US011912986B2

(12) United States Patent
Mali et al.

(10) Patent No.: US 11,912,986 B2
(45) Date of Patent: Feb. 27, 2024

(54) METHODS FOR SCREENING GENETIC PERTURBATIONS

(71) Applicant: The Regents of the University of California, Oakland, CA (US)

(72) Inventors: Prashant Mali, La Jolla, CA (US); Udit Parekh, La Jolla, CA (US); Yan Wu, La Jolla, CA (US); Kun Zhang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 274 days.

(21) Appl. No.: 17/028,836

(22) Filed: Sep. 22, 2020

(65) Prior Publication Data

US 2021/0108193 A1 Apr. 15, 2021

Related U.S. Application Data

(60) Provisional application No. 62/904,614, filed on Sep. 23, 2019.

(51) Int. Cl.
*C12N 15/10* (2006.01)
*C12N 5/071* (2010.01)
(Continued)

(52) U.S. Cl.
CPC .......... *C12N 15/1065* (2013.01); *A61K 35/44* (2013.01); *C12N 5/069* (2013.01);
(Continued)

(58) Field of Classification Search
CPC .... C12N 15/1065; C12N 5/069; C12N 15/86; C12N 2506/45; C12N 2740/15043; C12N 2740/15052; A61K 35/44
See application file for complete search history.

(56) References Cited

U.S. PATENT DOCUMENTS 5,591,624 A 1/1997 Barber et al.
6,365,150 B1 4/2002 Leboulch et al.
(Continued)

OTHER PUBLICATIONS

Parekh et al, 2018. Mapping Cellular Reprogramming via Pooled Overexpression Screens with Paired Fitness and Single-Cell RNA-Sequencing Readout. Cell Systems, 7, 548-555. (Year: 2018).*
(Continued)

*Primary Examiner* — Arthur S Leonard
*Assistant Examiner* — Jianjian Zhu
(74) *Attorney, Agent, or Firm* — Foley & Lardner LLP

(57) ABSTRACT

Understanding the complex effects of genetic perturbations on cellular state and fitness in human pluripotent stem cells (hPSCs) has been challenging using traditional pooled screening techniques which typically rely on unidimensional phenotypic readouts. Here, Applicants use barcoded open reading frame (ORF) overexpression libraries with a coupled single-cell RNA sequencing (scRNA-seq) and fitness screening approach, a technique we call SEUSS (ScalablE fUnctional Screening by Sequencing), to establish a comprehensive assaying platform. Using this system, Applicants perturbed hPSCs with a library of developmentally critical transcription factors (TFs), and assayed the impact of TF overexpression on fitness and transcriptomic cell state across multiple media conditions. Applicants further leveraged the versatility of the ORF library approach to systematically assay mutant gene libraries and also whole gene families. From the transcriptomic responses, Applicants built genetic co-perturbation networks to identify key altered gene modules. Strikingly, we found that KLF4 and SNAI2 have opposing effects on the pluripotency gene module, highlighting the power of this method to characterize the effects of genetic perturbations. From the fitness responses,
(Continued)

Applicants identified ETV2 as a driver of reprogramming towards an endothelial-like state.

13 Claims, 12 Drawing Sheets

Specification includes a Sequence Listing.

(51) Int. Cl.
*C12N 15/86* (2006.01)
*A61K 35/44* (2015.01)

(52) U.S. Cl.
CPC .......... *C12N 15/86* (2013.01); *C12N 2506/45* (2013.01); *C12N 2740/15043* (2013.01); *C12N 2740/15052* (2013.01)

(56) References Cited

U.S. PATENT DOCUMENTS

| | | | |
|---|---|---|---|
| 6,372,502 B1 | 4/2002 | Bank et al. |
| 6,475,786 B1 | 11/2002 | Bordignon et al. |
| 6,924,123 B2 | 8/2005 | Kingsman et al. |
| 6,995,919 B2 | 2/2006 | Kim |
| 7,056,699 B2 | 6/2006 | Kingsman et al. |
| 7,070,993 B2 | 7/2006 | Kaleko et al. |
| 7,070,994 B2 | 7/2006 | Barber et al. |
| 7,419,829 B2 | 9/2008 | Mitrophanous et al. |
| 7,442,551 B2 | 10/2008 | Kaleko et al. |

OTHER PUBLICATIONS

Sack et al, 2018, Profound Tissue Specificity in Proliferation Control Underlies Cancer Drivers and Aneuploidy Patterns, Cell 173, 499-514, e1-e13. (Year: 2018).*

Sack et al, 2018, Profound Tissue Specificity in Proliferation Control Underlies Cancer Drivers and Aneuploidy Patterns, Cell 173, 499-514. Supplemental table S1D. (Year: 2018).*

Elcheva et al. Direct induction of haematoendothelial programs in human pluripotent stem cells by transcriptional regulators. Nature Communications, 2014, 5: 4372. (Year: 2014).*

Morita et al. ETS transcription factor ETV2 directly converts human fibroblasts into functional endothelial cells. PNAS, 2015, 112(1):160-165. (Year: 2015).*

Adamson, et al., "A Multiplexed Single-Cell CRISPR Screening Platform Enables Systematic Dissection of the Unfolded Protein Response", Cell 167, 2016, pp. 1867-1882.

Castro, et al., "A novel function of the proneural factor Ascl1 in progenitor proliferation identified by genome-wide characterization of its targets", Genes & Development 25, 2011, pp. 930-945.

Chanda, et al., "Generation of Induced Neuronal Cells by the Single Reprogramming Factor ASCL1", Stem Cell Reports, 2014, vol. 3, pp. 282-296.

Datlinger, et al., "Pooled CRISPR screening with single-cell transcriptome readout", Nature Methods, 2016, vol. 14, No. 3, pp. 297-301.

Dixit, et al., "Perturb-seq: Dissecting molecular circuits with scalable single cell RNA profiling of pooled genetic screens", Cell, 2016, 167(7), pp. 1853-1866.

Fulton, et al., "TFCat: the curated catalog of mouse and human transcription factors", Genome Biology, 10(3):R29, 2009, 14 pages.

Hashimshony, et al., "CEL-Seq: Single-Cell RNA-Seq by Multiplexed Linear Amplification", Cell Reports, 2012, 2(3), pp. 666-673.

Islam, et al., "Characterization of the single-cell transcriptional landscape by highly multiplex RNA-seq", Genome Research, 2011, 21(7), pp. 1160-1167.

Jaitin, et al., "Dissecting Immune Circuits by Linking CRISPR-Pooled Screens with Single-Cell RNA-Seq", Cell 167, 2016, pp. 1883-1896.

Kolodziejczyk, et al., "The Technology and Biology of Single-Cell RNA Sequencing", Molecular Cell 58, 2015, pp. 610-620.

Liu, et al., "Critical and Reciprocal Regulation of KLF4 and SLUG in Transforming Growth Factor beta-Initiated Prostate Cancer Epithelial-Mesenchymal Transition", Molecular and Cellular Biology 32, 2012, pp. 941-953.

Macosko, et al., "Highly Parallel Genome-wide Expression Profiling of Individual Cells Using Nanoliter Droplets", Cell 161, 2015, pp. 1202-1214.

Mohr, et al., "Genomic Screening with RNAi: Results and Challenges", Annu. Rev. Biochem., 2010, 79, pp. 37-64.

Morita, et al., "ETS transcription factor ETV2 directly converts human fibroblasts into functional endothelial cells", PNAS, 2015, vol. 112, No. 1, pp. 160-165.

Nishiyama, et al., "Uncovering Early Response of Gene Regulatory Networks in ESCs by Systematic Induction of Transcription Factors", Cell Stem Cell 5, 2009, pp. 420-433.

Orkin, et al., "Chromatin Connections to Pluripotency and Cellular Reprogramming", Cell 145, 2011, pp. 835-850.

Ramsköld, et al., "Full-Length mRNA-Seq from single cell levels of RNA and individual circulating tumor cells", Nat. Biotechnol., Aug. 2012, 30(8), pp. 777-782.

Sasagawa, et al., "Quartz-Seq: a highly reproducible and sensitive single-cell RNA sequencing method, reveals non-genetic gene-expression heterogeneity", Genome Biology, 2013, 14(4):R31, 17 pages.

Shalem, et al., "High-throughput functional genomics using CRISPR-Cas9" Nat. Rev. Genet., 2015, 16(5), pp. 299-311.

Subramanian, et al., "Gene set enrichment analysis: A knowledge-based approach for interpreting genome-wide expression profiles", PNAS, 2005, vol. 102, No. 43, pp. 15545-15550.

Tang, et al., "mRNA-Seq whole-transcriptome analysis of a single cell", Nature Methods, vol. 6, No. 5, May 2009, pp. 377-382.

Treutlein, et al., "Dissecting direct reprogramming from fibroblast to neuron using single-cell RNA-seq", Nature, 2016 534(7607), pp. 391-395.

Xie, et al., Multiplexed Engineering and Analysis of Combinatorial Enhancer Activity in Single Cells, Molecular Cell 66, 2017, pp. 285-299.

* cited by examiner

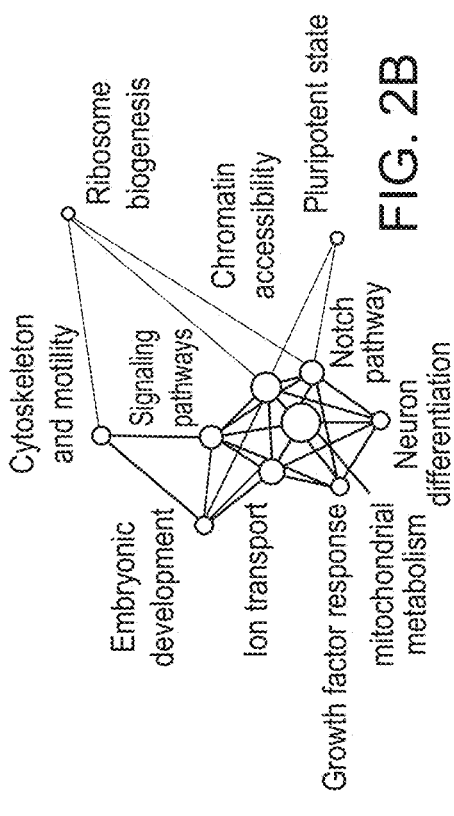
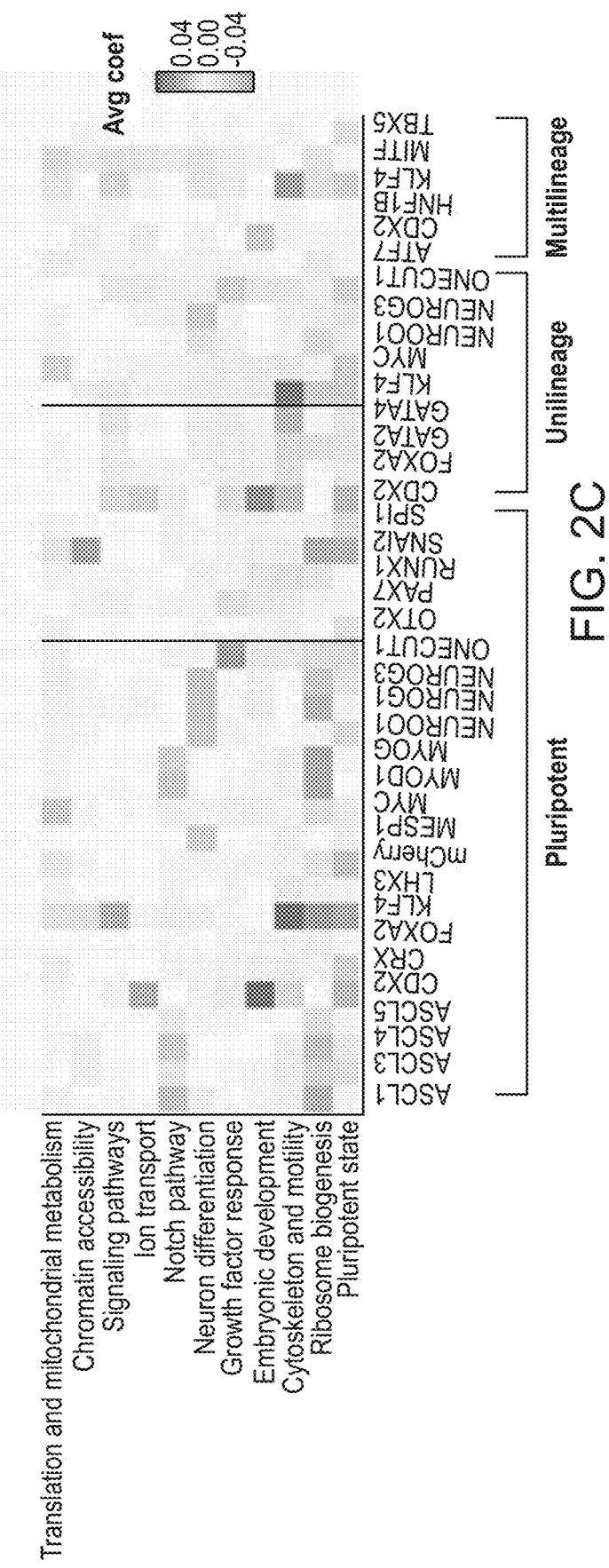
FIG. 2A
FIG. 2B
FIG. 2C

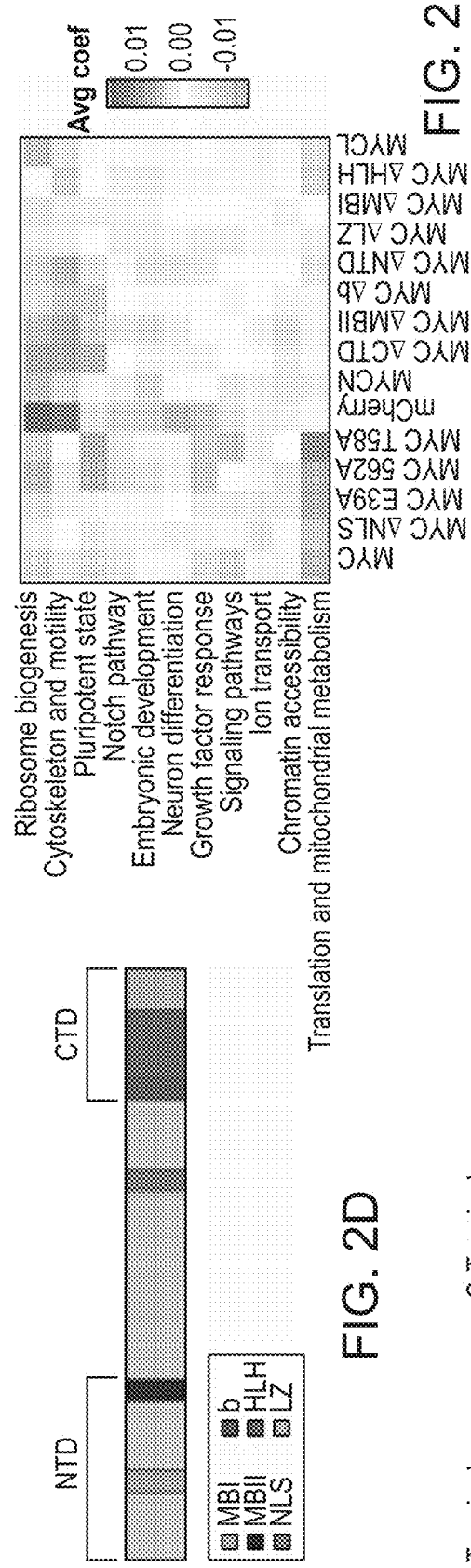
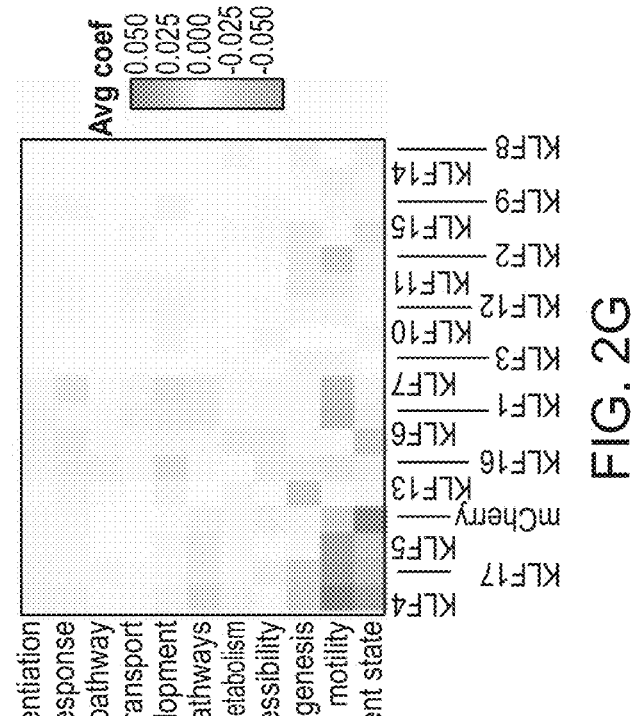
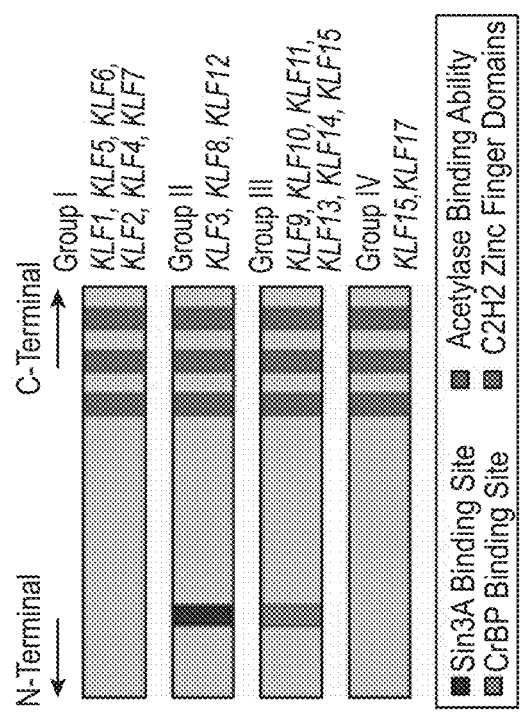
FIG. 2D, FIG. 2E, FIG. 2F, FIG. 2G

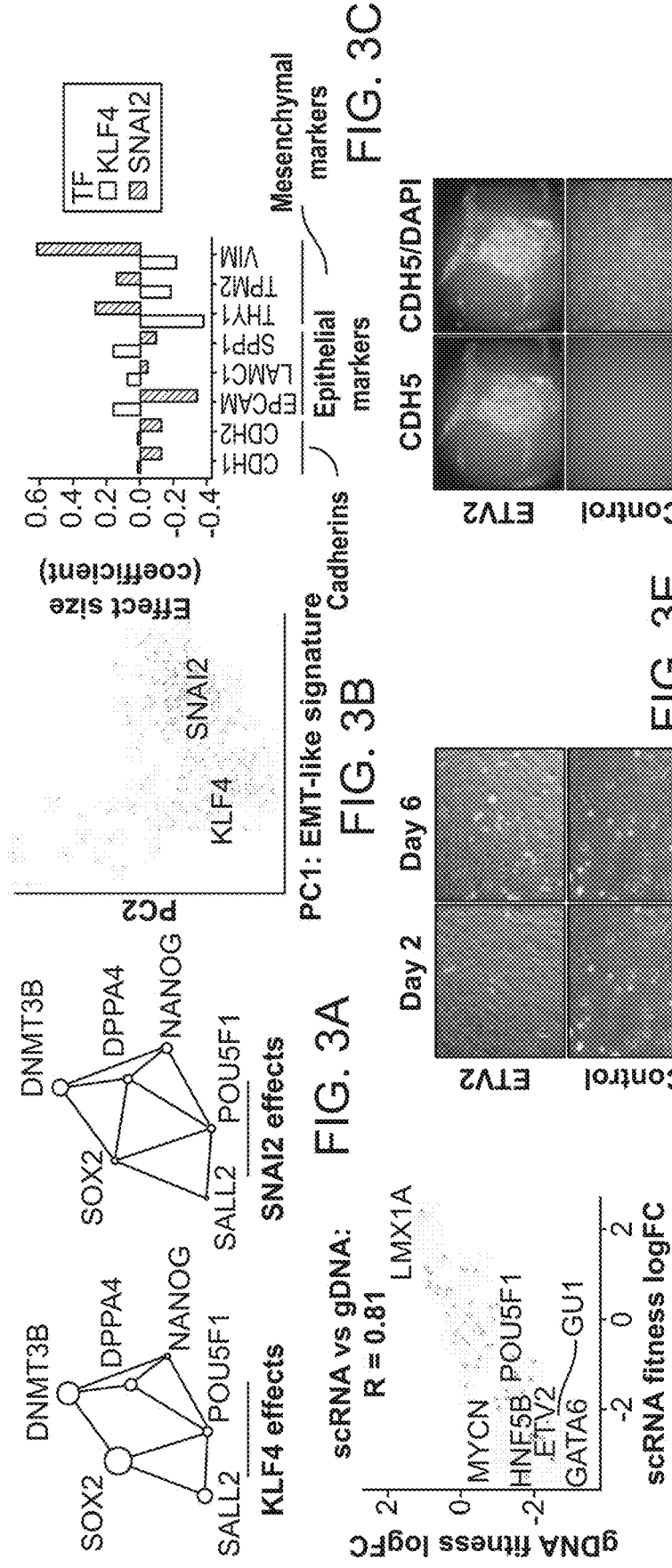

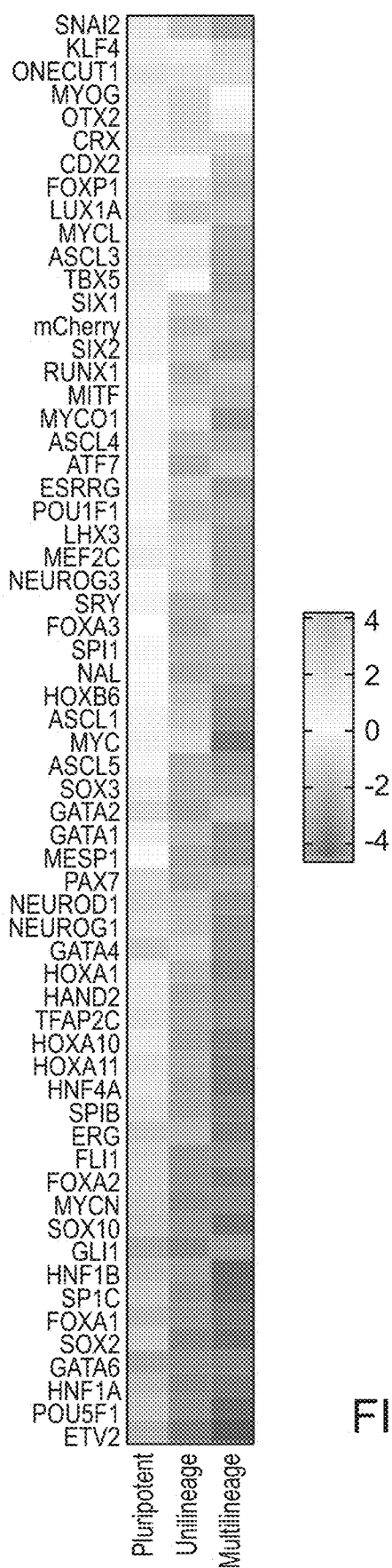
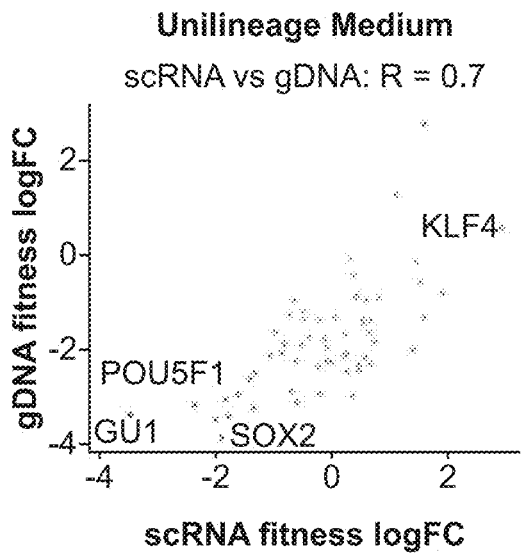
FIG. 5B
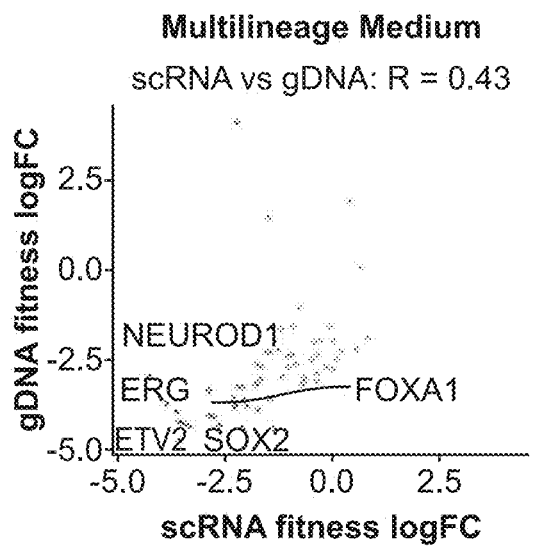
FIG. 5C
FIG. 5A

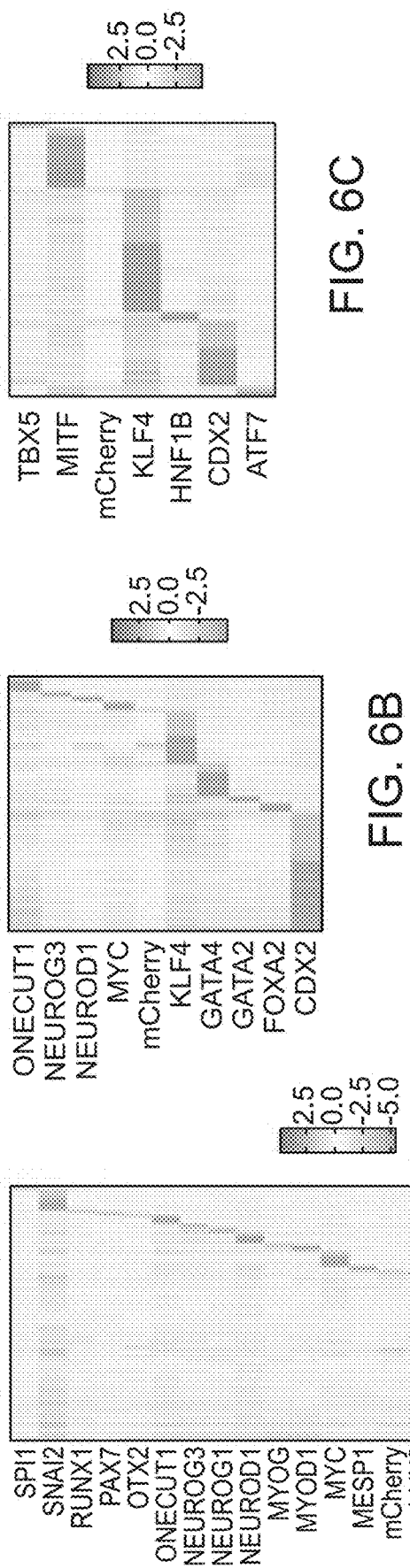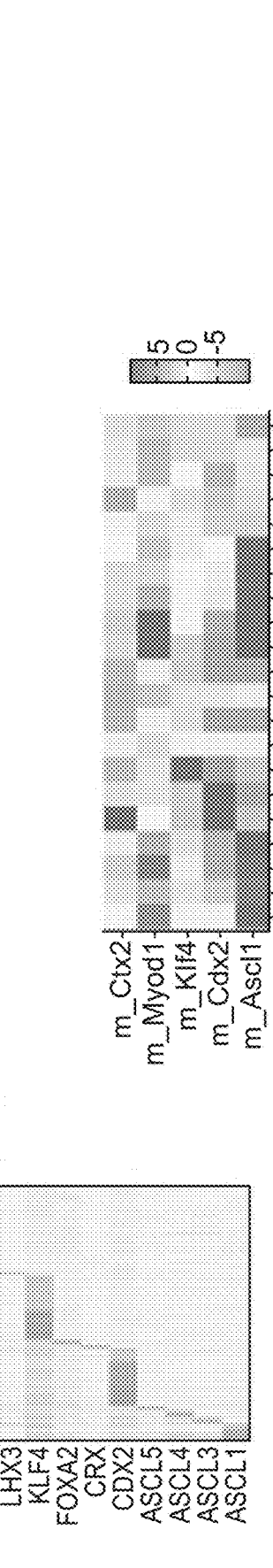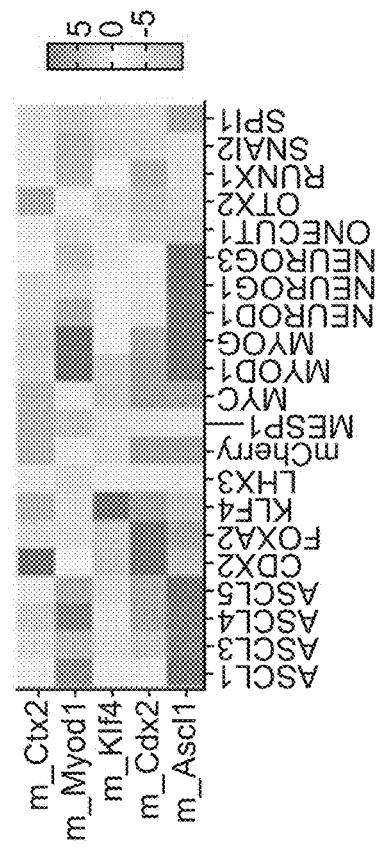

SEQUENCE LISTING

```
<160> NUMBER OF SEQ ID NOS: 130

<210> SEQ ID NO 1
<211> LENGTH: 1413
<212> TYPE: DNA
<213> ORGANISM: Homo sapiens

<400> SEQUENCE: 1
ttcctgttgc agataagccc agcttagccc agctgacccc agaccctctc ccctcactcc        60
ccccatgtcg caggatcgag accctgaggc agacagcccg ttcaccaagc cccccgcccc       120
gcccccatca ccccgtaaac ttctcccagc ctccgccctg ccctcaccca gcccgctgtt       180
ccccaagcct cgctccaagc ccacgccacc cctgcagcag ggcagcccca gaggccagca       240
cctatccccg aggctggggt cgaggctcgg ccccgccccct gcctctgcaa cttgagcctg      300
gctgcgaccc ctgctctgac gtctcggaaa attccccctt gcccaggccc ttgggggagg       360
gggtgcatgg tatgaaatgg ggctgagacc cccggctggg ggcagaggaa cccgccagag       420
aaggagccaa attaggcttc tgtttccctg atctggcact ccaaggggac acgccgacag       480
cgacagcaga gacatgctgg aaaggtacaa gctcatccct ggcaagcttc ccacagctgg       540
actggggctc cgcgttactg cacccagaag ttccatgggg ggcggagccc gactctcagg       600
ctcttccgtg gtccggggac tggacagaca tggcgtgcac agcctgggac tcttggagcg       660
gcgcctcgca gaccctgggc cccgcccctc tcggcccggg ccccatcccc gccgccggct       720
ccgaaggcgc cgcgggccag aactgcgtcc ccgtggcggg agaggccacc tcgtggtcgc       780
gcgcccaggc cgccgggagc aacaccagct gggactgttc tgtggggccc gacggcgata       840
cctactgggg cagtggcctg ggcggggagc cgcgcacgga ctgtaccatt tcgtggggcg       900
ggcccgcggg cccggactgt accacctcct ggaacccggg gctgcatgcg ggtggcacca       960
cctctttgaa gcggtaccag agctcagctc tcaccgtttg ctccgaaccg agcccgcagt      1020
cggaccgtgc cagtttggct cgatgcccca aaactaacca ccgaggtccc attcagctgt      1080
ggcagttcct cctggagctg ctccacgacg gggcgcgtag cagctgcatc cgttggactg      1140
gcaacagccg cgagttccag ctgtgcgacc ccaaagaggt ggctcggctg tggggcgagc      1200
gcaagagaaa gccgggcatg aattacgaga agctgagccg gggccttcgc tactactatc      1260
gccgcgacat cgtgcgcaag agcgggggc gaaagtacac gtaccgcttc ggggccgcg       1320 tgcccagcct agcctatccg gactgtgcgg gaggcggacg gggagcagag acacaataaa      1380
aattcccggt caaacctcaa aaaaaaaaa aaa                                    1413
```

<210> SEQ ID NO 2
<211> LENGTH: 1275
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| atgcccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgggatcagg tagcggtagc cgccgctccg ggctctgctc gccctcctac | 180 |
| gttgcggtca cacccttctc ccttcgggga gacaacgacg gcggtggcgg gagcttctcc | 240 |
| acggccgacc agctggagat ggtgaccgag ctgctgggag agacatggt gaaccagagt | 300 |
| ttcatctgcg acccggacga cgagaccttc atcaaaaaca tcatcatcca ggactgtatg | 360 |
| tggagcggct tctcggccgc cgccaagctc gtctcagaga gctggcctc ctaccaggct | 420 |
| gcgcgcaaag acagcggcag cccgaacccc gcccgcggcc acagcgtctg ctccacctcc | 480 |
| agcttgtacc tgcaggatct gagcgccgcc gcctcagagt gcatcgaccc ctcggtggtc | 540 |
| ttcccctacc ctctcaacga cagcagctcg cccaagtcct gcgcctcgca agactccagc | 600 |
| gccttctctc cgtcctcgga ttctctgctc tcctcgacgg agtcctcccc gcagggcagc | 660 |
| cccgagcccc tggtgctcca tgaggagaca ccgcccacca ccagcagcga ctctgaggag | 720 |
| gaacaagaag atgaggaaga aatcgatgtt gtttctgtgg aaaagaggca ggctcctggc | 780 |
| aaaaggtcag agtctggatc accttctgct ggaggccaca gcaaacctcc tcacagccca | 840 |
| ctggtcctca gaggtgcca cgtctccaca catcagcaca actacgcagc gcctccctcc | 900 |
| actcggaagg actatcctgc tgccaagagg gtcaagttgg acagtgtcag agtcctgaga | 960 |
| cagatcagca caaccgaaa atgcaccagc cccaggtcct cggacaccga ggagaatgtc | 1020 |
| aagaggcgaa cacacaacgt cttggagcgc cagaggagga acgagctaaa acggagcttt | 1080 |
| tttgccctgc gtgaccagat cccggagttg gaaaacaatg aaaaggcccc caaggtagtt | 1140 |
| atccttaaaa aagccacagc atacatcctg tccgtccaag cagaggagca aaagctcatt | 1200 |
| tctgaagagg acttgttgcg gaaacgacga gaacagttga acacaaaact gaacagcta | 1260 |
| cggaactctt gtgcg | 1275 |

<210> SEQ ID NO 3
<211> LENGTH: 1287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| atgcccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgcccagcga ggatatctgg aagaaattcg agctgctgcc caccccgccc | 180 |
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |

```
gacgagacct tcatcaaaaa catcggatca ggtagcggtc tcgtctcaga gaagctggcc      420
tcctaccagg ctgcgcgcaa agacagcggc agcccgaacc ccgcccgcgg ccacagcgtc      480
tgctccacct ccagcttgta cctgcaggat ctgagcgccg ccgcctcaga gtgcatcgac      540
ccctcggtgg tcttccccta ccctctcaac gacagcagct cgcccaagtc ctgcgcctcg      600
caagactcca gcgccttctc tccgtcctcg gattctctgc tctcctcgac ggagtcctcc      660
ccgcagggca gccccgagcc cctggtgctc catgaggaga caccgcccac caccagcagc      720
gactctgagg aggaacaaga agatgaggaa gaaatcgatg ttgtttctgt ggaaaagagg      780
caggctcctg gcaaaaggtc agagtctgga tcaccttctg ctggaggcca cagcaaacct      840
cctcacagcc cactggtcct caagaggtgc cacgtctcca catcagca caactacgca       900 gcgcctccct ccactcggaa ggactatcct gctgccaaga gggtcaagtt ggacagtgtc      960
agagtcctga cagatcag caacaaccga aaatgcacca gccccaggtc ctcggacacc      1020
gaggagaatg tcaagaggcg aacacacaac gtcttggagc gccagaggag gaacgagcta     1080
aaacggagct ttttgccct gcgtgaccag atcccgagt tggaaaacaa tgaaaaggcc      1140
cccaaggtag ttatccttaa aaaagccaca gcatacatcc tgtccgtcca agcagaggag     1200
caaaagctca tttctgaaga ggacttgttg cggaaacgac gagaacagtt gaaacacaaa     1260
cttgaacagc tacggaactc ttgtgcg                                         1287
```

<210> SEQ ID NO 4
<211> LENGTH: 1305
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgcccctca acgttagctt caccaacagg aactatgacc tcgactacga ctcggtgcag       60
ccgtatttct actgcgacga ggaggagaac ttctaccagc agcagcagca gagcgagctg      120
cagcccccgg cgcccagcga ggatatctgg aagaaattcg agctgctgcc cacccccgccc     180 ctgtccccta gccgccgctc cgggctctgc tcgccctcct acgttgcggt cacacccttc      240
tcccttcggg gagacaacga cggcggtggc gggagcttct ccacggccga ccagctggag      300
atggtgaccg agctgctggg aggagacatg gtgaaccaga gtttcatctg cgaccccgac      360
gacgagacct tcatcaaaaa catcatcatc caggactgta tgtggagcgg cttctcggcc      420
gccgccaagc tcgtctcaga gaagctggcc tcctaccagg ctgcgcgcaa agacagcggc      480
agcccgaacc ccgcccgcgg ccacagcgtc tgctccacct ccagcttgta cctgcaggat      540
ctgagcgccg ccgcctcaga gtgcatcgac ccctcggtgg tcttccccta ccctctcaac      600
gacagcagct cgcccaagtc ctgcgcctcg caagactcca gcgccttctc tccgtcctcg      660
gattctctgc tctcctcgac ggagtcctcc ccgcagggca gccccgagcc cctggtgctc      720
catgaggaga caccgcccac caccagcagc gactctgagg aggaacaaga agatgaggaa      780
gaaatcgatg ttgtttctgt ggaaaagagg caggctcctg gcaaaaggtc agagtctgga      840
tcaccttctg ctggaggcca cagcaaacct cctcacagcc cactggtcct caagaggtgc      900
cacgtctcca catcagca caactacgca gcgcctccct ccactcggaa ggactatgga       960
tcaggtagcg gtagtgtcag agtcctgaga cagatcagca acaaccgaaa atgcaccagc     1020
cccaggtcct cggacaccga ggagaatgtc aagaggcgaa cacacaacgt cttggagcgc     1080
```

| | |
|---|---|
| cagaggagga acgagctaaa acggagcttt tttgccctgc gtgaccagat cccggagttg | 1140 |
| gaaaacaatg aaaaggcccc caaggtagtt atccttaaaa aagccacagc atacatcctg | 1200 |
| tccgtccaag cagaggagca aaagctcatt tctgaagagg acttgttgcg aaacgacga | 1260 |
| gaacagttga aacacaaact tgaacagcta cggaactctt gtgcg | 1305 |

<210> SEQ ID NO 5
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | |
|---|---|
| atgccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgcccagcga ggatatctgg aagaaattcg agctgctgcc caccccgccc | 180 |
| ctgtcccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |
| gacgagacct tcatcaaaaa catcatcatc caggactgta tgtggagcgg cttctcggcc | 420 |
| gccgccaagc tcgtctcaga aagctggcc tcctaccagg ctgcgcgcaa agacagcggc | 480 |
| agcccgaacc ccgcccgcgg ccacagcgtc tgctccacct ccagcttgta cctgcaggat | 540 |
| ctgagcgccg ccgcctcaga gtgcatcgac ccctcggtgg tcttcccta ccctctcaac | 600 |
| gacagcagct cgcccaagtc ctgcgcctcg caagactcca cgccttctc tccgtcctcg | 660 |
| gattctctgc tctcctcgac ggagtcctcc ccgcagggca gccccgagcc cctggtgctc | 720 |
| catgaggaga caccgcccac caccagcagc gactctgagg aggaacaaga agatgaggaa | 780 |
| gaaatcgatg ttgtttctgt ggaaaagagg caggctcctg gcaaaaggtc agagtctgga | 840 |
| tcaccttctg ctggaggcca cagcaaacct cctcacagcc cactggtcct caagaggtgc | 900 |
| cacgtctcca cacatcagca caactacgca gcgcctccct ccactcggaa ggactatcct | 960 |
| gctgccaaga gggtcaagtt ggacagtgtc agagtcctga cagatcag caacaaccga | 1020 |
| aaatgcacca gccccaggtc ctcggacacc gaggagaatg tcggatcagg tagcggtgag | 1080 |
| ctaaaacgga gcttttttgc cctgcgtgac cagatcccgg agttggaaaa caatgaaaag | 1140 |
| gcccccaagg tagttatcct taaaaaagcc acagcataca tcctgtccgt ccaagcagag | 1200 |
| gagcaaaagc tcatttctga gaggacttg ttgcggaaac gacgagaaca gttgaaacac | 1260 |
| aaacttgaac agctacggaa ctcttgtgcg | 1290 |

<210> SEQ ID NO 6
<211> LENGTH: 1206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | |
|---|---|
| atgccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgcccagcga ggatatctgg aagaaattcg agctgctgcc caccccgccc | 180 |

| | |
|---|---|
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |
| gacgagacct tcatcaaaaa catcatcatc caggactgta tgtggagcgg cttctcggcc | 420 |
| gccgccaagc tcgtctcaga gaagctggcc tcctaccagg ctgcgcgcaa agacagcggc | 480 |
| agcccgaacc ccgccgcgg ccacagcgtc tgctccacct ccagcttgta cctgcaggat | 540 |
| ctgagcgccg ccgcctcaga gtgcatcgac ccctcggtgg tcttccccta ccctctcaac | 600 |
| gacagcagct cgcccaagtc ctgcgcctcg caagactcca gcgccttctc tccgtcctcg | 660 |
| gattctctgc tctcctcgac ggagtcctcc ccgcagggca gccccgagcc cctggtgctc | 720 |
| catgaggaga caccgcccac caccagcagc gactctgagg aggaacaaga agatgaggaa | 780 |
| gaaatcgatg ttgtttctgt ggaaaagagg caggctcctg gcaaaaggtc agagtctgga | 840 |
| tcaccttctg ctggaggcca cagcaaacct cctcacagcc cactggtcct caagaggtgc | 900 |
| cacgtctcca cacatcagca caactacgca gcgcctccct ccactcggaa ggactatcct | 960 |
| gctgccaaga gggtcaagtt ggacagtgtc agagtcctga cacagatcag caacaaccga | 1020 |
| aaatgcacca gccccaggtc ctcggacacc gaggagaatg tcaagaggcg aacacacaac | 1080 |
| gtcttggagc gccagaggag gaacggatca ggtagcggtc aaaagctcat ttctgaagag | 1140 |
| gacttgttgc ggaaacgacg agaacagttg aaacacaaac ttgaacagct acggaactct | 1200 |
| tgtgcg | 1206 |

<210> SEQ ID NO 7
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| atgcccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagccccgg cgcccagcga ggatatctgg aagaaattcg agctgctgcc caccccgccc | 180 |
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |
| gacgagacct tcatcaaaaa catcatcatc caggactgta tgtggagcgg cttctcggcc | 420 |
| gccgccaagc tcgtctcaga gaagctggcc tcctaccagg ctgcgcgcaa agacagcggc | 480 |
| agcccgaacc ccgccgcgg ccacagcgtc tgctccacct ccagcttgta cctgcaggat | 540 |
| ctgagcgccg ccgcctcaga gtgcatcgac ccctcggtgg tcttccccta ccctctcaac | 600 |
| gacagcagct cgcccaagtc ctgcgcctcg caagactcca gcgccttctc tccgtcctcg | 660 |
| gattctctgc tctcctcgac ggagtcctcc ccgcagggca gccccgagcc cctggtgctc | 720 |
| catgaggaga caccgcccac caccagcagc gactctgagg aggaacaaga agatgaggaa | 780 |
| gaaatcgatg ttgtttctgt ggaaaagagg caggctcctg gcaaaaggtc agagtctgga | 840 |
| tcaccttctg ctggaggcca cagcaaacct cctcacagcc cactggtcct caagaggtgc | 900 |
| cacgtctcca cacatcagca caactacgca gcgcctccct ccactcggaa ggactatcct | 960 |

| | |
|---|---|
| gctgccaaga gggtcaagtt ggacagtgtc agagtcctga gacagatcag caacaaccga | 1020 |
| aaatgcacca gcccaggtc ctcggacacc gaggagaatg tcaagaggcg aacacacaac | 1080 |
| gtcttggagc gccagaggag gaacgagcta aaacggagct tttttgccct gcgtgaccag | 1140 |
| atcccggagt tggaaaacaa tgaaaaggcc cccaaggtag ttatccttaa aaaagccaca | 1200 |
| gcatacatcc tgtccgtcca agcagaggag | 1230 |

<210> SEQ ID NO 8
<211> LENGTH: 906
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

| | |
|---|---|
| atgggatcag gtagcggtct cgtctcagag aagctggcct cctaccaggc tgcgcgcaaa | 60 |
| gacagcggca gcccgaaccc cgcccgcggc cacagcgtct gctccacctc cagcttgtac | 120 |
| ctgcaggatc tgagcgccgc cgcctcagag tgcatcgacc cctcggtggt cttcccctac | 180 |
| cctctcaacg cagcagctc gcccaagtcc tgcgcctcgc aagactccag cgccttctct | 240 |
| ccgtcctcgg attctctgct ctcctcgacg gagtcctccc cgcagggcag ccccgagccc | 300 |
| ctggtgctcc atgaggagac accgccacc accagcagcg actctgagga ggaacaagaa | 360 |
| gatgaggaag aaatcgatgt tgtttctgtg gaaagagggc aggctcctgg caaaaggtca | 420 |
| gagtctggat caccttctgc tggaggccac agcaaacctc ctcacagccc actggtcctc | 480 |
| aagaggtgcc acgtctccac acatcagcac aactacgcag cgcctcccc cactcggaag | 540 |
| gactatcctg ctgccaagag ggtcaagttg acagtgtca gagtcctgag acagatcagc | 600 |
| aacaaccgaa aatgcaccag ccccaggtcc tcggacaccg aggagaatgt caagaggcga | 660 |
| acacacaacg tcttggagcg ccagaggagg aacgagctaa aacggagctt ttttgccctg | 720 |
| cgtgaccaga tcccggagtt ggaaaacaat gaaaaggccc caaggtagt tatccttaaa | 780 |
| aaagccacag catacatcct gtccgtccaa gcagaggagc aaaagctcat ttctgaagag | 840 |
| gacttgttgc ggaaacgacg agaacagttg aaacacaaac ttgaacagct acggaactct | 900 |
| tgtgcg | 906 |

<210> SEQ ID NO 9
<211> LENGTH: 1062
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

| | |
|---|---|
| atgccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagcccccgg cgcccagcga ggatatctgg aagaaattcg agctgctgcc caccccgccc | 180 |
| ctgtccccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccagg tttcatctg cgaccccgga | 360 |
| gacgagacct tcatcaaaaa catcatcatc caggactgta tgtggagcgg cttctcggcc | 420 |

```
gccgccaagc tcgtctcaga gaagctggcc tcctaccagg ctgcgcgcaa agacagcggc      480
agcccgaacc ccgcccgcgg ccacagcgtc tgctccacct ccagcttgta cctgcaggat      540
ctgagcgccg ccgcctcaga gtgcatcgac ccctcggtgg tcttccccta ccctctcaac      600
gacagcagct cgcccaagtc ctgcgcctcg caagactcca gcgccttctc tccgtcctcg      660
gattctctgc tctcctcgac ggagtcctcc ccgcagggca gccccgagcc cctggtgctc      720
catgaggaga caccgcccac caccagcagc gactctgagg aggaacaaga agatgaggaa      780
gaaatcgatg ttgtttctgt ggaaaagagg caggctcctg gcaaaaggtc agagtctgga      840
tcaccttctg ctggaggcca cagcaaacct cctcacagcc cactggtcct caagaggtgc      900
cacgtctcca cacatcagca caactacgca gcgcctccct ccactcggaa ggactatcct      960
gctgccaaga gggtcaagtt ggacagtgtc agagtcctga cagatcag caacaaccga     1020 aaatgcacca gccccaggtc ctcggacacc gaggagaatg tc                        1062
```

<210> SEQ ID NO 10
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
atgcccctca acgttagctt caccaacagg aactatgacc tcgactacga ctcggtgcag       60
ccgtatttct actgcgacga ggaggagaac ttctaccagc agcagcagca gagcgcgctg      120 cagccccgg cgcccagcga ggatatctgg aagaaattcg agctgctgcc caccccgccc      180
ctgtccccta gccgccgctc cgggctctgc tcgccctcct acgttgcggt cacacccttc      240
tcccttcggg gagacaacga cggcgtggc gggagcttct ccacggccga ccagctggag      300
atggtgaccg agctgctggg aggagacatg gtgaaccaga gtttcatctg cgaccccgga      360
gacgagacct tcatcaaaaa catcatcatc caggactgta tgtggagcgg cttctcggcc      420
gccgccaagc tcgtctcaga gaagctggcc tcctaccagg ctgcgcgcaa agacagcggc      480
agcccgaacc ccgcccgcgg ccacagcgtc tgctccacct ccagcttgta cctgcaggat      540
ctgagcgccg ccgcctcaga gtgcatcgac ccctcggtgg tcttccccta ccctctcaac      600
gacagcagct cgcccaagtc ctgcgcctcg caagactcca gcgccttctc tccgtcctcg      660
gattctctgc tctcctcgac ggagtcctcc ccgcagggca gccccgagcc cctggtgctc      720
catgaggaga caccgcccac caccagcagc gactctgagg aggaacaaga agatgaggaa      780
gaaatcgatg ttgtttctgt ggaaaagagg caggctcctg gcaaaaggtc agagtctgga      840
tcaccttctg ctggaggcca cagcaaacct cctcacagcc cactggtcct caagaggtgc      900
cacgtctcca cacatcagca caactacgca gcgcctccct ccactcggaa ggactatcct      960
gctgccaaga gggtcaagtt ggacagtgtc agagtcctga cagatcag caacaaccga     1020 aaatgcacca gccccaggtc ctcggacacc gaggagaatg tcaagaggcg aacacacaac     1080
gtcttggagc gccagaggag gaacgagcta aaacggagct tttttgccct gcgtgaccag     1140
atcccggagt tggaaaacaa tgaaaaggcc cccaaggtag ttatccttaa aaaagccaca     1200
gcatacatcc tgtccgtcca agcagaggag caaaagctca tttctgaaga ggacttgttg     1260
cggaaacgac gagaacagtt gaaacacaaa cttgaacagc tacggaactc ttgtgcg        1317
```

<210> SEQ ID NO 11

<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

| | | | | |
|---|---|---|---|---|
| atgcccctca | acgttagctt | caccaacagg | aactatgacc tcgactacga ctcggtgcag | 60 |
| ccgtatttct | actgcgacga | ggaggagaac | ttctaccagc agcagcagca gagcgagctg | 120 |
| cagccccgg | cgcccagcga | ggatatctgg | aagaaattcg agctgctgcc cgccccgccc | 180 |
| ctgtccccta | gccgccgctc | cgggctctgc | tcgccctcct acgttgcggt cacacccttc | 240 |
| tcccttcggg | gagacaacga | cggcggtggc | gggagcttct ccacggccga ccagctggag | 300 |
| atggtgaccg | agctgctggg | aggagacatg | gtgaaccaga gtttcatctg cgacccggac | 360 |
| gacgagacct | tcatcaaaaa | catcatcatc | caggactgta tgtggagcgg cttctcggcc | 420 |
| gccgccaagc | tcgtctcaga | gaagctggcc | tcctaccagg ctgcgcgcaa agacagcggc | 480 |
| agcccgaacc | ccgcccgcgg | ccacagcgtc | tgctccacct ccagcttgta cctgcaggat | 540 |
| ctgagcgccg | ccgcctcaga | gtgcatcgac | ccctcggtgg tcttccccta ccctctcaac | 600 |
| gacagcagct | cgcccaagtc | ctgcgcctcg | caagactcca gcgccttctc tccgtcctcg | 660 |
| gattctctgc | tctcctcgac | ggagtcctcc | ccgcagggca gccccgagcc cctggtgctc | 720 |
| catgaggaga | caccgcccac | caccagcagc | gactctgagg aggaacaaga agatgaggaa | 780 |
| gaaatcgatg | ttgtttctgt | ggaaaagagg | caggctcctg gcaaaaggtc agagtctgga | 840 |
| tcaccttctg | ctggaggcca | cagcaaacct | cctcacagcc cactggtcct caagaggtgc | 900 |
| cacgtctcca | cacatcagca | caactacgca | gcgcctccct ccactcggaa ggactatcct | 960 |
| gctgccaaga | gggtcaagtt | ggacagtgtc | agagtcctga gacagatcag caacaaccga | 1020 |
| aaatgcacca | gccccaggtc | ctcggacacc | gaggagaatg tcaagaggcg aacacacaac | 1080 |
| gtcttggagc | gccagaggag | gaacgagcta | aaacggagct ttttgccct gcgtgaccag | 1140 |
| atcccggagt | tggaaaacaa | tgaaaaggcc | cccaaggtag ttatccttaa aaaagccaca | 1200 |
| gcatacatcc | tgtccgtcca | agcagaggag | caaaagctca tttctgaaga ggacttgttg | 1260 |
| cggaaacgac | gagaacagtt | gaaacacaaa | cttgaacagc tacggaactc ttgtgcg | 1317 |

<210> SEQ ID NO 12
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | | | | |
|---|---|---|---|---|
| atgcccctca | acgttagctt | caccaacagg | aactatgacc tcgactacga ctcggtgcag | 60 |
| ccgtatttct | actgcgacga | ggaggagaac | ttctaccagc agcagcagca gagcgagctg | 120 |
| cagccccgg | cgcccagcga | ggatatctgg | aagaaattcg agctgctgcc caccccgccc | 180 |
| ctggccccta | gccgccgctc | cgggctctgc | tcgccctcct acgttgcggt cacacccttc | 240 |
| tcccttcggg | gagacaacga | cggcggtggc | gggagcttct ccacggccga ccagctggag | 300 |
| atggtgaccg | agctgctggg | aggagacatg | gtgaaccaga gtttcatctg cgacccggac | 360 |
| gacgagacct | tcatcaaaaa | catcatcatc | caggactgta tgtggagcgg cttctcggcc | 420 |
| gccgccaagc | tcgtctcaga | gaagctggcc | tcctaccagg ctgcgcgcaa agacagcggc | 480 |

| | | |
|---|---|---|
| agcccgaacc cgcccgcgg ccacagcgtc tgctccacct ccagcttgta cctgcaggat | 540 | |
| ctgagcgccg ccgcctcaga gtgcatcgac ccctcgtgg tcttcccta ccctctcaac | 600 | |
| gacagcagct cgcccaagtc ctgcgcctcg caagactcca gcgccttctc tccgtcctcg | 660 | |
| gattctctgc tctcctcgac ggagtcctcc ccgcagggca gccccgagcc cctggtgctc | 720 | |
| catgaggaga caccgcccac caccagcagc gactctgagg aggaacaaga agatgaggaa | 780 | |
| gaaatcgatg ttgtttctgt ggaaaagagg caggctcctg gcaaaaggtc agagtctgga | 840 | |
| tcaccttctg ctggaggcca cagcaaacct cctcacagcc cactggtcct caagaggtgc | 900 | |
| cacgtctcca cacatcagca caactacgca gcgcctccct ccactcggaa ggactatcct | 960 | |
| gctgccaaga gggtcaagtt ggacagtgtc agagtcctga cagatcag caacaaccga | 1020 | |
| aaatgcacca gccccaggtc ctcggacacc gaggagaatg tcaagaggcg aacacacaac | 1080 | |
| gtcttggagc gccagaggag gaacgagcta aaacggagct tttttgccct gcgtgaccag | 1140 | |
| atcccggagt tggaaaacaa tgaaaaggcc cccaaggtag ttatccttaa aaaagccaca | 1200 | |
| gcatacatcc tgtccgtcca agcagaggag caaaagctca tttctgaaga ggacttgttg | 1260 | |
| cggaaacgac gagaacagtt gaaacacaaa cttgaacagc tacggaactc ttgtgcg | 1317 | |

<210> SEQ ID NO 13
<211> LENGTH: 1086
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | | |
|---|---|---|
| atggcgactg cggagacagc acttccatca atctcaacac tcactgcact ggggccattt | 60 | |
| ccagataccc aggacgattt ccttaagtgg tggcggtccg aagaggctca agacatggga | 120 | |
| cctggtccgc cggatcccac cgaacctcct ctgcatgtca aaagtgaaga tcagcctggc | 180 | |
| gaggaagagg atgacgaaag gggtgccgac gccacttggg acttggatct ctccttacc | 240 | |
| aatttctctg gtccggaacc tggcggggca ccacagacgt gcgctctcgc tccctcagaa | 300 | |
| gcgagcgggg ctcagtaccc accccctccc gaaactctgg gagcctatgc tgggggtcct | 360 | |
| ggactggtgg ctgggttgct tggtagtgag gaccattctg gctgggtacg cccgctttg | 420 | |
| agggccgcg ctccggacgc ctttgtggga ccggcgctcg ctcctgcacc ggctccggaa | 480 | |
| ccaaaagccc tcgcgctgca gcccgtgtac cccggacccg gagccggatc ctcaggggga | 540 | |
| tacttcccac ggaccggact cagcgttcca gcggcttccg gggcgccata cggattgttg | 600 | |
| agcggctacc cggctatgta tcccgctccc cagtaccaag gacacttcca attgttccgg | 660 | |
| ggtcttcaag ggcctgcgcc cgggcctgct accagtccca gtttcctcag ttgtctggga | 720 | |
| ccgggaactg ttggcactgg acttggcggg actgcagagg acccaggcgt tatagcagag | 780 | |
| acagcgccaa gtaaaagggg ccgacgaagc tgggccagga acgccaagc tgcgcacact | 840 | |
| tgtgcccatc caggttgcgg taaatcctac acgaagagca gtcatcttaa agcacatctt | 900 | |
| cgcacacaca cgggcgagaa gccctacgcc tgtacttggg aaggttgcgg ctggagattc | 960 | |
| gctagatctg acgagctcac ccggcattat cgaaaacaca ctggccagcg accgttccgg | 1020 | |
| tgccaactct gcccaagggc gttcagtcgc tcagatcatc tggctttgca tatgaagcga | 1080 | |
| cacctt | 1086 | |

<210> SEQ ID NO 14
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | | | | | |
|---|---|---|---|---|---|
| atggcccttag | tgaacccat | tcttcccagc | ttttccacgt | tcgcgtctcc | ttgccgagag | 60 |
| agaggccttc | aggaaaggtg | gccgagggct | gaacccgagt | ctggaggtac | ggatgatgat | 120 |
| cttaacagtg | tgctcgattt | catactctca | atgggactgg | acgggctggg | agcggaggca | 180 |
| gctcctgaac | caccaccacc | ccctccgccc | ccagcgtttt | actacccgga | gccaggtgcg | 240 |
| ccgccgccat | attcagcccc | ggcggtggc | ttggtgtccg | agctcctccg | gcctgaattg | 300 |
| gatgccccgc | tcggcccggc | gctgcatggt | agatttctgc | tcgcgcctcc | gggtcgactc | 360 |
| gttaaggctg | aacctcctga | ggctgatggt | ggaggtggct | acggatgtgc | ccccgggctt | 420 |
| acccgaggac | cgagaggtct | taagcgggaa | ggggcacctg | gcccggctgc | aagctgtatg | 480 |
| cgggggcccg | gtgggaggcc | tcccccgccc | cctgatacac | cccccttag | tccagatgga | 540 |
| ccagctcgac | ttcccgcacc | tggccccaga | gcgagtttcc | ccctccatt | tggaggaccg | 600 |
| gggtttggcg | ccccaggtcc | tggacttcac | tacgcccctc | ctgccccccc | agcttttggt | 660 |
| cttttcgacg | atgctgctgc | tgccgcagca | gccttgggcc | ttgcgccgcc | cgcagccagg | 720 |
| ggactgctca | cgccaccggc | aagccccctg | gagctccttg | aagccaagcc | gaagcgagga | 780 |
| cgcagatcat | ggccgcgcaa | gcggacagct | acgcatacct | gctcatatgc | gggctgcgga | 840 |
| aaaacctaca | caaagagttc | acaccttaaa | gcgcaccttc | gcacacacac | aggcgagaaa | 900 |
| ccatatcatt | gtaactggga | cggatgtgga | tggaaatttg | ctcggtctga | tgagcttacg | 960 |
| agacattatc | gaaagcatac | cggacatcgg | ccctttcaat | gccatctttg | tgacagagct | 1020 |
| ttttcccggt | ctgaccacct | cgctctgcac | atgaagaggc | acatg | | 1065 |

<210> SEQ ID NO 15
<211> LENGTH: 1035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | | | | | |
|---|---|---|---|---|---|
| atgctcatgt | tgacccagt | tcctgtcaag | caagaggcca | tggaccctgt | ctcagtgtca | 60 |
| tacccatcta | attacatgga | atccatgaag | cctaacaagt | atgggggtcat | ctactccaca | 120 |
| ccattgcctg | agaagttctt | tcagaccccca | gaaggtctgt | cgcacggaat | acagatggag | 180 |
| ccagtggacc | tcacggtgaa | caagcggagt | tcacccccctt | cggctgggaa | ttcgccctcc | 240 |
| tctctgaagt | tcccgtcctc | acaccggaga | gcctcgcctg | ggttgagcat | gccttcttcc | 300 |
| agcccaccga | taaaaaaata | ctacccccct | tctccaggcg | tgcagcccctt | cggcgtgccg | 360 |
| ctgtccatgc | caccagtgat | ggcagctgcc | ctctcgcggc | atggaatacg | gagcccgggg | 420 |
| atcctgcccg | tcatccagcc | ggtggtggtg | cagcccgtcc | cctttatgta | cacaagtcac | 480 |
| ctccagcagc | ctctcatggt | ctccttatcg | gaggagatgg | aaaattccag | tagtagcatg | 540 |
| caagtacctg | taattgaatc | atatgagaag | cctatatcac | agaaaaaaat | taaaatagaa | 600 |
| cctgggatcg | aaccacagag | gacagattat | tatcctgaag | aaatgtcacc | ccccttaatg | 660 |

| | |
|---|---|
| aactcagtgt cccccccgca agcattgttg caagagaatc acccttcggt catcgtgcag | 720 |
| cctgggaaga gacctttacc tgtggaatcc ccggatactc aaaggaagcg gaggatacac | 780 |
| agatgtgatt atgatggatg caacaaagtg tacactaaaa gctcccactt gaaagcacac | 840 |
| agaagaacac acacaggaga aaaccctac aaatgtacat gggaagggtg cacatggaag | 900 |
| tttgctcggt ctgatgaact aacaagacat ttccgaaaac atactggaat caaacctttc | 960 |
| cagtgcccgg actgtgaccg cagcttctcc cgttctgacc atcttgccct ccataggaaa | 1020 |
| cgccacatgc tagtc | 1035 |

<210> SEQ ID NO 16
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | |
|---|---|
| atggctacaa gggtgctgag catgagcgcc cgcctgggac ccgtgcccca gccgccggcg | 60 |
| ccgcaggacg agccggtgtt cgcgcagctc aagccggtgc tgggcgccgc gaatccggcc | 120 |
| cgcgacgcgg cgctcttccc cggcgaggag ctgaagcacg cgcaccaccg cccgcaggcg | 180 |
| cagcccgcgc ccgcgcaggc cccgcagccg gccagccgc cgccaccgg cccgcggctg | 240 |
| cctccagagg acctggtcca gacaagatgt gaaatggaga agtatctgac acctcagctt | 300 |
| cctccagttc ctataattcc agagcataaa agtatagac gagacagtgc ctcagtcgta | 360 |
| gaccagttct tcactgacac tgaagggtta ccttacagta tcaacatgaa cgtcttcctc | 420 |
| cctgacatca ctcacctgag aactggcctc tacaaatccc agagaccgtg cgtaacacac | 480 |
| atcaagacag aacctgttgc cattttcagc caccagagtg aaacgactgc ccctcctccg | 540 |
| gccccgaccc aggccctccc tgagttcacc agtatattca gctcacacca gaccgcagct | 600 |
| ccagaggtga acaatatttt catcaaacaa gaacttccta caccagatct tcatctttct | 660 |
| gtccctaccc agcagggcca cctgtaccag ctactgaata caccggatct agatatgccc | 720 |
| agttctacaa atcagacagc agcaatggac actcttaatg tttctatgtc agctgccatg | 780 |
| gcaggcctta acacacacac ctctgctgtt ccgcagactg cagtgaaaca attccagggc | 840 |
| atgccccctt gcacatacac aatgccaagt cagtttcttc cacaacaggc cacttacttt | 900 |
| cccccgtcac caccaagctc agagcctgga agtccagata acaagcaga gatgctccag | 960 |
| aatttaaccc cacctccatc ctatgctgct acaattgctt ctaaactggc aattcacaat | 1020 |
| ccaaatttac ccaccaccct gccagttaac tcacaaaaca tccaacctgt cagatacaat | 1080 |
| agaaggagta accccgattt ggagaaacga cgcatccact actgcgatta ccctggttgc | 1140 |
| acaaaagttt ataccaagtc ttctcattta aaagctcacc tgaggactca cactggtgaa | 1200 |
| aagccataca gtgtacctg ggaaggctgc gactggaggt tcgcgcgatc ggatgagctg | 1260 |
| acccgccact accggaagca cacaggcgcc aagcccttcc agtgcggggt gtgcaaccgc | 1320 |
| agcttctcgc gctctgacca cctggccctg catatgaaga ggcaccagaa c | 1371 |

<210> SEQ ID NO 17
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atggacgtgc tccccatgtg cagcatcttc caggagctcc agatcgtgca cgagaccggc        60
tacttctcgg cgctgccgtc tctggaggag tactggcaac agacctgcct agagctggaa       120
cgttacctcc agagcgagcc ctgctatgtt tcagcctcag aaatcaaatt tgacagccag       180
gaagatctgt ggaccaaaat cattctggct cgggagaaaa aggaggaatc gaactgaag        240
atatcttcca gtcctccaga ggacactctc atcagcccga gcttttgtta caacttagag       300
accaacagcc tgaactcaga tgtcagcagc gaatcctctg acagctccga ggaactttct       360
cccacggcca agtttacctc cgaccccatt ggcgaagttt tggtcagctc gggaaaattg       420
agctcctctg tcacctccac gcctccatct tctccggaac tgagcaggga accttctcaa       480
ctgtggggtt gcgtgcccgg ggagctgccc tcgccaggga aggtgcgcag cgggacttcg       540
gggaagccag gtgacaaggg aaatggcgat gcctcccccg acggcaggag gagggtgcac       600
cggtgccact ttaacggctg caggaaagtt tacaccaaaa gctcccactt gaaagcacac       660
cagcggacgc acacaggaga aaagccttac agatgctcat gggaagggtg tgagtggcgt       720
tttgcaagaa gtgatgagtt aaccaggcac ttccgaaagc acaccggggc caagcctttt       780
aaatgctccc actgtgacag gtgttttttcc aggtctgacc acctggccct gcacatgaag       840
aggcacctc                                                                849
```

<210> SEQ ID NO 18
<211> LENGTH: 906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
atggacgtgt tggctagtta tagtatattc caggagctac aacttgtcca cgacaccggc        60
tacttctcag ctttaccatc cctggaggag acctggcagc agacatgcct tgaattggaa       120
cgctacctac agacggagcc ccggaggatc tcagagacct ttggtgagga cttggactgt       180
ttcctccacg cttccctcc ccgtgcatt gaggaaagct tccgtcgctt agacccctg          240
ctgctccccg tggaagcggc catctgtgag aagagctcgg cagtggacat cttgctctct       300
cgggacaagt tgctatctga gacctgcctc agcctccagc cggccagctc ttctctagac       360
agctacacag ccgtcaacca ggcccagctc aacgcagtga cctcattaac gcccccatcg       420
tccctgagc tcagccgcca tctggtcaaa acctcacaaa ctctctctgc cgtggatggc       480
acggtgacgt tgaaactggt ggccaagaag gctgctctca gctccgtaaa ggtgggaggg       540
gtcgcaacag ctgcagcagc cgtgacggct gcgggggccg ttaagagtgg acagagcgac       600
agtgaccaag gagggctagg ggctgaagca tgtcccgaaa acaagaagag ggttcaccgc       660
tgtcagttta cgggtgccg gaaagtttat acaaaaagct cccacttaaa ggcccaccag       720
aggactcaca caggtgagaa gccttataag tgctcatggg agggatgtga gtggcgtttt       780
gcacgaagcg atgagctcac gaggcactac aggaaacaca caggtgcaaa gcccttcaaa       840
tgcaaccact gcgacaggtg ttttttccagg tctgaccatc ttgccctcca catgaagaga       900
catatc                                                                   906
```

<210> SEQ ID NO 19
<211> LENGTH: 1077

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atggtcgata tggataaact cataaacaac ttggaggtcc aacttaattc agaaggtggc      60
tcaatgcagg tattcaagca ggtcactgct tctgttcgga acagagatcc ccctgagata     120
gaatacagaa gtaatatgac ttctccaaca ctcctggatg ccaaccccat ggagaaccca     180
gcactgttta atgacatcaa gattgagccc ccagaagaac ttttggctag tgatttcagc     240
ctgccccaag tggaaccagt tgacctctcc tttcacaagc ccaaggctcc tctccagcct     300
gctagcatgc tacaagctcc aatacgtccc cccaagccac agtcttctcc ccagacccct     360
gtggtgtcca cgtcaacatc tgacatgagc acttcagcaa acattcctac tgttctgacc     420
ccaggctctg tcctgacctc ctctcagagc actggtagcc agcagatctt acatgtcatt     480
cacactatcc cctcagtcag tctgccaaat aagatgggtg gcctgaagac catcccagtg     540
gtagtgcagt ctctgcccat ggtgtatact actttgcctg cagatggggg ccctgcagcc     600
attacagtcc cactcattgg aggagatggt aaaaatgctg atcagtgaa agttgacccc      660 acctccatgt ctccactgga aattccaagt gacagtgagg agagtacaat tgagagtgga     720
tcctcagcct gcagagtct gcagggacta cagcaagaac cagcagcaat ggcccaaatg      780
cagggagaag agtcgcttga cttgaagaga agacggattc accaatgtga ctttgcagga     840
tgcagcaaag tgtacaccaa agctctcac ctgaaagctc accgcagaat ccatacagga      900
gagaagcctt ataaatgcac ctgggatggc tgctcctgga aatttgctcg ctcagatgag     960
ctcactcgcc atttccgcaa gcacacagge atcaagcctt tcggtgcac agactgcaac     1020 cgcagctttt ctcgttctga ccacctgtcc ctgcatcgcc gtcgccatga caccatg       1077

<210> SEQ ID NO 20
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgtccgcgg ccgcctacat ggacttcgtg gctgcccagt gtctggtttc catttcgaac      60
cgcgctgcgg tgccggagca tggggtcgct ccggacgccg agcggctgcg actacctgag     120
cgcgaggtga ccaaggagca cggtgacccg ggggacacct ggaaggatta ctgcacactg     180
gtcaccatcg ccaagagctt gttggacctg aacaagtacc gacccatcca gaccccctcc     240
gtgtgcagcg acagtctgga aagtccagat gaggatatgg atccgacag cgacgtgacc      300 accgaatctg ggtcgagtcc ttcccacagc cggaggagga acaggatcc tggcagcgcg     360 cccagcccgc tctccctcct ccatcctgga gtggctgcga aggggaaaca cgcctccgaa     420
aagaggcaca agtgcccta cagtggctgt gggaaagtct atggaaaatc ctcccatctc     480
aaagcccatt acagagtgca tacaggtgaa cggcccttc cctgcacgtg gccagactgc      540
cttaaaaagt tctcccgctc agacgagctg accgccact accggaccca cactggggaa     600
aagcagttcc gctgtccgct gtgtgagaag cgcttcatga ggagtgacca cctcacaaag     660
cacgcccggc ggcacaccga gttccacccc agcatgatca agcgatcgaa aaaggcgctg     720
```

```
                                                         gccaacgctt tg                                                  732

<210> SEQ ID NO 21
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgctcaact tcggtgcctc tctccagcag actgcggagg aaagaatgga aatgatttct        60
gaaaggccaa aagagagtat gtattcctgg aacaaaactg cagagaaaag tgattttgaa       120
gctgtagaag cacttatgtc aatgagctgc agttggaagt ctgattttaa gaaatacgtt       180
gaaaacagac tgttacacc agtatctgat ttgtcagagg aagagaatct gcttccggga        240
acacctgatt ttcatacaat cccagcattt tgtttgactc caccttacag tccttctgac       300
tttgaaccct ctcaagtgtc aaatctgatg gcaccagcgc catctactgt acacttcaag       360
tcactctcag atactgccaa acctcacatt gccgcacctt caaagagga agaaaagagc        420 ccagtatctg cccccaaact ccccaaagct caggcaacaa gtgtgattcg tcatacagct       480
gatgcccagc tatgtaacca ccagacctgc caatgaaag cagccagcat cctcaactat        540
cagaacaatt cttttagaag aagaacccac ctaaatgttg aggctgcaag aaagaacata      600
ccatgtgccg ctgtgtcacc aaacagatcc aaatgtgaga gaaacacagt ggcagatgtt      660
gatgagaaag caagtgctgc actttatgac ttttctgtgc cttcctcaga gacggtcatc      720
tgcaggtctc agccagcccc tgtgtcccca aacagaagt cagtgttggt ctctccacct       780
gcagtatctg caggggggagt gccacctatg ccggtcatct gccagatggt tcccttcct    840 gccaacaacc tgttgtgac aacagtcgtt cccagcactc ctcccagcca gccaccagcc      900
gtttgccccc ctgttgtgtt catgggcaca caagtcccca aaggcgctgt catgtttgtg     960 gtacccagc ccgttgtgca gagttcaaag cctccggtgg tgagcccgaa tggcaccaga     1020
ctctctccca ttgcccctgc tcctgggttt tcccctcag cagcaaaagt cactcctcag     1080
attgattcat caaggataag gagtcacatc tgtagccacc aggatgtgg caagacatac     1140 tttaaaagtt cccatctgaa ggcccacacg aggacgcaca caggagaaaa gcctttcagc    1200
tgtagctgga aaggttgtga aaggaggttt gcccgttctg atgaactgtc cagacacagg    1260
cgaacccaca cgggtgagaa gaaatttgcg tgccccatgt gtgaccggcg gttcatgagg    1320
agtgaccatt tgaccaagca tgcccggcgc catctatcag ccaagaagct accaaactgg    1380
cagatggaag tgagcaagct aaatgacatt gctctacctc caacccctgc tcccacacag    1440

<210> SEQ ID NO 22
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgcatactc ctgatttcgc tggacctgac gacgcccgag ccgtggacat tatggacatt        60
tgtgaatcta tactcgaaag aaagagacat gattcagagc gaagtacatg ctctatcctc       120
gagcaaacag acatggaggc ggtagaagct ctggtgtgca tgtccagttg gggtcagaga       180
tcccagaagg gggacttgct tagaatccga ccgcttactc cagtttccga tagcggcgac       240
```

```
gtaacaacta ctgttcatat ggacgcagcc acgcctgagc tgcccaaaga ctttcacagc    300
ctctcaactc tttgcatcac tccaccacag tcccccgatc ttgtcgaacc atcaacccgg    360
acccctgtta gcccgcaagt tacagattca aaggcgtgta ccgcgaccga tgttctgcag    420
agttcagcgg ttgtagcgcg ggcattgagc ggaggggctg aacgaggtct gttgggtctt    480
gaacccgtac cgagttctcc ttgtagagcc aagggtacta gtgttattcg gcataccggc    540
gagagtccgg cagcttgttt ccccaccata caaaccccag actgtcgcct tagtgattcc    600
cgggaagggg aggaacagct gttgggccac ttcgagacac ttcaagatac acacttgaca    660
gatagcttgc tgtccaccaa cctggtgtca tgtcaacctt gtttgcacaa gtccgggggt    720
ctccttctga ctgacaaagg tcaacaagcg ggatggcctg gcgctgtcca acatgcagt    780 cctaaaaact acgaaaatga tttgcctagg aaaaccacgc cgcttatcag tgtgagtgtt    840
cccgctccac ctgtcctgtg ccagatgatc cctgtaaccg ggcaatcatc tatgttgcct    900
gcgttcttga agcccccccc acaactgtcc gttggtacta ttcgcccgat ccttgcgcaa    960
gcagcgcccg ccccgcaacc cgtgttcgtg gggcccgctg tcccgcaggg tgcagtcatg   1020
ttggttcttc cccaggggc cctcccgcca ccagctccgt gtgcagcgaa tgtcatggct   1080
gccggaaaca cgaaattgtt gccccttgca cccgctccag ttttcataac gagctcacag   1140
aattgtgtgc cacaagtcga cttctcacga agacggaact atgtgtgctc tttcccaggt   1200
tgcagaaaaa catatttcaa atcctctcat ctgaaagcac atcttcggac ccatacagga   1260
gagaagcctt ttaattgtag ctgggatggc tgtgataaaa aattcgcaag aagtgatgag   1320
ctcagtcgac atcgcaggac gcataccggg gaaaaaaaat tcgtttgtcc agtttgtgac   1380
agaagattta tgaggtccga ccatctcacc aagcacgcgc gacgccacat gactacaaag   1440
aaaattcctg gctggcaagc cgaggtggga aaactcaacc gaatcgcttc cgctgaatcc   1500
cccggcagcc cgctggtaag tatgcctgcc agtgcc                             1536

<210> SEQ ID NO 23
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgaacattc acatgaagcg caagacgata aagaacatca atacattcga gaaccgaatg     60
ttgatgttgg atggcatgcc cgctgtacgg gtaaaaaccg agctcctgga gtctgaacaa    120
ggatccccaa acgtccacaa ctacccggat atggaggcag tgccgctctt gctcaacaat    180
gtgaagggag agccgcctga ggactctctc tccgtagatc atttccagac acagactgag    240
cccgtagatc tttcaattaa caaagccaga acatctccta ctgcggtaag ttcttctccc    300
gtaagtatga cagcaagtgc atctagtcca agttctacga gcactagcag ttcttcatct    360
agtagacttg ctagttcacc aacggtgatc acaagtgttt ctagcgccag cagcagctca    420
acggtactga ctcccggtcc actcgtggca agcgctagtg gcgtgggtgg ccaacaattt    480
ctccatatta ttcaccccgt gcctccgtct agtccgatga atctccagag caacaagctt    540
agtcacgtac ataggatccc cgtcgtcgtc cagtcagttc ccgtcgtcta cacagctgtg    600
cgatcccctg ggaatgtcaa taatactata gttgttcctt tgcttgagga tggtagggcg    660
catgggaaag cacagatgga ccccccgcgg cttgtcaccga gacagtctaa atccgatagt    720
```

```
gacgacgatg atttgcctaa cgtaacactg gactctgtga acgagaccgg gagtaccgct    780
ctgtcaatcg ctagggccgt acaggaggtc cacccaagcc ctgtgtcacg agtccgaggt    840
aacaggatga ataatcagaa atttccctgt agcatcagcc cattttctat agagtccact    900
cggagacagc gacgaagtga atcacccgac tccagaaaaa ggaggataca tcgctgtgac    960
tttgagggct gtaacaaggt ctacacaaaa agttcacacc tcaaggcgca tcgacggacg   1020
catactgggg aaaaaccgta caaatgcacc tgggagggat gcacgtggaa atttgcacgc   1080
tctgacgagt tgacacgcca ctatcgaaag catacgggcg taaagccgtt taaatgcgct   1140
gattgcgaca ggagttttag ccgctctgat caccttgctc ttcaccggag gcgacacatg   1200
cttgtt                                                              1206
```

<210> SEQ ID NO 24
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggctgcgg ctgcatatgt ggatcatttt gcggctgagt gcctggtgtc aatgtctagt     60
agagcggtgg tacacggtcc cagagaaggc ccagaatcac gcccagaggg cgccgccgtc    120
gctgcaacac cgacgctgcc tcgggtcgag gagcgccgcg acgggaagga cagtgcgtca    180
cttttcgtag tagcgagaat attggcagat ctgaatcaac aggctccagc acctgcgccc    240
gctgaacgcc gggagggcgc cgctgccaga aaggccagaa caccatgccg cttgccgcca    300
cctgcgccaa acccacaag tccaggtgcc gaaggtgcgg cggctgcccc tccttcaccg     360
gcctggtctg aaccagaacc agaggcaggt cttgaacctg agcgcgaacc cggccctgca    420
ggctctgggg aacctggcct gaggcagcgg gtgaggcgcg gccggagcag ggccgacctg    480
gaatcaccgc aaaggaaaca taaatgccat tatgctggtt gcgaaaaggt ttatggaaag    540
tcatcccacc tgaaagcaca cctccgcact cacacgggtg agcgacccttt tgcgtgttcc    600 tggcaagact gcaataaaaa gtttgctaga tctgatgaac ttgcacggca ttatcgaact    660
cataccggtg aaaagaagtt ctcatgccct atatgtgaga acggttcat gcgctctgac     720 cacttgacga acatgcaag acgacatgct aattttcatc cggggatgtt gcagagacgg     780 ggaggggggaa gtaggactgg aagtctctcc gactattccc gatccgacgc ttcctcacca    840
acgattagcc ccgcaagcag tccc                                           864
```

<210> SEQ ID NO 25
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgtcagccg cagtcgcatg ccttgattac ttcgcggccg agtgtcttgt ttccatgtca     60 gcggggggctg tcgttcacag aagaccacca gacccggagg gagcgggagg ggcagctgga    120
tctgaagtcg gcgcggctcc acctgaatca gcgcttcccg gccctggtcc tccaggtccc    180
gctagcgtgc cccaactccc acaagtgcct gctccgagtc ctggagcggg cggagcagcc    240
```

```
ccgcatctcc ttgcagcatc agtgtgggcc gatcttcgcg gaagctccgg ggagggctcc      300
tgggaaaaca gcggagaggc cccgcgagct tcaagcggct tttccgatcc aatcccttgc      360
agtgttcaaa ccccatgctc cgagctcgcg cccgcgtccg gagctgcggc agtgtgcgca      420
cctgaaagct catccgatgc gccggccgtt ccatctgcgc cagctgctcc cggtgcaccc      480
gcagcatctg gcggctttag tggtggagct cttggggcgg gtcccgcccc tgcggcggat      540
caagctcctc gcaggcgcag tgttacgccc gcagcaaaac ggcatcaatg cccctttcct      600
ggttgtacaa aagcatacta taagtcatcc catctcaaga gtcaccagag gacgcataca      660
ggtgagagac cttttagctg tgactggctc gattgcgaca agaaatttac gcggagcgac      720
gaacttgcgc ggcactaccg cactcacact ggagaaaaga ggttctcttg tcccctgtgt      780
cccaagcagt tctcacgcag tgatcacttg acaaaacatg ctaggagaca tccaacatac      840
catcccgaca tgatagagta tcgaggtagg cgacgcacac ctagaattga tcctccgctg      900
actagtgaag tcgagtcaag tgccagtgga agcggaccgg gtcccgcgcc ctcatttaca      960
acctgtctt                                                              969
```

<210> SEQ ID NO 26
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggtggacc acttacttcc agtggacgag aacttctcgt cgccaaaatg cccagttggg       60
tatctgggtg ataggctggt tggccggcgg gcatatcaca tgctgccctc acccgtctct      120
gaagatgaca gcgatgcctc cagcccctgc tcctgttcca gtcccgactc tcaagccctc      180
tgctcctgct atggtggagg cctgggcacc gagagccagg acagcatctt ggacttccta      240
ttgtcccagg ccacgctggg cagtggcggg ggcagcggca gtagcattgg ggccagcagt      300
ggccccgtgg cctgggggcc ctggcgaagg gcagcggccc ctgtgaaggg ggagcatttc      360
tgcttgcccg agtttccttt gggtgatcct gatgacgtcc cacggccctt ccagcctacc      420
ctggaggaga ttgaagagtt tctggaggag aacatggagc ctggagtcaa ggaggtccct      480
gagggcaaca gcaaggactt ggatgcctgc agccagctct cagctgggcc acacaagagc      540
cacctccatc ctgggtccag cgggagagag cgctgttccc ctccaccagg tggtgccagt      600
gcaggaggtg cccagggccc aggtgggggc cccacgcctg atggcccccat ccagtgttg      660 ctgcagatcc agcccgtgcc tgtgaagcag gaatcgggca cagggcctgc ctcccctggg      720
caagccccag agaatgtcaa ggttgcccag ctcctggtca catccagggg gcagaccttc      780
gcactcgtgc cccaggtggt accctcctcc aacttgaacc tgccctccaa gtttgtgcgc      840
attgcccctg tgcccattgc cgccaagcct gttggatcgg gacccctggg gcctggccct      900
gccggtctcc tcatgggcca aagttccccc aagaacccag ccgcagaact catcaaaatg      960
cacaaatgta ctttccctgg ctgcagcaag atgtacacac aaaagcagcca cctcaaggcc     1020 cacctgcgcc ggcacacggg tgagaagccc ttcgcctgca cctggccagg ctgcggctgg     1080
aggttctcgc gctctgacga gctgtcgcgg cacaggcgct cgcactcagg tgtgaagccg     1140
taccagtgtc ctgtgtgcga gaagaagttc gcgcggagcg accacctctc caagcacatc     1200
aaggtgcacc gcttcccgcg gagcagccgc tccgtgcgct ccgtgaac                  1248
```

<210> SEQ ID NO 27
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| atgtcagccg cggtcgcgtg cgtggattat tttgcagcag atgtgctgat ggcaatttca | 60 |
| tccggtgcag tagttcatcg cggaagacca ggtcctgagg gtgcggggcc tgcggccggg | 120 |
| ttggatgttc gcgccgcgcg cagggaagcc gcttctcccg gaacacctgg ccctcctcct | 180 |
| cctccgccgg cggcatcagg cccgggtcct ggtgcagctg cggctcctca cctgttggca | 240 |
| gcctccatac tggctgacct gcgagggggg ccaggcgctg cacctggtgg cgcgagtcca | 300 |
| gcaagttcca gctccgcggc gtcctccccg agtagtgggc gagctccggg cgcggcacct | 360 |
| tctgctgccg ctaaatcaca ccgatgccct ttcccagact gcgcgaaggc gtattataag | 420 |
| tccagtcatt tgaaatcaca cttgaggaca cataccggcg agagaccttt gcgtgcgac | 480 |
| tggcagggtt gtgataagaa atttgcgaga agcgacgaac tggcccgcca tcaccgcacc | 540 |
| cacacagggg aaaaaagatt ctcatgccca ctctgttcta agcgcttcac gcgaagcgac | 600 |
| catcttgcaa agcacgctag gagacaccct gggttccacc ccgacctctt gcgacgacct | 660 |
| ggcgcccggt ctactagccc gtctgactca ttgccgtgct ctctcgcagg gtcccctgct | 720 |
| ccgagccccg caccgtcccc agctcctgcc gggctt | 756 |

<210> SEQ ID NO 28
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

| atgtacggcc gaccgcaggc tgagatggaa caggaggctg gggagctgag ccggtggcag | 60 |
| gcggcgcacc aggctgccca ggataacgag aactcagcgc ccatcttgaa catgtcttca | 120 |
| tcttctggaa gctctggagt gcacacctct tggaaccaag gctaccaag cattcagcac | 180 |
| tttcctcaca gcgcagagat gctggggtcc cctttggtgt ctgttgaggc gccggggcag | 240 |
| aatgtgaatg aagggggggcc acagttcagt atgccactgc ctgagcgtgg tatgagctac | 300 |
| tgcccccaag cgactctcac tccttcccgg atgatttact gtcagagaat gtctcccct | 360 |
| cagcaagaga tgacgatttt cagtgggccc caactaatgc ccgtaggaga gcccaatatt | 420 |
| ccaagggtag ccaggcccct cggtgggaat ctaaggatgc cccccaatgg gctgccagtc | 480 |
| tcggcttcca ctggaatccc aataatgtcc cacactggga accctccagt gccttaccct | 540 |
| ggcctctcga cagtaccttc tgacgaaaca ttgttgggcc cgactgtgcc ttccactgag | 600 |
| gcccaggcag tgctcccctc catggctcag atgttgcccc gcaagatgc ccatgacctt | 660 |
| gggatgcccc cagctgagtc ccagtcattg ctggttttag gatctcagga ctctcttgtc | 720 |
| agtcagccag actctcaaga aggcccattt ctaccagagc agcccggacc tgctccacag | 780 |
| acagtagaga agaactccag gcctcaggaa gggactggta aaggggctc ctcagaggca | 840 |
| aggccttact gctgcaacta cgagaactgc ggaaaagctt ataccaaacg ctcccacctc | 900 |
| gtgagccacc agcgcaagca cacaggtgag aggccatatt cttgcaactg ggaaagttgt | 960 |

```
tcatggtctt tcttccgttc tgatgagctt agacgacata tgcgggtaca caccagatat    1020
cgaccatata aatgtgatca gtgcagccgg gagttcatga ggtctgacca tctcaagcaa    1080
caccagaaga ctcatcggcc gggaccctca gacccacagg ccaacaacaa caatggagag    1140
caggacagtc ctcctgctgc tggtcct                                        1167
```

```
<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ser Gly Ser Gly Ser
1               5

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtctcgtggg ctcggagatg tgtataagag acagagaact atttcctggc tgttacgcg     59

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acactctttc cctacacgac gctcttccga tctagaacta tttcctggct gttacgcg      58

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gactggagtt cagacgtgtg ctcttccgat cttgtcttcg ttgggagtga attagc        56

<210> SEQ ID NO 33
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atggtgagca agggcgagga ggataacatg gccatcatca aggagttcat gcgcttcaag    60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
```

```
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggccccgta      420 atgcagaaga agaccatggg ctgggaggcc tcctccgagc ggatgtaccc cgaggacggc     480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaag                  708
```

<210> SEQ ID NO 34
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggagtctt ctgctaaaat ggagtccgga ggcgcgggac aacaaccaca accgcaacca     60
caacaaccct tcctgccgcc ggccgcatgt ttttttcgcga ccgctgctgc tgctgcagcg    120
gcggcggctg ctgccgccgc gcaatccgcc caacagcaac aacaacaaca gcagcagcag    180
caacaagcgc ctcaacttcg acccgctgca gacgggcagc cctcagggg agggcacaag    240 agcgctccga agcaggttaa aaggcagagg agcagtagtc ccgaactgat gcgatgtaag    300
aggcgcctca attttagcgg ttttggttac tctttgcccc agcagcagcc ggctgccgta     360
gctcgccgaa atgagcggga aaggaaccgc gttaaacttg tgaatctcgg tttcgcgaca     420
cttcgagagc acgtaccaaa tggggcagct aacaagaaaa tgagtaaagt tgagacactg     480
cggtctgcag tggagtatat tagagctctt caacaattgc ttgacgagca cgatgccgta     540
tcagccgcat ttcaagccgg ggtgctgtcc ccaacaatat ctccgaacta cagcaatgat     600
cttaatagca tggcgggaag tcccgtttcc tcctactcct ctgatgaggg cagctacgac    660
cctctcagtc ccgaggagca agagcttctt gacttcacta actggttc                  708
```

<210> SEQ ID NO 35
<211> LENGTH: 573
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atgatggaca acagaggcaa ctctagtcta cctgacaaac ttcctatctt ccctgattct     60
gcccgcttgc cacttaccag gtccttctat ctggagccca tggtcacttt ccacgtgcac    120
ccagaggccc cggtgtcatc tccttactct gaggagctgc acggctgcc ttttcccagc     180 gactctctta tcctgggaaa ttacagtgaa ccctgcccct ctctttccc gatgccttat     240 ccaaattaca gagggtgcga gtactcctac gggccagcct tcacccggaa aaggaatgag     300
cgggaaaggc agcgggtgaa atgtgtcaat gaaggctacg cccagctccg acatcatctg     360
ccagaggagt atttggagaa gcgactcagc aaagtggaaa ccctcagagc tgcgatcaag    420
tacattaact acctgcagtc tcttctgtac cctgataaag ctgagacaaa gaataaccct    480
```

```
ggaaaagttt cctccatgat agcaaccacc agccaccatg ctgaccctat gttcagaatt    540
gtttgcccaa ctttcttgta caaagttgtc ccc                                 573
```

<210> SEQ ID NO 36
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atggagacgc gtaaaccggc ggaacggctg gccttgccat actcgctgcg caccgcgccc     60
ctgggcgttc cggggaccct gcccggactc ccgcggaggg accccctcag gtcgccctg    120 cgtctggacg ccgcgtgctg ggagtgggcg cgcagcggct gcgcacgggg atggcagtac    180
ttgcccgtgc cgctggacag cgccttcgag cccgccttcc tccgcaagcg caacgagcgc    240
gagcggcagc gggtgcgctg cgtgaacgag ggctatgcgc gcctccgaga ccacctgccc    300
cgggagctgg cagacaagcg cctcagcaaa gtggagacgc tccgcgctgc catcgactac    360
atcaagcacc tgcaggagct gctggagcgc caggcctggg ggctcgaggg gcggccggc    420 gccgtccccc agcgcagggc ggaatgcaac agcgacgggg agtccaaggc ctcttcggcg    480
ccttcgccca gcagcgagcc cgaggagggg ggcagc                              516
```

<210> SEQ ID NO 37
<211> LENGTH: 833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atgccgatgg gggcagcaga aagaggtgct gggccccaat catctgcagc accatgggct     60
ggttcagaaa aggcggcaaa gagagggcca tcaaaaagct ggtacccaag agctgctgca    120
tctgatgtca cgtgcccgac tggtggtgat ggagctgacc caaaacctgg acttttgga    180 ggtggtttag cttagggcc tgcgcccaga ggaacaatga ataataattt ctgcagggcc     240
cttgttgaca gaaggccttt aggaccccct tcatgtatgc aattaggtgt aatgccaccg    300
ccaagacaag cgcccctccc gccggctgaa ccccttggaa atgtacccttt cctcctatac    360 cctgccccga ctgaaccacc atattatgat gcatatgctg gtgttttccc atatgtgcct    420
ttccctggtg cttttggtgt atatgaatac ccttttgagc cggcttttat ccaaaagagg    480
aatgaaagag agacagagag agtgaagtgt gtgaatgaag atacgccag attgagaggc    540 catttgcctg gtgccctggc agaaaagaga ttatcaaaag ttgaaaccct gagggcggca    600
atcagatata taaatacct ccaagaactc ctttcatcag cacctgatgg atcgacacca    660
ccggcttcaa gaggtttacc tggaactgga ccatgccctg caccgcctgc tacaccaagg    720
ccagacagac ctggagatgg agaagcaaga gcaccttctt cccttgtccc tgaatcttct    780
gaatcatcat gttttcgcc ttcccctttt ttagaaagtg aagaatcctg gca            833
```

<210> SEQ ID NO 38
<211> LENGTH: 1482
<212> TYPE: DNA
<213> ORGANISM: Artificial Sequence
<220> FEATURE:

<223> OTHER INFORMATION: Description of Artificial Sequence: Synthetic
       polynucleotide

<400> SEQUENCE: 38

| | | | | | |
|---|---|---|---|---|---|
| atgggagacg | acagaccgtt | tgtgtgcaat | gccccgggct | gtggacagag | atttacaaac | 60 |
| gaggaccacc | tggcagttca | taaacacaag | catgagatga | cattgaaatt | tggcccagcc | 120 |
| cgaactgact | cagtcatcat | tgcagatcaa | acgcctactc | caactagatt | cctgaagaac | 180 |
| tgtgaggagg | tgggactctt | caatgaacta | gctagctcct | ttgaacatga | attcaagaaa | 240 |
| gctgcagatg | aggatgagaa | aaaggcaaga | agcaggactg | ttgccaaaaa | actggtggct | 300 |
| gctgctgggc | cccttgacat | gtctctgcct | tccacaccag | acatcaaaat | caaagaagaa | 360 |
| gagccagtgg | aggtagactc | atccccacct | gatagccctg | cctctagtcc | ctgttcccca | 420 |
| ccactgaagg | agaaggaggt | taccccaaag | cctgttctga | tctctacccc | cacacccacc | 480 |
| attgtacgtc | ctggctccct | gcctctccac | ttgggctatg | atccacttca | tccaacccct | 540 |
| ccctccccaa | cctctgtcat | cacacaggct | ccaccatcca | acaggcaaat | ggggtctccc | 600 |
| actggctccc | tccctcttgt | catgcatctt | gctaatggac | agaccatgcc | tgtgttgcca | 660 |
| gggcctccag | tacagatgcc | gtctgttata | tcgctggcca | gacctgtgtc | catggtgccc | 720 |
| aacattcctg | gtatccctgg | cccaccagtt | aacagtagtg | gctccatttc | tccctctggc | 780 |
| caccctatac | catcagaagc | caagatgaga | ctgaaagcca | ccctaactca | ccaagtctcc | 840 |
| tcaatcaatg | gtggttgtgg | aatggtggtg | ggtactgcca | gcaccatggt | gacagcccgc | 900 |
| ccagagcaga | gccagattct | catccagcac | cctgatgccc | catcccctgc | ccagccacag | 960 |
| gtctcaccag | ctcagcccac | ccctagtact | ggggggcgac | ggcggcgcac | agtagatgaa | 1020 |
| gatccagatg | agcgacggca | gcgctttctg | gagcgcaacc | gggctgcagc | ctcccgctgc | 1080 |
| cgccaaaagc | gaaagctgtg | ggtgtcctcc | ctagagaaga | aggccgaaga | actcacttct | 1140 |
| cagaacattc | agctgagtaa | tgaagtcaca | ttactacgca | atgaggtggc | ccagttgaaa | 1200 |
| cagctactgt | tagctcataa | agactgccca | gtcactgcac | tacagaaaaa | gactcaaggc | 1260 |
| tatttagaaa | gccccaagga | aagctcagag | ccaacgggtt | ctccagcccc | tgtgattcag | 1320 |
| cacagctcag | caacagcccc | tagcaatggc | ctcagtgttc | gctctgcagc | tgaagctgtg | 1380 |
| gccacctcgg | tcctcactca | gatggccagc | caaaggacag | aactgagcat | gccgatacaa | 1440 |
| tcgcatgtaa | tcatgacccc | acagtcccag | tctgcgggca | ga | | 1482 |

<210> SEQ ID NO 39
<211> LENGTH: 939
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 39

| | | | | | |
|---|---|---|---|---|---|
| atgtacgtga | gctacctcct | ggacaaggac | gtgagcatgt | accctagctc | cgtgcgccac | 60 |
| tctggcggcc | tcaacctggc | gccgcagaac | ttcgtcagcc | cccgcagta | cccggactac | 120 |
| ggcggttacc | acgtggcggc | cgcagctgca | cggcagcga | acttggacag | cgcgcagtcc | 180 |
| ccggggccat | cctggccggc | agcgtatggc | gccccactcc | gggaggactg | gaatggctac | 240 |
| gcgcccggag | gcgccgcggc | cgccgccaac | gccgtggctc | acggcctcaa | cggtggctcc | 300 |
| ccggccgcag | ccatgggcta | cagcagcccc | gcagactacc | atccgcacca | ccacccgcat | 360 |
| caccacccgc | accacccggc | cgccgcgcct | tcctgcgctt | ctgggctgct | gcaaacgctc | 420 |

```
aaccccggcc ctcctgggcc cgccgccacc gctgccgccg agcagctgtc tcccggcggc    480
cagcggcgga acctgtgcga gtggatgcgg aagccggcgc agcagtccct cggcagccaa    540
gtgaaaacca ggacgaaaga caaatatcga gtggtgtaca cggaccacca gcggctggag    600
ctggagaagg agtttcacta cagtcgctac atcaccatcc ggaggaaagc cgagctagcc    660
gccacgctgg ggctctctga gaggcaggtt aaaatctggt ttcagaaccg cagagcaaag    720
gagaggaaaa tcaacaagaa gaagttgcag cagcaacagc agcagcagcc accacagccg    780
cctccgccgc caccacagcc tccccagcct cagccaggtc ctctgagaag tgtcccagag    840
cccttgagtc cggtgtcttc cctgcaagcc tcagtgtctg gctctgtccc tggggttctg    900
gggccaactg ggggggtgct aaaccccacc gtcacccag                           939
```

<210> SEQ ID NO 40
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgatggcgt atatgaaccc ggggccccac tattctgtca acgccttggc cctaagtggc     60
cccagtgtgg atctgatgca ccaggctgtg ccctacccaa cgcccccag gaagcagcgg    120 cgggagcgca ccaccttcac ccggagccaa ctggaggagc tggaggcact gtttgccaag    180
acccagtacc cagacgtcta tgcccgtgag gaggtggctc tgaagatcaa tctgcctgag    240
tccagggttc aggtttggtt caagaaccgg agggctaaat gcaggcagca gcgacagcag    300
cagaaacagc agcagcagcc cccaggggc caggccaagg cccggcctgc caagaggaag    360
gcgggcacgt ccccaagacc ctccacagat gtgtgtccag accctctggg catctcagat    420
tcctacagtc cccctctgcc cggccctca ggctccccaa ccacggcagt ggccactgtg    480
tccatctgga gcccagcctc agagtccct ttgcctgagg cgcagcgggc tgggctggtg    540
gcctcagggc cgtctctgac ctccgccccc tatgccatga cctacgcccc ggcctccgct    600
ttctgctctt ccccctccgc ctatgggtct ccgagctcct atttcagcgg cctagacccc    660
tacctttctc ccatggtgcc ccagctaggg ggcccggctc ttagccccct ctctggcccc    720
tccgtgggac cttccctggc ccagtccccc acctccctat caggccagag ctatggcgcc    780
tacagccccg tggatagctt ggaattcaag gaccccacgg gcacctggaa attcacctac    840
aatcccatgg accctctgga ctacaaggat cagagtgcct ggaagtttca gatcttg      897
```

<210> SEQ ID NO 41
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggccagca ctattaagga agccttatca gttgtgagtg aggaccagtc gttgtttgag     60
tgtgcctacg gaacgccaca cctggctaag acagagatga ccgcgtcctc ctccagcgac    120
tatggacaga cttccaagat gagcccacgc gtccctcagc aggattggct gtctcaaccc    180
ccagccaggg tcaccatcaa aatggaatgt aaccctagcc aggtgaatgg ctcaaggaac    240
```

| | |
|---|---|
| tctcctgatg aatgcagtgt ggccaaaggc gggaagatgg tgggcagccc agacaccgtt | 300 |
| gggatgaact acggcagcta catggaggag aagcacatgc cacccccaaa catgaccacg | 360 |
| aacgagcgca gagttatcgt gccagcagat cctacgctat ggagtacaga ccatgtgcgg | 420 |
| cagtggctgg agtgggcggt gaaagaatat ggccttccag acgtcaacat cttgttattc | 480 |
| cagaacatcg atgggaagga actgtgcaag atgaccaagg acgacttcca gaggctcacc | 540 |
| cccagctaca atgccgacat ccttctctca catctccact acctcagaga gactcctctt | 600 |
| ccacatttga cttcagatga tgttgataaa gccttacaaa actctccacg gttaatgcat | 660 |
| gctagaaaca caggggtgc agcttttatt ttcccaaata cttcagtata tcctgaagct | 720 |
| acgcaaagaa ttacaactag gccagattta ccatatgagc cccccaggag atcagcctgg | 780 |
| accggtcacg gccaccccac gccccagtcg aaagctgctc aaccatctcc ttccacagtg | 840 |
| cccaaaactg aagaccagcg tcctcagtta gatccttatc agattcttgg accaacaagt | 900 |
| agccgccttg caaatccagg cagtggccag atccagcttt ggcagttcct cctggagctc | 960 |
| ctgtcggaca gctccaactc cagctgcatc acctgggaag caccaacgg ggagttcaag | 1020 |
| atgacggatc ccgacgaggt ggcccggcgc tggggagagc ggaagagcaa acccaacatg | 1080 |
| aactacgata agctcagccg cgccctccgt tactactatg acaagaacat catgaccaag | 1140 |
| gtccatggga agcgctacgc ctacaagttc gacttccacg ggatcgccca ggccctccag | 1200 |
| ccccaccccc cggagtcatc tctgtacaag taccccctcag acctcccgta catgggctcc | 1260 |
| tatcacgccc acccacagaa gatgaacttt gtggcgcccc accctccagc cctccccgtg | 1320 |
| acatcttcca gttttttgc tgccccaaac ccatactgga attcaccaac tgggggtata | 1380 |
| taccccaaca ctaggctccc caccagccat atgccttctc atctgggcac ttactac | 1437 |

<210> SEQ ID NO 42
<211> LENGTH: 1326
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 42

| | |
|---|---|
| atgtcaaaca aagatcgaca cattgattcc agctgttcgt ccttcatcaa gacggaacct | 60 |
| tccagcccag cctccctgac ggacagcgtc aaccaccaca gccctggtgg ctcttcagac | 120 |
| gccagtggga gctacagttc aaccatgaat ggccatcaga acggacttga ctcgccacct | 180 |
| ctctacccct ctgctcctat cctgggaggt agtgggcctg tcaggaaact gtatgatgac | 240 |
| tgctccagca ccattgttga agatccccag accaagtgtg aatacatgct caactcgatg | 300 |
| cccaagagac tgtgtttagt gtgtggtgac atcgcttctg gtaccactag tggggtagca | 360 |
| tcatgtgaag cctgcaaggc attcttcaag aggacaattc aaggcaatat agaatacagc | 420 |
| tgccctgcca cgaatgaatg tgaaatcaca aagcgcagac gtaaatcctg ccaggcttgc | 480 |
| cgcttcatga agtgtttaaa agtgggcatg ctgaaagaag gggtgcgtct tgacagagta | 540 |
| cgtggaggtc ggcagaagta caagcgcagg atagatgcgg agaacagccc atacctgaac | 600 |
| cctcagctgg ttcagccagc caaaaagcca ttgctctggt ctgatcctgc agataacaag | 660 |
| attgtctcac atttgttggt ggctgaaccg gagaagatct atgccatgcc tgaccctact | 720 |
| gtccccgaca gtgacatcaa agccctcact acactgtgtg acttggccga ccgagagttg | 780 |
| gtggttatca ttggatgggc gaagcatatt ccaggcttct ccacgctgtc cctggcggac | 840 |

| | |
|---|---|
| cagatgagcc ttctgcagag tgcttggatg gaaattttga tccttggtgt cgtataccgg | 900 |
| tctctttcgt ttgaggatga acttgtctat gcagacgatt atataatgga cgaagaccag | 960 |
| tccaaattag caggccttct tgatctaaat aatgctatcc tgcagctggt aaagaaatac | 1020 |
| aagagcatga agctggaaaa agaagaattt gtcaccctca agctatagc tcttgctaat | 1080 |
| tcagactcca tgcacataga agatgttgaa gccgttcaga agcttcagga tgtcttacat | 1140 |
| gaagcgctgc aggattatga agctggccag cacatggaag accctcgtcg agctggcaag | 1200 |
| atgctgatga cactgccact cctgaggcag acctctacca aggccgtgca gcatttctac | 1260 |
| aacatcaaac tagaaggcaa agtcccaatg cacaaacttt ttttggaaat gttggaggcc | 1320 |
| aaggtc | 1326 |

<210> SEQ ID NO 43
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

| | |
|---|---|
| atggatcttt ggaactggga tgaagcttcc cctcaagaag ttccccccgg aaataaactc | 60 |
| gcggggcttg gaagactccc tcgccttccg caacgcgtct ggggcggatg ccctggtgga | 120 |
| gcctcagcgg acccaaaccc tttgtctcca gcggaggggg caaagttggg tttctgcttc | 180 |
| ccggatcttg ctttgcaagg cgatactcca acggcgacgg cagagacctg ttggaaaggc | 240 |
| accagtagct ccctggccag ctttccgcag ctcgattggg ggtcagccct tctccatccc | 300 |
| gaagttccct gggggcgga acccgactcc caagcccttc cctggagtgg tgattggaca | 360 |
| gatatggcat gcacagcctg gacagttgg tccgggcgt cacagacatt gggaccagcc | 420 |
| ccacttggac cggggcctat ccccgcagca ggaagcgaag gagctgctgg tcagaactgt | 480 |
| gtgcccgtgg ctggtgaggc taccagttgg tccagggccc aggcagcagg cagtaacacc | 540 |
| agctgggatt gctcagtggg gcctgacggg gatacttatt ggggctctgg tcttggtgga | 600 |
| gaaccgagaa cggactgtac gataagttgg ggcggtccag ctgggcctga ttgtactacg | 660 |
| tcatggaatc ctggcttgca cgccggcggc acgacaagcc ttaagagata tcaaagttca | 720 |
| gcccttacag tttgctcaga accttccccg caaagtgacc gagcgtcact ggcgcgatgt | 780 |
| cctaaaacta atcatcgagg gccgatccag ttgtggcagt ttttgcttga actccttcac | 840 |
| gatggcgcga ggagcagttg catcagatgg accggtaaca gcagggagtt ccaattgtgt | 900 |
| gaccccaagg aagtggctcg actgtggggt gagcgcaaac ggaagcctgg tatgaattac | 960 |
| gaaaagttga gtaggggttt gcgatattac tataggcgcg catcgttcg aaagtccggt | 1020 |
| ggtcgaaagt acacatacag attcggcggt cgcgtaccat ctcttgcata ccctgattgc | 1080 |
| gcaggcgggg gtaggggtgc ggaaacacaa | 1110 |

<210> SEQ ID NO 44
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

| | |
|---|---|
| atggacggga ctattaagga ggctctgtcg gtggtgagcg acgaccagtc cctctttgac | 60 |

```
tcagcgtacg gagcggcagc ccatctcccc aaggccgaca tgactgcctc ggggagtcct      120
gactacgggc agcccccacaa gatcaacccc ctcccaccac agcaggagtg gatcaatcag     180
ccagtgaggg tcaacgtcaa gcgggagtat gaccacatga atggatccag ggagtctccg     240
gtggactgca gcgttagcaa atgcagcaag ctggtgggcg gaggcgagtc caaccccatg     300
aactacaaca gctatatgga cgagaagaat ggccccccctc ctcccaacat gaccaccaac    360
gagaggagag tcatcgtccc cgcagacccc acactgtgga cacaggagca tgtgaggcaa    420
tggctggagt gggccataaa ggagtacagc ttgatggaga tcgacacatc cttttccag     480 aacatggatg gcaaggaact tgtaaaatg aacaaggagg acttcctccg cgccaccacc    540
ctctacaaca cggaagtgct gttgtcacac ctcagttacc tcagggaaag ttcactgctg    600
gcctataata caacctccca caccgaccaa tcctcacgat tgagtgtcaa agaagaccct    660
tcttatgact cagtcagaag aggagcttgg ggcaataaca tgaattctgg cctcaacaaa   720
agtcctcccc ttggaggggc acaaacgatc agtaagaata cagagcaacg gccccagcca   780
gatccgtatc agatcctggg cccgaccagc agtcgcctag ccaaccctgg aagcgggcag   840
atccagctgt ggcaattcct cctggagctg ctctccgaca cgccaacgc cagctgtatc    900 acctgggagg ggaccaacgg ggagttcaaa atgacggacc ccgatgaggt ggccaggcgc   960
tggggcgagc ggaaaagcaa gcccaacatg aattacgaca agctgagccg ggccctccgt  1020
tattactatg ataaaaacat tatgaccaaa gtgcacggca aagatatgc ttacaaattt    1080 gacttccacg gcattgccca ggctctgcag ccacatccga ccgagtcgtc catgtacaag   1140 taccttctg acatctccta catgccttcc taccatgccc accagcagaa ggtgaacttt    1200
gtccctcccc atccatcctc catgcctgtc acttcctcca gcttctttgg agccgcatca   1260
caatactgga cctcccccac gggggaatc taccccaacc caacgtccc ccgccatcct    1320 aacacccacg tgccttcaca cttaggcagc tactac                              1356
```

<210> SEQ ID NO 45
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atgttgggca ccgtgaagat ggaggggcat gagacaagcg actggaattc ctactacgcg      60
gatacccaag aagcgtattc ttcagttccc gtaagcaata tgaactccgg attggggagc     120
atgaatagta tgaacacgta tatgacaatg aatacgatga ccaccagcgg caacatgaca    180
ccggcctcct ttaatatgtc atatgcgaac cctggtcttg gcgctggcct ctcaccaggt    240
gcggtcgctg gaatgcccgg ggggagcgcc ggagcgatga actccatgac cgctgcgggc   300
gtgacggcca tgggtacggc cctgtcaccc agtggaatgg gagctatggg ggcccagcaa    360
gccgcctcaa tgaatggatt ggggccctat gccgcggcga tgaatccctg catgtcccct   420
atggcttatg ccccccagcaa tttgggtcgc agtagagccg gcgtggtgg cgatgccaaa   480 accttcaagc gaagttatcc tcatgcgaag cctccttatt catatatatc cttgattacg   540
atggcgatac agcaggcccc gtctaagatg ctgactctga gtgagatata ccagtggatc  600
atggaccttt tccttactac ccggcaaaac caacagagat ggcaaaactc aatacgccat   660 agccttttcct tcaatgattg ctttgtcaaa gtcgctcgga gccctgacaa gcccggtaaa   720
```

```
gggtcctatt ggacccttca tccagatagc ggcaatatgt tcgagaatgg ttgttatctt      780
agacggcaga aacgattcaa atgtgagaaa cagccaggtg ccggcggtgg tggcggcagc      840
ggttcaggcg gaagtggtgc caagggtggg cctgagtcta gaaaagaccc cagcggagca      900
agcaatccaa gcgcggactc tcccctgcac cgcggtgttc atggtaagac aggtcagctt      960
gagggggcgc ctgctccagg cccggctgcg tcaccgcaaa cactggacca tagtggagct     1020
acagcgaccg gaggtgcttc agaactcaag acgcctgcgt cctccactgc gcctccgatc     1080
tccagtggtc ccggtgcact tgcctctgtt cctgcatctc atccagcaca cggactcgcg     1140
ccgcacgagt cccagctcca tttgaaaggg gacccacact acagctttaa ccacccattc     1200
tctattaaca atttgatgtc atcctcagaa cagcagcata aactcgactt caaagcctat     1260
gaacaggccc tgcagtattc tccatatggc tctacacttc ctgcttctct tccattgggg     1320
tctgcaagtg tgacaacgcg ctccccaatc gagccaagtg ccctcgagcc tgcttattat     1380
caaggagtat attcccgacc agttttgaat acaagt                               1416

<210> SEQ ID NO 46
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atgctgggag cggtgaagat ggaagggcac gagccgtccg actggagcag ctactatgca       60
gagcccgagg gctactcctc cgtgagcaac atgaacgccg gcctggggat gaacggcatg      120
aacacgtaca tgagcatgtc ggcggccgcc atgggcagcg gctcgggcaa catgagcgcg      180
ggctccatga acatgtcgtc gtacgtgggc gctggcatga gcccgtccct ggcggggatg      240
tcccccggcg cgggcgccat ggcgggcatg ggcggctcgg ccggggcggc tggcgtggcg      300
ggcatggggc cgcacttgag tcccagcctg agcccgctcg gggggcaggc ggccggggcc      360
atgggcggcc tggccccccta cgccaacatg aactccatga ccccatgta cgggcaggcg      420 ggcctgagcc gcgcccgcga ccccaagacc tacaggcgca gctacacgca cgcaaagccg      480
ccctactcgt acatctcgct catcaccatg gccatccagc agagcccaa caagatgctg      540 acgctgagcg agatctacca gtggatcatg gacctcttcc ccttctaccg gcagaaccag      600
cagcgctggc agaactccat ccgccactcg ctctccttca cgactgtttt cctgaaggtg      660
ccccgctcgc ccgacaagcc cggcaagggc tccttctgga ccctgcaccc tgactcgggc      720
aacatgttcg agaacggctg ctacctgcgc gccagaagc gcttcaagtg cgagaagcag      780
ctggcgctga aggaggccgc aggcgccgcc ggcagcggca agaaggcggc cgccggggcc      840
caggcctcac aggctcaact cggggaggcc gccgggccgg cctccgagac tccgcgggc      900 accgagtcgc ctcactcgag cgcctccccg tgccaggagc acaagcgagg gggcctggga      960
gagctgaagg ggacgccggc tgcggcgctg agccccccag agcggcgcc ctctcccggg     1020 cagcagcagc aggccgcggc ccacctgctg ggccgcccc accacccggg cctgccgcct     1080
gaggcccacc tgaagccgga acaccactac gccttcaacc accgttctc catcaacaac     1140 ctcatgtcct cggagcagca gcaccaccac agccaccacc accaccagcc cacaaaatg     1200 gacctcaagg cctacgaaca ggtgatgcac taccccggct acggttcccc catgcctggc     1260
agcttggcca tgggccccggt cacgaacaaa acgggcctgg acgcctcgcc cctggccgca     1320
```
gatacctcct actaccaggg ggtgtactcc cggcccatta tgaactcctc tttg    1374

<210> SEQ ID NO 47
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atgctgggct cagtgaagat ggaggcccat gacctggccg agtggagcta ctacccggag    60
gcgggcgagg tctactcgcc ggtgacccca gtgcccacca tggcccccct caactcctac   120
atgaccctga tcctctaag ctctccctat cccctgggg ggctccctgc ctccccactg    180
ccctcaggac ccctggcacc cccagcacct gcagcccccc tggggcccac tttcccaggc    240
ctgggtgtca gcggtggcag cagcagctcc gggtacgggg ccccgggtcc tgggctggtg    300
cacgggaagg agatgccgaa ggggtatcgg cggcccctgg cacacgccaa gccaccgtat    360
tcctatatct cactcatcac catggccatc cagcaggcgc cgggcaagat gctgaccttg    420
agtgaaatct accagtggat catggacctc ttcccttact accgggagaa tcagcagcgc    480
tggcagaact ccattcgcca ctcgctgtct ttcaacgact gcttcgtcaa ggtggcgcgt    540
tccccagaca agcctggcaa gggctcctac tgggccctac accccagctc agggaacatg    600
tttgagaatg gctgctacct gcgccgccag aaacgcttca agctggagga aaggtgaaa    660 aaaggggca gcggggctgc caccaccacc aggaacggga cagggtctgc tgcctcgacc    720 accaccccg cggccacagt cacctccccg ccccagcccc cgcctccagc cctgagcct    780 gaggcccagg gcggggaaga tgtggggget ctggactgtg gctcacccgc ttcctccaca    840
ccctatttca ctggcctgga gctcccaggg gagctgaagc tggacgcgcc ctacaacttc    900
aaccaccctt tctccatcaa caacctaatg tcagaacaga caccagcacc tcccaaactg    960
gacgtggggt ttgggggcta cggggctgaa ggtgggagc ctggagtcta ctaccaggc    1020 ctctattccc gctctttgct taatgcatcc                                    1050

<210> SEQ ID NO 48
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atgatgcaag aatctgggac tgagacaaaa agtaacggtt cagccatcca gaatgggtcg    60
ggcggcagca accacttact agagtgcggc ggtcttcggg aggggcggtc caacggagag   120
acgccggccg tggacatcgg ggcagctgac ctcgcccacg cccagcagca gcagcaacag    180
tggcatctca taaaccatca gccctctagg agtcccagca gttggcttaa gagactaatt    240
tcaagccctt gggagttgga agtcctgcag gtccccttgt ggggagcagt tgctgagacg    300
aagatgagtg gacctgtgtg tcagcctaac ccttccccat tt                       342

<210> SEQ ID NO 49
<211> LENGTH: 1005
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 49

```
atggagttcc ctggcctggg gtccctgggg acctcagagc ccctccccca gtttgtggat      60
cctgctctgg tgtcctccac accagaatca ggggttttct tccctctgg gcctgagggc      120
ttggatgcag cagcttcctc cactgccccg agcacagcca ccgctgcagc tgcggcactg    180
gcctactaca gggacgctga ggcctacaga cactccccag tctttcaggt gtacccattg    240
ctcaactgta tggaggggat cccagggggc tcaccatatg ccggctgggc ctacggcaag    300
acggggctct accctgcctc aactgtgtgt cccacccgcg aggactctcc tccccaggcc    360
gtggaagatc tggatggaaa aggcagcacc agcttcctgg agctttgaa gacagagcgg    420
ctgagcccag acctcctgac cctgggacct gcactgcctt catcactccc tgtccccaat    480
agtgcttatg ggggccctga cttttccagt accttctttt ctcccaccgg gagccccctc    540
aattcagcag cctattcctc tcccaagctt cgtggaactc tccccctgcc tccctgtgag    600
gccagggagt gtgtgaactg cggagcaaca gccactccac tgtggcggag ggacaggaca    660
ggccactacc tatgcaacgc ctgcggcctc tatcacaaga tgaatgggca gaacaggccc    720
ctcatccggc ccaagaagcg cctgattgtc agtaaacggg caggtactca gtgcaccaac    780
tgccagacga ccaccacgac actgtggcgg agaaatgcca gtggggatcc cgtgtgcaat    840
gcctgcggcc tctactacaa gctacaccac cagcactact gtggtggctc cgctcagctc    900
atgagggcac agagcatggc ctccagagga ggggtggtgt ccttctcctc ttgtagccag    960
aattctggac aacccaagtc tctgggcccc aggcaccccc tggct                   1005
```

<210> SEQ ID NO 50
<211> LENGTH: 1440
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50

```
atggaggtgg cgccggagca gccgcgctgg atggcgcacc cggccgtgct gaatgcgcag     60
caccccgact cacaccaccc gggcctggcg cacaactaca tggaacccgc gcagctgctg   120
cctccagacg aggtggacgt cttcttcaat cacctcgact cgcagggcaa cccctactat    180
gccaaccccg ctcacgcgcg ggcgcgcgtc tcctacagcc ccgcgcacgc ccgcctgacc    240
ggaggccaga tgtgccgccc acacttgttg cacagcccgg gtttgccctg gctggacggg    300
ggcaaagcag ccctctctgc cgctgcggcc caccaccaca cccctggac cgtgagcccc    360
ttctccaaga cgccactgca cccctcagct gctggaggcc ctggaggccc actctctgtg    420
tacccagggg ctggggtgg gagcggggga ggcagcggga gctcagtggc ctccctcacc    480
cctacagcaa cccactctgg ctcccacctt ttcggcttcc cacccacgcc acccaaagaa    540
gtgtctcctg accctagcac cacgggggct gcgtctccag cctcatcttc cgcgggggt    600
agtgcagccc gaggagagga caaggacggc gtcaagtacc aggtgtcact gacggagagc    660
atgaagatgg aaagtggcag tccctgcgc ccaggcctag ctactatggg cacccagcct    720
gctacacacc accccatccc cacctacccc tcctatgtgc cggcggctgc ccacgactac    780
agcagcggac tcttccaccc cggaggcttc ctggggggac cggcctccag cttcaccct    840
aagcagcgca gcaaggctcg ttcctgttca gaaggccggg agtgtgtcaa ctgtggggcc    900
```

```
acagccaccc ctctctggcg gcgggacggc accggccact acctgtgcaa tgcctgtggc      960
ctctaccaca agatgaatgg gcagaaccga ccactcatca agcccaagcg aagactgtcg     1020
gccgccagaa gagccggcac ctgttgtgca aattgtcaga cgacaaccac caccttatgg     1080
cgccgaaacg ccaacgggga ccctgtctgc aacgcctgtg gcctctacta caagctgcac     1140
aatgttaaca ggccactgac catgaagaag aagggatcc agactcggaa ccggaagatg     1200
tccaacaagt ccaagaagag caagaaaggg gcggagtgct tcgaggagct gtcaaagtgc     1260
atgcaggaga agtcatcccc cttcagtgca gctgccctgg ctggacacat ggcacctgtg     1320
ggccacctcc cgcccttcag ccactccgga cacatcctgc ccactccgac gcccatccac     1380
ccctcctcca gcctctcctt cggccacccc cacccgtcca gcatggtgac cgccatgggc     1440
```

<210> SEQ ID NO 51
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
atgtaccaga gcctggctat ggctgctaat catggacctc cccctggagc ctatgaagcc       60
ggaggacctg gcgcttttat gcatggagct ggcgccgctt cttctcccgt gtatgtgcct      120
acacctagag tgcccagcag cgtgctgggc ctttcttatc ttcagggagg aggagcagga      180
tctgcttctg gcggagcttc aggcggatct tctggaggcg ctgcttcagg tgctggacct      240
ggaactcaac agggatctcc tggatggtca caggcaggag ctgatggagc cgcttatacc      300
cctcctcctg tgagcccag gtttagcttt cctggcacaa caggctcttt agctgccgct      360
gctgctgcag ccgcagctag agaagcagct gcatattcta gtggcggagg agctgctgga      420
gccggcttag ctggaagaga gcagtacgga agagccggat ttgccggaag ctatagcagc      480
ccttaccctg cctatatggc cgatgttggc gcatcttggg cagccgccgc agcagcttct      540
gcaggacctt ttgactcacc tgtgcttcac tctctgcctg gcagagctaa tcctgccgcc      600
agacatccca acctggacat gttcgacgac ttcagcgagg gcagagaatg cgtgaactgc      660
ggagccatga gcacccccct ttggagaaga gacggcaccg gccactacct ttgcaatgcc      720
tgtggcctgt accacaagat gaacggcatc aacagacccc tgatcaagcc ccagagaaga      780
ctgagcgcta gcagaagagt gggcctgtcc tgcgccaatt gccagaccac aaccaccaca      840
ctgtggagga gaaatgccga gggcgagcct gtgtgtaacg cctgtggact gtacatgaag      900
ctgcacggcg tgcccagacc tctggccatg agaaaggagg gcatccagac cagaaagaga      960
aagcccaaga acctgaacaa gagcaagacc cccgctgctc cttctggaag cgagagcctg     1020
cctccagcct ctggagccag cagcaatagc tctaacgcca ccacatcttc ttctgaggag     1080
atgaggccca tcaaaaccga gccaggcctg agcagccact acggcacag ctctagcgtg     1140 agccagactt ttagcgtgtc tgccatgtca ggccacggac ctagcattca ccctgtgctg     1200
agcgccctga gttgagccc acagggctat gcttctcctg tgtctcagag ccctcagacc     1260
tccagcaagc aggactcctg gaattctctg gtgctggccg acagccacgg cgatatcatc     1320
accgcc                                                               1326
```

<210> SEQ ID NO 52
<211> LENGTH: 1785

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | | | | | |
|---|---|---|---|---|---|
| atggccctga | ccgacggcgg | atggtgtctc | cctaaaagat | tcggcgccgc | tggcgctgat | 60 |
| gcttctgaca | gcagagcctt | ccccgctagg | gaacccagca | caccacctag | ccccatcagc | 120 |
| agctcaagct | ctagctgtag | cagaggcgga | gagagaggac | ctggaggcgc | ttctaactgc | 180 |
| ggcacacctc | agctggatac | agaagccgcc | gccggaccac | cagccagatc | tcttttactt | 240 |
| agcagctacg | ccagccaccc | ttttggcgct | cctcatggac | cctctgctcc | tggtgtggcc | 300 |
| ggacctggcg | gaaacctgag | ctcttgggag | gaccttctgc | tgtttaccga | cctggaccag | 360 |
| gctgccaccg | ctagcaagct | tctgtggagc | agcaggggcg | ctaagctgag | cccttttgcc | 420 |
| cctgagcagc | ccgaggagat | gtaccagacc | ctggctgctt | taagtctcca | gggacctgcc | 480 |
| gcttatgacg | agcccctgg | tggatttgtt | cactcagcgg | cagcagccgc | agctgctgca | 540 |
| gccgctgcca | gctcacctgt | gtatgtgcct | accacaagag | tgggcagcat | gttacctgga | 600 |
| cttccttacc | atctgcaggg | cagcggaagc | ggccctgcta | accatgccgg | aggagctgga | 660 |
| gctcaccccg | gatggcctca | ggcttctgca | gattctcctc | cttatggatc | tggaggagga | 720 |
| gcagctggag | ggggagctgc | aggaccaggt | ggagccggaa | gcgcagcagc | acatgtgtct | 780 |
| gccagatttc | cctatagccc | tagccctcct | atggccaatg | gcgctgctag | agaacccgga | 840 |
| ggatatgctg | cggcaggctc | tggcggcgct | ggcggagttt | ctggaggtgg | atcttcactg | 900 |
| gccgctatgg | gaggaagaga | gcctcagtac | tcttctctga | gcgccgctag | accactgaac | 960 |
| ggcacctatc | atcaccacca | ccatcaccat | catcatcacc | ccagcccta | ctcccttat | 1020 |
| gtgggagccc | cccttacacc | cgcttggcct | gccggcccct | tcgagacacc | tgtgctgcac | 1080 |
| agccttcagt | ctagagctgg | cgcaccttta | ccagtgccta | gaggcccctc | tgccgacttg | 1140 |
| ctggaggatc | tgagcgagag | cagagagtgc | gtgaactgtg | gcagcatcca | gacacccctg | 1200 |
| tggagaagag | acggcaccgg | ccactacctg | tgcaacgctt | gcggcctgta | cagcaagatg | 1260 |
| aatgggctga | gcagacccct | gatcaagccc | cagaagaggg | tgcccagcag | cagacggctg | 1320 |
| ggactgagct | gcgccaactg | tcataccaca | caaccacac | tgtggcggag | aaacgccgag | 1380 |
| ggcgagcccg | tgtgtaacgc | ctgcggcctt | tacatgaagc | tgcacggcgt | gcccagacct | 1440 |
| ctggccatga | agaaggaggg | aatccagacc | agaaagagaa | agcccaagaa | catcaacaag | 1500 |
| agcaagacct | gcagcggcaa | cagcaacaac | agcatcccca | tgaccccac | cagcacatct | 1560 |
| agcaacagcg | acgactgtag | caagaacaca | tcacctacca | cccagcccac | agctagcgga | 1620 |
| gccggcgccc | ccgtgatgac | aggcgccgga | gagtccacaa | atcccgagaa | tagcgaactg | 1680 |
| aagtactctg | gacaggacgg | actgtatatc | ggcgtgagcc | tggcttctcc | cgccgaggtg | 1740 |
| accagctctg | tcagacctga | ctcttggtgt | gccctcgccc | tggcc | 1785 |

<210> SEQ ID NO 53
<211> LENGTH: 3318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgttcaact cgatgacccc accaccaatc agtagctatg cgagccctg ctgtctccgg    60 cccctcccca gtcaggggc ccccagtgtg gggacagaag gactgtctgg cccgcccttc   120
tgccaccaag ctaacctcat gtccggcccc cacagttatg ggccagccag agagaccaac   180
agctgcaccg agggcccact cttttcttct ccccggagtg cagtcaagtt gaccaagaag   240
cgggcactgt ccatctcacc tctgtcggat gccagcctgg acctgcagac ggttatccgc   300
acctcaccca gctccctcgt agctttcatc aactcgcgat gcacatctcc aggaggctcc   360
tacggtcatc tctccattgg caccatgagc ccatctctgg gattcccagc ccagatgaat   420
caccaaaaag ggccctcgcc ttcctttggg gtccagcctt gtggtcccca tgactctgcc   480
cggggtggga tgatcccaca tcctcagtcc cggggaccct tcccaacttg ccagctgaag   540
tctgagctgg acatgctggt tggcaagtgc cgggaggaac ccttggaagg tgatatgtcc   600
agccccaact ccacaggcat acaggatccc ctgttgggga tgctggatgg gcgggaggac   660
ctcgagagag aggagaagcg tgagcctgaa tctgtgtatg aaactgactg ccgttgggat   720
ggctgcagcc aggaatttga ctcccaagag cagctggtgc accacatcaa cagcgagcac   780
atccacgggg agcggaagga gttcgtgtgc cactgggggg gctgctccag ggagctgagg   840
cccttcaaag cccagtacat gctggtggtt cacatgcgca gacacactgg cgagaagcca   900
cacaagtgca cgtttgaagg gtgccggaag tcatactcac gcctcgaaaa cctgaagacg   960
cacctgcggt cacacacggg tgagaagcca tacatgtgtg agcacgaggg ctgcagtaaa  1020
gccttcagca atgccagtga ccgagccaag caccagaatc ggacccattc caatgagaag  1080
ccgtatgtat gtaagctccc tggctgcacc aaacgctata cagatcctag ctcgctgcga  1140
aaacatgtca agacagtgca tggtcctgac gcccatgtga ccaaacggca ccgtggggat  1200 ggcccctgc ctcgggcacc atccatttct acagtggagc ccaagaggga gcggaagga  1260 ggtcccatca gggaggaaag cagactgact gtgccagagg gtgccatgaa gccacagcca  1320
agccctgggg cccagtcatc ctgcagcagt gaccactccc cggcagggag tgcagccaat  1380
acagacagtg gtgtggaaat gactggcaat gcaggggca gcactgaaga cctctccagc  1440
ttggacgagg gaccttgcat tgctggcact ggtctgtcca ctcttcgccg ccttgagaac  1500
ctcaggctgg accagctaca tcaactccgg ccaatagga cccggggtct caaactgccc  1560
agcttgtccc acaccggtac cactgtgtcc cgccgcgtgg gccccccagt ctctcttgaa  1620
cgccgcagca gcagctccag cagcatcagc tctgcctata ctgtcagccg ccgctcctcc  1680
ctggcctctc cttcccccc tggctcccca ccagagaatg gagcatcctc cctgcctggc  1740
cttatgcctg cccagcacta cctgcttcgg gcaagatatg cttcagccag aggggtggt  1800 acttcgccca ctgcagcatc cagcctggat cggataggtg gtcttcccat gcctccttgg  1860
agaagccgag ccgagtatcc aggatacaac cccaatgcag gggtcacccg gagggccagt  1920
gacccagccc aggctgctga ccgtcctgct ccagctagag tccagaggtt caagagcctg  1980
ggctgtgtcc atacccccacc cactgtggca ggggaggac agaactttga tccttacctc  2040
ccaacctctg tctactcacc acagcccccc agcatcactg agaatgctgc catggatgct  2100
agagggctac aggaagagcc agaagttggg acctccatgg tgggcagtgg tctgaacccc  2160
tatatggact cccacctac tgatactctg ggatatgggg gacctgaagg ggcagcagct  2220
gagccttatg gagcgagggg tccaggctct ctgcctcttg ggcctggtcc acccaccaac  2280
tatgccccca cccctgtcc ccagcaggcc tcatatcctg accccaccca agaaacatgg  2340
ggtgagttcc cttcccactc tgggctgtac ccaggcccca aggctctagg tggaacctac  2400
```

```
agccagtgtc ctcgacttga acattatgga caagtgcaag tcaagccaga acagggtgc     2460 ccagtggggt ctgactccac aggactggca ccctgcctca atgccaccc cagtgagggg    2520 cccccacatc cacagcctct cttttcccat taccccagc cctctcctcc caatatctc     2580 cagtcaggcc cctataccca gccaccccct gattatcttc cttcagaacc caggccttgc    2640
ctggactttg attccccac ccattccaca gggcagctca aggctcagct tgtgtgtaat    2700
tatgttcaat ctcaacagga gctactgtgg gagggtgggg gcagggaaga tgcccccgcc   2760
caggaacctt cctaccagag tcccaagttt ctgggggggtt cccaggttag cccaagccgt  2820
gctaaagctc cagtgaacac atatggacct ggctttggac ccaacttgcc caatcacaag   2880
tcaggttcct atcccacccc ttcaccatgc catgaaaatt ttgtagtggg ggcaaatagg   2940
gcttcacata gggcagcagc accacctcga cttctgcccc cattgcccac ttgctatggg   3000
cctctcaaag tgggaggcac aaaccccagc tgtggtcatc ctgaggtggg caggctagga   3060
gggggtcctg ccttgtaccc tcctcccgaa ggacaggtat gtaaccccct ggactctctt   3120
gatcttgaca acactcagct ggactttgtg gctattctgg atgagcccca ggggctgagt   3180
cctcctcctt cccatgatca gcggggcagc tctggacata ccccacctcc ctctgggccc   3240
cccaacatgg ctgtgggcaa catgagtgtc ttactgagat ccctacctgg ggaaacagaa   3300
ttcctcaact ctagtgcc                                                 3318

<210> SEQ ID NO 54
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgagtctgg taggtggttt tccccaccac ccggtggtgc accacgaggg ctacccgttt      60
gccgccgccg ccgccgccag ccgctgcagc catgaggaga cccctactt ccatggctgg     120 ctcatcggcc accccgagat gtcgcccccc gactacagca tggccctgtc ctacagcccc    180
gagtatgcca gcggcaccgc caaccgcaag gagcggcgca ggactcagag catcaacagc    240
gccttcgccg aactgcgcga gtgcatcccc aacgtacccg ccgacaccaa actctccaaa    300
atcaagaccc tgcgcctggc caccagctac atcgcctacc tcatggacct gctggccaag    360
gacgaccaga atggcgaggc ggaggccttc aaggcagaga tcaagaagac cgacgtgaaa    420
gaggagaaga ggaagaagga gctgaacgaa atcttgaaaa gcacagtgag cagcaacgac    480
aagaaaacca aaggccggac gggctggccg cagcacgtct gggccctgga gctcaagcag    540

<210> SEQ ID NO 55
<211> LENGTH: 1896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atggtttcta aactgagcca gctgcagacg gagctcctgg cggccctgct ggagtcaggg      60
ctgagcaaag aggcactgct ccaggcactg gtgagccgg ggccctacct cctggctgga     120
gaaggccccc tggacaaggg ggagtcctgc ggcggcggtc gaggggagct ggctgagctg    180
```

```
cccaatgggc tgggggagac tcggggctcc gaggacgaga cggacgacga tggggaagac    240
ttcacgccac ccatcctcaa agagctggag aacctcagcc ctgaggaggc ggcccaccag    300
aaagccgtgg tggagaccct tctgcaggag gacccgtggc gtgtggcgaa gatggtcaag    360
tcctacctgc agcagcacaa catcccacag cgggaggtgg tcgataccac tggcctcaac    420
cagtcccacc tgtcccaaca cctcaacaag ggcactccca tgaagacgca gaagcgggcc    480
gccctgtaca cctggtacgt ccgcaagcag cgagaggtgg cgcagcagtt cacccatgca    540
gggcagggag ggctgattga agagcccaca ggtgatgagc taccaaccaa gaaggggcgg    600
aggaaccgtt tcaagtgggg cccagcatcc cagcagatcc tgttccaggc ctatgagagg    660
cagaagaacc ctagcaagga ggagcgagag acgctagtgg aggagtgcaa tagggcggaa    720
tgcatccaga gagggtgtc cccatcacag gcacaggggc tggctccaa cctcgtcacg     780 gaggtgcgtg tctacaactg gtttgccaac cggcgcaaag aagaagcctt ccggcacaag    840
ctggccatgg acacgtacag cgggccccc ccagggccag gcccgggacc tgcgctgccc     900
gctcacagct cccctggcct gcctccacct gccctctccc ccagtaaggt ccacggtgtg    960
cgctatggac agcctgcgac cagtgagact gcagaagtac cctcaagcag cggcggtccc   1020
ttagtgacag tgtctacacc cctccaccaa gtgtccccca cgggcctgga gcccagccac   1080
agcctgctga gtacagaagc caagctggtc tcagcagctg ggggccccct ccccctgtc    1140 agcaccctga cagcactgca cagcttggag cagacatccc caggcctcaa ccagcagccc    1200
cagaacctca tcatggcctc acttcctggg gtcatgacca cgggcctgg tgagcctgcc    1260 tccctgggtc ctacgttcac caacacaggt gcctccaccc tggtcatcgg cctggcctcc    1320
acgcaggcac agagtgtgcc ggtcatcaac agcatgggca gcagcctgac caccctgcag    1380
cccgtccagt ctcccagcc gctgcacccc tcctaccagc agccgctcat gccacctgtg    1440
cagagccatg tgacccagag ccccttcatg gccaccatgg ctcagctgca gagcccccac    1500
gccctctaca gccacaagcc cgaggtggcc cagtacaccc acacaggcct gctcccgcag    1560
actatgctca tcaccgacac caccaacctg agcgccctgg ccagcctcac gcccaccaag    1620
caggtcttca cctcagacac tgaggcctcc agtgagtccg ggcttcacac gccggcatct    1680
caggccacca ccctccacgt ccccagccag gaccctgccg gcatccagca cctgcagccg    1740
gcccaccggc tcagcgccag ccccacagtg tcctccagca gcctggtgct gtaccagagc    1800
tcagactcca gcaatggcca gagccaccctg ctgccatcca accacagcgt catcgagacc    1860
ttcatctcca cccagatggc ctcttcctcc cagttg                             1896
```

<210> SEQ ID NO 56
<211> LENGTH: 1671
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atggttagca aactgacatc cctccagcag gaacttcttt ctgccctcct ctccagtggg     60
gtaaccaaag aggtactggt ccaggctttg gaggagttgc tcccctcacc gaattttggt    120
gtaaagttgg agactctccc cctctcccct ggttctggag cagagccgga tactaaaccg    180
gtatttcata cgcttacaaa cggacacgca aagggtcggc tttcaggtga cgaagggtct    240
gaggacggcg atgattatga cacccccgccc atcctcaaag aactgcaggc ccttaataca    300
```

```
gaggaagcgg cggagcagcg agctgaagtt gacagaatgc tctcagaaga tccgtggaga        360
gctgcgaaaa tgattaaggg atatatgcag caacataaca ttccccagag agaggtagtt        420
gatgttaccg gccttaacca gagccacctg tctcagcatc tcaataaggg tactcctatg        480
aaaacacaga agcgagcggc cctttacaca tggtacgtgc ggaagcaacg agaaattctc        540
cgacagttca atcagacagt acaatcttca gggaacatga cggataaaag ctcacaggat        600
cagctcttgt ttctcttccc cgagttcagc caacagtccc acggtccagg tcaatctgat        660
gatgcttgca gtgaacctac aaacaaaaaa atgaggagga acaggtttaa atggggaccg        720
gcctctcagc agatactgta ccaagcgtac gatcggcaga aaaacccaag caaagaggag        780
cgcgaggcat tggtcgagga gtgtaatcgg gccgagtgct gcaacgggg tgtaagtcct         840
agcaaagccc atggtctcgg ctcaaacttg gtcacggagg tgagggtata taattggttt        900
gccaacaggc ggaaggagga agcattccgg caaaagctgg cgatggatgc ctactcaagc        960
aaccagacac atagcctcaa ccctctgttg tcacacgggt cccctcatca ccaaccttct       1020
tcctctccac ccaacaaact ttctggtgtc cgatattccc agcaggggaa caacgagata       1080
acatcttcct ctactataag tcatcacgga aattctgcaa tggtaacgtc acagagtgtg       1140
ttgcaacagg tatcacccgc gtctcttgat ccaggccaca atctgttgag ccctgacgga       1200
aagatgatct ctgtttctgg tggcggactc ccgccggtct ccacacttac caacatacat       1260
agtctcagtc atcataatcc tcagcagagc caaaacctga tatgactcc tcttagcgga        1320
gtgatggcta ttgcgcaatc tttgaacacc tcacaagcac aatctgtacc cgtcataaac       1380
agcgtagcgg gctcattggc ggcgctccaa ccagtgcagt tctcccagca gctccattca       1440
ccccatcaac agcctctgat gcagcagagc cctggtagtc acatggctca acagccgttc       1500
atggcagctg tcactcagct ccagaactcc catatgtatg cccacaagca agaaccacca       1560
caatacagtc acacatcaag attccccagt gctatggttg ttactgacac atcctctatc       1620
tcaactctga cgaacatgtc cagtagtaaa caatgtcctc tgcaagcatg g                1671
```

<210> SEQ ID NO 57
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
atgcgactct ccaaaaccct cgtcgacatg gacatggccg actacagtgc tgcactggac         60
ccagcctaca ccaccctgga atttgagaat gtgcaggtgt tgacgatggg caatgacacg        120
tccccatcag aaggcaccaa cctcaacgcg cccaacagcc tggtgtcag cgccctgtgt         180
gccatctgcg ggaccgggc cacgggcaaa cactacggtg cctcgagctg tgacggctgc        240
aagggcttct tccggaggag cgtgcggaag aaccacatgt actcctgcag atttagccgg        300
cagtgcgtgg tggacaaaga caagaggaac cagtgccgct actgcaggct caagaaatgc        360
ttccgggctg gcatgaagaa ggaagccgtc cagaatgagc gggaccggat cagcactcga        420
aggtcaagct atgaggacag cagcctgccc tccatcaatg cgctcctgca ggcggaggtc        480
ctgtcccgac agatcaccct ccccgtctcc gggatcaacg gcgacattcg ggcgaagaag        540
attgccagca tcgcagatgt gtgtgagtcc atgaaggagc agctgctggt tctcgttgag        600
tgggccaagt acatcccagc tttctgcgag ctcccccctgg acgaccaggt ggccctgctc        660
```

| | |
|---|---|
| agagcccatg ctggcgagca cctgctgctc ggagccacca agagatccat ggtgttcaag | 720 |
| gacgtgctgc tcctaggcaa tgactacatt gtccctcggc actgcccgga gctggcggag | 780 |
| atgagccggg tgtccatacg catccttgac gagctggtgc tgcccttcca ggagctgcag | 840 |
| atcgatgaca atgagtatgc ctacctcaaa gccatcatct tctttgaccc agatgccaag | 900 |
| gggctgagcg atccagggaa gatcaagcgg ctgcgttccc aggtgcaggt gagcttggag | 960 |
| gactacatca cgaccgcca gtatgactcg cgtggccgct ttggagagct gctgctgctg | 1020 |
| ctgcccacct tgcagagcat cacctggcag atgatcgagc agatccagtt catcaagctc | 1080 |
| ttcggcatgg ccaagattga caacctgttg caggagatgc tgctgggagg tccgtgccaa | 1140 |
| gcccaggagg ggcggggttg gagtggggac tccccaggag acaggcctca cacagtgagc | 1200 |
| tcaccccctca gctccttggc ttccccactg tgccgctttg gcaagttgc t | 1251 |

<210> SEQ ID NO 58
<211> LENGTH: 1005
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58

| | |
|---|---|
| atggacaacg cgcggatgaa ttccttcctc gagtacccaa ttttgtctag tggagacagt | 60 |
| ggcacttgca gtgcccgagc ctatccatca gaccacagaa ttacaacatt ccaaagctgt | 120 |
| gcggtgtcag ccaacagttg cggcggagac gaccgcttcc tggtcggaag aggggttcaa | 180 |
| attggatcac ctcaccatca ccatcaccac caccatcacc accccaacc ggcgacttac | 240 |
| caaaccagcg gcaatttggg cgtgagctat agccattcct catgtggacc ttcctatggg | 300 |
| tctcagaatt ctccgcccc ttatagccca tacgccctga ccaagaggc cgatgtatca | 360 |
| ggaggctatc cccagtgcgc gccagcggtt tactcaggta atctttctag cccgatggtc | 420 |
| cagcaccacc atcaccatca aggttatgcc ggcggtgcag tcggatcccc acaatacata | 480 |
| caccatagtt acggccaaga gcaccaatcc ctggccctcg ctacatataa caactcactg | 540 |
| tctccgcttc atgcttccca ccaagaagct tgtcggagtc cgcctcaga aacttcctct | 600 |
| ccagctcaga cttttgattg gatgaaggtc aagcggaatc cgcctaaaac gggcaaagta | 660 |
| ggtgaatatg ctatttggg acagcctaat gctgtccgca ccaatttcac aacaaaacag | 720 |
| cttactgaac tcgagaagga atttcatttt aataagtatt tgactcgagc gagacgagtc | 780 |
| gaaatcgccg ctagtcttca acttaacgag acccaggtta agatatggtt ccagaacaga | 840 |
| agaatgaaac aaaaaaagcg ggagaaggaa ggactcctcc ctatatcacc agccacaccc | 900 |
| ccaggtaacg acgagaaggc ggaggaatct tcagagaaga gttccagctc cccttgtgtt | 960 |
| ccttctcctg gtagctcaac cagcgatacc ctcacgacga gtcac | 1005 |

<210> SEQ ID NO 59
<211> LENGTH: 282
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59

| | |
|---|---|
| atgtgtcaag gcaattccaa aggtgaaaac gcagccaact ggctcacggc aaagagtggt | 60 |
| cggaagaagc gctgcccta cacgaagcac cagacactgg agctggagaa ggagtttctg | 120 |

```
ttcaatatgt accttactcg agagcggcgc ctagagatta gccgcagcgt ccacctcacg    180
gacagacaag tgaaaatctg gtttcagaac cgcaggatga aactgaagaa atgaatcga    240 gaaaaccgga tccgggagct cacagccaac tttaattttt cc                     282
```

<210> SEQ ID NO 60
<211> LENGTH: 942
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atggattttg atgagcgtgg tccctgctcc tctaacatgt atttgccaag ttgtacttac    60
tacgtctcgg gtccagattt ctccagcctc ccttcttttc tgccccagac cccgtcttcg   120
cgcccaatga catactccta ctcctccaac ctgccccagg tccaacccgt gcgcgaagtg   180
accttcagag agtacgccat tgagcccgcc actaaatggc accccgcgg caatctggcc    240 cactgctact ccgcggagga gctcgtgcac agagactgcc tgcaggcgcc cagcgcggcc   300
ggcgtgcctg cgacgtgct ggccaagagc tcggccaacg tctaccacca ccccaccccc    360
gcagtctcgt ccaatttcta tagcaccgtg gcaggaacg gcgtcctgcc acaggctttc    420
gaccagtttt cgagacagc ctacggcacc ccggaaaacc tcgcctcctc cgactacccc    480
ggggacaaga gcgccgagaa ggggcccccg gcggccacgg cgacctccgc ggcggcggcg    540
gcggctgcaa cggcgcgcc ggcaacttca agttcggaca cgcgcggcgg cggcggctgc    600
cgggagatgg cggcggcagc agaggagaaa gagcggcggc ggcgccccga gagcagcagc   660
agccccgagt cgtcttccgg ccacactgag gacaaggccg gcggctccag tggccaacgc   720
acccgcaaaa agcgctgccc ctataccaag taccagatcc gagagctgga acgggagttc    780
ttcttcagcg tctacattaa caagagaag cgcctgcaac tgtcccgcat gctcaacctc    840
actgatcgtc aagtcaaaat ctggtttcag aacaggagaa tgaaggaaaa aaaaattaac    900
agagaccgtt tacagtacta ctcagcaaat ccactcctct tg                     942
```

<210> SEQ ID NO 61
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atgagttcct atttcgtgaa ctccaccttc cccgtcactc tggccagcgg gcaggagtcc    60
ttcctgggcc agctaccgct ctattcgtcg ggctatgcgg acccgctgag acattacccc   120
gcgccctacg ggccagggcc gggccaggac aagggctttg ccacttcctc ctattacccg   180
ccggcgggcg gtggctacgg ccgagcggcg ccctgcgact acgggccggc gccggccttc    240
taccgcgaga aagagtcggc ctgcgcactc tccggcgccg acgagcagcc cccgttccac    300
cccgagccgc ggaagtcgga ctgcgcgcag gacaagagcg tgttcggcga cacagaagag    360
cagaagtgct ccactccggt ctacccgtgg atgcagcgga tgaattcgtg caacagttcc    420
tcctttgggc ccagcggccg gcgaggccgc cagacataca cacgttacca gacgctggag    480
ctggagaagg agtttcacta caatcgctac ctgacgcggc ggcggcgcat cgagatcgcg    540
```

-continued

| | |
|---|---|
| cacgccctgt gcctgacgga gaggcagatc aagatatggt tccagaaccg acgcatgaag | 600 |
| tggaaaaagg agagcaaact gctcagcgcg tctcagctca gtgccgagga ggaggaagaa | 660 |
| aaacaggccg ag | 672 |

<210> SEQ ID NO 62
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

| | |
|---|---|
| atggctgtca gcgacgcgct gctcccatct ttctccacgt tcgcgtctgg cccggcggga | 60 |
| agggagaaga cactgcgtca agcaggtgcc ccgaataacc gctggcggga ggagctctcc | 120 |
| cacatgaagc gacttccccc agtgcttccc ggccgcccct atgacctggc ggcggcgacc | 180 |
| gtggccacag acctggagag cggcggagcc ggtgcggctt cgcggcggta gcaacctggcg | 240 |
| cccctacctc ggagagagac cgaggagttc aacgatctcc tggacctgga ctttattctc | 300 |
| tccaattcgc tgacccatcc tccggagtca gtggccgcca ccgtgtcctc gtcagcgtca | 360 |
| gcctcctctt cgtcgtcgcc gtcgagcagc ggccctgcca gcgcgccctc cacctgcagc | 420 |
| ttcacctatc cgatccgggc cgggaacgac ccgggcgtgg cgccgggcgg cacgggcgga | 480 |
| ggcctcctct atgcaggga gtccgctccc cctccgacgg ctcccttcaa cctggcggac | 540 |
| atcaacgacg tgagcccctc gggcggcttc gtggccgagc tcctgcggcc agaattggac | 600 |
| ccggtgtaca ttccgccgca gcagccgcag ccgccaggtg gcgggctgat gggcaagttc | 660 |
| gtgctgaagg cgtcgctgag cgcccctggc agcgagtacg gcagcccgtc ggtcatcagc | 720 |
| gtcagcaaag gcagccctga cggcagccac ccggtggtgg tggcgcccta caacggcggg | 780 |
| ccgccgcgca cgtgccccaa gatcaagcag gaggcggtct cttcgtgcac ccacttgggc | 840 |
| gctggacccc ctctcagcaa tggccaccgg ccggctgcac acgacttccc cctggggcgg | 900 |
| cagctcccca gcaggactac cccgaccctg ggtcttgagg aagtgctgag cagcagggac | 960 |
| tgtcaccctg ccctgccgct tcctccccggc ttccatcccc acccgggggcc caattaccca | 1020 |
| tccttcctgc ccgatcagat gcagccgcaa gtcccgccgc tccattacca agagctcatg | 1080 |
| ccacccggtt cctgcatgcc agaggagccc aagccaaaga ggggaagacg atcgtggccc | 1140 |
| cggaaaagga ccgccaccca cacttgtgat tacgcgggct gcggcaaaac ctacacaaag | 1200 |
| agttcccatc tcaaggcaca cctgcgaacc cacacaggtg agaaaccttta ccactgtgac | 1260 |
| tgggacggct gtggatggaa attcgcccgc tcagatgaac tgaccaggca ctaccgtaaa | 1320 |
| cacacggggc accgcccgtt ccagtgccaa aaatgcgacc gagcatttc caggtcggac | 1380 |
| cacctcgcct tacacatgaa gaggcatttt | 1410 |

<210> SEQ ID NO 63
<211> LENGTH: 1236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

| | |
|---|---|
| atggaggcgc gcggggagct gggcccggcc cgggagtcgg cggaggcga cctgctgcta | 60 |
| gcactgctgg cgcggagggc ggacctgcgc cgagagatcc cgctgtgcgc tggctgtgac | 120 |

```
cagcacatcc tggaccgctt catcctcaag gctctggacc gccactggca cagcaagtgt      180
ctcaagtgca gcgactgcca cacgccactg gccgagcgct gcttcagccg aggggagagc      240
gtttactgca aggacgactt tttcaagcgc ttcgggacca agtgcgccgc gtgccagctg      300
ggcatcccgc ccacgcaggt ggtgcgccgc gcccaggact cgtgtaccac cctgcactgc      360
tttgcctgcg tcgtgtgcaa gcggcagctg ccacgggcg acgagttcta cctcatggag       420
gacagccggc tcgtgtgcaa ggcggactac gaaaccgcca agcagcgaga ggccgaggcc      480
acggccaagc ggccgcgcac gaccatcacc gccaagcagc tggagacgct gaagagcgct      540
tacaacacct cgcccaagcc ggcgcgccac gtgcgcgagc agctctcgtc cgagacgggc      600
ctggacatgc gcgtggtgca ggtttggttc cagaaccgcc gggccaagga agaggctg       660 aagaaggacg ccggccggca gcgctggggg cagtatttcc gcaacatgaa gcgctcccgc      720
ggcggctcca agtcggacaa ggacagcgtt caggagggg aggacagcga cgctgaggtc       780
tccttccccg atgagccttc cttggcggaa atgggcccgg ccaatggcct ctacgggagc      840 tgggggaac ccacccaggc cttgggccgg ccctcgggag ccctgggcaa cttctccctg       900
gagcatggag gcctggcagg cccagagcag taccgagagc tgcgtcccgg cagcccctac      960
ggtgtccccc catccccgc cgccccgcag agcctccctg gccccagcc cctcctctcc       1020 agcctggtgt acccagacac cagcttgggc cttgtgccct cgggagcccc cggcgggccc      1080
ccacccatga gggtgctggc agggaacgga cccagttctg acctatccac ggggagcagc      1140
gggggttacc ccgacttccc tgccagcccc gcctcctggc tggatgaggt agaccacgct      1200
cagttctcag gcctcatggg cccagctttc ttgtac                                1236

<210> SEQ ID NO 64
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggaaggaa tcatgaaccc ctacacggct ctgcccaccc cacagcagct cctggccatc      60
gagcagagtg tctacagctc agatcccttc gacagggtc tcaccccacc ccagatgcct        120
ggagaccaca tgcacccta tggtgccgag cccctttcc atgacctgga tagcgacgac        180
acctccctca gtaacctggg tgactgtttc ctagcaacct cagaagctgg gcctctgcag      240
tccagagtgg gaaaccccat tgaccatctg tactccatgc agaattctta cttcacatct       300

<210> SEQ ID NO 65
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggggagaa aaagattca gattacgagg attatggatg aacgtaacag acaggtgaca        60
tttacaaaga ggaaatttgg gttgatgaag aaggcttatg agctgagcgt gctgtgtgac      120
tgtgagattg cgctgatcat cttcaacagc accaacaagc tgttccagta tgccagcacc      180
gacatggaca aagtgcttct caagtacacg gagtacaacg agccgcatga gagccggaca      240
```

```
aactcagaca tcgtggagac gttgagaaag aagggcctta atggctgtga cagcccagac    300
cccgatgcgg acgattccgt aggtcacagc cctgagtctg aggacaagta caggaaaatt    360
aacgaagata ttgatctaat gatcagcagg caaagattgt gtgctgttcc acctcccaac    420
ttcgagatgc cagtctccat cccagtgtcc agccacaaca gtttggtgta cagcaaccct    480
gtcagctcac tgggaaaccc caacctattg ccactggctc accttctct gcagaggaat     540 agtatgtctc ctggtgtaac acatcgacct ccaagtgcag gtaacacagg tggtctgatg    600
ggtggagacc tcacgtctgg tgcaggcacc agtgcaggga acgggtatgg caatccccga    660
aactcaccag gtctgctggt ctcacctggt aacttgaaca agaatatgca agcaaaatct    720
cctcccccaa tgaatttagg aatgaataac cgtaaaccag atctccgagt tcttattcca    780
ccaggcagca agaatacgat gccatcagtg tctgaggatg tcgacctgct tttgaatcaa    840 aggataaaata actcccagtc ggctcagtca ttggctaccc cagtggtttc cgtagcaact    900
cctactttac caggacaagg aatggggagga tatccatcag ccatttcaac aacatatggt    960
accgagtact ctctgagtag tgcagacctg tcatctctgt ctgggtttaa caccgccagc   1020
gctcttcacc ttggttcagt aactggctgg caacagcaac acctacataa catgccacca   1080
tctgccctca gtcagttggg agcttgcact agcactcatt tatctcagag ttcaaatctc   1140
tccctgcctt ctactcaaag cctcaacatc aagtcagaac ctgtttctcc tcctagagac   1200
cgtaccacca ccccttcgag ataccacaa cacacgcgcc acgaggcggg gagatctcct    1260
gttgacagct tgagcagctg tagcagttcg tacgacggga gcgaccgaga ggatcaccgg   1320
aacgaattcc actcccccat tggactcacc agaccttcgc cggacgaaag ggaaagtccc   1380
tcagtcaagc gcatgcgact ttctgaagga tgggcaaca                          1419
```

<210> SEQ ID NO 66
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atggcccagc cctgtgccc gccgctctcc gagtcctgga tgctctctgc ggcctggggc     60
ccaactcggc ggccgccgcc ctccgacaag gactgcggcc gctccctcgt ctcgtcccca    120
gactcatggg gcagcacccc agccgacagc cccgtggcga gcccgcgcg gccaggcacc    180 ctccgggacc cccgcgcccc ctccgtaggt aggcgcggcg cgcgcagcag ccgcctgggc    240
agcgggcaga ggcagagcgc cagtgagcgg gagaaactgc gcatgcgcac gctggcccgc    300
gccctgcacg agctgcgccg ctttctaccg ccgtccgtgg cgcccgcggg ccagagcctg    360
accaagatcg agacgctgcg cctggctatc cgctatatcg ccacctgtc ggccgtgcta    420 ggcctcagcg aggagagtct ccagcgccgg tgccggcagc gcggtgacgc ggggtccct   480 cggggctgcc cgctgtgccc cgacgactgc cccgcgcaga tgcagacacg gacgcaggct    540
gaggggcagg ggcaggggcg cgggctgggc ctggtatccg ccgtccgcgc cggggcgtcc    600 tgggatccc cgcctgcctg ccccggagcc cgagctgcac ccgagccgcg cgacccgcct    660
gcgctgttcg ccgaggcggc gtgcccggaa gggcaggcga tggagccaag cccaccgtcc    720
ccgctccttc cggcgacgt gctggctctg ttgagacct ggatgcccct ctcgcctctg     780
gagtggctgc ctgaggagcc caagttg                                       807
```

<210> SEQ ID NO 67
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

| | |
|---|---|
| atgctggaaa tgctagaata taatcactat caggtgcaga cccacctcga aaacccacc | 60 |
| aagtaccaca tacagcaagc ccaacggcag caggtaaagc agtacctttc taccacttta | 120 |
| gcaaataaac atgccaacca agtcctgagc ttgccatgtc caaaccagcc tggcgatcat | 180 |
| gtcatgccac cggtgccggg gagcagcgca cccaacagcc catggctat gcttacgctt | 240 |
| aactccaact gtgaaaaaga gggatttttat aagtttgaag agcaaaacag ggcagagagc | 300 |
| gagtgcccag gcatgaacac acattcacga gcgtcctgta tgcagatgga tgatgtaatc | 360 |
| gatgacatca ttagcctaga atcaagttat aatgaggaaa tcttgggctt gatggatcct | 420 |
| gctttgcaaa tggcaaatac gttgcctgtc tcgggaaact tgattgatct ttatggaaac | 480 |
| caaggtctgc ccccaccagg cctcaccatc agcaactcct gtccagccaa ccttcccaac | 540 |
| ataaaaggg agctcacaga gtctgaagca agagcactgg ccaagagag gcagaaaaag | 600 |
| gacaatcaca acctgattga acgaagaaga agatttaaca taaatgaccg cattaaagaa | 660 |
| ctaggtactt tgattcccaa gtcaaatgat ccagacatgc gctggaacaa gggaaccatc | 720 |
| ttaaaagcat ccgtggacta tatccgaaag ttgcaacgag aacagcaacg cgcaaaagaa | 780 |
| cttgaaaacc gacagaagaa actggagcac gccaaccggc atttgttgct cagaatacag | 840 |
| gaacttgaaa tgcaggctcg agctcatgga ctttcccctta ttccatccac gggtctctgc | 900 |
| tctccagatt tggtgaatcg gatcatcaag caagaacccg ttcttgagaa ctgcagccaa | 960 |
| gacctccttc agcatcatgc agacctaacc tgtacaacaa ctctcgatct cacggatggc | 1020 |
| accatcacct tcaacaacaa cctcggaact gggactgagg ccaaccaagc ctatagtgtc | 1080 |
| cccacaaaaa tgggatccaa actggaagac atcctgatgg acgacaccct ttctcccgtc | 1140 |
| ggtgtcactg atccactcct ttcctcagtg tcccccggag cttccaaaac aagcagccgg | 1200 |
| aggagcagta tgagcatgga agagacggag cacacttgt | 1239 |

<210> SEQ ID NO 68
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

| | |
|---|---|
| atgccctca acgttagctt caccaacagg aactatgacc tcgactacga ctcggtgcag | 60 |
| ccgtatttct actgcgacga ggaggagaac ttctaccagc agcagcagca gagcgagctg | 120 |
| cagccccgg cgcccagcga ggatatctgg aagaaattcg agctgctgcc caccccgccc | 180 |
| ctgtcccta gccgccgctc cgggctctgc tcgccctcct acgttgcggt cacacccttc | 240 |
| tcccttcggg gagacaacga cggcggtggc gggagcttct ccacggccga ccagctggag | 300 |
| atggtgaccg agctgctggg aggagacatg gtgaaccaga gtttcatctg cgacccggac | 360 |
| gacgagacct tcatcaaaaa catcatcatc caggactgta tgtggagcgg cttctcggcc | 420 |
| gccgccaagc tcgtctcaga gaagctggcc tcctaccagg ctgcgcgcaa agacagcggc | 480 |

| | |
|---|---|
| agcccgaacc ccgcccgcgg ccacagcgtc tgctccacct ccagcttgta cctgcaggat | 540 |
| ctgagcgccg ccgcctcaga gtgcatcgac ccctcggtgg tcttccccta ccctctcaac | 600 |
| gacagcagct cgcccaagtc ctgcgcctcg caagactcca gcgccttctc tccgtcctcg | 660 |
| gattctctgc tctcctcgac ggagtcctcc ccgcagggca gccccgagcc cctggtgctc | 720 |
| catgaggaga caccgcccac caccagcagc gactctgagg aggaacaaga agatgaggaa | 780 |
| gaaatcgatg ttgtttctgt ggaaaagagg caggctcctg gcaaaaggtc agagtctgga | 840 |
| tcaccttctg ctggaggcca gcaaaacct cctcacagcc cactggtcct caagaggtgc | 900 |
| cacgtctcca cacatcagca caactacgca gcgcctccct ccactcggaa ggactatcct | 960 |
| gctgccaaga gggtcaagtt ggacagtgtc agagtcctga cagatcag caacaaccga | 1020 |
| aaatgcacca gccccaggtc ctcggacacc gaggagaatg tcaagaggcg aacacacaac | 1080 |
| gtcttggagc gccagaggag gaacgagcta aaacggagct ttttgccct gcgtgaccag | 1140 |
| atcccggagt tggaaaacaa tgaaaaggcc cccaaggtag ttatccttaa aaaagccaca | 1200 |
| gcatacatcc tgtccgtcca agcagaggag caaaagctca tttctgaaga ggacttgttg | 1260 |
| cggaaacgac gagaacagtt gaaacacaaa cttgaacagc tacggaactc ttgtgcg | 1317 |

<210> SEQ ID NO 69
<211> LENGTH: 618
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

| | |
|---|---|
| atggactacg actcgtacca gcactatttc tacgactatg actgcgggga ggatttctac | 60 |
| cgctccacgg cgcccagcga ggacatctgg aagaaattcg agctggtgcc atcgcccccc | 120 |
| acgtcgccgc cctggggctt gggtcccggc gcaggggacc cggcccccgg gattggtccc | 180 |
| ccggagccgt ggcccggagg gtgcaccgga gacgaagcgg aatcccgggg ccactcgaaa | 240 |
| ggctggggca ggaactacgc ctccatcata cgccgtgact gcatgtggag cggcttctcg | 300 |
| gcccgggaac ggctggagag agctgtgagc gaccggctcg ctcctggcgc gccccggggg | 360 |
| aacccgccca aggcgtccgc cgccccggac tgcactccca gcctcgaagc cggcaacccg | 420 |
| gcgcccgccg cccccctgtcc gctgggcgaa cccaagaccc aggcctgctc cgggtccgag | 480 |
| agcccaagcg actcgggtaa ggacctcccc gagccatcca agaggggggcc acccccatggg | 540 |
| tggccaaagc tctgcccctg cctgaggtca ggcattggct cttctcaagc tcttgggcca | 600 |
| tctccgcctc tctttggc | 618 |

<210> SEQ ID NO 70
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

| | |
|---|---|
| atgccgagtt gttccacgtc tacgatgcca ggaatgatat gcaagaaccc cgacttggag | 60 |
| tttgactctt tgcaaccatg cttttatccg gatgaagacg actttatttt cggcggcccg | 120 |
| gacagcaccc ctcctggaga ggacatctgg aaaaaattcg aacttttgcc tacaccccca | 180 |

| | |
|---|---|
| ctcagtccct ctcgaggatt tgcggaacac agcagtgaac cgccgtcttg ggtgacagag | 240 |
| atgctcctcg agaacgaatt gtggggaagc cctgcggagg aagacgcttt cgggctcggt | 300 |
| ggactcggag gtctcacgcc gaacccagtc atactgcagg attgcatgtg gtctggattc | 360 |
| tcagctcggg agaagctgga acgggcagtt tctgagaaac tccaacatgg ccggggccct | 420 |
| ccaacagcgg gttctaccgc acagtcccct ggtgctggag ccgctagtcc cgcggggaga | 480 |
| ggccatgggg gcgcggcagg agcgggtagg gccggcgctg cgttgcctgc tgagcttgcg | 540 |
| caccccgccg ctgaatgtgt agatcccgcg gtagtgtttc cgttccccgt taataagcga | 600 |
| gaaccggcac cggtgccagc cgctcctgcg tctgcacccg cggcaggtcc tgctgtcgcc | 660 |
| tcaggagcag gtattgccgc tcctgcaggg gcaccaggag tagcccctcc aaggcccggc | 720 |
| ggtaggcaaa cctccggcgg cgaccacaaa gcactctcaa cgagcggaga ggatacactg | 780 |
| tccgatagtg atgacgagga cgacgaagag gaggacgagg aggaggagat agatgttgtc | 840 |
| acggtcgaga agcgaaggag ttcttcaaat acaaaagcgg taacgacatt cacgataaca | 900 |
| gtaagaccta agaacgcagc cctcggtcca gggcgggccc agtccagtga gcttatactt | 960 |
| aagcgctgcc tgccgattca ccagcagcat aactacgcgg ccctagtccc ctacgttgag | 1020 |
| agcgaggatg ccccccaca aaaaaaaata agtctgaag cgtcccccg cccctgaaa | 1080 |
| tccgtaatcc ccccaaaggc gaagtcactc agtcccagga attcagattc cgaggactcc | 1140 |
| gaacggcggc ggaatcataa catacttgag agacaacgac gcaatgacct gaggtcttct | 1200 |
| tttttgaccc tccgagatca cgtccccgag ctggttaaga atgagaaagc tgcgaaggta | 1260 |
| gtcatactga aaaaggccac cgagtatgtc catagtttgc aagctgagga gcaccagctt | 1320 |
| ctccttgaaa aggagaaact tcaggcacga caacagcaat tgctgaaaaa gattgagcat | 1380 |
| gcacgcactt gt | 1392 |

<210> SEQ ID NO 71
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

| | |
|---|---|
| atggagctac tgtcgccacc gctccgcgac gtagacctga cggcccccga cggctctctc | 60 |
| tgctcctttg ccacaacgga cgacttctat gacgacccgt gtttcgactc cccggacctg | 120 |
| cgcttcttcg aagacctgga cccgcgcctg atgcacgtgg gcgcgctcct gaaacccgaa | 180 |
| gagcactcgc acttccccgc ggcggtgcac ccggccccgg gcgcacgtga ggacgagcat | 240 |
| gtgcgcgcgc ccagcgggca ccaccaggcg ggccgctgcc tactgtgggc ctgcaaggcg | 300 |
| tgcaagcgca agaccaccaa cgccgaccgc cgcaaggccg ccaccatgcg cgagcggcgc | 360 |
| cgcctgagca aagtaaatga ggcctttgag acactcaagc gctgcacgtc gagcaatcca | 420 |
| aaccagcggt tgcccaaggt ggagatcctg cgcaacgcca tccgctatat cgagggcctg | 480 |
| caggctctgc tgcgcgacca ggacgccgcg ccccctggcg ccgcagccgc cttctatgcg | 540 |
| ccgggcccgc tgccccgggg ccgcggcggc gagcactaca gcggcgactc cgacgcgtcc | 600 |
| agcccgcgct ccaactgctc cgacggcatg atggactaca gcggcccccc gagcggcgcc | 660 |
| cggcggcgga actgctacga aggcgcctac tacaacgagg cgcccagcga acccaggccc | 720 |
| gggaagagtg cggcggtgtc gagcctagac tgcctgtcca gcatcgtgga gcgcatctcc | 780 |

| | |
|---|---|
| accgagagcc ctgcggcgcc cgccctcctg ctggcggacg tgccttctga gtcgcctccg | 840 |
| cgcaggcaag aggctgccgc ccccagcgag ggagagagca gcggcgaccc cacccagtca | 900 |
| ccggacgccg ccccgcagtg ccctgcgggt gcgaacccca acccgatata ccaggtgctc | 960 |

<210> SEQ ID NO 72
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | |
|---|---|
| atggagctgt atgagacatc cccctacttc taccaggaac cccgcttcta tgatggggaa | 60 |
| aactacctgc ctgtccacct ccagggcttc gaaccaccag gctacgagcg gacggagctc | 120 |
| accctgagcc ccgaggcccc agggccccct gaggacaagg ggctggggac ccccgagcac | 180 |
| tgtccaggcc agtgcctgcc gtgggcgtgt aaggtgtgta agaggaagtc ggtgtccgtg | 240 |
| gaccggcggc gggcggccac actgagggag aagcgcaggc tcaagaaggt gaatgaggcc | 300 |
| ttcgaggccc tgaagagaag caccctgctc aaccccaacc agcggctgcc caaggtggag | 360 |
| atcctgcgca gtgccatcca gtacatcgag cgcctccagg ccctgctcag ctccctcaac | 420 |
| caggaggagc gtgaccctcc gctaccgggg ggggcgggc cccagccagg ggtgcccagc | 480 |
| gaatgcagct ctcacagcgc ctcctgcagt ccagagtggg gcagtgcact ggagttcagc | 540 |
| gccaacccag gggatcatct gctcacggct gaccctacag atgcccacaa cctgcactcc | 600 |
| ctcacctcca tcgtggacag catcacagtg gaagatgtgt ctgtggcctt cccagatgaa | 660 |
| accatgccca ac | 672 |

<210> SEQ ID NO 73
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| atgaccaaat cgtacagcga gagtgggctg atgggcgagc tcagccccca aggtcctcca | 60 |
| agctggacag acgagtgtct cagttctcag gacgaggagc acgaggcaga caagaaggag | 120 |
| gacgacctcg aagccatgaa cgcagaggag gactcactga ggaacggggg agaggaggag | 180 |
| gacgaagatg aggacctgga agaggaggaa gaagaggaag gaggatgag cgatcaaaag | 240 |
| cccaagagac gcggccccaa aaagaagaag atgactaagg ctcgcctgga gcgttttaaa | 300 |
| ttgagacgca tgaaggctaa cgcccgggag cggaaccgca tgcacggact gaacgcggcg | 360 |
| ctagacaacc tgcgcaaggt ggtgccttgc tattctaaga cgcagaagct gtccaaaatc | 420 |
| gagactctgc gcttggccaa gaactacatc tgggctctgt cggagatcct gcgctcaggc | 480 |
| aaaagcccag acctggtctc cttcgttcag acgctttgca agggcttatc ccaacccacc | 540 |
| accaacctgg ttgcgggctg cctgcaactc aatcctcgga cttttctgcc tgagcagaac | 600 |
| caggacatgc cccccacct gccgacggcc agcgcttcct tccctgtaca ccctactcc | 660 |
| taccagtcgc ctgggctgcc cagtccgcct tacggtacca tggacagctc ccatgtcttc | 720 |
| cacgttaagc ctccgccgca cgcctacagc gcagcgctgg agcccttctt tgaaagccct | 780 |
| ctgactgatt gcaccagccc ttcctttgat ggaccctca gcccgccgct cagcatcaat | 840 |

```
ggcaacttct ctttcaaaca cgaaccgtcc gccgagtttg agaaaaatta tgcctttacc      900
atgcactatc ctgcagcgac actggcaggg gcccaaagcc acggatcaat cttctcaggc      960
accgctgccc ctcgctgcga gatccccata gacaatatta tgtccttcga tagccattca     1020
catcatgagc gagtcatgag tgcccagctc aatgccatat ttcatgat                  1068
```

<210> SEQ ID NO 74
<211> LENGTH: 711
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 74

```
atgccagccc gccttgagac ctgcatctcc gacctcgact gcgccagcag cagcggcagt       60
gacctatccg gcttcctcac cgacgaggaa gactgtgcca gactccaaca ggcagcctcc      120
gcttcggggc cgcccgcgcc ggcccgcagg ggcgcgccca atatctcccg ggcgtctgag      180
gttccagggg cacaggacga cgagcaggag aggcggcggc gccgcggccg gacgcgggtc      240
cgctccgagg cgctgctgca ctcgctgcgc aggagccggc gcgtcaaggc caacgatcgc      300
gagcgcaacc gcatgcacaa cttgaacgcg gccctggacg cactgcgcag cgtgctgccc      360
tcgttccccg acgacaccaa gctcaccaaa atcgagacgt gcgcttcgc ctacaactac       420 atctgggctc tggccgagac actgcgcctg gcggatcaag ggctgccgg aggcggtgcc       480 cgggagcgcc tcctgccgcc gcagtgcgtc cctgcctgc ccggtccccc aagcccgcc       540 agcgacgcgg agtcctgggg ctcaggtgcc gccgccgcct cccgctctc tgacccagt       600 agcccagccg cctccgaaga cttcacctac cgccccggcg accctgtttt ctccttccca      660
agcctgccca aagacttgct ccacacaacg ccctgtttca ttccttacca c               711
```

<210> SEQ ID NO 75
<211> LENGTH: 642
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 75

```
atgacaccac aaccatctgg tgctcccaca gtccaggtga cgcgagagac tgaaagatca       60
ttcccacgcg cgtccgagga tgaggtgaca tgtccaacta gcgcaccccc ctctcctacc      120
cggacccgcg ggaattgtgc tgaggccgaa gagggaggat gcagaggagc accaaggaaa      180
cttcgagccc gacggggtgg aagaagccgc cccaagtctg agctcgccct tagcaagcag      240
cgccgcagtc ggaggaaaaa ggcaaacgac cgggaaagga ataggatgca taatcttaat      300
tctgctctgg acgctctgcg aggcgtactt cctactttcc cggatgacgc gaaattgacc      360
aagatagaga ctctccggtt tgcacataat tacatctggg ctcttacaca aacactgaga      420
attgccgatc acagtcttta cgctcttgag ccacccgccc cgcactgtgg cgagctgggt      480
agccccggcg gctctcctgg agactggggg tctttgtatt ctcctgtcag ccaagcggga      540
tctttgagtc cggctgccag tctcgaagaa agacccggac tccttggagc gacttttttca      600 gcatgtctgt ccctggctc attggctttc tcagacttt tg                          642
```

<210> SEQ ID NO 76

<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
atggccctgc ctcccagccc gctggccatg gaatatgtca atgactttga cttgatgaag      60
tttgaggtaa agcgggaacc ctctgagggc cgacctggcc cacctacagc ctcactggga     120
tccacacctt acagctcagt gcctccttca cccaccttca gtgaaccagg catggtaggg     180
gcaaccgagg gtacacgacc aggtttggag gagctgtact ggcttgctac cctgcagcag     240
cagcttgggg ctggggaggc attgggactg agtcctgaag aggccatgga gctactgcaa     300
ggtcagggcc cagtccctgt tgatggaccc catggttact acccagggag cccagaggag     360
acaggagccc agcacgttca gttggcagag cggttttccg acgcggcgct tgtctcgatg     420
tctgtgcgag aactaaaccg gcagctgcgg ggatgcggga gagacgaggc tctacgactg     480
aagcagaggc gtcgaacgct gaagaaccgt ggctatgcgc aagcatgtcg ttccaagagg     540
ctgcaacaga ggcgaggtct tgaggccgag cgcgcccgtc ttgcagccca gctagatgcg     600
ctacgagctg aagtagcacg tttggcaaga gagcgagatc tctacaaggc tcgctgtgac     660
cggctaacct cgagtggccc cgggtccggg gatccctccc accttttcct ctgcccaact     720
ttcttgtaca aagttgtccc c                                               741
```

<210> SEQ ID NO 77
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
atgaacgcgc agctgaccat ggaagcgatc ggcgagctgc acggggtgag ccatgagccg      60
gtgcccgccc ctgccgacct gctgggcgga agccccacg cgcgcagctc cgtggcgcac      120
cgcggcagcc acctgccccc cgcgcacccg cgctccatgg gcatggcgtc cctgctggac     180
ggcggcagcg gcggcggaga ttaccaccac caccaccggg cccctgagca gcctggcc      240
ggccccctgc atcccaccat gaccatggcc tgcgagactc cccaggtat gagcatgccc     300
accacctaca ccaccttgac ccctctgcag ccgctgcctc ccatctccac agtctcggac     360
aagttccccc accatcacca ccaccaccat caccaccacc acccgcacca ccaccagcgc     420
ctggcgggca acgtgagcgg tagcttcacg ctcatgcggg atgagcgcgg gctggcctcc     480
atgaataacc tctataccc ctaccacaag gacgtggccg gcatgggcca gagcctctcg     540
cccctctcca gctccggtct gggcagcatc acaactccc agcaagggct ccccactat     600
gcccaccgg gggccgccat gcccaccgac aagatgctca cccccaacgg cttcgaagcc     660
caccaccgg ccatgctcgg ccgccacggg gagcagcacc tcacgcccac ctcggccggc     720
atggtgccca tcaacggcct tcctccgcac catccccacg cccacctgaa cgcccaggc     780
cacgggcaac tcctgggcac agcccgggag cccaaccctt cggtgaccgg cgcgcaggtc     840
agcaatggaa gtaattcagg gcagatggaa gagatcaata ccaagaggt ggcgcagcgt     900
atcaccaccg agctcaagcg ctacagcatc ccacaggcca tcttcgcgca gagggtgctc     960
tgccgctccc agggggaccct ctcggacctg ctgcgcaacc ccaaaccctg gagcaaactc    1020
```

```
aaatccggcc gggagacctt ccggaggatg tggaagtggc tgcaggagcc ggagttccag    1080
cgcatgtccg cgctccgctt agcagcatgc aaaaggaaag aacaagaaca tgggaaggat    1140
agaggcaaca cacccaaaaa gcccaggttg gtcttcacag atgtccagcg tcgaactcta    1200
catgcaatat tcaaggaaaa taagcgtcca tccaaagaat tgcaaatcac catttcccag    1260
cagctggggt tggagctgag cactgtcagc aacttcttca tgaacgcaag aaggaggagt    1320
ctggacaagt ggcaggacga gggcagctcc aattcaggca actcatcttc ttcatcaagc    1380
acttgtacca aagca                                                      1395
```

<210> SEQ ID NO 78
<211> LENGTH: 891
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
atgatgtctt atcttaagca accgccttac gcagtcaatg ggctgagtct gaccacttcg     60
ggtatggact tgctgcaccc ctccgtgggc tacccggggc cctgggcttc ttgtcccgca    120 gccaccccc ggaaacagcg ccgggagagg acgacgttca ctcgggcgca gctagatgtg    180
ctggaagcac tgtttgccaa gacccggtac ccagacatct tcatgcgaga ggaggtggca    240
ctgaaaatca acttgcccga gtcgagggtg caggtatggt ttaagaatcg aagagctaag    300
tgccgccaac aacagcaaca acagcagaat ggaggtcaaa acaaagtgag acctgccaaa    360
aagaagacat ctccagctcg ggaagtgagt tcagagagtg gaacaagtgg ccaattcact    420
cccccctcta gcacctcagt cccgaccatt gccagcagca gtgctcctgt gtctatctgg    480
agcccagctt ccatctcccc actgtcagat cccttgtcca cctcctcttc ctgcatgcag    540
aggtcctatc ccatgaccta tactcaggct tcaggttata gtcaaggata tgctggctca    600
acttcctact ttgggggcat ggactgtgga tcatatttga cccctatgca tcaccagctt    660
cccggaccag gggccacact cagtcccatg ggtaccaatg cagtcaccag ccatctcaat    720
cagtccccag cttctctttc cacccaggga tatggagctt caagcttggg ttttaactca    780
accactgatt gcttggatta taaggaccaa actgcctcct ggaagcttaa cttcaatgct    840
gactgcttgg attataaaga tcagacatcc tcgtggaaat tccaggtttt g             891
```

<210> SEQ ID NO 79
<211> LENGTH: 1554
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atggcggccc ttcccggcac ggtaccgaga atgatgcggc cggctccggg gcagaactac     60
ccccgcacgg gattcccttt ggaagtgtcc accccgcttg ccaaggccg ggtcaatcag     120 ctgggagggg tcttcatcaa tgggcgaccc ctgcctaacc acatccgcca aagatagtg    180 gagatggccc accatggcat ccggccctgt gtcatctccc gacagctgcg tgtctcccac    240
ggctgcgtct ccaagattct ttgccgctac caggagaccg gtccatccg gcctggggcc    300 atcggcggca gcaagcccag acaggtggcg actccggatg tagagaaaaa gattgaggag    360
```

```
tacaagaggg aaaacccagg catgttcagc tgggagatcc gggacaggct gctgaaggat      420
gggcactgtg accgaagcac tgtgccctca gtgagttcga ttagccgcgt gctcagaatc      480
aagttcggga agaaagagga ggaggatgaa gcggacaaga aggaggacga cggcgaaaag      540
aaggccaaac acagcatcga cggcatcctg ggcgacaaag gaaccggct ggacgagggc       600 tcggatgtgg agtcggaacc tgacctccca ctgaagcgca agcagcgacg cagtcggacc      660
acattcacgg ccgagcagct ggaggagctg gagaaggcct ttgagaggac ccactaccca      720
gacatataca cccgcgagga gctggcgcag aggaccaagc tgacagaggc gcgtgtgcag      780
gtctggttca gtaaccgccg cgcccgttgg cgtaagcagg caggagccaa ccagctggcg      840
gcgttcaacc accttctgcc aggaggcttc ccgcccaccg gcatgccac gctgcccccc       900 taccagctgc cggactccac ctaccccacc accaccatct cccaagatgg ggcagcact       960 gtgcaccggc ctcagcccct gccaccgtcc accatgcacc agggcgggct ggctgcagcg     1020
gctgcagccg ccgacaccag ctctgcctac ggagcccgcc acagcttctc cagctactct     1080
gacagcttca tgaatccggc ggcgcccttcc aaccacatga acccggtcag caacggcctg    1140
tctcctcagg tgatgagcat cttgggcaac cccagtgcgg tgccccgca gccacaggct      1200 gacttctcca tctccccgct gcatggcggc ctggactcgg ccacctccat ctcagccagc     1260
tgcagccagc gggccgactc catcaagcca ggagacagcc tgcccacctc ccaggcctac     1320
tgcccaccca cctacagcac caccggctac agcgtggacc ccgtggccgg ctatcagtac     1380
ggccagtacg gccagagtga gtgcctggtg ccctgggcgt cccccgtccc cattccttct     1440
cccaccccca gggcctcctg cttgtttatg gagagctaca aggtggtgtc agggtgggga     1500
atgtccattt cacagatgga aaaattgaag tccagccaga tggaacagtt cacc          1554
```

<210> SEQ ID NO 80
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atgagttgcc aagcttttac ttcggctgat acctttatac ctctgaattc tgacgcctct       60
gcaactctgc ctctgataat gcatcacagt gctgccgagt gtctaccagt ctccaaccat      120
gccaccaatg tgatgtctac agcaacagga cttcattatt ctgttccttc ctgtcattat      180
ggaaaccagc catcaaccta tggagtgatg gcaggtagtt aaccccttg tctttataaa       240 tttcctgacc acaccttgag tcatggattt cctcctatac accagcctct tctggcagag      300
gaccccacag ctgctgattt caagcaggaa ctcaggcgga aaagtaaatt ggtggaagag      360
ccaatagaca tggattctcc agaaatcaga gaacttgaaa agtttgccaa tgaatttaaa      420
gtgagacgaa ttaaattagg atacacccag acaaatgttg gggaggccct ggcagctgtg      480
catggctctg aattcagtca acaacaatc tgccgatttg aaaatctgca gctcagcttt       540
aaaaatgcat gcaaactgaa agcaatatta tccaaatggc tggaggaagc tgagcaagta      600
ggagctttgt acaatgaaaa agtgggagca atgaaagga aagaaaacg aagaacaact        660 ataagcattg ctgctaaaga tgctctggag agacactttg agaacagaa taaaccttct       720 tctcaagaga tcatgaggat ggctgaagaa ctgaatctgg agaagaagt agtaagagtt       780 tggttttgca accggaggca gagagaaaaa cgggtgaaaa caagtctgaa tcagagttta      840
```

```
ttttctattt ctaaggaaca tcttgagtgc agatcaggcc tcatgggccc agctttcttg    900
tac                                                                  903
```

<210> SEQ ID NO 81
<211> LENGTH: 1080
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atggcgggac acctggcttc agattttgcc ttctcgcccc ctccaggtgg tggaggtgat     60
gggccagggg ggccggagcc gggctgggtt gatcctcgga cctggctaag cttccaaggc    120
cctcctggag ggccaggaat cgggccgggg gttgggccag gctctgaggt gtgggggatt    180
cccccatgcc ccccgccgta tgagttctgt gggggatgg cgtactgtgg ccccaggtt     240 ggagtggggc tagtgcccca aggcggcttg gagacctctc agcctgaggg cgaagcagga    300
gtcggggtgg agagcaactc cgatgggcc tccccggagc cctgcaccgt caccctggt    360 gccgtgaagc tggagaagga gaagctggag caaaacccgg aggagtccca ggacatcaaa    420
gctctgcaga agaactcga gcaatttgcc aagctcctga gcagaagag gatcaccctg    480 ggatatacac aggccgatgt ggggctcacc ctgggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga aagagaaagc gaaccagtat cgagaaccga    720
gtgagaggca acctggagaa tttgttcctg cagtgcccga aacccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gccccatttt    960
ggtaccccag gctatgggag ccctcacttc actgcactgt actcctcggt cccttttccct   1020 gagggggaag cctttcccc tgtctctgtc accactctgg gctctcccat gcattcaaac   1080
```

<210> SEQ ID NO 82
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atggcttcag acagcatatt tgagtcattt ccttcgtacc cacagtgctt catgagagaa     60
tgcatacttg gaatgaatcc ttctagagac gtccacgatg ccagcacgag ccgccgcttc    120
acgccgccct tccaccgcgct gagcccaggc aagatgagcg aggcgttgcc gctgggcgcc    180
ccggacgccg gcgctgccct ggccggcaag ctgaggagcg gcgaccgcag catggtggag    240
gtgctggccg accacccggg cgagctggtg cgcaccgaca gccccaactt cctctgctcc    300
gtgctgccta cgcactggcg ctgcaacaag accctgccca tcgctttcaa ggtggtggcc    360
ctaggggatg ttccagatgg cactctggtc actgtgatgg ctggcaatga tgaaaactac    420
tcggctgagc tgaaaatgc taccgcagcc atgaagaacc aggttgcaag atttaatgac    480
ctcaggtttg tcggtcgaag tggaagaggg aaaagcttca ctctgaccat cactgtcttc    540
```

```
acaaacccac cgcaagtcgc cacctaccac agagccatca aaatcacagt ggatgggccc      600
cgagaacctc gaagacatcg gcagaaacta gatgatcaga ccaagcccgg gagcttgtcc      660 tttccgagc ggctcagtga actggagcag ctgcggcgca cagccatgag ggtcagccca       720
caccacccag cccccacgcc caaccctcgt gcctccctga accactccac tgcctttaac      780
cctcagcctc agagtcagat gcaggataca aggcagatcc aaccatcccc accgtggtcc      840
tacgatcagt cctaccaata cctgggatcc attgcctctc cttctgtgca cccagcaacg      900
cccatttcac ctggacgtgc cagcggcatg acaaccctct gcagaaact tccagtcga        960 ctctcaacgg cacccgacct gacagcgttc agcgacccgc gccagttccc cgcgctgccc     1020
tccatctccg accccgcat gcactatcca ggcgccttca cctactcccc gacgccggtc      1080
acctcgggca tcggcatcgg catgtcggcc atgggctcgg ccacgcgcta ccacacctac     1140
ctgccgccgc cctaccccgg ctcgtcgcaa gcgcagggag gcccgttcca agccagctcg     1200
ccctcctacc acctgtacta cggcgcctcg gccggctcct accagttctc catggtgggc     1260
ggcgagcgct cgccgccgcg catcctgccg ccctgcacca acgcctccac cggctccgcg     1320
ctgctcaacc ccagcctccc gaaccagagc gacgtggtgg aggccgaggg cagccacagc     1380
aactccccca ccaacatggc gccctccgcg cgcctggagg aggccgtgtg gaggccctac     1440

<210> SEQ ID NO 83
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atgtcgatgc tgccgtcgtt tggctttacg caggagcaag tggcgtgcgt gtgcgaggtt       60
ctgcagcaag gcggaaacct ggagcgcctg ggcaggttcc tgtggtcact gccgcctgc      120 gaccacctgc acaagaacga gagcgtactc aaggccaagg cggtggtcgc cttccaccgc     180
ggcaacttcc gtgagctcta caagatcctg gagagccacc agttctcgcc tcacaaccac     240
cccaaactgc agcaactgtg gctgaaggcg cattacgtgg aggccgagaa gctgtgcggc     300
cgacccctgg gcgccgtggg caaatatcgg gtgcgccgaa aatttccact gccgcgcacc     360
atctgggacg gcgaggagac cagctactgc ttcaaggaga agtcgagggg tgtcctgcgg     420
gagtggtacg cgcacaatcc ctacccatcg ccgcgtgaga agcgggagct ggccgaggcc     480
accggcctca ccaccaccca ggtcagcaac tggtttaaga accggaggca agagaccgg      540 gccgcggagg ccaaggaaag ggagaacacc gaaaacaata actcctcctc caacaagcag    600
aaccaactct ctcctctgga aggggcaag ccgctcatgt ccagctcaga agaggaattc      660
tcacctcccc aaagtccaga ccagaactcg gtccttctgc tgcagggcaa tatgggccac    720
gccaggagct caaactattc tctcccgggc ttaacagcct cgcagcccag tcacggcctg    780
cagacccacc agcatcagct ccaagactct ctgctcggcc cctcacctc cagtctggtg     840 gacttggggt cc                                                          852

<210> SEQ ID NO 84
<211> LENGTH: 873
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 84

```
atgtccatgc tgcccaccct cggcttcacg caggagcaag tggcgtgcgt gtgcgaggtg      60
ctgcagcagg gcggcaacat cgagcggctg ggccgcttcc tgtggtcgct gcccgcctgc     120
gagcaccttc acaagaatga aagcgtgctc aaggccaagg ccgtggtggc cttccaccgc     180
ggcaacttcc gcgagctcta caagatcctg gagagccacc agttctcgcc gcacaaccac     240
gccaagctgc agcagctgtg gctcaaggca cactacatcg aggcggagaa gctgcgcggc     300
cgaccctgg gcgccgtggg caaataccgc gtgcgccgca aattcccgct gccgcgctcc      360
atctgggacg gcgaggagac cagctactgc ttcaaggaaa agagtcgcag cgtgctgcgc     420
gagtggtacg cgcacaaccc ctacccttca ccccgcgaga gcgtgagct gacggaggcc      480
acgggcctca ccaccacaca ggtcagcaac tggttcaaga accggcggca gcgcgaccgg     540
gcggccgagg ccaaggaaag ggagaacaac gagaactcca attctaacag ccacaacccg     600
ctgaatggca gcggcaagtc ggtgttaggc agctcggagat gagaagac tccatcgggg      660
acgccagacc actcatcatc cagccccgca ctgctcctca gcccgccgcc cctgggctg      720
ccgtccctgc acagctgggg ccaccctccg ggccccagcg cagtgccagt gccggtgcca     780
ggcggaggtg gagcggaccc actgcaacac accatggcc tgcaggactc catcctcaac      840
cccatgtcag ccaacctcgt ggacctgggc tcc                                   873
```

<210> SEQ ID NO 85
<211> LENGTH: 804
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgccgcgct ccttcctggt caagaagcat ttcaacgcct ccaaaaagcc aaactacagc      60
gaactggaca cacatacagt gattatttcc ccgtatctct atgagagtta ctccatgcct     120
gtcataccac aaccagagat cctcagctca ggagcataca gccccatcac tgtgtggact     180
accgctgctc cattccacgc ccagctaccc aatggcctct ctcctctttc cggatactcc     240
tcatctttgg ggcgagtgag tcccccctcct ccatctgaca cctcctccaa ggaccacagt     300
ggctcagaaa gccccattag tgatgaagag gaaagactac agtccaagct ttcagacccc     360
catgccattg aagctgaaaa gtttcagtgc aatttatgca ataagaccta ttcaactttt     420
tctgggctgg ccaaacataa gcagctgcac tgcgatgccc agtctagaaa atctttcagc     480
tgtaaatact gtgacaagga atatgtgagc ctgggcgccc tgaagatgca tattcggacc     540
cacacattac cttgtgtttg caagatctgc ggcaaggcgt tttcagacc tggttgctt      600
caaggacaca ttagaactca cacggggag aagccttttt cttgccctca ctgcaacaga     660
gcatttgcag acaggtcaaa tctgagggct catctgcaga cccattctga tgtaaagaaa     720
taccagtgca aaaactgctc caaaaccttc tccagaatgt ctctcctgca caaacatgag     780
gaatctggct gctgtgtagc acac                                             804
```

<210> SEQ ID NO 86
<211> LENGTH: 1398
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 86

```
atggcggagg agcaggacct atcggaggtg gagctgagcc ccgtgggctc ggaggagccc      60
cgctgcctgt ccccggggag cgcgccctcg ctagggcccg acggcggcgg cggcggatcg     120
ggcctgcgag ccagcccggg gccaggcgag ctgggcaagg tcaagaagga gcagcaggac     180
ggcgaggcgc acgatgacaa gttccccgtg tgcatccgcg aggccgtcag ccaggtgctc     240
agcggctacg actggacgct ggtgcccatg cccgtgcgcg tcaacggcgc cagcaaaagc     300
aagccgcacg tcaagcggcc catgaacgcc ttcatggtgt gggctcaggc agcgcgcagg     360
aagctcgcgg accagtaccc gcacctgcac aacgctgagc tcagcaagac gctgggcaag     420
ctctggaggc tgctgaacga aagtgacaag cgccccttca tcgaggaggc tgagcggctc     480
cgtatgcagc acaagaaaga ccacccggac tacaagtacc agcccaggcg gcggaagaac     540
gggaaggccg cccagggcga ggcggagtgc cccgtggggg aggccgagca aggtgggacc     600
gccgccatcc aggcccacta caagagcgcc cacttggacc accggcaccc aggagagggc     660
tcccccatgt cagatgggaa ccccgagcac ccctcaggcc agagccatgg cccacccacc     720
cctccaacca ccccgaagac agagctgcag tcgggcaagg cagacccgaa gcgggacggg     780
cgctccatgg gggagggcgg gaagcctcac atcgacttcg gcaacgtgga cattggtgag     840
atcagccacg aggtaatgtc caacatggag acctttgatg tggctgagtt ggaccagtac     900
ctgccgccca tgggcaccc aggccatgtg agcagctact cagcagccgg ctatgggctg     960
ggcagtgccc tggccgtggc cagtggacac tccgcctgga tctccaagcc accaggcgtg    1020
gctctgccca cggtctcacc acctggtgtg gatgccaaag cccaggtgaa gacagagacc    1080
gcggggcccc aggggccccc acactacacc gaccagccat ccacctcaca gatcgcctac    1140
acctccctca gcctgcccca ctatggctca gccttcccct ccatctcccg cccccagttt    1200
gactactctg accatcagcc ctcaggaccc tattatggcc actcgggcca ggcctctggc    1260
ctctactcgg ccttctccta tatgggggcc tcgcagcggc ccctctacac ggccatctct    1320
gaccccagcc cctcagggcc ccagtcccac agccccacac actgggagca gccagtatat    1380
acgacactgt cccggccc                                                  1398
```

<210> SEQ ID NO 87
<211> LENGTH: 951
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87

```
atgtacaaca tgatggagac ggagctgaag ccgccggggcc cgcagcaaac ttcgggggc      60
ggcggcggca actccaccgc ggcggcggcc ggcggcaacc agaaaaacag cccggaccgc     120
gtcaagcggc ccatgaatgc cttcatggtg tggtcccgcg gcagcggcg caagatggcc     180
caggagaacc ccaagatgca caactcggag atcagcaagc gctgggcgc cgagtggaaa     240
cttttgtcgg agacggagaa gcggccgttc atcgacgagg ctaagcggct gcgagcgctg     300
cacatgaagg agcacccgga ttataaatac cggccccggc ggaaaaccaa gacgctcatg     360
aagaaggata agtacacgct gcccggcggg ctgctggccc ccggcggcaa tagcatggcg     420
agcggggtcg gggtgggcgc cggcctgggc gcgggcgtga accagcgcat ggacagttac     480
```

```
gcgcacatga acggctggag caacggcagc tacagcatga tgcaggacca gctgggctac      540
ccgcagcacc cgggcctcaa tgcgcacggc gcagcgcaga tgcagcccat gcaccgctac      600
gacgtgagcg ccctgcagta caactccatg accagctcgc agacctacat gaacggctcg      660
cccacctaca gcatgtccta ctcgcagcag ggcacccctg gcatggctct tggctccatg      720
ggttcggtgg tcaagtccga ggccagctcc agccccctg tggttacctc ttcctcccac        780
tccagggcgc cctgccaggc cggggacctc cgggacatga tcagcatgta tctccccggc      840
gccgaggtgc cggaacccgc cgcccccagc agacttcaca tgtcccagca ctaccagagc      900
ggcccggtgc ccggcacggc cattaacggc acactgcccc tctcacacat g               951
```

<210> SEQ ID NO 88
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
atgcgacctg ttcgagagaa ctcatcaggt gcgagaagcc cgcgggttcc tgctgatttg      60
gcgcggagca ttttgataag cctacccttc ccgccggact cgctggccca caggccccca      120
agctccgctc cgacggagtc ccagggcctt ttcaccgtgg ccgctccagc cccgggagcg      180
ccttctcctc ccgccacgct ggcgcacctt cttcccgccc cggcaatgta cagccttctg      240
gagactgaac tcaagaaccc cgtagggaca cccacacaag cggcgggcac cggcggcccc      300
gcagccccgg gaggcgcagg caagagtagt gcgaacgcag ccggcggcgc gaactcgggc      360
ggcggcagca gcgtggtgc gagcggaggt ggcggggta cagaccagga ccgtgtgaaa        420
cggcccatga acgccttcat ggtatggtcc cgcgggcagc ggcgcaaaat ggccctggag      480
aaccccaaga tgcacaattc tgagatcagc aagcgcttgg gcgccgactg gaaactgctg      540
accgacgccg agaagcgacc attcatcgac gaggccaagc gacttcgcgc cgtgcacatg      600
aaggagtatc cggactacaa gtaccgaccg cgccgcaaga ccaagacgct gctcaagaaa      660
gataagtact ccctgcccag cggcctcctg cctccggtg ccgcggccgc cgccgccgct       720
gccgcggccg cagccgctgc cgccagcagt ccggtgggcg tgggccagcg cctggacacg      780
tacacgcacg tgaacggctg ggccaacggc gcgtactcgc tggtgcagga gcagctgggc      840
tacgcgcagc ccccgagcat gagcagcccc ccgccgccgc ccgcgctgcc gccgatgcac      900
cgctacgaca tggccggcct gcagtacagc ccaatgatgc cgcccggcgc tcagagctac      960
atgaacgtcg ctgccgcggc cgccgccgcc tcgggctacg ggggcatggc gccctcagcc      1020
acagcagccg cggccgccgc ctacgggcag cagcccgcca ccgccgcggc cgcagctgcg      1080
gccgcagccg ccatgagcct gggccccatg ggctcggtag tgaagtctga gcccagctcg      1140
ccgccgcccg ccatcgcatc gcactctcag cgcgcgtgcc tcggcgacct gcgcgacatg      1200
atcagcatgt acctgccacc cggcggggac gcggccgacg ccgcctctcc gctgcccggc      1260
ggtcgcctgc acggcgtgca ccagcactac cagggcgccg ggactgcagt caacggaacg      1320
gtgccgctga cccacatc                                                    1338
```

<210> SEQ ID NO 89
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| | | | | | |
|---|---|---|---|---|---|
| atgttacagg | cgtgcaaaat | ggaagggttt | cccctcgtcc | cccctcagcc | atcagaagac | 60 |
| ctggtgccct | atgacacgga | tctataccaa | cgccaaacgc | acgagtatta | ccctatctc | 120 |
| agcagtgatg | gggagagcca | tagcgaccat | tactgggact | ccaccccca | ccacgtgcac | 180 |
| agcgagttcg | agagcttcgc | cgagaacaac | ttcacggagc | tccagagcgt | gcagccccg | 240 |
| cagctgcagc | agctctaccg | ccacatggag | ctggagcaga | tgcacgtcct | cgatacccc | 300 |
| atggtgccac | cccatcccag | tcttggccac | caggtctcct | acctgccccg | gatgtgcctc | 360 |
| cagtacccat | ccctgtcccc | agcccagccc | agctcagatg | aggaggaggg | cgagcggcag | 420 |
| agccccccac | tggaggtgtc | tgacggcgag | gcggatggcc | tggagcccgg | gcctgggctc | 480 |
| ctgcctgggg | agacaggcag | caagaagaag | atccgcctgt | accagttcct | gttggacctg | 540 |
| ctccgcagcg | gcgacatgaa | ggacagcatc | tggtgggtgg | acaaggacaa | gggccacttc | 600 |
| cagttctcgt | ccaagcacaa | ggaggcgctg | gcgcaccgct | ggggcatcca | gaagggcaac | 660 |
| cgcaagaaga | tgacctacca | gaagatggcg | cgcgcgctgc | gcaactacgg | caagacgggc | 720 |
| gaggtcaaga | aggtgaagaa | gaagctcacc | taccagttca | gcggcgaagt | gctgggccgc | 780 |
| ggggggcctgg | ccgagcggcg | ccacccgccc | cac | | | 813 |

<210> SEQ ID NO 90
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

| | | | | | |
|---|---|---|---|---|---|
| atgctcgccc | tggaggctgc | acagctcgac | gggccacact | tcagctgtct | gtacccagat | 60 |
| ggcgtcttct | atgacctgga | cagctgcaag | cattccagct | accctgattc | agaggggggct | 120 |
| cctgactccc | tgtgggactg | gactgtggcc | ccacctgtcc | cagccacccc | ctatgaagcc | 180 |
| ttcgacccgg | cagcagccgc | ttttagccac | ccccaggctg | cccagctctg | ctacgaaccc | 240 |
| cccacctaca | gccctgcagg | gaacctcgaa | ctggccccca | gctggaggc | cccggggcct | 300 |
| ggcctccccg | cataccccac | ggagaacttc | gctagccaga | ccctggttcc | cccggcatat | 360 |
| gccccgtacc | ccagccctgt | gctatcagag | gaggaagact | taccgttgga | cagccctgcc | 420 |
| ctggaggtct | cggacagcga | gtcggatgag | gccctcgtgg | ctggccccga | ggggaaggga | 480 |
| tccgaggcag | ggactcgcaa | gaagctgcgc | ctgtaccagt | tcctgctggg | gctactgacg | 540 |
| cgcggggaca | tgcgtgagtg | cgtgtggtgg | gtggagccag | gcgccggcgt | cttccagttc | 600 |
| tcctccaagc | acaaggaact | cctggcgcgc | gctggggcc | agcagaaggg | gaaccgcaag | 660 |
| cgcatgacct | accagaagct | ggcgcgcgcc | ctccgaaact | acgccaagac | cggcgagatc | 720 |
| cgcaaggtca | agcgcaagct | cacctaccag | ttcgacagcg | cgctgctgcc | tgcagtccgc | 780 |
| cgggccttg | | | | | | 789 |

<210> SEQ ID NO 91
<211> LENGTH: 744
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 91

| | | | | |
|---|---|---|---|---|
| atgacgtgtg | ttgaacaaga | caagctgggt | caagcatttg | aagatgcttt tgaggttctg | 60 |
| aggcaacatt | caactggaga | tcttcagtac | tcgccagatt | acagaaatta cctggcttta | 120 |
| atcaaccatc | gtcctcatgt | caaaggaaat | tccagctgct | atggagtgtt gcctacagag | 180 |
| gagcctgtct | ataattggag | aacggtaatt | aacagtgctg | cggacttcta ttttgaagga | 240 |
| aatattcatc | aatctctgca | gaacataact | gaaaaccagc | tggtacaacc cactcttctc | 300 |
| cagcaaaagg | ggggaaaagg | caggaagaag | ctccgactgt | ttgaatacct tcacgaatcc | 360 |
| ctgtataatc | cggagatggc | atcttgtatt | cagtgggtag | ataaaaccaa aggcatcttt | 420 |
| cagtttgtat | caaaaaacaa | agaaaaactt | gccgagcttt | ggggggaaaag aaaaggcaac | 480 |
| aggaagacca | tgacttacca | gaaaatggcc | agggcactca | gaaattacgg aagaagtggg | 540 |
| gaaattacca | aaatccggag | gaagctgact | taccagttca | gtgaggccat tctccaaaga | 600 |
| ctctctccat | cctatttcct | ggggaaagag | atcttctatt | cacagtgtgt tcaacctgat | 660 |
| caagaatatc | tcagtttaaa | taactggaat | gcaaattata | attatacata tgccaattac | 720 |
| catgagctaa | atcaccatga | ttgc | | | 744 |

<210> SEQ ID NO 92
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| | | | | |
|---|---|---|---|---|
| atgcaatcat | atgcttctgc | tatgttaagc | gtattcaaca | gcgatgatta cagtccagct | 60 |
| gtgcaagaga | atattcccgc | tctccggaga | agctcttcct | tcctttgcac tgaaagctgt | 120 |
| aactctaagt | atcagtgtga | acgggagaa | acagtaaag | gcaacgtcca ggatagagtg | 180 |
| aagcgaccca | tgaacgcatt | catcgtgtgg | tctcgcgatc | agaggcgcaa gatggctcta | 240 |
| gagaatccca | gaatgcgaaa | ctcagagatc | agcaagcagc | tgggatacca gtggaaaatg | 300 |
| cttactgaag | ccgaaaaatg | gccattcttc | caggaggcac | agaaattaca ggccatgcac | 360 |
| agagagaaat | acccgaatta | taagtatcga | cctcgtcgga | aggcgaagat gctgccgaag | 420 |
| aattgcagtt | tgcttcccgc | agatcccgct | tcggtactct | gcagcgaagt gcaactggac | 480 |
| aacaggttgt | acagggatga | ctgtacgaaa | gccacacact | caagaatgga gcaccagcta | 540 |
| ggccacttac | cgcccatcaa | cgcagccagc | tcaccgcagc | aacgggaccg ctacagccac | 600 |
| tggacaaagc | tg | | | | 612 |

<210> SEQ ID NO 93
<211> LENGTH: 1557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

| | | | | |
|---|---|---|---|---|
| atggccgacg | cagacgaggg | cttttggcctg | gcgcacacgc | tctggagcc tgacgcaaaa | 60 |
| gacctgccct | gcgattcgaa | acccgagagc | gcgctcgggg | cccccagcaa gtccccgtcg | 120 |

| | |
|---|---|
| tccccgcagg ccgccttcac ccagcagggc atggagggaa tcaaagtgtt tctccatgaa | 180 |
| agagaactgt ggctaaaatt ccacgaagtg ggcacggaaa tgatcataac caaggctgga | 240 |
| aggcggatgt ttcccagtta caaagtgaag gtgacgggcc ttaatcccaa aacgaagtac | 300 |
| attcttctca tggacattgt acctgccgac gatcacagat acaaattcgc agataataaa | 360 |
| tggtctgtga cgggcaaagc tgagcccgcc atgcctggcc gcctgtacgt gcacccagac | 420 |
| tcccccgcca ccggggcgca ttggatgagg cagctcgtct ccttccagaa actcaagctc | 480 |
| accaacaacc acctggaccc atttgggcat attattctaa attccatgca caaataccag | 540 |
| cctagattac acatcgtgaa agcggatgaa aataatggat ttggctcaaa aaatacagcg | 600 |
| ttctgcactc acgtctttcc tgagactgcg tttatagcag tgacttccta ccagaaccac | 660 |
| aagatcacgc aattaaagat tgagaataat ccctttgcca aaggatttcg ggcagtgat | 720 |
| gacatggagc tgcacagaat gtcaagaatg caaagtaaag aatatcccgt ggtccccagg | 780 |
| agcaccgtga ggcaaaaagt ggcctccaac cacagtcctt tcagcagcga gtctcgagct | 840 |
| ctctccacct catccaattt ggggtcccaa taccagtgtg agaatggtgt ttccggcccc | 900 |
| tcccaggacc tcctgcctcc acccaaccca tacccactgc cccaggagca tagccaaatt | 960 |
| taccattgta ccaagaggaa agaggaagaa tgttccacca cagaccatcc ctataagaag | 1020 |
| ccctacatgg agacatcacc cagtgaagaa gattccttct accgctctag ctatccacag | 1080 |
| cagcagggcc tgggtgcctc ctacaggaca gagtcggcac agcggcaagc ttgcatgtat | 1140 |
| gccagctctg cgccccccag cgagcctgtg cccagcctag aggacatcag ctgcaacacg | 1200 |
| tggccaagca tgccttccta cagcagctgc accgtcacca ccgtgcagcc catggacagg | 1260 |
| ctaccctacc agcacttctc cgctcacttc acctcggggc ccctggtccc tcggctggct | 1320 |
| ggcatggcca accatggctc cccacagctg ggagagggaa tgttccagca ccagacctcc | 1380 |
| gtggcccacc agcctgtggt caggcagtgt gggcctcaga ctggcctgca gtcccctggc | 1440 |
| acccttcagc cccctgagtt cctctactct catggcgtgc caaggactct atcccctcat | 1500 |
| cagtaccact ctgtgcacgg agttggcatg gtgccagagt ggagcgacaa tagcttg | 1557 |

<210> SEQ ID NO 94
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

| | |
|---|---|
| atgttgtgga aaataaccga taatgtcaag tacgaagagg actgcgagga tcgccacgac | 60 |
| gggagcagca atgggaatcc gcgggtcccc cacctctcct ccgccgggca gcacctctac | 120 |
| agccccgcgc caccctctc ccacactgga gtcgccgaat atcagccgcc accctacttt | 180 |
| cccccctccct accagcagct ggcctactcc cagtcggccg accctactc gcatctgggg | 240 |
| gaagcgtacg ccgccgccat caaccccctg caccagccgg cgcccacagg cagccagcag | 300 |
| caggcctggc ccggccgcca gagccaggag ggagcggggc tgccctcgca ccacggcgc | 360 |
| ccggccggcc tactgcccca cctctccggg ctggaggcgg cgcggtgag cgcccgcagg | 420 |
| gatgcctacc gccgctccga cctgctgctg cccacgcac acgccctgga tgccgcgggc | 480 |
| ctggccgaga acctggggct ccacgacatg cctcaccaga tggacgaggt gcagaatgtc | 540 |
| gacgaccagc acctgttgct gcacgatcag acagtcattc gcaaaggtcc catttccatg | 600 |

```
accaagaacc ctctgaacct ccctgtcag aaggagctgg tgggggccgt aatgaacccc    660
actgaggtct tctgctcagt ccctggaaga ttgtcgctcc tcagctctac gtctaaatac    720
aaagtgacag tggctgaagt acagaggcga ctgtccccac ctgaatgctt aaatgcctcg    780
ttactgggag gtgttctcag aagagccaaa tcgaaaaatg gaggccggtc cttgcgggag    840
aagttggaca agattgggtt gaatcttccg gccgggaggc ggaaagccgc tcatgtgact    900
ctcctgacat ccttagtaga aggtgaagct gttcatttgg ctagggactt tgcctatgtc    960
tgtgaagccg aatttcctag taaccagtg gcagaatatt taaccagacc tcatcttgga   1020
ggacgaaatg agatggcagc taggaagaac atgctattgg cggcccagca actgtgtaaa   1080
gaattcacag aacttctcag ccaagaccgg acacccatg ggaccagcag gctcgcccca   1140
gtcttggaga cgaacataca gaactgcttg tctcatttca gcctgattac ccacgggttt   1200
ggcagccagg ccatctgtgc cgcggtgtct gccctgcaga actacatcaa agaagccctg   1260
attgtcatag acaaatccta catgaaccct ggagaccaga gtccagctga ttctaacaaa   1320
accctggaga aaatggagaa acacaggaaa                                    1350
```

<210> SEQ ID NO 95
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
agaccacgcc tctgtcatgt accaaatc                                        28

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ggtcagcagc atcgtggtca acataac                                         27

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tctccgtggt cctgaagcag acata                                           25

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agccatgtgg tctctctggt tgtgtatg                                        28

```
<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tttgtgggcc tgaagaaaac t                                              21

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cttgaatccc gaatggaaag gg                                             22

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tacagcatgt cctactcgca g                                              21

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gagtccattg ctgttggaac cg                                             22

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cagcggaaac cccaacagtt a                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gacctccaca gagaagtcga g                                              21

<210> SEQ ID NO 105
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
agtccactga gtaccggaga c                                              21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cgagagctac acgttcacgg                                                20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
agccaacctt aactgaggag t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgatcctgac tgcgatgaga g                                              21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggcaacgtgg cctttctac                                                 20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gaagtttcgc agacctgaca t                                              21

<210> SEQ ID NO 111
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
atcgctctcc tgctaacagt c                                           21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctgagacccg agcagagttt g                                           21

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cacgatctca tacctggcct gcttc                                       25

<210> SEQ ID NO 114
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tggagcagga caggttcagt ctttca                                      26

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aggttgctgc tggtgaggtc att                                         23

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtttgagtgg tgccgtactg gtagga                                      26

<210> SEQ ID NO 117
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 117
agggctgtcc tgaataagca g                                           21

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gtgtatatcc cagggtgatc ctc                                         23

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gaggaagagg taaccacagg g                                           21

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
atgtccctct tgtcgccaac ct                                          22

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gagggtcagt agaacatgcg t                                           21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122 tgccttttc ttagggcaga g                                            21

<210> SEQ ID NO 123
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 123
catttcacgc atctggcgtt c                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gggtgtcgag ggaaaaatag g                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ggcaagttga ttggagggat g                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cttgtctgtt cttctgaccc c                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
agtggcagtt acccattcct g                                              21

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gtatgcacca ttcaactcct cg                                             22

<210> SEQ ID NO 129
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 129
ctcgtactgg atgggtgaac t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tgaatctcga cgttctcctc c                                              21
```

METHODS FOR SCREENING GENETIC PERTURBATIONS

CROSS-REFERENCE TO RELATED APPLICATION

This application claims priority to 35 U.S.C. § 119(e) of U.S. Provisional Application Ser. No. 62/904,614, filed Sep. 23, 2019, the content of which is hereby incorporated by reference its entirety.

This invention was made with government support under HG009285 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 14, 2020, is named 114198-0152_SL.txt and is 155,507 bytes in size.

BACKGROUND

Cellular reprogramming by the overexpression of transcription factors (TF), has widely impacted biological research, from the direct conversion of adult somatic cells to the induction of pluripotent stem cells, and the differentiation of hPSCs. To date, the choice of TFs that drive such reprogramming has been through a combination of the knowledge of their role in development and cellular transformation, and systematic trial-and-error. These challenges highlight the need for the development of a scalable screening method to assess the effects of TF overexpression. Such a screening method would have broad applicability in advancing a fundamental understanding of reprogramming, and as a means for the discovery of novel reprogramming factors. This disclosure addresses this need and provides related advantages as well.

SUMMARY

Described herein is a comprehensive high-throughput platform to determine an optimal method to drive the differentiation of pluripotent cells to specific somatic lineages. In some aspects, the platform utilizes a novel open reading frame (ORF) gene overexpression vector library of developmentally critical transcription factors. The platform builds genetic co-perturbation networks to identified key altered gene modules and identifies key reprogramming/differentiation drivers from transcriptomic responses. The platform enabled identification of the key role of (previously not recognized) transcription factor ETV2 in reprogramming towards an endothelial state.

Thus, in one aspect, provided herein are isolated nucleic acids comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF. In some embodiments, the TF ORF encodes a developmentally critical TF.

In another aspect, provided herein is a TF screening library comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF. In some embodiments, the TF ORF encodes a developmentally critical TF, optionally selected from the TFs listed in Table 1.

In some embodiments, the TF screening library comprises, consists of, or consists essentially of at least 10, at least 20, at least 30, at least 40, at least 50, at least 60, at least 70, at least 80, at least 90, or at least 100 nucleic acids or vectors, wherein each nucleic acid or vector comprises, consists of, or consists essentially of a distinct nucleic acid encoding a TF ORF.

In some embodiments, the TF screening library further comprises, consists of, or consists essentially of a nucleic acid encoding a selectable marker. In some embodiments, the TF screening library further comprises, consists of, or consists essentially of a nucleic acid encoding an expression control element. In some embodiments, the expression control element is a promoter or a long terminal repeat (LTR). In some embodiments, the TF screening library further comprises, consists of, or consists essentially of a nucleic acid encoding a translation elongation factor, optionally wherein the translation elongation factor is Ef1a.

In some embodiments, the vector is a retroviral vector, optionally a lentiviral vector.

In another aspect, provided herein is a viral packaging system comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF; or a TF screening library; and a packaging plasmid.

In another aspect, provided herein is a method for producing a viral particle, the method comprising, consisting of, or consisting essentially of transfecting a packaging cell line with a viral packaging system comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF; or a TF screening library; and a packaging plasmid under conditions suitable to package the vector or the TF screening library into a viral particle. In another aspect, also provided herein is a viral particle produced by this method, and optionally a carrier. In another aspect, also provided herein is an isolated cell comprising a nucleic acid, vector, or particle as described herein, and optionally a carrier.

In another aspect, provided herein is a kit comprising, consisting of, or consisting essentially of at least one of (a) a nucleic acid or vector according to any of the embodiments described herein; and/or (b) a TF screening library according to any of the embodiments described herein; and/or (c) a viral packaging system according to any of the embodiments described herein; and/or (d) a viral particle according to any of the embodiments described herein; and/or (e) an isolated cell according to any of the embodiments described herein, and optionally instructions for use.

In another aspect, provided herein is a method of performing a high throughput gene activation screen, the method comprising, consisting of, or consisting essentially of: (a) transducing a target cell with the viral particle according to any of the embodiments described herein; and (b) performing scRNA-seq on the transduced target cell to identify the nucleic acid barcode. In some embodiments, the method further comprises or consists of determining a fitness effect in the transduced target cell. In some embodiments, the method further comprises or consists of identifying a co-perturbation network. In some embodiments, the method further comprises or consists of identifying a functional gene module. In some embodiments, the target cell is a stem cell. In some embodiments, the stem cell is an embryonic stem cell (ESC) or an induced pluripotent stem cell (iPSC). In some embodiments, the target cell is a mammalian cell, optionally wherein the mammalian cell is an equine, bovine, canine, murine, porcine, feline, or human cell. In a particular embodiment, the target cell is a human cell.

In other aspects, also provided herein is a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell. In some embodiments, ectopic expression of ETV2 is induced by transducing the stem cell with a vector comprising a nucleic acid encoding ETV2 and a nucleic acid encoding an expression control element. In some embodiments, the stem cell is an ESC or an iPSC. In some embodiments, the stem cell is a mammalian cell, optionally wherein the mammalian cell is an equine, bovine, canine, murine, porcine, feline, or human cell. In some embodiments, the stem cell is a human cell. In some embodiments, the stem cell has been genetically modified. In some embodiments, the method further comprises or consists of genetically modifying the stem cell or the endothelial cell.

In further aspect, also provided herein is an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, and optionally a carrier. In some embodiments, the endothelial cell expresses at least one of CDH5, PECAM1, or VWF.

In another aspect, also provided herein is a population of endothelial cells produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, and optionally a carrier.

In some aspects, provided herein is a composition comprising, consisting of, or consisting essentially of an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, or a population of endothelial cells produced according to a method described herein, and one or more of: a pharmaceutically acceptable carrier, a cryopreservative or a preservative. In some embodiments, the carrier is a pharmaceutically acceptable carrier. In some embodiments, the cryopreservative is suitable for long term storage of the composition at a temperature ranging from $-200°$ C. to $0°$ C., from $-80°$ C. to $0°$ C., from $-20°$ C. to $0°$ C., or from $0°$ C. to $10°$ C.

In some aspects, provided herein is a method of treating a subject in need thereof, the method comprising, consisting of, or consisting essentially of administering an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, or a population of endothelial cells produced according to a method described herein, or a composition comprising, consisting of, or consisting essentially of the endothelial cell or population and a carrier to the subject. In some embodiments of the method, an effective amount of the endothelial cell, population, or composition is administered to the subject. In some embodiments, the endothelial cell or population is allogenic or autologous to the subject being treated.

In some embodiments of the method, the subject has a wound, a corneal disease or condition, a myocardial infarction, or a vascular disease or condition. In some embodiments, the subject has a corneal disease or condition. In some embodiments, the administration is local or systemic. In some embodiments, the endothelial cell, population, or composition is administered to the subject's eye.

In some embodiments of the method, the subject is a mammal and the mammal is an equine, bovine, canine, murine, porcine, feline, or human. In some embodiments, the mammal is a human. In some embodiments, the endothelial cells are autologous or allogeneic to the subject being treated.

BRIEF DESCRIPTION OF THE FIGURES

(FIG. 1A) Schematic of experimental and analytical framework for evaluation of effects of transcription factor (TF) overexpression in hPSCs: Individual TFs are cloned into the barcoded ORF overexpression vector, pooled and packaged into lentiviral libraries for transduction of hPSCs. Transduced cells are harvested at a fixed time point to be assayed as single cells using droplet based scRNA-seq to evaluate transcriptomic changes. Cells are genotyped by amplifying the overexpression transcript from scRNA-seq cDNA prior to fragmentation and library construction, and identifying the overexpressed TF barcode for each cell. The cell count for each genotype is used to estimate fitness. Gene expression matrices from scRNA-seq are used to obtain differential gene expression and clustering signatures which in turn are used for evaluation of cell state reprogramming and gene regulatory network analysis. (FIG. 1B) Fitness effect of TFs: log fold change of individual TFs, calculated as cell counts normalized against plasmid library read counts. (FIG. 1C) t-SNE projection (left panel), and cluster enrichment of significant TFs in clusters (right panel) from screens in pluripotent stem cell medium. (FIG. 1D) t-SNE projection (left panel), and cluster enrichment of significant TFs in clusters (right panel) from screens in unilineage (endothelial) growth medium. (FIG. 1E) t-SNE projection (left panel), and enrichment of significant TFs in clusters (right panel) from screens in multilineage differentiation medium. (FIG. 1F) Number of differentially expressed genes for TFs across different growth media. The TFs in (FIG. 1C), (FIG. 1D), (FIG. 1E) and (FIG. 1F) were chosen as significant with the following criteria: cluster enrichment with a false discovery rate (FDR) of less than $10^{-6}$ and a cluster enrichment profile different from control (mCherry) with a FDR less than $10^{-6}$, or if the TF drove differential expression of more than 100 genes.

FIGS. 2A-2G: Effect of TF overexpression on gene-to-gene co-perturbation network (FIG. 2A) Schematic for gene-gene co-perturbation network analysis: A SNN network is built from the linear model coefficients and the network is then segmented into gene modules. Genes have a highly weighted edge between them if they respond similarly to TF overexpression. (FIG. 2B) Gene module network: Node size indicates the number of genes in the module; Edge size indicates distance between modules. (FIG. 2C) Effect of TF overexpression on gene modules: (FIG. 2D) Schematic of functional domains of c-MYC: MYC Box I (MBI) and MYC Box II (II) which are essential for transactivation of target genes are housed in the amino-terminal domain (NTD); the basic (b) helix-loop-helix (HLH) leucine zipper (LZ) motif, which is required for heterodimerization with the MAX protein is housed in the carboxy-terminal domain (CTD); the nuclear localization signal domain (NLS) is located in the central region of the protein. (FIG. 2E) Effect of MYC mutant overexpression on gene modules. (FIG. 2F) Schematic of KLF gene family protein structure grouped by common structural and functional features (FIG. 2G) Effect of KLF family overexpression on gene modules. For heatmaps in (FIG. 2C), (FIG. 2E), (FIG. 2F), effect size was calculated as the average of the linear model coefficients for a given TF perturbation across all genes within a module.

FIGS. 3A-3H: Elucidating effects of KLF4, SNAI2 and ETV2 (FIG. 3A) Effect of KLF4 and SNAI2 on a subnetwork of the pluripotent state module, encompassing key pluripotency regulators. Node size indicates the effect size; blue nodes are downregulated, red nodes are upregulated. (FIG. 3B) PC plot of performing PCA on 200 genes from the Hallmark Epithelial Mesenchymal Transition geneset from MSigDB[42]. PC1 corresponds to an EMT-like signature. (FIG. 3C) Effect of KLF4 and SNAI2 on selected epithelial and mesenchymal markers, including key Cadherin genes. (FIG. 3D) Correlation between fitness estimate from scRNA-seq genotype counts and bulk fitness estimate from gDNA in hPSC medium. (FIG. 3E) Morphology change for cells transduced with either ETV2 or mCherry in EGM. (FIG. 3F) Immunofluorescence micrograph of CDH5 labelled day 6 ETV2- or mCherry-transduced cells. (FIG. 3G) qRT-PCR analysis of signature endothelial genes CDH5, PECAM1, VWF and KDR, at day 6 post-transduction. Data were normalized to GAPDH and expressed relative to control cells in pluripotent stem cell medium. (FIG. 3H) Tube formation assay for day 6 ETV2- or mCherry-transduced cells

FIGS. 5A-5C: Fitness analysis from genomic DNA and correlation with fitness from scRNA-seq genotyped cell counts (FIG. 5A) Log fold-change of TF read counts amplified from genomic DNA vs plasmid library control (FIG. 5B) Log fold change of TF counts vs plasmid library control for genomic DNA reads vs cell counts fitness for: (FIG. 5B) Unilineage medium (endothelial growth medium) (FIG. 5C) Multilineage medium.

FIGS. 6A-6D: Differential gene expression analysis of significant TFs (FIG. 6A) Heatmap of differentially expressed genes for significant TFs in hPSC medium. (FIG. 6B) Heatmap of differentially expressed genes for significant TFs in endothelial growth medium. (FIG. 6C) Heatmap of differentially expressed genes for significant TFs in multilineage medium (FIG. 6D) Heatmap showing signed log p-values of enrichment for differentially expressed homologous genes in mESCs upon overexpression of TFs[25]. ASCL1, CDX2, KLF4, MYOD1, and OTX2 display a high degree of overlap with overexpression of their homologs in mESCs.

(FIGS. 7A-7E) Correlation between significant hits in the combined hPSC dataset with hits in each individual dataset. (FIG. 7F) Correlation of hits between the two multilineage datasets.

(FIG. 8A) Correlation of the number of differentially expressed genes for each TF vs the fitness effect (log-FC) for hPSC medium (FIG. 8B) Correlation of the number of differentially expressed genes for each TF vs the fitness effect (log-FC) for endothelial medium (FIG. 8C) Correlation of the number of differentially expressed genes for each TF vs the fitness effect (log-FC) for multilineage medium.

(FIG. 9B) qRT-PCR analysis of signature cadherins during EMT: CDH1 and CDH2 at day 5 post-transduction in pluripotent stem cell medium. (FIG. 9C) qRT-PCR analysis of signature epithelial marker genes during EMT: EPCAM, LAMC1 and SPP1 at day 5 post-transduction in pluripotent stem cell medium. (FIG. 9D) qRT-PCR analysis of signature mesenchymal marker genes during EMT: TPM2, THY1 and VIM at day 5 post-transduction in pluripotent stem cell medium. Data for all assays were normalized to GAPDH and expressed relative to control cells.

(FIG. 10A) Correlation of KLF4 effects in the KLF family screen with KLF4 effects in the hPSC screen. (FIG. 10B) Correlation of MYC effects in the MYC mutants screen with KLF4 effects in the hPSC screen.

DETAILED DESCRIPTION

Figure 1A:
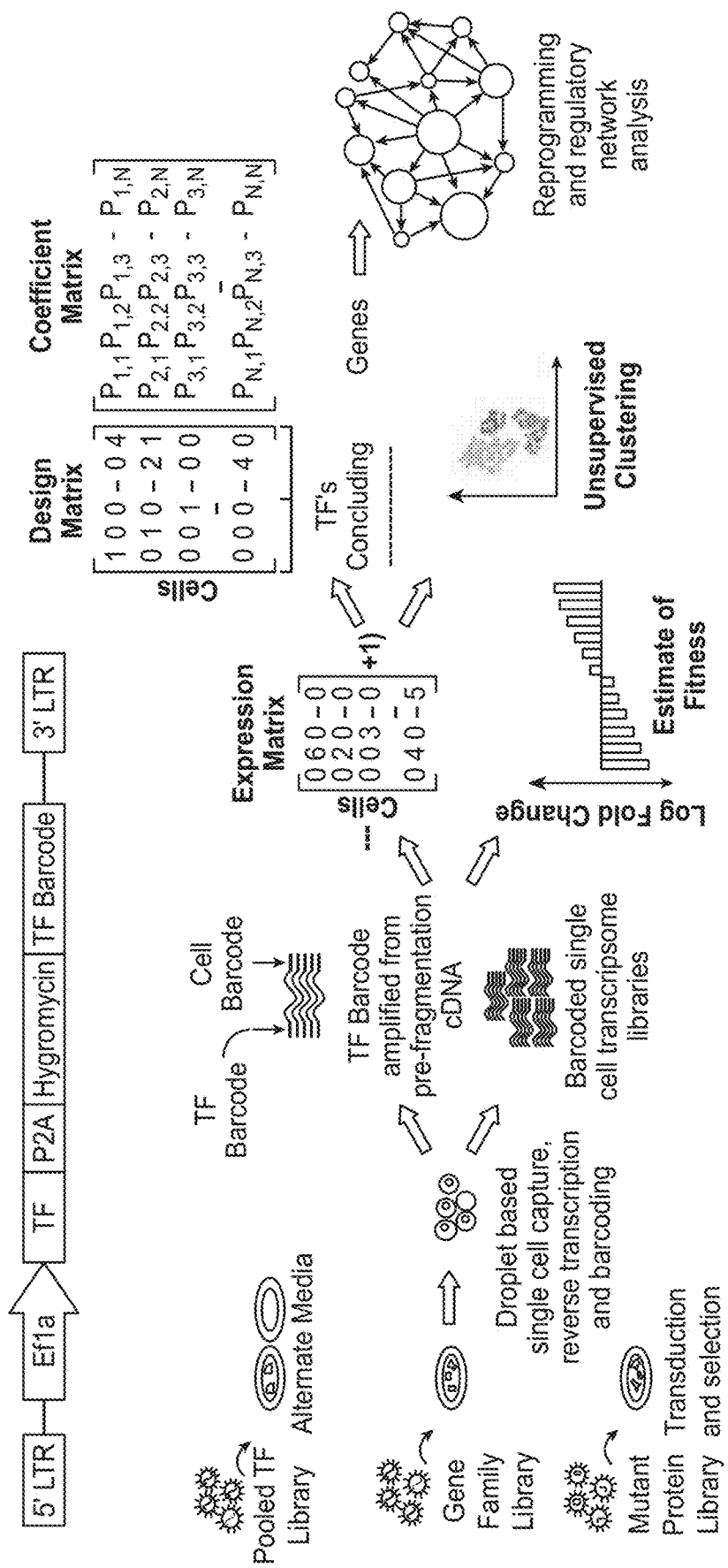
FIGS. 1A-1F: SEUSS workflow and identification of significant TFs from fitness and scRNA-seq analysis.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach;

Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)); Sohail (ed.) (2004) Gene Silencing by RNA Interference: Technology and Application (CRC Press).

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transition terms are within the scope of this disclosure.

As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus.

A "viral vector" is defined as a recombinantly produced virus or viral particle that comprises a nucleic acid to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

Lentiviral vectors of this disclosure include vectors based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to this disclosure may be based on a genetically or otherwise (e.g. by specific choice of packaging cell system) altered version of a particular retrovirus.

That the vector particle according to the disclosure is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

The term "an expression control element" as used herein, intends a polynucleotide that is operatively linked to a target polynucleotide to be transcribed, and facilitates the expression of the target polynucleotide. A promoter is an example of an expression control element.

The term "promoter" refers to a nucleic acid sequence (e.g., a region of genomic DNA) that initiates transcription of a particular gene. The promoter includes the core promoter, which is the minimal portion of the promoter required to properly initiate transcription and can also include regulatory elements such as transcription factor binding sites. The regulatory elements may promote transcription or inhibit transcription. Regulatory elements in the promoter can be binding sites for transcriptional activators or transcriptional repressors. A promoter can be constitutive or inducible. A constitutive promoter refers to one that is always active and/or constantly directs transcription of a gene above a basal level of transcription. An inducible promoter is one which is capable of being induced by a molecule or a factor added to the cell or expressed in the cell. An inducible promoter may still produce a basal level of transcription in the absence of induction, but induction typically leads to significantly more production of the protein. Non-tissue specific promoters include but are not limited to human cytomegalovirus (CMV), CMV enhancer/chicken β-actin (CBA) promoter, Rous sarcoma virus (RSV), simian virus 40 (SV40) and mammalian elongation factor 1α (EF1α), are non-specific promoters and are commonly used in gene therapy vectors. Promoters can also be tissue specific. A tissue specific promoter allows for the production of a protein in a certain population of cells that have the appropriate transcriptional factors to activate the promoter.

A "target cell" as used herein, shall intend a cell containing the genome into which polynucleotides that are operatively linked to an expression control element are to be integrated. Cells that are infected with a lentivirus or susceptible to lentiviral infection are non-limiting examples of target cells.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "polynucleotide," "nucleic acid," and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells or tissues that are isolated from other cells or tissues and is meant to encompass both cultured and engineered cells or tissues.

As used herein, "stem cell" defines a cell with the ability to divide for indefinite periods in culture and give rise to specialized cells. At this time and for convenience, stem cells are categorized as somatic (adult), embryonic or induced pluripotent stem cells. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4.

The term "culturing" refers to the in vitro propagation of cells or organisms on or in synthetic culture conditions such as culture media of various kinds. In some aspects, the medium is changed daily. It is understood that the descendants of a cell grown in culture may not be completely identical (i.e., morphologically, genetically, or phenotypically) to the parent cell. By "expanded" is meant any proliferation, growth, or division of cells. Disclosed herein are culture methods that support differentiation by in inclusion of nutrients and effector molecules necessary to promote or support the differentiation of stem cells into differentiated cells.

"Differentiation" describes the process whereby an unspecialized cell acquires the features of a specialized cell such as a heart, liver, pancreas, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell and may also include maturation or development of the cell. As used herein, "a cell that differentiates into pancreatic beta cell" defines any cell that can become a committed pancreatic cells that produces insulin. Non-limiting examples of cells that are capable of differentiating into endothelial cells include embryonic stem cells, pluripotent stem cells, induced pluripotent stem cells (iPSCs), mesenchymal stem cell, hematopoietic stem cells, and adipose stem cells.

As used herein, a "pluripotent cell" defines a less differentiated cell that can give rise to at least two distinct (genotypically and/or phenotypically) further differentiated progeny cells. In another aspect, a "pluripotent cell" includes an Induced Pluripotent Stem Cell (iPSC) which is an artificially derived stem cell from a non-pluripotent cell, typically an adult somatic cell, produced by inducing expression of one or more stem cell specific genes.

A "composition" is intended to encompass a combination of active agent and another "carrier," e.g., compound or composition, inert (for example, a detectable agent or label) or active, such as an adjuvant, diluent, binder, stabilizer, buffers, salts, lipophilic solvents, preservative, adjuvant or the like. Compositions may include stabilizers and preservatives. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. For examples of carriers, stabilizers and adjuvants, see Martin (1975) Remington's Pharm. Sci., 15th Ed. (Mack Publ. Co., Easton). Carriers also include biocompatible scaffolds, pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myo-inositol.

A population of cells intends a collection of more than one cell that is identical (clonal) or non-identical in phenotype and/or genotype.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by assaying for expression of a pre-selected cell surface marker or other marker.

An "effective amount" is an amount sufficient to effect beneficial or desired results. In the context of a therapeutic cell, population, or composition, the term "effective amount" as used herein refers to the amount to alleviate at least one or more symptom of a disease, disorder, or condition (e.g., corneal condition), and relates to a sufficient amount of the cell, population, or composition to provide the desired effect (e.g., repair of the cornea). An effective amount as used herein would also include an amount sufficient to delay the development of a disease, disorder, or condition symptom, alter the course of disease, disorder, or condition symptom (for example but not limited to, slow the progression of corneal degradation), or reverse a symptom of a disease, disorder, or condition. Thus, it is not possible to specify the exact "effective amount." However, for any given case, an appropriate "effective amount" can be determined by one of ordinary skill in the art using only routine experimentation.

An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. The dosage can be determined by a physician and adjusted, as necessary, to suit observed effects of the treatment. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo. Consistent with this definition, as used herein, the term "therapeutically effective amount" is an amount sufficient to achieve the result of the method.

The term "administration" shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

An "enriched population" of cells intends a substantially homogenous population of cells having certain defined characteristics. The cells are greater than 60%, or alternatively greater than 65%, or alternatively greater than 70%, or alternatively greater than 75%, or alternatively greater than 80%, or alternatively greater than 85%, or alternatively greater than 90%, or alternatively greater than 95%, or alternatively greater than 98% identical in the defined characteristics. In one aspect, the substantially homogenous population of cells express markers that correlate with pluripotent cell identity such as expression of stem-cell specific genes like OCT4 and NANOG. In another aspect, the substantially homogenous population of cells express markers that are correlated with definitive endoderm cell identity such SOX17, CXCR4, FOXA2, and GATA4. In another aspect, the substantially homogenous population of cells express markers that are correlated with posterior foregut cell identity such as HNF1β, HNF4A while suppressing expression of HHEX, HOXA3, CDX2, OCT4, and NANOG. In another aspect, the substantially homogenous population of cells express markers that are correlated with pancreatic progenitor cell identity such as PDX1 (pancreatic duodenal homeobox gene 1). In another aspect, the substantially homogenous population of cells express markers that are correlated with endocrine pancreas cell identity such as NKX6.1, NEURO-D1, and NGN3. In yet another aspect, the substantially homogenous population of cells express markers that are correlated with islet precursor cell identity such as INS. This population may further be identified by its ability to secrete C-peptide.

A "gene" refers to a polynucleotide containing at least one open reading frame that is capable of encoding a particular RNA, polypeptide, or protein after being transcribed and/or translated. The term "express" refers to the production of a gene product. As used herein, "expression" refers to the process by which polynucleotides are transcribed into RNA and/or the process by which the transcribed RNA such as mRNA is subsequently being translated into peptides, polypeptides, or proteins. If the polynucleotide is derived from genomic DNA, expression may include splicing of the mRNA in a eukaryotic cell. A "gene product" or alternatively a "gene expression product" refers to the amino acid (e.g., peptide or polypeptide) or functional RNA (e.g. a tRNA, miRNA, rRNA, or shRNA) generated when a gene is transcribed and translated.

The term "treating" (or "treatment") of a pancreatic or immune disorder or condition refers to ameliorating the effects of, or delaying, halting or reversing the progress of, or delaying or preventing the onset of, a pancreatic or immune condition such as diabetes, pre-diabetes, juvenile onset (Type I) diabetes mellitus, including pediatric insulin-dependent diabetes mellitus (IDDM), and adult onset diabetes mellitus (Type II diabetes). Treatment includes preventing the disease or condition (i.e., causing the clinical symptoms of the disease not to develop in a patient that may be predisposed to the disease but does not yet experience or display symptoms of the disease), inhibiting the disease or condition (i.e., arresting or reducing the development of the disease or its clinical symptoms), or relieving the disease or condition (i.e., causing regression of the disease or its clinical symptoms).

A mammalian stem cell, as used herein, intends a stem cell having an origin from a mammal. Non-limiting examples include, e.g., a murine, a canine, an equine, a simian and a human. An animal stem cell intends a stem cell having an origin from an animal, e.g., a mammalian stem cell.

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the methods and compositions disclosed herein are also useful for veterinary treatment of companion mammals, exotic animals and domesticated animals, including mammals, rodents, and the like which is susceptible to diabetes or other immune or pancreatic diseases or conditions. In one embodiment, the mammals include horses, dogs, and cats. In another embodiment of the present disclosure, the human is an adolescent or infant under the age of eighteen years.

An immature stem cell, as compared to a mature stem cell, intends a phenotype wherein the cell expresses or fails to express one or more markers of a mature phenotype. Examples of such are known in the art, e.g., telomerase length or the expression of actin for mature cardiomyocytes derived or differentiated from a less mature phenotype such as an embryonic stem cell. An immature beta cell intends a pancreatic cell that has insulin secretory granules but lacks GSIS. In contrast, mature beta cells typically are positive for GSIS and have low lactate dehydrogenase (LDH).

Descriptive Embodiments

Understanding the complex effects of genetic perturbations on cellular state and fitness in human pluripotent stem cells (hPSCs) has been challenging using traditional pooled screening techniques which typically rely on unidimensional phenotypic readouts. Here, Applicants use barcoded open reading frame (ORF) overexpression libraries with a coupled single-cell RNA sequencing (scRNA-seq) and fitness screening approach, a technique Applicants call SEUSS (ScalablE fUnctional Screening by Sequencing), to establish a comprehensive assaying platform. Using this system, Applicants perturbed hPSCs with a library of developmentally critical transcription factors (TFs), and assayed the impact of TF overexpression on fitness and transcriptomic cell state across multiple media conditions. Applicants further leveraged the versatility of the ORF library approach to systematically assay mutant gene libraries and also whole gene families. From the transcriptomic responses, Applicants built genetic co-perturbation networks to identify key altered gene modules. Strikingly, Applicants found that KLF4 and SNAI2 have opposing effects on the pluripotency gene module, highlighting the power of Applicants' method to characterize the effects of genetic perturbations. From the fitness responses, Applicants identified ETV2 as a driver of reprogramming towards an endothelial-like state.

Isolated Nucleic Acids and Transcription Factor Screening Libraries

This disclosure provides isolated polynucleotides or nucleic acids comprising, consisting of, or consisting essentially of (a) a polynucleotide or nucleic acid encoding a transcription factor (TF) open reading frame (ORF); (b) a nucleic acid barcode, and (c) an optional vector comprising (a) and (b); wherein the nucleic acid barcode is located 3' to the TF ORF.

Transcription factors are proteins that bind (directly or indirectly through recruitment factors) to enhancer or promoter regions of DNA (e.g. a genome) and interact to activate, repress, or maintain the current level of transcription of a particular gene or genetic locus. Many transcription factors can bind to specific DNA sequences. Non-limiting examples of TFs can be found at TFCat (Genome Biol. 2009; 10(3): R29).

An ORF refers to the part of a gene or polynucleotide that has the potential to be transcribed and/or translated. ORFs span intron/exon regions, which in some embodiments can be spliced together after transcription of the ORF to yield a final mRNA for protein translation. Thus, ORFs include both introns and exons, when applicable. In some embodiments, an ORF is a continuous stretch of codons that contain a start codon and a stop codon. In some embodiments, the transcription termination site is located after the ORF, beyond the translation stop codon.

In some embodiments, the TF ORF encodes a developmentally critical TF. As used herein, "developmentally critical" refers to a transcription factor that regulates development and/or differentiation by modulating transcription. Regulation may include, for example, suppression of one or more specific developmental or differentiation gene expression programs, activation of one or more specific developmental or differentiation gene expression programs, and/or maintenance of a specific level of activation or suppression of a specific developmental or differentiation program. For example, a developmentally critical transcription factor may function upstream of a lineage-specific gene network and direct a stem or progenitor cell to differentiate into that specific cell lineage. Examples of developmentally critical TFs include but are not limited to ASCL1, ASCL3, ASCL4, ASCL5, ATF7, CDX2, CRX, ERG, ESRRG, ETV2, FLI1, FOXA1, FOXA2, FOXA3, FOXP1, GATA1, GATA2, GATA4, GATA6, GLI1, HAND2, HNF1A, HNF1B, HNF4A, HOXA1, HOXA10, HOXA11, HOXB6, KLF4, LHX3, LMX1A, MEF2C, MESP1, MITF, MYC, MYCL, MYCN, MYOD1, MYOG, NEUROD1, NEUROG1, NEUROG3, NRL, ONECUT1, OTX2, PAX7, POU1F1, POU5F1, RUNX, SIX1, SIX2, SNAI2, SOX10, SOX2, SOX3, SPI1, SPIB, SPIC, SRY, TBX5, and TFAP2C.

In some embodiments, the vector is a retroviral vector, optionally a lentiviral vector.

This disclosure provides a vector comprising, or alternatively consisting essentially of, or yet further consisting of a viral backbone. In one aspect, the viral backbone contains essential nucleic acids or sequences for integration into a target cell's genome. In one aspect, the essential nucleic acids necessary for integration of the genome of the target cell include at the 5' and 3' ends the minimal LTR regions required for integration of the vector.

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, equine infectious anaemia virus (EIAV), simian immunodeficiency virus (SIV), feline immunodeficiency virus (FIV), and human immunodeficiency virus (HIV). Alternatively, it is contemplated that other retrovirus can be used as a basis for a vector backbone such murine leukemia virus (MLV). It will be evident that a viral vector need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

In another aspect, provided herein is a TF screening library comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF. In some embodiments, the TF ORF encodes a developmentally critical TF, optionally selected from the TFs listed in Table 1.

In some embodiments, the TF screening library comprises, consists of, or consists essentially of at least 10, at least 20, at least 30, at least 40, at least 50, at least 60, at least 70, at least 80, at least 90, or at least 100 nucleic acids or vectors, wherein each nucleic acid or vector comprises, consists of, or consists essentially of a distinct nucleic acid encoding a TF ORF.

In some embodiments, the TF screening library further comprises, consists of, or consists essentially of a nucleic acid encoding a selectable marker (e.g., hygromycin). In some embodiments, the TF screening library further comprises, consists of, or consists essentially of a nucleic acid encoding an expression control element. In some embodiments, the expression control element is a promoter or a long terminal repeat (LTR). In some embodiments, the TF screening library further comprises, consists of, or consists essentially of a nucleic acid encoding a translation elongation factor, optionally wherein the translation elongation factor is Ef1a.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

In another aspect, provided herein is a viral packaging system comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF; or aTF screening library; and a packaging plasmid.

In another aspect, provided herein is a method for producing a viral particle, the method comprising, consisting of, or consisting essentially of transfecting a packaging cell line with a viral packaging system comprising, consisting of, or consisting essentially of at least one isolated nucleic acid comprising, consisting of, or consisting essentially of (a) a nucleic acid encoding a transcription factor (TF) open reading frame (ORF); (b) a nucleic acid barcode, and (c) an optional vector comprising (a) and (b); wherein the nucleic acid barcode is located 3' to the TF ORF; or aTF screening library; and a packaging plasmid under conditions suitable to package the vector or the TF screening library into a viral particle. In another aspect, also provided herein is a viral particle produced by this method, and optionally a carrier. In another aspect, also provided herein is an isolated cell comprising a nucleic acid, vector, or particle as described herein, and optionally a carrier.

Retroviral vectors for use in the methods and compositions described herein include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemi®, manufactured by Open Biosystems; and pLV, lab generated and used by Charité Medical School, Institute of Virology (CBF), Berlin, Germany.

This invention also provides the suitable packaging cell line. In one aspect, the packaging cell line is the HEK-293 cell line. Other suitable cell lines are known in the art, for example, described in the patent literature within U.S. Pat. Nos. 7,070,994; 6,995,919; 6,475,786; 6,372,502; 6,365,150 and 5,591,624, each incorporated herein by reference.

Yet further provided is an isolated cell or population of cells, comprising, or alternatively consisting essentially of, or yet further consisting of, a retroviral particle of this invention, which in one aspect, is a viral particle. In one aspect, the isolated host cell is a packaging cell line.

Kits

In another aspect, provided herein is a kit comprising, consisting of, or consisting essentially of at least one of (a) a nucleic acid or vector according to any of the embodiments described herein; and/or (b) a TF screening library according to any of the embodiments described herein; and/or (c) a viral packaging system according to any of the embodiments described herein; and/or (d) a viral particle according to any of the embodiments described herein; and/or (e) an isolated cell according to any of the embodiments described herein, and optionally instructions for use.

High Throughput Gene Activation Screens

In another aspect, provided herein is a method of performing a high throughput gene activation screen, the method comprising, consisting of, or consisting essentially of: (a) transducing a target cell with the viral particle according to any of the embodiments described herein; and (b) performing single cell RNA sequencing (scRNA-seq) on the transduced target cell to identify the nucleic acid barcode.

In some embodiments, scRNA-seq methods comprise the following steps: isolation of single cell and RNA, reverse transcription (RT), optional amplification, library generation, and sequencing. Several scRNA-seq protocols appropriate for use with the disclosed methods have been published: Tang et al. (Nat Methods. 6 (5): 377-82) STRT (Islam, S. et al. (2011). Genome Res. 21 (7): 1160-7), SMART-seq (Ramskold, D. et al. (2012). Nat. Biotechnol. 30 (8): 777-82) CEL-seq (Hashimshony, T. et al. (2012) Cell Rep. 2 (3): 666-73), and Quartz-seq (Sasagawa, Y. et al. (2013) Genome Biol. 14 (4): R31).

In some embodiments, the method further comprises or consists of determining a fitness effect in the transduced target cell. Fitness effects include but are not limited to effects on cell proliferation, effects on cell viability, effects on rate of senescence, effects on apoptosis, effects on DNA repair mechanisms, effects on genome stability, effects on gene transcription, and effects on stress response. In some embodiments, fitness effects are calculated from genomic DNA or mRNA reads, In some embodiments, the method further comprises or consists of identifying a co-perturbation network. In some embodiments, the method further comprises or consists of identifying a functional gene module. In some embodiments, the target cell is a stem cell. In some embodiments, the stem cell is an embryonic stem cell (ESC) or an induced pluripotent stem cell (iPSC). In some embodiments, the target cell is a mammalian cell, optionally wherein the mammalian cell is an equine, bovine, canine, murine, porcine, feline, or human cell. In a particular embodiment, the target cell is a human cell.

Endothelial Differentiation Methods and Compositions

Also provided herein is a method driving or directing differentiation of a stem cell into an endothelial cell, the method comprising, consisting of, or consisting essentially of inducing ectopic expression of ETV2 (Ets variant 2, Entrez gene: 2116) in a stem cell under conditions suitable to support differentiation of the stem cell into an endothelial cell.

In some embodiments, ectopic expression of ETV2 is induced by transducing the stem cell with a vector (e.g., AAV) comprising a nucleic acid encoding ETV2 and a nucleic acid encoding an expression control element. In other embodiments, the vector encodes an open reading frame of ETV2. In other embodiments, the vector encodes a cDNA of ETV2 (RefSeq: NM 001300974; NM 001304549; NM 014209). A non-limiting example of the sequence of an ETV2 cDNA is provided:

(SEQ ID NO: 1)

```
   1  ttcctgttgc agataagccc agcttagccc agctgacccc agacctctc ccctcactcc
  61  ccccatgtcg caggatcgag accctgaggc agacagcccg ttcaccaagc ccccgcccc
 121  gcccccatca cccgtaaac ttctcccagc ctccgccctg ccctcaccca gcccgctgtt
 181  ccccaagcct cgctccaagc ccacgccacc cctgcagcag ggcagcccca gaggccagca
 241  cctatccccg aggctggggt cgaggctcgg ccccgcccct gcctctgcaa cttgagcctg
 301  gctgcgaccc ctgtctgac gtctcggaaa attcccctt gcccaggccc ttgggggagg
 361  gggtgcatgg tatgaaatgg ggctgagacc cccggctggg ggcagaggaa cccgccagag
 421  aaggagccaa attaggcttc tgtttccctg atctggcact ccaaggggac acgccgacag
 481  cgacagcaga gacatgctgg aaaggtacaa gctcatccct ggcaagcttc ccacagctgg
 541  actggggctc cgcgttactg cacccagaag ttccatgggg ggcggagccc gactctcagg
 601  ctcttccgtg gtccggggac tggacagaca tggcgtgcac agcctgggac tcttggagcg
 661  gcgcctcgca gaccctgggc cccgcccctc tcggcccggg ccccatcccc gccgccggct
 721  ccgaaggcgc cgcgggccag aactgcgtcc ccgtggcggg agaggccacc tcgtggtcgc
 781  gcgcccaggc cgccgggagc aacaccagct gggactgttc tgtggggccc gacggcgata
 841  cctactgggg cagtggcctg ggcggggagc cgcgcacgga ctgtaccatt tcgtggggcg
 901  ggcccgcggg cccggactgt accacctcct ggaacccggg gctgcatgcg ggtggcacca
 961  cctctttgaa gcggtaccag agctcagctc tcaccgtttg ctccgaaccg agcccgcagt
1021  cggaccgtgc cagtttggct cgatgcccca aaactaacca ccgaggtccc attcagctgt
1081  ggcagttcct cctggagctg ctccacgacg gggcgcgtag cagctgcatc cgttggactg
1141  gcaacagccg cgagttccag ctgtgcgacc ccaaagaggt ggctcggctg tggggcgagc
1201  gcaagagaaa gccgggcatg aattacgaga agctgagccg gggccttcgc tactactatc
1261  gccgcgacat cgtgcgcaag agcggggggc gaaagtacac gtaccgcttc ggggccgcg
1321  tgcccagcct agcctatccg gactgtgcgg gaggcggacg gggagcagag acacaataaa
1381  aattcccggt caaacctcaa aaaaaaaaa aaa
```

In some embodiments, the stem cell is an ESC or an iPSC. In some embodiments, the stem cell is a mammalian cell, optionally wherein the mammalian cell is an equine, bovine, canine, murine, porcine, feline, or human cell. In some embodiments, the stem cell is a human cell. In some embodiments, the stem cell has been genetically modified. In some embodiments, the method further comprises or consists of genetically modifying the stem cell or the endothelial cell.

In further aspect, also provided herein is an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, and optionally a carrier. In some embodiments, the endothelial cell expresses at least one of CDH5 (VE-Cadherin, Entrez gene: 1003; RefSeq: NM 001114117, NM 00179, PECAM1 (Platelet endothelial cell adhesion molecule, Entrez gene: 5175; RefSeq: NM 000442), or VWF (Von Willebrand Factor, Entrez gene: 7450, RefSeq: NM 000552).

In another aspect, also provided herein is a population of endothelial cells produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, and optionally a carrier.

In some aspects, provided herein is a composition comprising, consisting of, or consisting essentially of an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, or a population of endothelial cells produced according to a method described herein, and one or more of: a pharmaceutically acceptable carrier, a cryopreservative or a preservative. In some embodiments, the carrier is a pharmaceutically acceptable carrier. In some embodiments, the cryopreservative is suitable for long term storage of the composition at a temperature ranging from −200° C. to 0° C., from −80° C. to 0° C., from −20° C. to 0° C., or from 0° C. to 10° C.

Methods of Treatment

In some aspects, provided herein is a method of treating a subject in need thereof, the method comprising, consisting of, or consisting essentially of administering an endothelial cell produced by a method driving differentiation of a stem cell into an endothelial cell, the method comprising, consisting of, or consisting essentially of inducing ectopic expression of ETV2 in a stem cell under conditions suitable to support differentiation of the stem cell into an endothelial cell, or a population of endothelial cells produced according to a method described herein, or a composition comprising, consisting of, or consisting essentially of the endothelial cell or population and a carrier to the subject. In some embodiments of the method, an effective amount of the endothelial cell, population, or composition is administered to the subject. In some embodiments, the endothelial cell or population is allogenic or autologous to the subject being treated. In one aspect, the treatment excludes prevention.

In some embodiments of the method, the subject has a wound, a corneal disease or condition, a myocardial infarction, or a vascular disease or condition. In some embodiments, the subject has a corneal disease or condition. In some embodiments, the administration is local or systemic. In some embodiments, the endothelial cell, population, or composition is administered to the subject's eye.

An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. The dosage can be determined by a physician and adjusted, as necessary, to suit observed effects of the treatment. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to achieve the result of the method.

The term "administration" shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

In some embodiments of the method, the subject is a mammal and the mammal is an equine, bovine, canine, murine, porcine, feline, or human. In some embodiments, the mammal is a human. In some embodiments, the endothelial cells are autologous or allogeneic to the subject being treated.

Having been generally described herein, the follow examples are provided to further illustrate this invention.

Example 1

Recently, screens combining genetic perturbations with scRNA-seq readouts have emerged as promising alternatives to traditional screens, enabling high-throughput, high-content screening by profiling the transcriptomes of tens of thousands of individual cells simultaneously. Unlike array-based methods scRNA-seq screens are scalable, while unlike traditional pooled screening techniques, they enable direct readout of cell state changes. In addition, they also enable the evaluation of heterogeneous cellular response to perturbations. While several groups have demonstrated CRISPR-Cas9 based knock-out and knock-down scRNA-seq screens, to Applicants' knowledge, gene activation screens have yet to be demonstrated.

Here, Applicants use barcoded ORF overexpression libraries with a coupled scRNA-seq and fitness screen, a technique Applicants call SEUSS, to systematically overexpress TFs and assay both, the transcriptomic and fitness effects on hPSCs. Applicants chose open-reading frame (ORF) constructs for several reasons, namely that ORF constructs yield strong, stable expression of the gene of interest, enable the ability to express a targeted isoform of the gene, and allow for the ability to express engineered or mutant forms of the gene, aspects otherwise not accessible through endogenous gene activation. Applicants screened a pooled library of TFs that are either developmentally critical, specific to key lineages, or are pioneer factors capable of binding closed chromatin (Table 1). From the transcriptomic readouts, Applicants built a gene-gene co-perturbation network, segmented the network genes into functional gene modules, and used these gene modules to also elucidate the impact of TF overexpression on the pluripotent cell state. Notably, Applicants also leveraged the versatility of the ORF library approach and SEUSS to systematically assay mutant gene libraries (MYC) and whole gene families (KLF). Finally, Applicants also leveraged the complementary fitness information via SEUSS to ascertain that ETV2 is a novel reprogramming factor for hPSCs, whose overexpression yields rapid differentiation towards the endothelial lineage.

Figure 4:
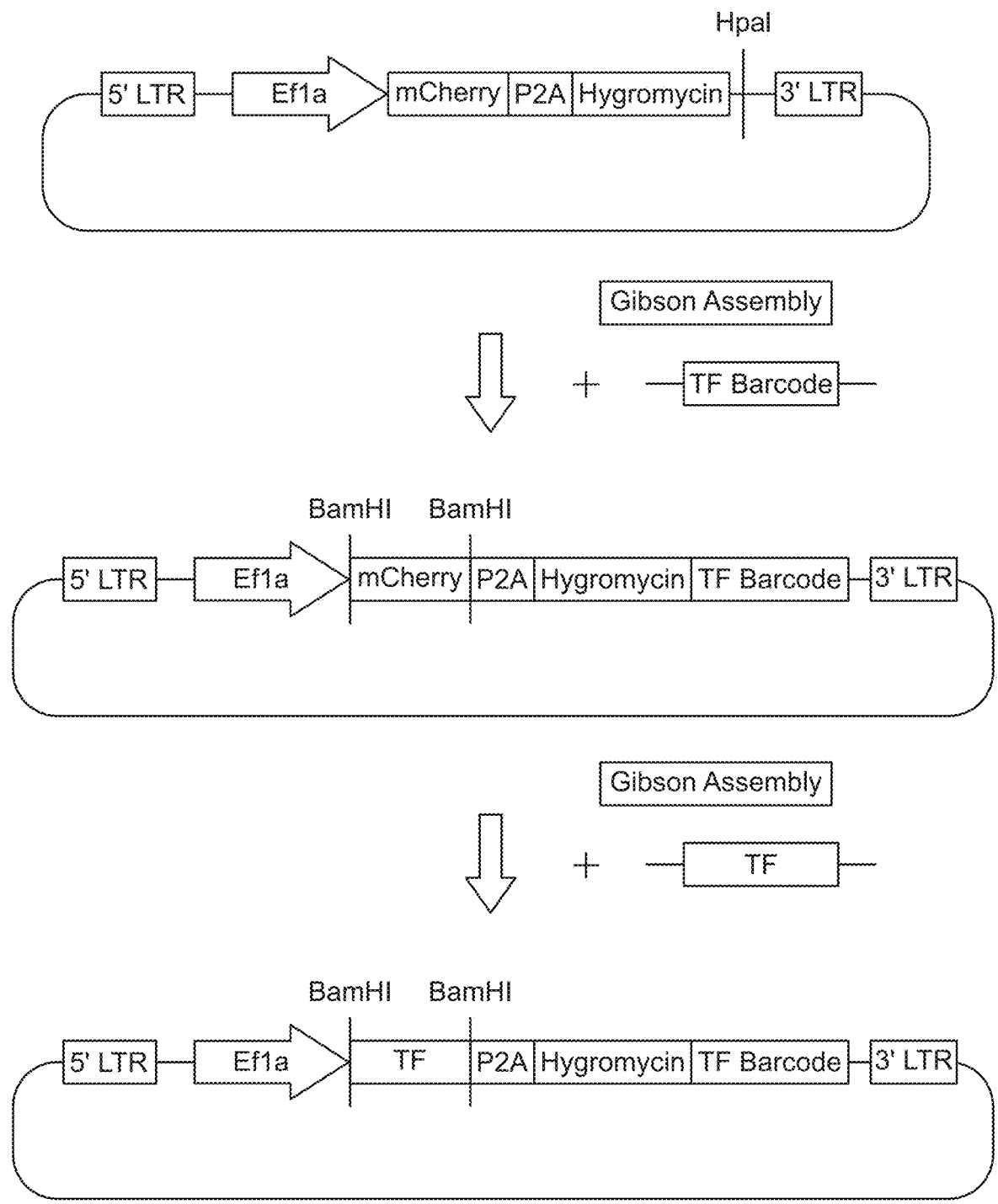
FIG. 4: Schematic of cloning strategy for synthesis of barcoded ORF vectors. The construction involved two steps: (i) insertion of a pool of barcodes into the backbone after digestion with HpaI, (ii) individually substituting mCherry with TFs after digestion with BamHI.

Applicants designed Applicants' ORF overexpression vector such that each TF was paired with a unique 20 bp barcode sequence located downstream of the 3' end of a hygromycin resistance transgene (FIG. 1A, FIG. 4), and 200 bp upstream of the lentiviral 3'-long terminal repeat (LTR) region. This yields a polyadenylated transcript bearing the barcode proximal to the 3' end, thereby facilitating efficient capture and detection in scRNA-seq. To construct the ORF library, transcription factors were amplified out of a multi-tissue human cDNA pool or directly synthesized as double-stranded DNA fragments, and individually cloned into the backbone vector (FIG. 4). The final library consisted of 61 developmentally critical or pioneer TFs (Table 1). Applicants chose this library size to ensure that within a single scRNA-seq run of up to 10,000 cells, each perturbation was represented by at least 50-100 cells. However, SEUSS can be scaled up to include all known TFs.

Applicants conducted the overexpression screens by transducing lentiviral ORF libraries into human embryonic stem cells (hESCs), maintaining them under antibiotic selection for 5 days after transduction, for screens in hPSC medium, and 6 days after transduction, for screens in unlineage (endothelial) and multilineage (high serum) medium, and then performing scRNA-seq on the transduced and selected cells. TF barcodes were recovered and associated with scRNA-seq cell barcodes by targeted amplification from the unfragmented cDNA, allowing genotyping of each cell for downstream analysis (FIG. 1A). Genotyped cell counts, although an under-sampling of the bulk population, also allowed Applicants to obtain an estimate of fitness, which was strongly correlated with bulk fitness obtained from genomic DNA (FIG. 1A, FIG. 3D, FIGS. 5A-5C).

Figure 1B:
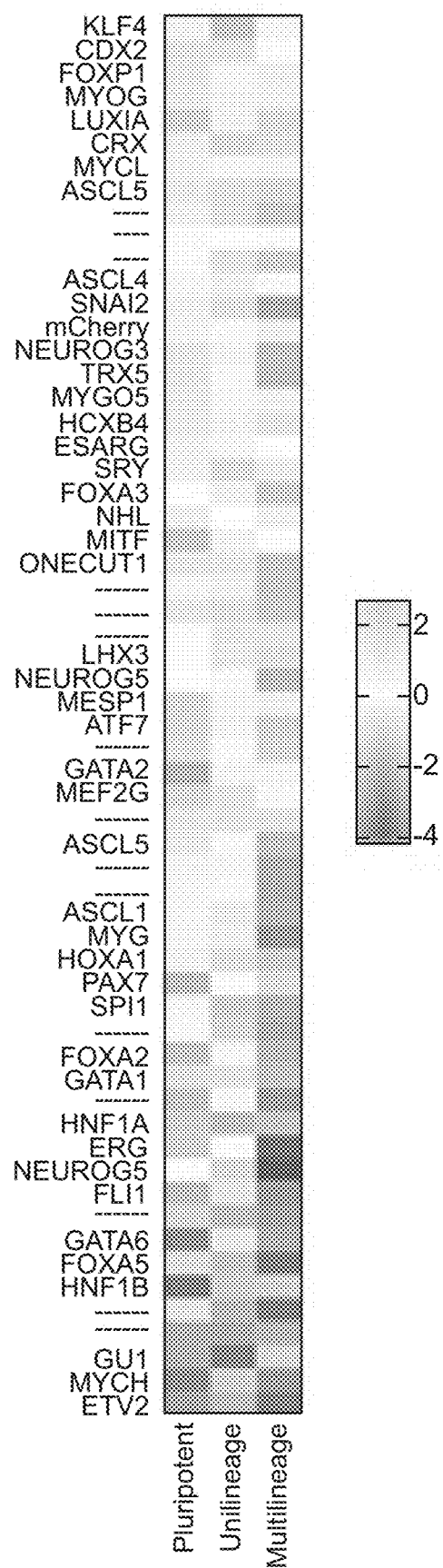
Figure 1C:
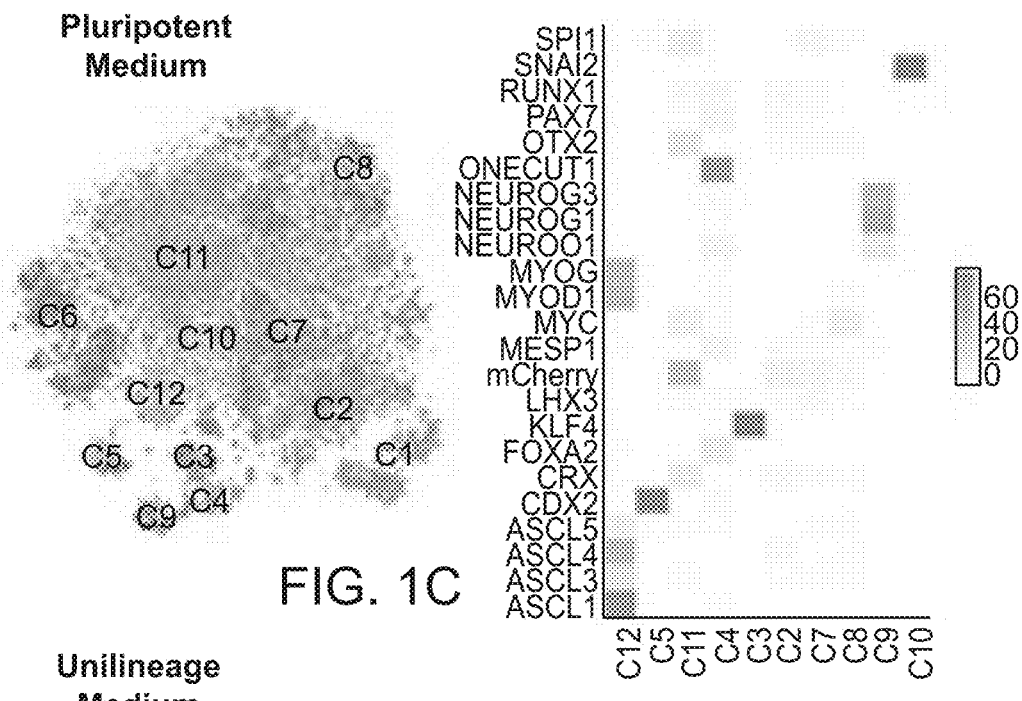
Figure 1D:
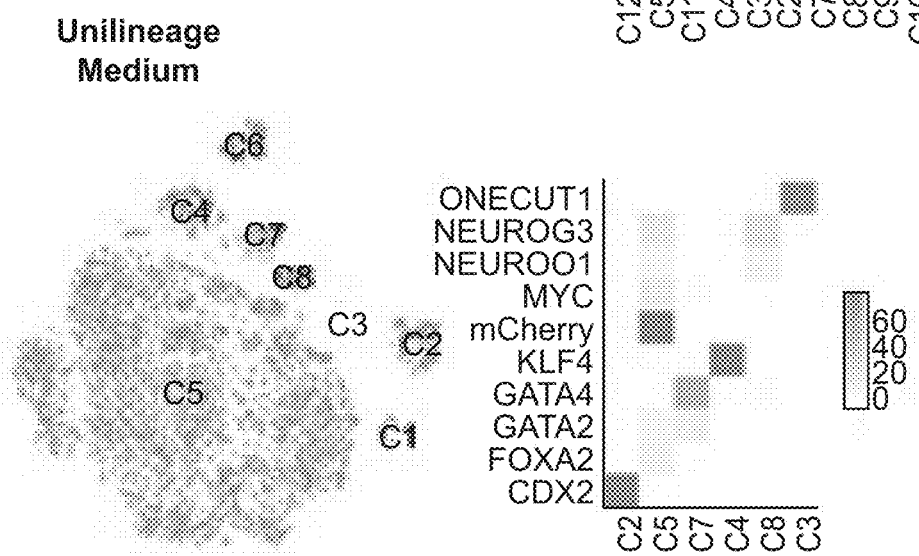
Figure 1E:
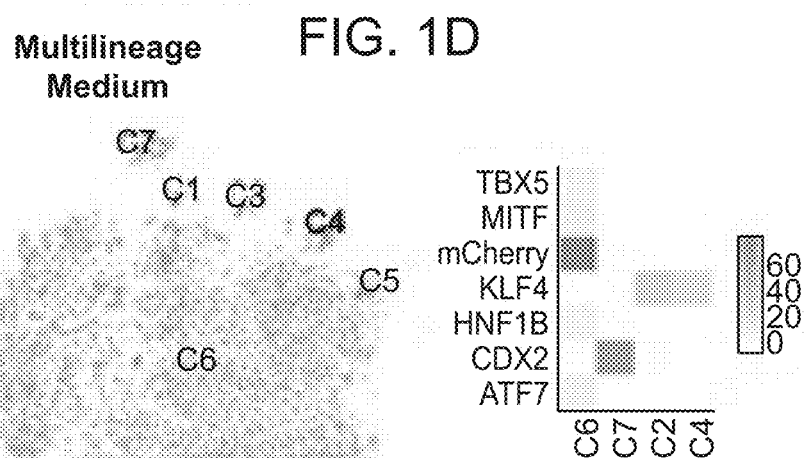
Figure 1F:
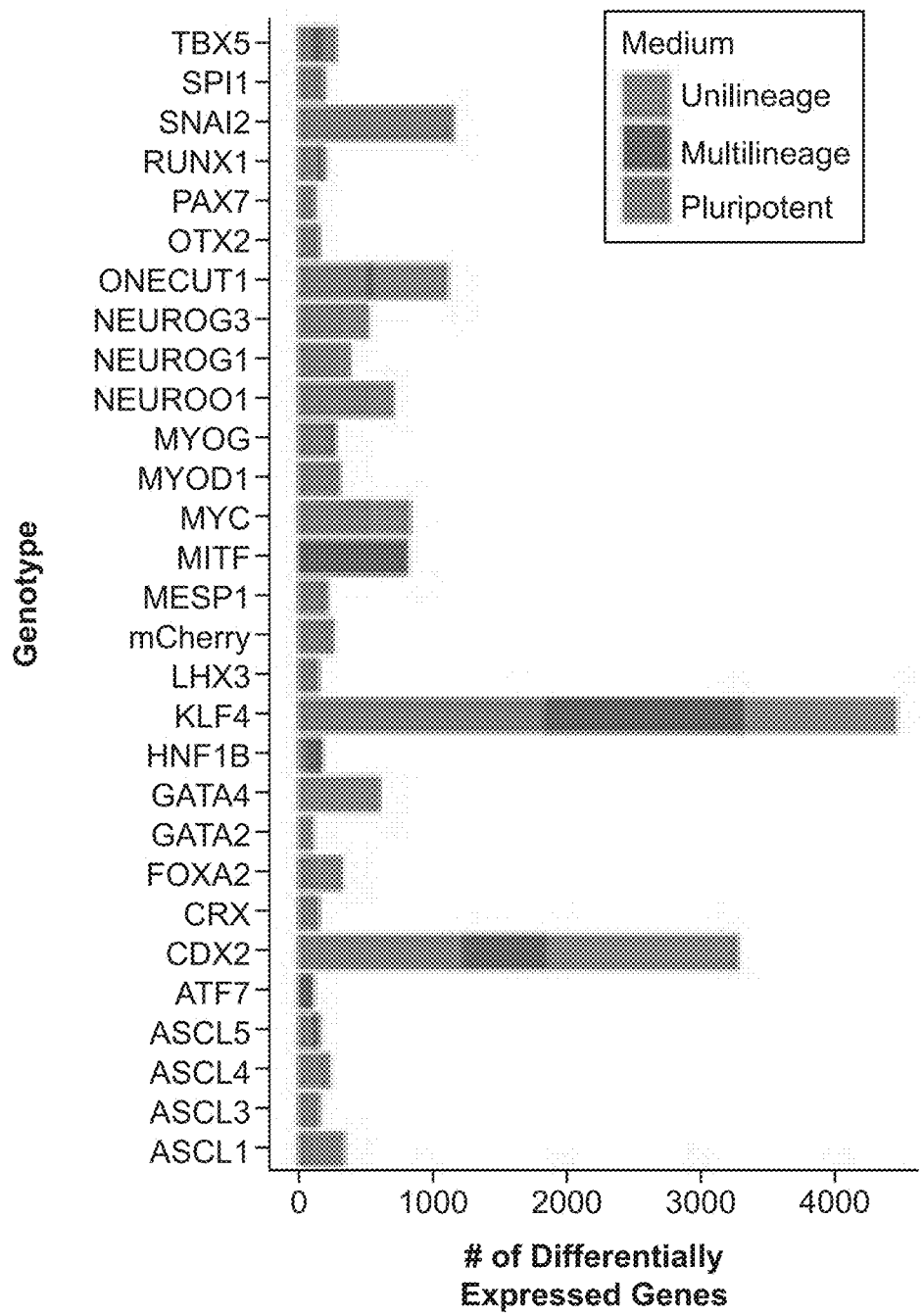

To analyze the effect of the TF perturbations, Applicants used the Seurat computational pipeline to cluster the cells from the scRNA-seq expression matrix (FIG. 1C, FIG. 1D, FIG. 1E). In parallel, a linear model was used to identify genes whose expression levels are appreciably changed by the perturbation. To select TFs for downstream analysis, Applicants calculated over-enrichment of TFs in clusters using Fisher's exact test (FIG. 1C, FIG. 1D, FIG. 1E). Subsequently, Applicants focused Applicants' analysis on TFs that were either significantly enriched for at least one cluster (FDR<$10^{-6}$), or had at least 100 significant differentially expressed genes. For TFs that had significant over-enrichment in a cluster, Applicants repeated the linear regression analysis, only including cells that fell into enriched clusters (FIG. 1F).

Figure 7A:
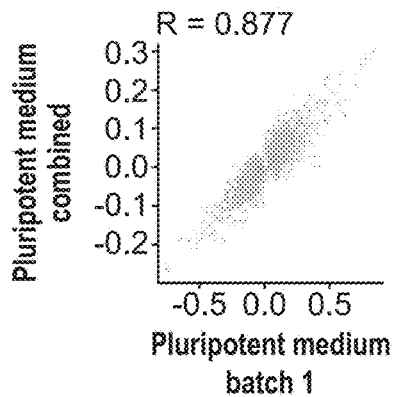
FIGS. 7A-7F: Correlation between aggregated samples. For all plots, correlation was between the coefficients of significant hits, with a hit being defined as a gene—TF pair with the following significance criteria: (FDR<0.05, |coef|>0.025).
Figure 7B:
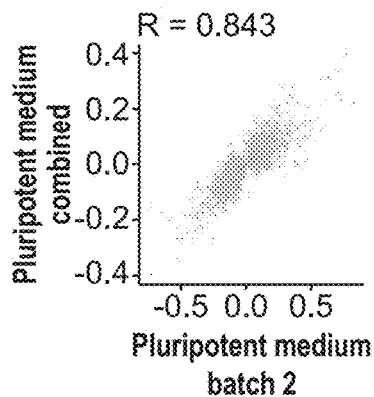
Figure 7C:
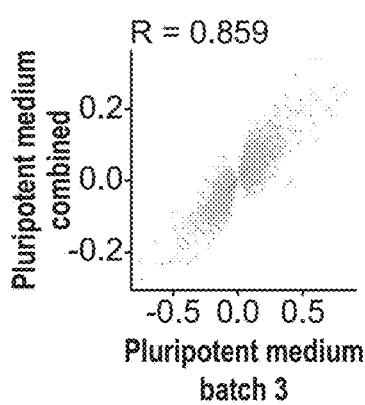
Figure 7D:
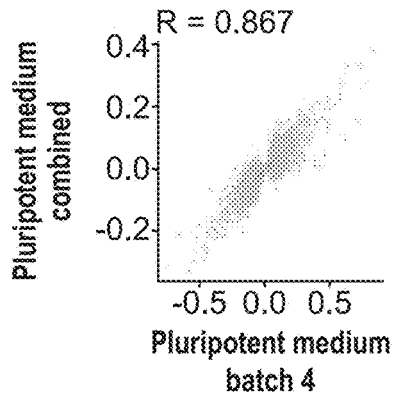
Figure 7E:
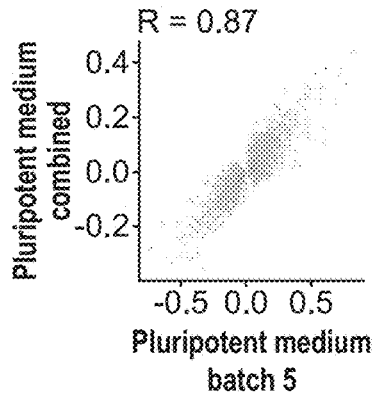
Figure 7F:
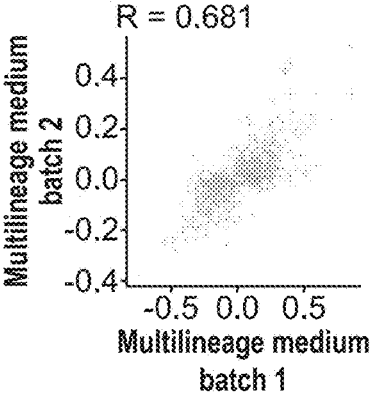
Figure 8A:
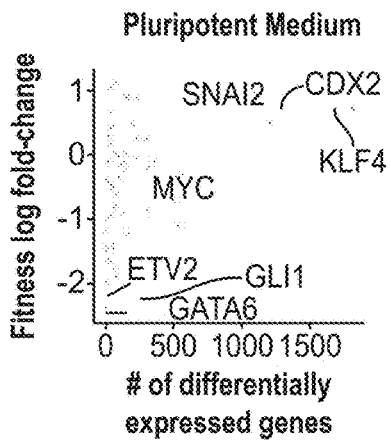
FIGS. 8A-8C: Correlation between fitness and transcriptomic effects.
Figure 8B:
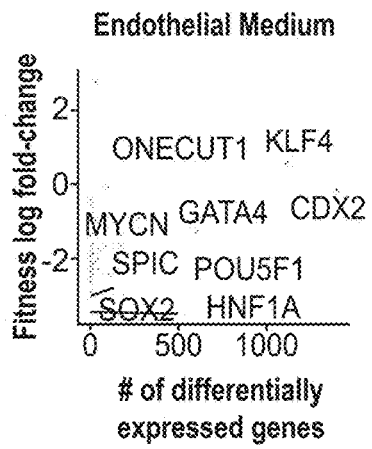
Figure 8C:
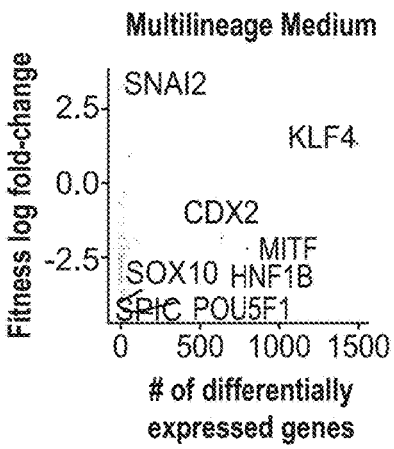
Figure 9A:
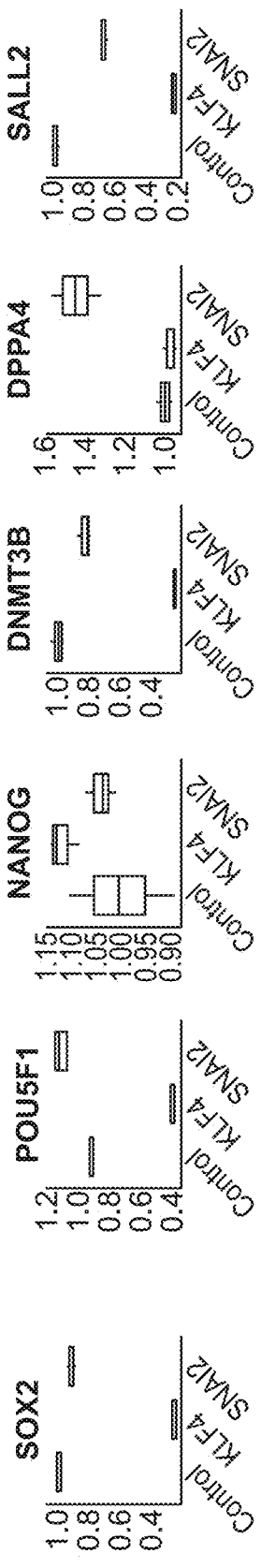
FIGS. 9A-9D: Confirmatory assays for effects of KLF4 and SNAI2 on key genes in the pluripotency network and involved in EMT (FIG. 9A) qRT-PCR analysis of signature pluripotency network genes SOX2, POU5F1, NANOG, DNMT3B, DPPA4 and SALL2 at day 5 post-transduction in in pluripotent stem cell medium.
Figure 9B:
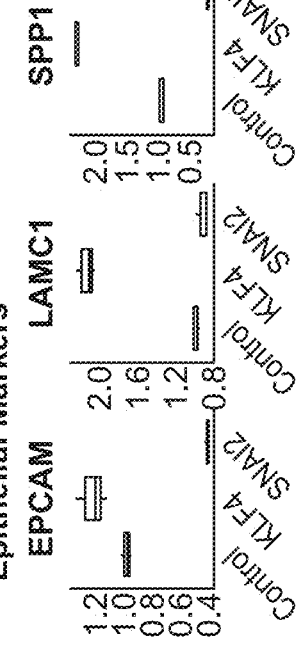
Figure 9C:
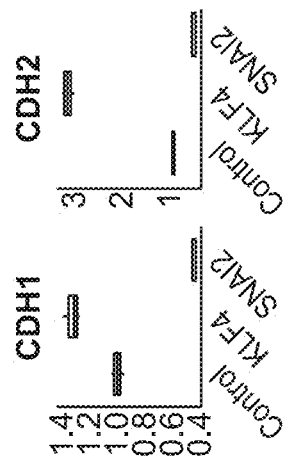
Figure 9D:
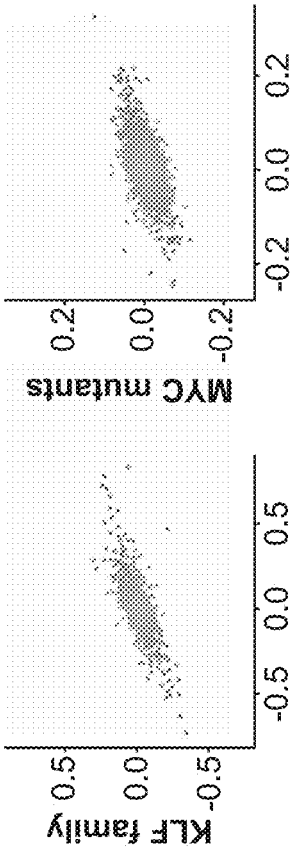
Figure 10A:
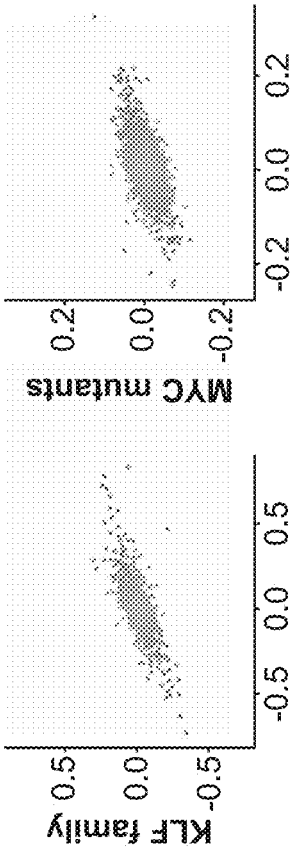
FIGS. 10A-10B: Correlation of KLF4 and MYC effects across samples.
Figure 10B:
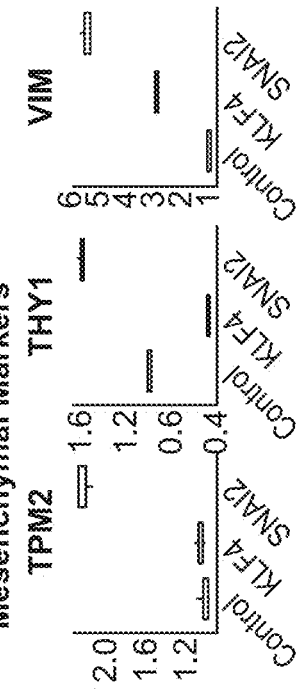

This framework was used to conduct screens in hPSC medium, aggregating 12,873 cells across five samples. Applicants found that these independent experiments were well correlated with the combined dataset (Pearson R>0.84), implying overall reproducibility and the absence of strong batch effects (FIGS. 7A-7E). To study the interplay of ORF overexpression with growth media conditions, Applicants also conducted screens in a unilineage medium, specifically endothelial growth medium, on 5,646 cells and in a multi-lineage (ML) differentiation medium, specifically a high serum growth medium, on 3476 cells (Table 3). Two samples were aggregated for analysis in the ML medium, again showing good correlation (FIG. 7F; Pearson R=0.68).

From Applicants' screen in hPSC medium, Applicants found that transcriptomic changes do not necessarily correlate with changes in fitness (FIG. 5), thus Applicants' coupled screening method enables a more comprehensive profiling of impacts on both fitness and cell state. Among the most significantly depleted TFs, was the haemato-endothelial master regulator ETV2, (FIG. 3D, FIG. 5), which guided Applicants' choice of EGM for a unilineage medium screen.

Applicants find that certain TFs show consistent effects across all media conditions (CDX2, KLF4), while some TFs have medium-specific effects. For instance, SNAI2 effects were specific to hPSC medium, MITF to ML medium, and GATA4 to EGM (FIG. 1F). To benchmark Applicants' results, Applicants compared expression profiles for significant TFs in hPSC medium with a previously reported bulk RNA-seq screen of TF perturbations in mESCs. For TFs present in both datasets, Applicants found a strong overlap, suggesting the effectiveness of Applicants' screen for studying perturbations (FIG. 6D).

To interpret the effects of the significant TFs, Applicants used the regression coefficients of the linear model to build a weighted gene-to-gene co-perturbation network, where genes with a highly weighted edge between them respond to TF perturbations in a similar manner (FIG. 2A). Using this network, Applicants identified 11 altered gene modules via a modularity optimization graph clustering algorithm. Many of these gene modules showed a strong enrichment for Gene Ontology (GO) terms, and gene module identity was assigned using GO enrichment paired with manual inspection of genes in each module. In this network, Applicants found that the pluripotency gene module and the chromatin accessibility module are highly interconnected, reflecting the relationship between those two biological processes (FIG. 2B), and suggesting that this network may serve as a resource to understand the cascading effects of genetic perturbations (FIG. 2B, Table 5).

Applicants next calculated the effect of each significant TF on the gene modules (FIG. 2C). Applicants found that the annotated neural specifiers NEUROD1, NEUROG1, and NEUROG3, which show similar cluster enrichment and differential expression patterns, upregulate the neuron differentiation module, consistent with their known effects. ASCL1 and MYOD1, which also show similarity in clustering and expression patterns, upregulate the Notch pathway module (FIG. 2C). This similarity between ASCL1 and MYOD1 may be due to a myogenic program initiated by ASCL1. Notably, for the TFs with consistent effects across medium conditions, Applicants find that both CDX2 and KLF4 strongly downregulate the pluripotency gene module, while CDX2 also upregulates the embryonic development gene module, potentially reflecting its role in trophectoderm development, and KLF4 tends to upregulate the cytoskeleton and motility gene modules.

Next, since in Applicants' screens MYC was found to drive significant transcriptomic changes in hPSC medium in its wild type form (FIG. 1F), Applicants chose to focus on it in demonstrating the ability of Applicants' platform to also systematically screen mutant forms of proteins. Specifically, Applicants constructed a library of mutant MYC proteins, where functional domains were systematically deleted (FIG. 2D), or mutations at known hotspots were incorporated (Glu-39, Thr-58 and Ser-62). Screening this library in pluripotent stem cell medium, Applicants found that while some variants, such as known hotspot mutations, as well as deletion of the nuclear localization signal (NLS) sequence maintain an effect similar to the wild type MYC, a majority of the other mutant forms show a greater overlap with the control mCherry-transduced cells, suggesting the essential requirement of the mapped domains for function of MYC in hPSCs (FIG. 2E).

MYC Mutants Library:

| GENE | SEQUENCE | SEQ ID NO: | MUTATION |
|---|---|---|---|
| MYC ΔMBI | ATGCCCCTCAACGTTAGCTTCACCAACAGGAACTATGACC TCGACTACGACTCGGTGCAGCCGTATTTCTACTGCGACGA GGAGGAGAACTTCTACCAGCAGCAGCAGCAGAGCGAGCT GCAGCCCCGGCGGGATCAGGTAGCGGTAGCCGCCGCTC CGGGCTCTGCTCGCCCTCCTACGTTGCGGTCACACCCTTCT CCCTTCGGGGAGACAACGACGGCGGTGGCGGGAGCTTCT CCACGGCCGACCAGCTGGAGATGGTGACCGAGCTGCTGG GAGGAGACATGGTGAACCAGAGTTTCATCTGCGACCCGG ACGACGAGACCTTCATCAAAAACATCATCATCCAGGACTG TATGTGGAGCGGCTTCTCGGCCGCCGCCAAGCTCGTCTCA GAGAAGCTGGCCTCCTACCAGGCTGCGCGCAAAGACAGC GGCAGCCCGAACCCCGCCCGCGGCCACAGCGTCTGCTCCA | 2 | Deletion of MYC Box I |

| GENE | SEQUENCE | SEQ ID NO: | MUTATION |
| --- | --- | --- | --- |
| | CCTCCAGCTTGTACCTGCAGGATCTGAGCGCCGCCGCCTC<br>AGAGTGCATCGACCCCTCGGTGGTCTTCCCCTACCCTCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTCAAGAGGCGAAC<br>ACACAACGTCTTGGAGCGCCAGAGGAGGAACGAGCTAAA<br>ACGGAGCTTTTTTGCCCTGCGTGACCAGATCCCGGAGTTG<br>GAAAACAATGAAAAGGCCCCCAAGGTAGTTATCCTTAAA<br>AAAGCCACAGCATACATCCTGTCCGTCCAAGCAGAGGAG<br>CAAAAGCTCATTTCTGAAGAGGACTTGTTGCGGAAACGAC<br>GAGAACAGTTGAAACACAAACTTGAACAGCTACGGAACT<br>CTTGTGCG | | |
| c-MYC ΔMBII | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGAGCT<br>GCAGCCCCCGGCGCCCAGCGAGGATATCTGGAAGAAATT<br>CGAGCTGCTGCCCACCCCGCCCCTGTCCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCGGATCAGGTAGC<br>GGTCTCGTCTCAGAGAAGCTGGCCTCCTACCAGGCTGCGC<br>GCAAAGACAGCGGCAGCCCGAACCCCGCCCGCGGCCACA<br>GCGTCTGCTCCACCTCCAGCTTGTACCTGCAGGATCTGAG<br>CGCCGCCGCCTCAGAGTGCATCGACCCCTCGGTGGTCTTC<br>CCCTACCCTCTCAACGACAGCAGCTCGCCCAAGTCCTGCG<br>CCTCGCAAGACTCCAGCGCCTTCTCTCCGTCCTCGGATTCT<br>CTGCTCTCCTCGACGGAGTCCTCCCCGCAGGGCAGCCCCG<br>AGCCCCTGGTGCTCCATGAGGAGACACCGCCCACCACCAG<br>CAGCGACTCTGAGGAGGAACAAGAAGATGAGGAAGAAAT<br>CGATGTTGTTTCTGTGGAAAAGAGGCAGGCTCCTGGCAAA<br>AGGTCAGAGTCTGGATCACCTTCTGCTGGAGGCCACAGCA<br>AACCTCCTCACAGCCCACTGGTCCTCAAGAGGTGCCACGT<br>CTCCACACATCAGCACAACTACGCAGCGCCTCCCTCCACT<br>CGGAAGGACTATCCTGCTGCCAAGAGGGTCAAGTTGGAC<br>AGTGTCAGAGTCCTGAGACAGATCAGCAACAACCGAAAA<br>TGCACCAGCCCCAGGTCCTCGGACACCGAGGAGAATGTC<br>AAGAGGCGAACACACAACGTCTTGGAGCGCCAGAGGAGG<br>AACGAGCTAAAACGGAGCTTTTTTGCCCTGCGTGACCAGA<br>TCCCGGAGTTGGAAAACAATGAAAAGGCCCCCAAGGTAG<br>TTATCCTTAAAAAAGCCACAGCATACATCCTGTCCGTCCA<br>AGCAGAGGAGCAAAAGCTCATTTCTGAAGAGGACTTGTT<br>GCGGAAACGACGAGAACAGTTGAAACACAAACTTGAACA<br>GCTACGGAACTCTTGTGCG | 3 | Deletion of MYC Box II |
| MYC ΔNLS | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGAGCT<br>GCAGCCCCCGGCGCCCAGCGAGGATATCTGGAAGAAATT<br>CGAGCTGCTGCCCACCCCGCCCCTGTCCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCATCATCCAGGACT<br>GTATGTGGAGCGGCTTCTCGGCCGCCGCCAAGCTCGTCTC<br>AGAGAAGCTGGCCTCCTACCAGGCTGCGCGCAAAGACAG<br>CGGCAGCCCGAACCCCGCCCGCGGCCACAGCGTCTGCTCC<br>ACCTCCAGCTTGTACCTGCAGGATCTGAGCGCCGCCGCCT<br>CAGAGTGCATCGACCCCTCGGTGGTCTTCCCCTACCCTCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT | 4 | Deletion of nuclear localization signal sequence |

| GENE | SEQUENCE | SEQ ID NO: | MUTATION |
|---|---|---|---|
| | CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATGGATCAGGTAGCGGTAGTGTCAGAGTCCTGAGACAGA<br>TCAGCAACAACCGAAAATGCACCAGCCCCAGGTCCTCGG<br>ACACCGAGGAGAATGTCAAGAGGCGAACACACAACGTCT<br>TGGAGCGCCAGAGGAGGAACGAGCTAAAACGGAGCTTTT<br>TTGCCCTGCGTGACCAGATCCCGGAGTTGGAAAACAATGA<br>AAAGGCCCCCAAGGTAGTTATCCTTAAAAAAGCCACAGC<br>ATACATCCTGTCCGTCCAAGCAGAGGAGCAAAAGCTCATT<br>TCTGAAGAGGACTTGTTGCGGAAACGACGAGAACAGTTG<br>AAACACAAACTTGAACAGCTACGGAACTCTTGTGCG | | |
| MYC<br>Δb | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGAGCT<br>GCAGCCCCCGGCGCCCAGCGAGGATATCTGGAAGAAATT<br>CGAGCTGCTGCCCACCCCGCCCCTGTCCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCATCATCCAGGACT<br>GTATGTGGAGCGGCTTCTCGGCCGCCGCCAAGCTCGTCTC<br>AGAGAAGCTGGCCTCCTACCAGGCTGCGCGCAAAGACAG<br>CGGCAGCCCGAACCCCGCCCGCGGCCACAGCGTCTGCTCC<br>ACCTCCAGCTTGTACCTGCAGGATCTGAGCGCCGCCGCCT<br>CAGAGTGCATCGACCCTCGGTGGTCTTCCCCTACCCTCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTCGGATCAGGTAG<br>CGGTGAGCTAAAACGGAGCTTTTTTGCCCTGCGTGACCAG<br>ATCCCGGAGTTGGAAAACAATGAAAAGGCCCCCAAGGTA<br>GTTATCCTTAAAAAAGCCACAGCATACATCCTGTCCGTCC<br>AAGCAGAGGAGCAAAAGCTCATTTCTGAAGAGGACTTGT<br>TGCGGAAACGACGAGAACAGTTGAAACACAAACTTGAAC<br>AGCTACGGAACTCTTGTGCG | 5 | Deletion of basic<br>motif |
| MYC<br>ΔHLH | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGAGCT<br>GCAGCCCCCGGCGCCCAGCGAGGATATCTGGAAGAAATT<br>CGAGCTGCTGCCCACCCCGCCCCTGTCCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCATCATCCAGGACT<br>GTATGTGGAGCGGCTTCTCGGCCGCCGCCAAGCTCGTCTC<br>AGAGAAGCTGGCCTCCTACCAGGCTGCGCGCAAAGACAG<br>CGGCAGCCCGAACCCCGCCCGCGGCCACAGCGTCTGCTCC<br>ACCTCCAGCTTGTACCTGCAGGATCTGAGCGCCGCCGCCT<br>CAGAGTGCATCGACCCTCGGTGGTCTTCCCCTACCCTCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTCAAGAGGCGAAC<br>ACACAACGTCTTGGAGCGCCAGAGGAGGAACGGATCAGG | 6 | Deletion of helix-<br>loop-helix motif |

-continued

| GENE | SEQUENCE | SEQ ID NO: | MUTATION |
|---|---|---|---|
| | TAGCGGTCAAAAGCTCATTTCTGAAGAGGACTTGTTGCGG AAACGACGAGAACAGTTGAAACACAAACTTGAACAGCTA CGGAACTCTTGTGCG | | |
| MYC ΔLZ | ATGCCCCTCAACGTTAGCTTCACCAACAGGAACTATGACC TCGACTACGACTCGGTGCAGCCGTATTTCTACTGCGACGA GGAGGAGAACTTCTACCAGCAGCAGCAGCAGAGCGAGCT GCAGCCCCCGGCGCCCAGCGAGGATATCTGGAAGAAATT CGAGCTGCTGCCCACCCCGCCCCTGTCCCCTAGCCGCCGC TCCGGGCTCTGCTCGCCCTCCTACGTTGCGGTCACACCCTT CTCCCTTCGGGGAGACAACGACGGCGGTGGCGGGAGCTT CTCCACGGCCGACCAGCTGGAGATGGTGACCGAGCTGCTG GGAGGAGACATGGTGAACCAGAGTTTCATCTGCGACCCG GACGACGAGACCTTCATCAAAAACATCATCATCCAGGACT GTATGTGGAGCGGCTTCTCGGCCGCCGCCAAGCTCGTCTC AGAGAAGCTGGCCTCCTACCAGGCTGCGCGCAAAGACAG CGGCAGCCCGAACCCCGCCCGCGGCCACAGCGTCTGCTCC ACCTCCAGCTTGTACCTGCAGGATCTGAGCGCCGCCGCCT CAGAGTGCATCGACCCCTCGGTGGTCTTCCCCTACCCTCTC AACGACAGCAGCTCGCCCAAGTCCTGCGCCTCGCAAGACT CCAGCGCCTTCTCTCCGTCCTCGGATTCTCTGCTCTCCTCG ACGGAGTCCTCCCCGCAGGGCAGCCCCGAGCCCCTGGTGC TCCATGAGGAGACACCGCCCACCACCAGCAGCGACTCTG AGGAGGAACAAGAAGATGAGGAAGAAATCGATGTTGTTT CTGTGGAAAAGAGGCAGGCTCCTGGCAAAAGGTCAGAGT CTGGATCACCTTCTGCTGGAGGCCACAGCAAACCTCCTCA CAGCCCACTGGTCCTCAAGAGGTGCCACGTCTCCACACAT CAGCACAACTACGCAGCGCCTCCCTCCACTCGGAAGGACT ATCCTGCTGCCAAGAGGGTCAAGTTGGACAGTGTCAGAGT CCTGAGACAGATCAGCAACAACCGAAAATGCACCAGCCC CAGGTCCTCGGACACCGAGGAGAATGTCAAGAGGCGAAC ACACAACGTCTTGGAGCGCCAGAGGAGGAACGAGCTAAA ACGGAGCTTTTTTGCCCTGCGTGACCAGATCCCGGAGTTG GAAAACAATGAAAAGGCCCCCAAGGTAGTTATCCTTAAA AAAGCCACAGCATACATCCTGTCCGTCCAAGCAGAGGAG | 7 | Deletion of leucine zipper motif |
| MYC ΔNTD | ATGGGATCAGGTAGCGGTCTCGTCTCAGAGAAGCTGGCCT CCTACCAGGCTGCGCGCAAAGACAGCGGCAGCCCGAACC CCGCCCGCGGCCACAGCGTCTGCTCCACCTCCAGCTTGTA CCTGCAGGATCTGAGCGCCGCCGCCTCAGAGTGCATCGAC CCCTCGGTGGTCTTCCCCTACCCTCTCAACGACAGCAGCT CGCCCAAGTCCTGCGCCTCGCAAGACTCCAGCGCCTTCTC TCCGTCCTCGGATTCTCTGCTCTCCTCGACGGAGTCCTCCC CGCAGGGCAGCCCCGAGCCCCTGGTGCTCCATGAGGAGA CACCGCCCACCACCAGCAGCGACTCTGAGGAGGAACAAG AAGATGAGGAAGAAATCGATGTTGTTTCTGTGGAAAAGA GGCAGGCTCCTGGCAAAAGGTCAGAGTCTGGATCACCTTC TGCTGGAGGCCACAGCAAACCTCCTCACAGCCCACTGGTC CTCAAGAGGTGCCACGTCTCCACACATCAGCACAACTACG CAGCGCCTCCCTCCACTCGGAAGGACTATCCTGCTGCCAA GAGGGTCAAGTTGGACAGTGTCAGAGTCCTGAGACAGAT CAGCAACAACCGAAAATGCACCAGCCCCAGGTCCTCGGA CACCGAGGAGAATGTCAAGAGGCGAACACACAACGTCTT GGAGCGCCAGAGGAGGAACGAGCTAAAACGGAGCTTTTT TGCCCTGCGTGACCAGATCCCGGAGTTGGAAAACAATGA AAAGGCCCCCAAGGTAGTTATCCTTAAAAAAGCCACAGC ATACATCCTGTCCGTCCAAGCAGAGGAGCAAAAGCTCATT TCTGAAGAGGACTTGTTGCGGAAACGACGAGAACAGTTG AAACACAAACTTGAACAGCTACGGAACTCTTGTGCG | 8 | Deletion of amino-terminal domain: Housing MYC Box I and II |
| MYC ΔCTD | ATGCCCCTCAACGTTAGCTTCACCAACAGGAACTATGACC TCGACTACGACTCGGTGCAGCCGTATTTCTACTGCGACGA GGAGGAGAACTTCTACCAGCAGCAGCAGCAGAGCGAGCT GCAGCCCCCGGCGCCCAGCGAGGATATCTGGAAGAAATT CGAGCTGCTGCCCACCCCGCCCCTGTCCCCTAGCCGCCGC TCCGGGCTCTGCTCGCCCTCCTACGTTGCGGTCACACCCTT CTCCCTTCGGGGAGACAACGACGGCGGTGGCGGGAGCTT CTCCACGGCCGACCAGCTGGAGATGGTGACCGAGCTGCTG GGAGGAGACATGGTGAACCAGAGTTTCATCTGCGACCCG GACGACGAGACCTTCATCAAAAACATCATCATCCAGGACT GTATGTGGAGCGGCTTCTCGGCCGCCGCCAAGCTCGTCTC AGAGAAGCTGGCCTCCTACCAGGCTGCGCGCAAAGACAG CGGCAGCCCGAACCCCGCCCGCGGCCACAGCGTCTGCTCC ACCTCCAGCTTGTACCTGCAGGATCTGAGCGCCGCCGCCT CAGAGTGCATCGACCCCTCGGTGGTCTTCCCCTACCCTCTC AACGACAGCAGCTCGCCCAAGTCCTGCGCCTCGCAAGACT | 9 | Deletion of carboxy-terminal domain: Housing basic helix-loop-helix leucine zipper motif, governing heterodimerization with MAX protein |

-continued

| GENE | SEQUENCE | SEQ ID NO: | MUTATION |
|---|---|---|---|
| | CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTC | | |
| MYC<br>Glu39Ala | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGCgCT<br>GCAGCCCCCGGCGCCCAGCGAGGATATCTGGAAGAAATT<br>CGAGCTGCTGCCCACCCCGCCCCTGTCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCATCATCCAGGACT<br>GTATGTGGAGCGGCTTCTCGGCCGCCGCCAAGCTCGTCTC<br>AGAGAAGCTGGCCTCCTACCAGGCTGCGCGCAAAGACAG<br>CGGCAGCCCGAACCCCGCCCGCGGCCACAGCGTCTGCTCC<br>ACCTCCAGCTTGTACCTGCAGGATCTGAGCGCCGCCGCCT<br>CAGAGTGCATCGACCCCTCGGTGGTCTTCCCCTACCCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTCAAGAGGCGAAC<br>ACACAACGTCTTGGAGCGCCAGAGGAGGAACGAGCTAAA<br>ACGGAGCTTTTTTGCCCTGCGTGACCAGATCCCGGAGTTG<br>GAAAACAATGAAAAGGCCCCCAAGGTAGTTATCCTTAAA<br>AAAGCCACAGCATACATCCTGTCCGTCCAAGCAGAGGAG<br>CAAAAGCTCATTTCTGAAGAGGACTTGTTGCGGAAACGAC<br>GAGAACAGTTGAAACACAAACTTGAACAGCTACGGAACT<br>CTTGTGCG | 10 | Point mutation changing Glutamic Acid to Alanine at amino acid 39 |
| MYC<br>Thr58Ala | ATGCCCCTCAACGTTAGCTTCACCAACAGGAACTATGACC<br>TCGACTACGACTCGGTGCAGCCGTATTTCTACTGCGACGA<br>GGAGGAGAACTTCTACCAGCAGCAGCAGCAGAGCGAGCT<br>GCAGCCCCCGGCGCCCAGCGAGGATATCTGGAAGAAATT<br>CGAGCTGCTGCCCGCCCCGCCCCTGTCCCTAGCCGCCGC<br>TCCGGGCTCTGCTCGCCCTCCTACGTTGCGGTCACACCCTT<br>CTCCCTTCGGGGAGACAACGACGGCGGTGGCGGGAGCTT<br>CTCCACGGCCGACCAGCTGGAGATGGTGACCGAGCTGCTG<br>GGAGGAGACATGGTGAACCAGAGTTTCATCTGCGACCCG<br>GACGACGAGACCTTCATCAAAAACATCATCATCCAGGACT<br>GTATGTGGAGCGGCTTCTCGGCCGCCGCCAAGCTCGTCTC<br>AGAGAAGCTGGCCTCCTACCAGGCTGCGCGCAAAGACAG<br>CGGCAGCCCGAACCCCGCCCGCGGCCACAGCGTCTGCTCC<br>ACCTCCAGCTTGTACCTGCAGGATCTGAGCGCCGCCGCCT<br>CAGAGTGCATCGACCCCTCGGTGGTCTTCCCCTACCCTC<br>AACGACAGCAGCTCGCCCAAGTCCTGCGCCTCGCAAGACT<br>CCAGCGCCTTCTCTCCGTCCTCGGATTCTCTGCTCTCCTCG<br>ACGGAGTCCTCCCCGCAGGGCAGCCCCGAGCCCCTGGTGC<br>TCCATGAGGAGACACCGCCCACCACCAGCAGCGACTCTG<br>AGGAGGAACAAGAAGATGAGGAAGAAATCGATGTTGTTT<br>CTGTGGAAAAGAGGCAGGCTCCTGGCAAAAGGTCAGAGT<br>CTGGATCACCTTCTGCTGGAGGCCACAGCAAACCTCCTCA<br>CAGCCCACTGGTCCTCAAGAGGTGCCACGTCTCCACACAT<br>CAGCACAACTACGCAGCGCCTCCCTCCACTCGGAAGGACT<br>ATCCTGCTGCCAAGAGGGTCAAGTTGGACAGTGTCAGAGT<br>CCTGAGACAGATCAGCAACAACCGAAAATGCACCAGCCC<br>CAGGTCCTCGGACACCGAGGAGAATGTCAAGAGGCGAAC<br>ACACAACGTCTTGGAGCGCCAGAGGAGGAACGAGCTAAA<br>ACGGAGCTTTTTTGCCCTGCGTGACCAGATCCCGGAGTTG | 11 | Point mutation changing Threonine to Alanine at amino acid 58 |

| GENE | SEQUENCE | SEQ ID NO: | MUTATION |
|---|---|---|---|
| | GAAAACAATGAAAAGGCCCCCAAGGTAGTTATCCTTAAA AAAGCCACAGCATACATCCTGTCCGTCCAAGCAGAGGAG CAAAAGCTCATTTCTGAAGAGGACTTGTTGCGGAAACGAC GAGAACAGTTGAAACACAAACTTGAACAGCTACGGAACT CTTGTGCG | | |
| MYC Ser62Ala | ATGCCCCTCAACGTTAGCTTCACCAACAGGAACTATGACC TCGACTACGACTCGGTGCAGCCGTATTTCTACTGCGACGA GGAGGAGAACTTCTACCAGCAGCAGCAGCAGAGCGAGCT GCAGCCCCCGGCGCCCAGCGAGGATATCTGGAAGAAATT CGAGCTGCTGCCCACCCCGCCCCTGGCCCCTAGCCGCCGC TCCGGGCTCTGCTCGCCCTCCTACGTTGCGGTCACACCCTT CTCCCTTCGGGGAGACAACGACGGCGGTGGCGGGAGCTT CTCCACGGCCGACCAGCTGGAGATGGTGACCGAGCTGCTG GGAGGAGACATGGTGAACCAGAGTTTCATCTGCGACCCG GACGACGAGACCTTCATCAAAAACATCATCATCCAGGACT GTATGTGGAGCGGCTTCTCGGCCGCCGCCAAGCTCGTCTC AGAGAAGCTGGCCTCCTACCAGGCTGCGCGCAAAGACAG CGGCAGCCCGAACCCCGCCCGCGGCCACAGCGTCTGCTCC ACCTCCAGCTTGTACCTGCAGGATCTGAGCGCCGCCGCCT CAGAGTGCATCGACCCCTCGGTGGTCTTCCCCTACCCTCTC AACGACAGCAGCTCGCCCAAGTCCTGCGCCTCGCAAGACT CCAGCGCCTTCTCTCCGTCCTCGGATTCTCTGCTCTCCTCG ACGGAGTCCTCCCCGCAGGGCAGCCCCGAGCCCCTGGTGC TCCATGAGGAGACACCGCCCACCACCAGCAGCGACTCTG AGGAGGAACAAGAAGATGAGGAAGAAATCGATGTTGTTT CTGTGGAAAAGAGGCAGGCTCCTGGCAAAAGGTCAGAGT CTGGATCACCTTCTGCTGGAGGCCACAGCAAACCTCCTCA CAGCCCACTGGTCCTCAAGAGGTGCCACGTCTCCACACAT CAGCACAACTACGCAGCGCCTCCCTCCACTCGGAAGGACT ATCCTGCTGCCAAGAGGGTCAAGTTGGACAGTGTCAGAGT CCTGAGACAGATCAGCAACAACCGAAAATGCACCAGCCC CAGGTCCTCGGACACCGAGGAGAATGTCAAGAGGCGAAC ACACAACGTCTTGGAGCGCCAGAGGAGGAACGAGCTAAA ACGGAGCTTTTTTGCCCTGCGTGACCAGATCCCGGAGTTG GAAAACAATGAAAAGGCCCCCAAGGTAGTTATCCTTAAA AAAGCCACAGCATACATCCTGTCCGTCCAAGCAGAGGAG CAAAAGCTCATTTCTGAAGAGGACTTGTTGCGGAAACGAC GAGAACAGTTGAAACACAAACTTGAACAGCTACGGAACT CTTGTGCG | 12 | Point mutation changing Serine to Alanine at amino acid 58 |

Additionally, the consistent and strong effects of KLF4 overexpression motivated the investigation of the full KLF zinc finger transcription factor family (FIG. 2F) as a demonstration of the utility of Applicants' technique in studying patterns of perturbation effects across gene families. A screen including all 17 members of the KLF family was conducted in pluripotent stem cell medium. Gene module analysis showed that KLF5 and KLF17 also have similar effects as KLF4 (FIG. 2G), which may reflect their similar role in promoting or maintaining epithelial cell states. On the other hand, unlike most of the KLF family, KLF13 and KLF16 fail to activate the cytoskeleton and motility module (FIG. 2G).

KLF Family Library

| GENE | SEQUENCE | SEQ ID NO: |
|---|---|---|
| KLF1 | ATGGCGACTGCGGAGACAGCACTTCCATCAATCTCAACACTCACTGCACTG GGGCCATTTCCAGATACCCAGGACGATTTCCTTAAGTGGTGGCGGTCCGAA GAGGCTCAAGACATGGGACCTGGTCCGCCGGATCCCACCGAACCTCCTCTG CATGTCAAAAGTGAAGATCAGCCTGGCGAGGAAGAGGATGACGAAAGGG GTGCCGACGCCACTTGGGACTTGGATCTTCTCCTTACCAATTTCTCTGGTCC GGAACCTGGCGGGGCACCACAGACGTGCGCTCTCGCTCCCTCAGAAGCGA GCGGGGCTCAGTACCCACCCCCTCCCGAAACTCTGGGAGCCTATGCTGGGG GTCCTGGACTGGTGGCTGGGTTGCTTGGTAGTGAGGACCATTCTGGCTGGG TACGCCCCGCTTTGAGGGCCCGCGCTCCGGACGCCTTTGTGGGACCGGCGC TCGCTCCTGCACCGGCTCCGGAACCAAAAGCCCTCGCGCTGCAGCCCGTGT ACCCCGGACCCGGAGCCGGATCCTCAGGGGGATACTTCCCACGGACCGGA CTCAGCGTTCCAGCGGCTTCCGGGGCGCCATACGGATTGTTGAGCGGCTAC CCGGCTATGTATCCCGCTCCCCAGTACCAAGGACACTTCCAATTGTTCCGG GGTCTTCAAGGGCCTGCGCCCGGGCCTGCTACCAGTCCCAGTTTCCTCAGT TGTCTGGGACCGGGAACTGTTGGCACTGGACTTGGCGGGACTGCAGAGGA CCCAGGCGTTATAGCAGAGACAGCGCCAAGTAAAAGGGGCCGACGAAGCT GGGCCAGGAAACGCCAAGCTGCGCACACTTGTGCCCATCCAGGTTGCGGT AAATCCTACACGAAGAGCAGTCATCTTAAAGCACATCTTCGCACACACAC GGGCGAGAAGCCCTACGCCTGTACTTGGGAAGGTTGCGGCTGGAGATTCG CTAGATCTGACGAGCTCACCCGGCATTATCGAAAACACACTGGCCAGCGA | 13 |

| GENE | SEQUENCE | SEQ ID NO: |
|---|---|---|
| | CCGTTCCGGTGCCAACTCTGCCCAAGGGCGTTCAGTCGCTCAGATCATCTG<br>GCTTTGCATATGAAGCGACACCTT | |
| KLF2 | ATGGCCCTTAGTGAACCCATTCTTCCCAGCTTTTCCACGTTCGCGTCTCCTT<br>GCCGAGAGAGAGGCCTTCAGGAAAGGTGGCCGAGGGCTGAACCCGAGTCT<br>GGAGGTACGGATGATGATCTTAACAGTGTGCTCGATTTCATACTCTCAATG<br>GGACTGGACGGGCTGGGAGCGGAGGCAGCTCCTGAACCACCACCACCCCC<br>TCCGCCCCAGCGTTTTACTACCCGGAGCCAGGTGCGCCGCCGCCATATTC<br>AGCCCCGGCGGGTGGCTTGGTGTCCGAGCTCCTCCGGCCTGAATTGGATGC<br>CCCGCTCGGCCCGGCGCTGCATGGTAGATTTCTGCTCGCGCCTCCGGGTCG<br>ACTCGTTAAGGCTGAACCTCCTGAGGCTGATGGTGGAGGTGGCTACGGAT<br>GTGCCCCCGGGCTTACCCGAGGACCGAGAGGTCTTAAGCGGGAAGGGGCA<br>CCTGGCCCGGCTGCAAGCTGTATGCGGGGCCCGGTGGGAGGCCTCCCCC<br>GCCCCCTGATACACCCCCCCTTAGTCCAGATGGACCAGCTCGACTTCCCGC<br>ACCTGGCCCCAGAGCGAGTTTCCCCCCTCCATTTGGAGGACCGGGGTTTGG<br>CGCCCCAGGTCCTGGACTTCACTACGCCCCTCCTGCCCCCCCAGCTTTTGGT<br>CTTTTCGACGATGCTGCTGCTGCCGCAGCAGCCTTGGGCCTTGCGCCGCCC<br>GCAGCCAGGGGACTGCTCACGCCACCGGCAAGCCCCTGGAGCTCCTTGA<br>AGCCAAGCCGAAGCGAGGACGCAGATCATGGCCGCGCAAGCGGACAGCT<br>ACGCATACCTGCTCATATGCGGGCTGCGGAAAAACCTACACAAAGAGTTC<br>ACACCTTAAAGCGCACCTCGCACACACACAGGCGAGAAACCATATCATT<br>GTAACTGGGACGGATGTGGATGGAAATTTGCTCGGTCTGATGAGCTTACGA<br>GACATTATCGAAAGCATACCGGACATCGGCCCTTTCAATGCCATCTTTGTG<br>ACAGAGCTTTTTCCCGGTCTGACCACCTCGCTCTGCACATGAAGAGGCACA<br>TG | 14 |
| KLF3 | ATGCTCATGTTTGACCCAGTTCCTGTCAAGCAAGAGGCCATGGACCCTGTC<br>TCAGTGTCATACCCATCTAATTACATGGAATCCATGAAGCCTAACAAGTAT<br>GGGGTCATCTACTCCACACCATTGCCTGAGAAGTTCTTTCAGACCCCAGAA<br>GGTCTGTCGCACGGAATACAGATGGAGCCAGTGGACCTCACGGTGAACAA<br>GCGGAGTTCACCCCCTTCGGCTGGGAATTCGCCCTCCTCTCTGAAGTTCCC<br>GTCCTCACACCGGAGAGCCTCGCCTGGGTTGAGCATGCCTTCTTCCAGCCC<br>ACCGATAAAAAAATACTCACCCCCTTCTCCAGGCGTGCAGCCCTTCGGCGT<br>GCCGCTGTCCATGCCACCAGTGATGGCAGCTGCCCTCTCGCGGCATGGAAT<br>ACGGAGCCCGGGGATCCTGCCCGTCATCCAGCCGGTGGTGGTGCAGCCCG<br>TCCCCTTTATGTACACAAGTCACCTCCAGCAGCCTCTCATGGTCTCCTTATC<br>GGAGGAGATGGAAAATTCCAGTAGTAGCATGCAAGTACCTGTAATTGAAT<br>CATATGAGAAGCCTATATCACAGAAAAAAATTAAAATAGAACCTGGGATC<br>GAACCACAGAGGACAGATTATTATCCTGAAGAAATGTCACCCCCCTTAATG<br>AACTCAGTGTCCCCCCCGCAAGCATTGTTGCAAGAGAATCACCCCTTCGGTC<br>ATCGTGCAGCCTGGGAAGAGACCTTTACCTGTGAATCCCCGGATACTCAA<br>AGGAAGCGGAGGATACACAGATGTGATTATGATGGATGCAACAAAGTGTA<br>CACTAAAAGCTCCCACTTGAAAGCACACAGAAGAACACACACAGGAGAAA<br>AACCCTACAAATGTACATGGGAAGGGTGCACATGGAAGTTTGCTCGGTCT<br>GATGAACTAACAAGACATTTCCGAAAACATACTGGAATCAAACCTTTCCA<br>GTGCCCGGACTGTGACCGCAGCTTCTCCCGTTCTGACCATCTTGCCCTCCAT<br>AGGAAACGCCACATGCTAGTC | 15 |
| KLF5 | ATGGCTACAAGGGTGCTGAGCATGAGCGCCCGCCTGGGACCCGTGCCCCA<br>GCCGCCGGCGCCGCAGGACGAGCCGGTGTTCGCGCAGCTCAAGCCGGTGC<br>TGGGCGCCGCGAATCCGGCCCGCGACGCGGCGCTCTTCCCCGGCGAGGAG<br>CTGAAGCACGCGCACCACCGCCCGCAGGCGCAGCCCGCGCCCGCAGGC<br>CCCGCAGCCGGCCCAGCCGCCCGCCACCGGCCCGCGGCTGCCTCCAGAGG<br>ACCTGGTCCAGACAAGATGTGAAATGGAGAAGTATCTGACACCTCAGCTT<br>CCTCCAGTTCCTATAATTCCAGAGCATAAAAAGTATAGACGAGACAGTGCC<br>TCAGTCGTAGACCAGTTCTTCACTGACACTGAAGGGGTTACCTTACAGTATC<br>AACATGAACGTCTTCCTCCCTGACATCACTCACCTGAGAACTGGCCTCTAC<br>AAATCCCAGAGACCGTGCGTAACACACATCAAGACAGAACCTGTTGCCAT<br>TTTCAGCCACCAGAGTGAAACGACTGCCCCTCCTCCGGCCCCGACCCAGGC<br>CCTCCCTGAGTTCACCAGTATATTCAGCTCACACCAGACCGCAGCTCCAGA<br>GGTGAACAATATTTTCATCAAACAAGAACTTCCTACACCAGATCTTCATCT<br>TTCTGTCCCTACCCAGCAGGGCCACCTGTACCAGCTACTGAATACACCGGA<br>TCTAGATATGCCCAGTTCTACAAATCAGACAGCAGCAATGGACACTCTTAA<br>TGTTTCTATGTCAGCTGCCATGGCAGGCCTTAACACACACACCTCTGCTGTT<br>CCGCAGACTGCAGTGAAACAATTCCAGGGCATGCCCCCTTGCACATACAC<br>AATGCCAAGTCAGTTTCTTCCACAACAGGCCACTTACTTTCCCCCGTCACC<br>ACCAAGCTCAGAGCCTGGAAGTCAGATAGACAAGCAGAGATGCTCCAGA<br>ATTTAACCCCACCTCCATCCTATGCTGCTACAATTGCTTCTAAACTGGCAAT<br>TCACAATCCAAATTTACCCACCACCCTGCCAGTTAACTCACAAAACATCCA<br>ACCTGTCAGATACAATAGAAGGAGTAACCCCGATTTGGAGAAACGACGCA<br>TCCACTACTGCGATTACCCTGGTTGCACAAAAGTTTATACCAAGTCTTCTC<br>ATTTAAAAGCTCACCTGAGGACTCACACTGGTGAAAAGCCATACAAGTGT<br>ACCTGGGAAGGCTGCGACTGGAGGTTCGCGCGATCGGATGAGCTGACCCG<br>CCACTACCGGAAGCACACAGGCGCCAAGCCCTTCCAGTGCGGGGTGTGCA<br>ACCGCAGCTTCTCGCGCTCTGACCACCTGGCCCTGCATATGAAGAGGCACC<br>AGAAC | 16 |

| GENE | SEQUENCE | SEQ ID NO: |
|---|---|---|
| KLF6 | ATGGACGTGCTCCCCATGTGCAGCATCTTCCAGGAGCTCCAGATCGTGCAC<br>GAGACCGGCTACTTCTCGGCGCTGCCGTCTCTGGAGGAGTACTGGCAACAG<br>ACCTGCCTAGAGCTGGAACGTTACCTCCAGAGCGAGCCCTGCTATGTTTCA<br>GCCTCAGAAATCAAATTTGACAGCCAGGAAGATCTGTGGACCAAAATCAT<br>TCTGGCTCGGGAGAAAAAGGAGGAATCCGAACTGAAGATATCTTCCAGTC<br>CTCCAGAGGACACTCTCATCAGCCCGAGCTTTTGTTACAACTTAGAGACCA<br>ACAGCCTGAACTCAGATGTCAGCAGCGAATCCTCTGACAGCTCCGAGGAA<br>CTTTCTCCCACGGCCAAGTTTACCTCCGACCCCATTGGCGAAGTTTTGGTCA<br>GCTCGGGAAATTGAGCTCCTCTGTCACCTCCACGCCTCCATCTTCTCCGG<br>AACTGAGCAGGGAACCTTCTCAACTGTGGGGTTGCGTGCCCGGGGAGCTG<br>CCCTCGCCAGGGAAGGTGCGCAGCGGGACTTCGGGGAAGCCAGGTGACAA<br>GGGAAATGGCGATGCCTCCCCCGACGGCAGGAGGAGGGTGCACCGGTGCC<br>ACTTTAACGGCTGCAGGAAAGTTTACACCAAAAGCTCCCACTTGAAAGCA<br>CACCAGCGGACGCACACAGGAGAAAAGCCTTACAGATGCTCATGGGAAGG<br>GTGTGAGTGGCGTTTTGCAAGAAGTGATGAGTTAACCAGGCACTTCCGAA<br>AGCACACCGGGGCCAAGCCTTTTAAATGCTCCCACTGTGACAGGTGTTTTT<br>CCAGGTCTGACCACCTGGCCCTGCACATGAAGAGGCACCTC | 17 |
| KLF7 | ATGGACGTGTTGGCTAGTTATAGTATATTCCAGGAGCTACAACTTGTCCAC<br>GACACCGGCTACTTCTCAGCTTTACCATCCCTGGAGGAGACCTGGCAGCAG<br>ACATGCCTTGAATTGGAACGCTACCTACAGACGGAGCCCCGGAGGATCTC<br>AGAGACCTTTGGTGAGGACTTGGACTGTTTCCTCCACGCTTCCCCTCCCCC<br>GTGCATTGAGGAAAGCTTCCGTCGCTTAGACCCCCTGCTGCTCCCCGTGGA<br>AGCGGCCATCTGTGAGAAGAGCTCGGCAGTGGACATCTTGCTCTCTCGGGA<br>CAAGTTGCTATCTGAGACCTGCCTCAGCCTCCAGCCGGCCAGCTCTTCTCT<br>AGACAGCTACACAGCCGTCAACCAGGCCCAGCTCAACGCAGTGACCTCAT<br>TAACGCCCCCATCGTCCCTGAGCTCAGCCGCCATCTGGTCAAAACCTCAC<br>AAACTCTCTCTGCCGTGGATGGCACGGTGACGTTGAAACTGGTGGCCAAG<br>AAGGCTGCTCTCAGCTCCGTAAAGGTGGGAGGGGTCGCAACAGCTGCAGC<br>AGCCGTGACGGCTGCGGGGGCCGTTAAGAGTGGACAGAGCGACAGTGACC<br>AAGGAGGGCTAGGGGCTGAAGCATGTCCCGAAAACAAGAAGAGGGTTCA<br>CCGCTGTCAGTTTAACGGGTGCCGGAAAGTTTATACAAAAAGCTCCCACTT<br>AAAGGCCCACCAGAGGACTCACACAGGTGAGAAGCCTTATAAGTGCTCAT<br>GGGAGGGATGTGAGTGGCGTTTTGCACGAAGCGATGAGCTCACGAGGCAC<br>TACAGGAAACACACAGGTGCAAAGCCCTTCAAATGCAACCACTGCGACAG<br>GTGTTTTTCCAGGTCTGACCATCTTGCCCTCCACATGAAGAGACATATC | 18 |
| KLF8 | ATGGTCGATATGGATAAACTCATAAACAACTTGGAGGTCCAACTTAATTCA<br>GAAGGTGGCTCAATGCAGGTATTCAAGCAGGTCACTGCTTCTGTTCGGAAC<br>AGAGATCCCCCTGAGATAGAATACAGAAGTAATATGACTTCTCCAACACTC<br>CTGGATGCCAACCCCATGGAGAACCCAGCACTGTTTAATGACATCAAGATT<br>GAGCCCCCAGAAGAACTTTTGGCTAGTGATTTCAGCCTGCCCCAAGTGGAA<br>CCAGTTGACCTCTCCTTTCACAAGCCCAAGGCTCCTCTCCAGCCTGCTAGC<br>ATGCTACAAGCTCCAATACGTCCCCCCAAGCCACAGTCTTCTCCCCAGACC<br>CTTGTGGTGTCCACGTCAACATCTGACATGAGCACTTCAGCAAACATTCCT<br>ACTGTTCTGACCCCAGGCTCTGTCCTGACCTCCTCTCAGAGCACTGGTAGC<br>CAGCAGATCTTACATGTCATTCACACTATCCCCTCAGTCAGTCTGCCAAAT<br>AAGATGGGTGGCCTGAAGACCATCCCAGTGGTAGTGCAGTCTCTGCCCATG<br>GTGTATACTACTTTGCCTGCAGATGGGGGCCCTGCAGCCATTACAGTCCCA<br>CTCATTGGAGGAGATGGTAAAAATGCTGGATCAGTGAAAGTTGACCCCAC<br>CTCCATGTCTCCACTGGAAATTCCAAGTGACAGTGAGGAGAGTACAATTGA<br>GAGTGGATCCTCAGCCTTGCAGAGTCTGCAGGGACTACAGCAAGAACCAG<br>CAGCAATGGCCCAAATGCAGGGAGAAGAGTCGCTTGACTTGAAGAGAAGA<br>CGGATTCACCAATGTGACTTTGCAGGATGCAGCAAAGTGTACACCAAAAG<br>CTCTCACCTGAAAGCTCACCGCAGAATCCATACAGGAGGAGAAGCCTTATA<br>AATGCACCTGGGATGGCTGCTCCTGGAAATTTGCTCGCTCAGATGAGCTCA<br>CTCGCCATTTCCGCAAGCACACAGGCATCAAGCCTTTTCGGTGCACAGACT<br>GCAACCGCAGCTTTTCTCGTTCTGACCACCTGTCCCTGCATCGCCGTCGCCA<br>TGACACCATG | 19 |
| KLF9 | ATGTCCGCGGCCGCCTACATGGACTTCGTGGCTGCCCAGTGTCTGGTTTCC<br>ATTTCGAACCGCGCTGCGGTGCCGGAGCATGGGTCGCTCCGGACGCCGA<br>GCGGCTGCGACTACCTGAGCGCGAGGTGACCAAGGAGCACGGTGACCCGG<br>GGGACACCTGGAAGGATTACTGCACACTGGTCACCATCGCCAAGAGCTTG<br>TTGGACCTGAACAAGTACCGACCCATCCAGACCCCCTCCGTGTGCAGCGAC<br>AGTCTGGAAAGTCCAGATGAGGATATGGGATCCGACAGCGACGTGACCAC<br>CGAATCTGGGTCGAGTCCTTCCCACAGCCCGGAGGAGACAGGATCCTG<br>GCAGCGCGCCCAGCCCGCTCTCCCTCCTCCATCCTGGAGTGGCTGCGAAGG<br>GGAAACACGCCTCCGAAAAGAGGCACAAGTGCCCCTACAGTGGCTGTGGG<br>AAAGTCTATGGAAAATCCTCCCATCTCAAAGCCCATTACAGAGTGCATACA<br>GGTGAACGGCCCTTTCCCTGCACGTGGCCAGACTGCCTTAAAAAGTTCTCC<br>CGCTCAGACGAGCTGACCCGCCACTACCGGACCCACACTGGGGAAAAGCA<br>GTTCCGCTGTCCGCTGTGTGAGAAGCGCTTCATGAGGAGTGACCACCTCAC<br>AAAGCACGCCCGGCGGCACACCGAGTTCCACCCCAGCATGATCAAGCGAT<br>CGAAAAAGGCGCTGGCCAACGCTTTG | 20 |

-continued

| GENE | SEQUENCE | SEQ ID NO: |
|---|---|---|
| KLF10 | ATGCTCAACTTCGGTGCCTCTCTCCAGCAGACTGCGGAGGAAAGAATGGA AATGATTTCTGAAAGGCCAAAAGAGAGTATGTATTCCTGGAACAAAACTG CAGAGAAAAGTGATTTTGAAGCTGTAGAAGCACTTATGTCAATGAGCTGC AGTTGGAAGTCTGATTTTAAGAAATACGTTGAAAACAGACCTGTTACACCA GTATCTGATTTGTCAGAGGAAGAGAATCTGCTTCCGGGAACACCTGATTTT CATACAATCCCAGCATTTTGTTTGACTCCACCTTACAGTCCTTCTGACTTTG AACCCTCTCAAGTGTCAAATCTGATGGCACCAGCGCCATCTACTGTACACT TCAAGTCACTCTCAGATACTGCCAAACCTCACATTGCCGCACCTTTCAAAG AGGAAGAAAAGAGCCCAGTATCTGCCCCCAAACTCCCCAAAGCTCAGGCA ACAAGTGTGATTCGTCATACAGCTGATGCCCAGCTATGTAACCACCAGACC TGCCCAATGAAAGCAGCCAGCATCCTCAACTATCAGAACAATTCTTTTAGA AGAAGAACCCACCTAAATGTTGAGGCTGCAAGAAAGAACATACCATGTGC CGCTGTGTCACCAAACAGATCCAAATGTGAGAGAAACACAGTGGCAGATG TTGATGAGAAAGCAAGTGCTGCACTTTATGACTTTTCTGTGCCTTCCTCAG AGACGGTCATCTGCAGGTCTCAGCCAGCCCCTGTGTCCCCACAACAGAAGT CAGTGTTGGTCTCTCCACCTGCAGTATCTGCAGGGGAGTGCCACCTATGC CGGTCATCTGCCAGATGGTTCCCCTTCCTGCCAACAACCCTGTTGTGACAA CAGTCGTTCCCAGCACTCCTCCCAGCCAGCCACCAGCCGTTTGCCCCCCTG TTGTGTTCATGGGCACACAAGTCCCCAAAGGCGCTGTCATGTTTGTGGTAC CCCAGCCCGTTGTGCAGAGTTCAAAGCCTCCGGTGGTGAGCCCGAATGGC ACCAGACTCTCTCCCATTGCCCCTGCTCCTGGGTTTTCCCCTTCAGCAGCAA AAGTCACTCCTCAGATTGATTCATCAAGGATAAGGAGTCACATCTGTAGCC ACCCAGGATGTGGCAAGACATACTTTAAAAGTTCCCATCTGAAGGCCCAC ACGAGGACGCACACAGGAGAAAAGCCTTTCAGCTGTAGCTGGAAAGGTTG TGAAAGGAGGTTTGCCCCGTTCTGATGAACTGTCCAGACACAGGCGAACCC ACACGGGTGAGAAGAAATTTGCGTGCCCCATGTGTGACCGGCGGTTCATG AGGAGTGACCATTTGACCAAGCATGCCCGGCGCCATCTATCAGCCAAGAA GCTACCAAACTGGCAGATGGAAGTGAGCAAGCTAAATGACATTGCTCTAC CTCCAACCCCTGCTCCCACACAG | 21 |
| KLF11 | ATGCATACTCCTGATTTCGCTGGACCTGACGACGCCCGAGCCGTGGACATT ATGGACATTTGTGAATCTATACTCGAAAGAAAGAGACATGATTCAGAGCG AAGTACATGCTCTATCCTCGAGCAAACAGACATGGAGGCGGTAGAAGCTC TGGTGTGCATGTCCAGTTGGGGTCAGAGATCCCAGAAGGGGGACTTGCTTA GAATCCGACCGCTTACTCCAGTTTCCGATAGCGGCGACGTAACAACTACTG TTCATATGGACGCAGCCACGCCTGAGCTGCCCAAAGACTTTCACAGCCTCT CAACTCTTTGCATCACTCCACCACAGTCCCCCGATCTTGTCGAACCATCAA CCCGGACCCCTGTTAGCCCGGCAAGTTACAGATTCAAAGGCGTGTACCGCGA CCGATGTTCTGCAGAGTTCAGCGGTTGTAGCGCGGGCATTGAGCGGAGGG GCTGAACGAGGTCTGTTGGGTCTTGAACCCGTACCGAGTTCTCCTTGTAGA GCCAAGGGTACTAGTGTTATTCGGCATACCGGCGAGAGTCCGGCAGCTTGT TTCCCCACCATACAAACCCCAGACTGTCGCCTTAGTGATTCCCGGGAAGGG GAGGAACAGCTGTTGGGCCACTTCGAGACACTTCAAGATACACACTTGAC AGATAGCTTGCTGTCCACCAACCTGGTGTCATGTCAACCTTGTTTGCACAA GTCCGGGGGTCTCCTTCTGACTGACAAAGGTCAACAAGCGGGATGGCCTG GCGCTGTCCAAACATGCAGTCCTAAAAACTACGAAAATGATTTGCCTAGG AAAACCACGCCGCTTATCAGTGTGAGTGTTCCCGCTCCACCTGTCCTGTGC CAGATGATCCCTGTAACCGGGCAATCATCTATGTTGCCTGCGTTCTTGAAG CCCCCCCCCACAACTGTCCGTTGGTACTGTTCGCCCGATCCTTGCGCAAGCA GCGCCCGCCCCGCAACCCGTGTTCGTGGGGCCCGCTGTCCCGCAGGGTGCA GTCATGTTGGTTCTTCCCCAGGGGGCCCTCCCGCCACCAGCTCCGTGTGCA GCGAATGTCATGGCTGCCGGAAACACGAATTGTTGCCCCTTGCACCCGCT CCAGTTTTCATAACGAGCTCACAGAATTGTGTGCCACAAGTCGACTTCTCA CGAAGACGGAACTATGTGTGCTCTTTCCCAGGTTGCAGAAAAACATATTTC AAATCCTCTCATCTGAAAGCACATCTTCGGACCCATACAGGAGAGAAGCCT TTTAATTGTAGCTGGGATGGCTGTGATAAAAAAATTCGCAAGAAGTGATGA GCTCAGTCGACATCGCAGGACGCATACCGGGGAAAAAAAATTCGTTTGTC CAGTTTGTGACAGAAGATTTATGAGGTCCGACCATCTCACCAAGCACGCGC GACGCCACATGACTACAAAGAAAATTCCTGGCTGGCAAGCCGAGGTGGGA AAACTCAACCGAATCGCTTCCGCTGAATCCCCCGGCAGCCCGCTGGTAAGT ATGCCTGCCAGTGCC | 22 |
| KLF12 | ATGAACATTCACATGAAGCGCAAGACGATAAAGAACATCAATACATTCGA GAACCGAATGTTGATGTTGGATGGCATGCCCGCTGTACGGGTAAAAACCG AGCTCCTGGAGTCTGAACAAGGATCCCCAAACGTCCACAACTACCCGGAT ATGGAGGCAGTGCCGCTCTTGCTCAACAATGTGAAGGGAGAGCCGCCTGA GGACTCTCTCTCCGTAGATCATTTCCAGACACAGACTGAGCCCGTAGATCT TTCAATTAACAAAGCCAGAACATCTCCTACTGCGGTAAGTTCTTCTCCCGT AAGTATGACAGCAAGTGCATCTAGTCCAAGTTCTACGAGCACTAGCAGTTC TTCATCTAGTAGACTTGCTAGTTCACCAACGGTGATCACAAGTGTTTCTAG CGCCAGCAGCAGCTCAACGGTACTGACTCCCGGTCCACTCGTGGCAAGCG CTAGTGGCGTGGGTGCCAACAATTTCTCCATATTATTCACCCCGTGCCTC CGTCTAGTCCGATGAATCTCCAGAGCAACAAGCTTAGTCACGTACATAGGA TCCCCGTCGTCGTCCAGTCAGTTCCCGTCGTCTACACAGCTGTGCGATCCCC TGGGAATGTCAATAATACTATAGTTGTTCCTTTGCTTGAGGATGGTAGGGG | 23 |

| GENE | SEQUENCE | SEQ ID NO: |
|---|---|---|
| | CCATGGGAAAGCACAGATGGACCCCCGCGGCTTGTCACCGAGACAGTCTA<br>AATCCGATAGTGACGACGATGATTTGCCTAACGTAACACTGGACTCTGTGA<br>ACGAGACCGGGAGTACCGCTCTGTCAATCGCTAGGGCCGTACAGGAGGTC<br>CACCCAAGCCCTGTGTCACGAGTCCGAGGTAACAGGATGAATAATCAGAA<br>ATTTCCCTGTAGCATCAGCCCATTTTCTATAGAGTCCACTCGGAGACAGCG<br>ACGAAGTGAATCACCCGACTCCAGAAAAAGGAGGATACATCGCTGTGACT<br>TTGAGGGCTGTAACAAGGTCTACACAAAAAGTTCACACCTCAAGGCGCAT<br>CGACGGACGCATACTGGGGAAAAACCGTACAAATGCACCTGGGAGGGATG<br>CACGTGGAAATTTGCACGCTCTGACGAGTTGACACGCCACTATCGAAAGC<br>ATACGGGCGTAAAGCCGTTTAAATGCGCTGATTGCGACAGGAGTTTTAGCC<br>GCTCTGATCACCTTGCTCTTCACCGGAGGCGACACATGCTTGTT | |
| KLF13 | ATGGCTGCGGCTGCATATGTGGATCATTTTGCGGCTGAGTGCCTGGTGTCA<br>ATGTCTAGTAGAGCGGTGGTACACGGTCCCAGAGAAGGCCCAGAATCACG<br>CCCAGAGGGCGCCGCCGTCGCTGCAACACCGACGCTGCCTCGGGTCGAGG<br>AGCGCCGCGACGGGAAGGACAGTGCGTCACTTTTCGTAGTAGCGAGAATA<br>TTGGCAGATCTGAATCAACAGGCTCCAGCACCTGCGCCCGCTGAACGCCG<br>GGAGGGCGCCGCTGCCAGAAAGGCCAGAACACCATGCCGCTTGCCGCCAC<br>CTGCGCCAGAACCCACAAGTCCAGGTGCCGAAGGTGCGGCGGCTGCCCCT<br>CCTTCACCGGCCTGGTCTGAACCAGAACCAGAGGCAGGTCTTGAACCTGA<br>GCGCGAACCCGGCCCTGCAGGCTCTGGGGAACCTGGCCTGAGGCAGCGGG<br>TGAGGCGCGGCCGGAGCAGGGCCGACCTGGAATCACCGCAAAGGAAACAT<br>AAATGCCATTATGCTGGTTGCGAAAAGGTTTATGGAAAGTCATCCCACCTG<br>AAAGCACACCTCCGCACTCACACGGGTGAGCGACCTTTTGCGTGTTCCTGG<br>CAAGACTGCAATAAAAAGTTTGCTAGATCTGATGAACTTGCACGGCATTAT<br>CGAACTCATACCGGTGAAAAGAAGTTCTCATGCCCTATATGTGAGAAACG<br>GTTCATGCGCTCTGACCACTTGACGAAACATGCAAGACGACATGCTAATTT<br>TCATCCGGGGATGTTGCAGAGACGGGGAGGGGGAAGTAGGACTGGAAGTC<br>TCTCCGACTATTCCCGATCCGACGCTTCCTCACCAACGATTAGCCCCGCAA<br>GCAGTCCC | 24 |
| KLF14 | ATGTCAGCCGCAGTCGCATGCCTTGATTACTTCGCGGCCGAGTGTCTTGTTT<br>CCATGTCAGCGGGGGCTGTCGTTCACAGAAGACCACCAGACCCGGAGGGA<br>GCGGGAGGGGCAGCTGGATCTGAAGTCGGCGCGGCTCCACCTGAATCAGC<br>GCTTCCCGGCCTGGTCCTCCAGGTCCCGCTAGCGTGCCCCAACTCCCACA<br>AGTGCCTGCTCCGAGTCCTGGAGCGGGCGGAGCAGCCCCGCATCTCCTTGC<br>AGCATCAGTGTGGGCCGATCTTCGCGGAAGCTCCGGGGAGGGCTCCTGGG<br>AAAACAGCGGAGAGGCCCCGCGAGCTTCAAGCGGCTTTTCCGATCCAATC<br>CCTTGCAGTGTTCAAACCCCATGCTCCGAGCTCGCGCCCGCGTCCGGAGCT<br>GCGGCAGTGTGCGCACCTGAAAGCTCATCCGATGCGCCGGCCGTTCCATCT<br>GCGCCAGCTGCTCCCGGTGCACCCGCAGCATCTGCGGCTTTAGTGGTGGA<br>GCTCTTGGGCGGGTCCCGCCCCTGCGGCGGATCAAGCTCCTCGCAGGCGC<br>AGTGTTACGCCCGCAGCAAAACGGCATCAATGCCCCTTTCCTGGTTGTACA<br>AAAGCATACTATAAGTCATCCCATCTCAAGAGTCACCGAGGACGCATAC<br>AGGTGAGAGACCTTTTAGCTGTGACTGGCTCGATTGCGACAAGAAATTTAC<br>GCGGAGCGACGAACTTGCGCGGCACTACCGCACTCACACTGGAGAAAAGA<br>GGTTCTCTTGTCCCCTGTGTCCCAAGCAGTTCTCACGCAGTGATCACTTGAC<br>AAAACATGCTAGGAGACATCCAACATACCATCCCGACATGATAGAGTATC<br>GAGGTAGGCGACGCACACCTAGAATTGATCCTCCGCTGACTAGTGAAGTC<br>GAGTCAAGTGCCAGTGGAAGCGGACCGGGTCCCGCGCCCTCATTTACAAC<br>CTGTCTT | 25 |
| KLF15 | ATGGTGGACCACTTACTTCCAGTGGACGAGAACTTCTCGTCGCCAAAATGC<br>CCAGTTGGGTATCTGGGTGATAGGCTGGTTGGCCGGCGGGCATATCACATG<br>CTGCCCTCACCCGTCTCTGAAGATGACAGCGATGCCTCCAGCCCCTGCTCC<br>TGTTCCAGTCCCGACTCTCAAGCCCTCTGCTCCTGCTATGGTGGAGGCCTG<br>GGCACCGAGAGCCAGGACAGCATCTTGGACTTCCTATTGTCCCAGGCCACG<br>CTGGGCAGTGGCGGGGGCAGCGGCAGTAGCATTGGGGCAGCAGTGGCCC<br>CGTGGCCTGGGGGCCCTGGCGAAGGGCAGCGGCCCCTGTGAAGGGGGAGC<br>ATTTCTGCTTGCCCGAGTTTCCTTTGGGTGATCCTGATGACGTCCCACGGCC<br>CTTCCAGCCTACCCTGGAGGAGATTGAAGAGTTTCTGGAGGAGAACATGG<br>AGCCTGGAGTCAAGGAGGTCCCTGAGGGCAACAGCAAGGACTTGGATGCC<br>TGCAGCCAGCTCTCAGCTGGGCCACACAAGAGCCACCTCCATCCTGGGTCC<br>AGCGGGAGAGAGCGCTGTTCCCCTCCACCAGGTGGTGCCAGTGCAGGAGG<br>TGCCCAGGGCCCAGGTGGGGCCCCACGCCTGATGGCCCCATCCCAGTGTT<br>GCTGCAGATCCAGCCCGTGCCTGTGAAGCAGGAATCGGGCACAGGGCCTG<br>CCTCCCCTGGGCAAGCCCCAGAGAATGTCAAGGTTGCCCAGCTCCTGGTCA<br>ACATCCAGGGGCAGACCTTCGCACTCGTGCCCCAGGTGGTACCCTCCTCCA<br>ACTTGAACCTGCCCCTCCAAGTTTGTGCGCATTGCCCCTGTGCCCATTGCCGC<br>CAAGCCTGTTGGATCGGGACCCCTGGGGCCTGGCCCTGCCGGTCTCTTCAT<br>GGGCCAGAAGTTCCCCAAGAACCCAGCCGCAGAACTCATCAAAATGCACA<br>AATGTACTTTCCCTGGCTGCAGCAAGATGTACACCAAAAGCAGCCACCTCA<br>AGGCCCACCTGCGCCGGCACACGGGTGAGAAGCCCTTCGCCTGCACCTGG<br>CCAGGCTGCGGCTGGAGGTTCTCGCGCTCTGACGAGCTGTCGCGGCACAG<br>GCGCTCGCACTCAGGTGTGAAGCCGTACCAGTGTCCTGTGTGCGAGAAGA<br>AGTTCGCGCGGAGCGACCACCTCTCCAAGCACATCAAGGTGCACCGCTTCC | 26 |

| GENE | SEQUENCE | SEQ ID NO: |
|---|---|---|
| | CGCGGAGCAGCCGCTCCGTGCGCTCCGTGAAC | |
| KLF16 | ATGTCAGCCGCGGTCGCGTGCGTGGATTATTTTGCAGCAGATGTGCTGATG<br>GCAATTTCATCCGGTGCAGTAGTTCATCGCGGAAGACCAGGTCCTGAGGGT<br>GCGGGGCCTGCGGCCGGGTTGGATGTTCGCGCCGCGCGCAGGGAAGCCGC<br>TTCTCCCGGAACACCTGGCCCTCCTCCTCCTCCGCCGGCGGCATCAGGCCC<br>GGGTCCTGGTGCAGCTGCGGCTCCTCACCTGTTGGCAGCCTCCATACTGGC<br>TGACCTGCGAGGGGGGCCAGGCGCTGCACCTGGTGGCGCGAGTCCAGCAA<br>GTTCCAGCTCCGCGGCGTCCTCCCCGAGTAGTGGGCGAGCTCCGGGCGCGG<br>CACCTTCTGCTGCCGCTAAATCACACCGATGCCCTTTCCCAGACTGCGCGA<br>AGGCGTATTATAAGTCCAGTCATTTGAAATCACACTTGAGGACACATACCG<br>GCGAGAGACCTTTTGCGTGCGACTGGCAGGGTTGTGATAAGAAATTTGCG<br>AGAAGCGACGAACTGGCCCGCCATCACCGCACCCACACAGGGGAAAAAA<br>GATTCTCATGCCCACTCTGTTCTAAGCGCTTCACGCGAAGCGACCATCTTG<br>CAAAGCACGCTAGGAGACACCCTGGGTTCCACCCCGACCTCTTGCGACGA<br>CCTGGCGCCCGGTCTACTAGCCCGTCTGACTCATTGCCGTGCTCTCTCGCA<br>GGGTCCCCTGCTCCGAGCCCCGCACCGTCCCCAGCTCCTGCCGGGCTT | 27 |
| KLF17 | ATGTACGGCCGACCGCAGGCTGAGATGGAACAGGAGGCTGGGGAGCTGAG<br>CCGGTGGCAGGCGGCGCACCAGGCTGCCCAGGATAACGAGAACTCAGCGC<br>CCATCTTGAACATGTCTTCATCTTCTGGAAGCTCTGGAGTGCACACCTCTTG<br>GAACCAAGGCCTACCAAGCATTCAGCACTTTCCTCACAGCGCAGAGATGCT<br>GGGGTCCCCTTTGGTGTCTGTTGAGGCGCCGGGGCAGAATGTGAATGAAG<br>GGGGGCCACAGTTCAGTATGCCACTGCCTGAGCGTGGTATGAGCTACTGCC<br>CCCAAGCGACTCTCACTCCTTCCCGGATGATTTACTGTCAGAGAATGTCTC<br>CCCCTCAGCAAGAGATGACGATTTTCAGTGGGCCCCAACTAATGCCCGTAG<br>GAGAGCCCAATATTCCAAGGGTAGCCAGGCCCTTCGGTGGGAATCTAAGG<br>ATGCCCCCCAATGGGCTGCCAGTCTCGGCTTCCACTGGAATCCCAATAATG<br>TCCCACACTGGGAACCCTCCAGTGCCTTACCCTGGCCTCTCGACAGTACCT<br>TCTGACGAAACATTGTTGGGCCCGACTGTGCCTTCCACTGAGGCCCAGGCA<br>GTGCTCCCCTCCATGGCTCAGATGTTGCCCCCGCAAGATGCCCATGACCTT<br>GGGATGCCCCCAGCTGAGTCCCAGTCATTGCTGGTTTTAGGATCTCAGGAC<br>TCTCTTGTCAGTCAGCCAGACTCTCAAGAAGGCCCATTTCTACCAGAGCAG<br>CCCGGACCTGCTCCACAGACAGTAGAGAAGAACTCCAGGCCTCAGGAAGG<br>GACTGGTAGAAGGGGCTCCTCAGAGGCAAGGCCTTACTGCTGCAACTACG<br>AGAACTGCGGAAAAGCTTATACCAAACGCTCCCACCTCGTGAGCCACCAG<br>CGCAAGCACACAGGTGAGAGGCCATATTCTTGCAACTGGGAAAGTTGTTC<br>ATGGTCTTTCTTCCGTTCTGATGAGCTTAGACGACATATGCGGGTACACAC<br>CAGATATCGACCATATAAATGTGATCAGTGCAGCCGGGAGTTCATGAGGT<br>CTGACCATCTCAAGCAACACCAGAAGACTCATCGGCCGGGACCCTCAGAC<br>CCACAGGCCAACAACAACAATGGAGAGCAGGACAGTCCTCCTGCTGCTGG<br>TCCT | 28 |

To further demonstrate the applicability of the network analysis to uncover novel phenomena, Applicants focused on two TFs, SNAI2 and KLF4, which seemed to have opposite effects on the pluripotency module. Since KLF4 and SNAI2 are known to play critical and opposing roles in epithelial-mesenchymal transition (EMT) Applicants assessed whether they cause changes along an EMT-like axis in hPSCs as well. A PCA analysis using 200 genes from a consensus EMT geneset from MSigDB demonstrated a distinct stratification of KLF4-transduced cells towards an epithelial-like state and SNAI2-transduced cells towards a mesenchymal-like state. The scRNA-seq data also demonstrates expression level changes in signature genes consistent with EMT (FIG. 3C), which Applicants confirmed with qRT-PCR (FIG. 9).

Finally, Applicants chose to focus on ETV2, which has the greatest average fitness loss across all medium conditions (FIG. 1B), as an exemplary case for investigation of a TF showing markedly reduced fitness in all medium conditions. Applicants hypothesized that the reduced fitness could be due to a proliferation disadvantage if ETV2-transduced cells are undergoing massive reprogramming without division. Focused experiments revealed that while ETV2-transduced cells undergo extensive cell death in pluripotent medium, there is a morphology change, indicative of an endothelial phenotype, in endothelial medium (FIG. 3E). Confirmatory qRT-PCR assays demonstrated a strong upregulation of the key endothelial markers CDH5, PECAM1 and VWF (FIG. 3F). Immunofluorescence revealed a distinct distribution of CDH5, with greater localization at cell-cell junctions (FIG. 3G), consistent with known results. In addition, functional testing confirmed tube formation (FIG. 3H), suggesting that a single TF, ETV2, may be able to drive reprogramming from a pluripotent to an endothelial-like state.

To Applicants' knowledge, this is the first demonstration of a high-throughput gene over-expression screening approach that can simultaneously assay both fitness and transcriptome-wide effects. Applicants' use of ORF overexpression drove strong phenotypic effects, allowing Applicants to capture subtle transcriptomic signals. Additionally, Applicants demonstrated the versatility of the SEUSS screening platform, by assaying mutant forms of a single TF, and assaying all the TFs in a gene family to uncover patterns and differences. Applicants note that the effects of gene overexpression are context dependent. In Applicants' assays, since hPSCs were transduced with pooled libraries, transcriptomic changes driven by cell-cell interactions could increase variability, even supporting the survival of certain cells or disrupting the pluripotent state of control cells. Applicants also assume, in aggregating multiple batches from independent experiments, that each batch is relatively similar. Additionally, while Applicants believe the gene co-perturbation network is a valuable resource, it is dependent on the set of perturbations and conditions used in the experiment.

Taken together, SEUSS has broad applicability to study the effects of overexpression in diverse cell types and contexts; it may be extended to novel applications such as high-throughput screening of large-scale protein mutagenesis, and is amenable to scale-up. In combination with other methods of genetic and epigenetic perturbation it may allow Applicants to generate a comprehensive understanding of the pluripotent and differentiation landscape.

Example 1 Methods

Cell Culture

H1 hESC cell line was maintained under feeder-free conditions in mTeSR1 medium (Stem Cell Technologies). Prior to passaging, tissue-culture plates were coated with growth factor-reduced Matrigel (Corning) diluted in DMEM/F-12 medium (Thermo Fisher Scientific) and incubated for 30 minutes at 37° C., 5% $CO_2$. Cells were dissociated and passaged using the dissociation reagent Versene (Thermo Fisher Scientific).

Library Preparation

A lentiviral backbone plasmid was constructed containing the EF1α promoter, mCherry transgene flanked by BamHI restriction sites, followed by a P2A peptide and hygromycin resistance enzyme gene immediately downstream. Each transcription factor in the library was individually inserted in place of the mCherry transgene. Since the ectopically expressed transcription factor would lack a poly-adenylation tail due to the presence of the 2A peptide immediately downstream of it, the transcript will not be captured during single-cell transcriptome sequencing which relies on binding the poly-adenylation tail of mRNA. Thus, a barcode sequence was introduced to allow for identification of the ectopically expressed transcription factor. The backbone was digested with HpaI, and a pool of 20 bp long barcodes with flanking sequences compatible with the HpaI site, was inserted immediately downstream of the hygromycin resistance gene by Gibson assembly. The vector was constructed such that the barcodes were located only 200 bp upstream of the 3'-LTR region. This design enabled the barcodes to be transcribed near the poly-adenylation tail of the transcripts and a high fraction of barcodes to be captured during sample processing for scRNA-seq.

To create the transcription factor library, individual transcription factors were PCR amplified out of a human cDNA pool (Promega Corporation) or obtained as synthesized double-stranded DNA fragments (gBlocks, IDT Inc) with flanking sequences compatible with the BamHI restriction sites. MYC mutants were obtained as gBlocks with a 6-amino acid GSGSGS linker (SEQ ID NO: 29) substituted in place of deleted domains (Table 1). The lentiviral backbone was digested with BamHI HF (New England Biolabs) at 37° C. for 3 hours in a reaction consisting of: lentiviral backbone, 4 µg, CutSmart buffer, 5 µl, BamHI, 0.625 µl, $H_2O$ up to 50 µl. After digestion, the vector was purified using a QIAquick PCR Purification Kit (Qiagen). Each transcription factor vector was then individually assembled via Gibson assembly. The Gibson assembly reactions were set up as follows: 100 ng digested lentiviral backbone, 3:10 molar ratio of transcription factor insert, 2× Gibson assembly master mix (New England Biolabs), $H_2O$ up to 20 µl. After incubation at 50° C. for 1 h, the product was transformed into One Shot Stbl3 chemically competent *Escherichia coli* (Invitrogen). A fraction (150 µL) of cultures was spread on carbenicillin (50 µg/ml) LB plates and incubated overnight at 37° C. Individual colonies were picked, introduced into 5 ml of carbenicillin (50 µg/ml) LB medium and incubated overnight in a shaker at 37° C. The plasmid DNA was then extracted with a QIAprep Spin Miniprep Kit (Qiagen), and Sanger sequenced to verify correct assembly of the vector and to extract barcode sequences.

To assemble the library, individual transcription factor vectors were pooled together in an equal mass ratio along with a control vector containing the mCherry transgene which constituted 10% of the final pool.

Viral Production

HEK 293T cells were maintained in high glucose DMEM supplemented with 10% fetal bovine serum (FBS). In order to produce lentivirus particles, cells were seeded in a 15 cm dish 1 day prior to transfection, such that they were 60-70% confluent at the time of transfection. For each 15 cm dish 36 µl of Lipofectamine 2000 (Life Technologies) was added to 1.5 ml of Opti-MEM (Life Technologies). Separately 3 µg of pMD2.G (Addgene no. 12259), 12 µg of pCMV delta R8.2 (Addgene no. 12263) and 9 µg of an individual vector or pooled vector library was added to 1.5 ml of Opti-MEM. After 5 minutes of incubation at room temperature, the Lipofectamine 2000 and DNA solutions were mixed and incubated at room temperature for 30 minutes. During the incubation period, medium in each 15 cm dish was replaced with 25 ml of fresh, pre-warmed medium. After the incubation period, the mixture was added dropwise to each dish of HEK 293T cells. Supernatant containing the viral particles was harvested after 48 and 72 hours, filtered with 0.45 µm filters (Steriflip, Millipore), and further concentrated using Amicon Ultra-15 centrifugal ultrafilters with a 100,000 NMWL cutoff (Millipore) to a final volume of 600-800 µl, divided into aliquots and frozen at −80° C.

Viral Transduction

For viral transduction, on day −1, H1 cells were dissociated to a single cell suspension using Accutase (Innovative Cell Technologies) and seeded into Matrigel-coated plates in mTeSR containing ROCK inhibitor, Y-27632 (10 µM, Sigma-Aldrich). For transduction with the TF library, cells were seeded into 10 cm dishes at a density of $6\times10^6$ cells for screens conducted in mTeSR or $4.5\times10^6$ cells for screens conducted in endothelial growth medium (EGM) or multi-lineage (ML) medium (DMEM+20% FBS.) For transduction with individual transcription factors cells were seeded at a density of $4\times10^5$ cells per well of a 12 well plate for experiments conducted in mTeSR or $3\times10^5$ cells per well for experiments conducted in the alternate media.

On day 0, medium was replaced with fresh mTeSR to allow cells to recover for 6-8 hours. Recovered cells were then transduced with lentivirus added to fresh mTeSR containing polybrene (5 µg/ml, Millipore). On day 1, medium was replaced with the appropriate fresh medium: mTeSR, endothelial growth medium or high glucose DMEM+20% FBS. Hygromycin (Thermo Fisher Scientific) selection was started from day 2 onward at a selection dose of 50 µg/ml, medium containing hygromycin was replaced daily.

Single Cell Library Preparation

For screens conducted in mTeSR cells were harvested 5 days after transduction while for alternate media, EGM or ML, cells were harvested 6 days after transduction with the TF library. Cells were dissociated to single cell suspensions using Accutase (Innovative Cell Technologies). For samples sorted with magnetically assisted cell sorting (MACS), cells were labelled with anti-TRA-1-60 antibodies or with dead cell removal microbeads and sorted as per manufacturer's instructions (Miltenyi Biotec). Samples were then resuspended in 1×PBS with 0.04% BSA at a concentration between 600-2000 per µl. Samples were loaded on the 10× Chromium system and processed as per manufacturer's instructions (10× Genomics). Unused cells were centrifuged at 300 rcf for 5 minutes and stored as pellets at −80° C. until extraction of genomic DNA.

Single cell libraries were prepared as per the manufacturer's instructions using the Single Cell 3' Reagent Kit v2 (10× Genomics). Prior to fragmentation, a fraction of the sample post-cDNA amplification was used to amplify the transcripts containing both the TF barcode and cell barcode.

Barcode Amplification

Barcodes were amplified from cDNA generated by the single cell system as well as from genomic DNA from cells not used for single cell sequencing. Barcodes were amplified from both types of samples and prepared for deep sequencing through a two-step PCR process.

For amplification of barcodes from cDNA, the first step was performed as three separate 50 µl reactions for each sample. 2 µl of the cDNA was input per reaction with Kapa Hifi Hotstart ReadyMix (Kapa Biosystems). The PCR primers used were, Nexterai7_TF_Barcode_F: GTCTCGTGGGCTCGGAGATGTGTATAAGA-GACAGAGAACTATTTCCTGGCTGTTACGCG (SEQ ID NO: 30) and NEBNext Universal PCR Primer for Illumina (New England Biolabs). The thermocycling parameters were 95° C. for 3 min; 26-28 cycles of 98° C. for 20 s; 65° C. for 15 s; and 72° C. for 30 s; and a final extension of 72° C. for 5 min. The numbers of cycles were tested to ensure that they fell within the linear phase of amplification. Amplicons (~500 bp) of 3 reactions for each sample were pooled, size-selected and purified with Agencourt AMPure XP beads at a 0.8 ratio. The second step of PCR was performed with two separate 50 µl reactions with 50 ng of first step purified PCR product per reaction. Nextera XT Index primers were used to attach Illumina adapters and indices to the samples. The thermocycling parameters were: 95° C. for 3 min; 6-8 cycles of (98° C. for 20 s; 65° C. for 15 s; 72° C. for 30 s); and 72° C. for 5 min. The amplicons from these two reactions for each sample were pooled, size-selected and purified with Agencourt AMPure XP beads at a 0.8 ratio. The purified second-step PCR library was quantified by Qubit dsDNA HS assay (Thermo Fisher Scientific) and used for downstream sequencing on an Illumina HiSeq platform.

For amplification of barcodes from genomic DNA, genomic DNA was extracted from stored cell pellets with a DNeasy Blood and Tissue Kit (Qiagen). The first step PCR was performed as three separate 50 µl reactions for each sample. 2 µg of genomic DNA was input per reaction with Kapa Hifi Hotstart ReadyMix. The PCR primers used were, NGS_TF-Barcode_F: ACACTCTTTCCCTA-CACGACGCTCTTCCGATCTAGAACTAT-TTCCTGGCTGTTACGCG (SEQ ID NO: 31) and NGS_TF-Barcode_R: GACTGGAGTTCA-GACGTGTGCTCTTCCGATCTTGTCTTCGTTGG-GAGTGAATTAGC (SEQ ID NO: 32). The thermocycling parameters were: 95° C. for 3 min; 26-28 cycles of 98° C. for 20 s; 55° C. for 15 s; and 72° C. for 30 s; and a final extension of 72° C. for 5 min. The numbers of cycles were tested to ensure that they fell within the linear phase of amplification. Amplicons (200 bp) of 3 reactions for each sample were pooled, size-selected with Agencourt AMPure XP beads (Beckman Coulter, Inc.) at a ratio of 0.8, and the supernatant from this was further size-selected and purified at a ratio of 1.6. The second step of PCR was performed as two separate 50 µl reactions with 50 ng of first step purified PCR product per reaction. Next Multiplex Oligos for Illumina (New England Biolabs) Index primers were used to attach Illumina adapters and indices to the samples. The thermocycling parameters were: 95° C. for 3 min; 6 cycles of (98° C. for 20 s; 65° C. for 20 s; 72° C. for 30 s); and 72° C. for 2 min. The amplicons from these two reactions for each sample were pooled, size-selected with Agencourt AMPure XP beads at a ratio of 0.8, and the supernatant from this was further size-selected and purified at a ratio of 1.6. The purified second-step PCR library was quantified by Qubit dsDNA HS assay (Thermo Fisher Scientific) and used for downstream sequencing on an Illumina MiSeq platform.

Single Cell RNA-Seq Processing and Genotype Deconvolution

Using the 10× genomics CellRanger pipeline [citation], Applicants aligned Fastq files to hg38, counted UMIs to generate counts matrices, and aggregated samples across 10× runs with cellranger aggr. All cellranger commands were run using default settings.

To assign one or more transcription factor genotypes to each cell, Applicants aligned the plasmid barcode reads to hg38 using BWA, and then labeled each read with its corresponding cell and UMI tags. To remove potential chimeric reads, Applicants used a two-step filtering process. First, Applicants only kept UMIs that made up at least 0.5% of the total amount of reads for each cell. Applicants then counted the number of UMIs and reads for each plasmid barcode within each cell, and only assigned that cell any barcode that contained at least 10% of the cell's read and UMI counts. Barcodes were mapped to transcription factors within one edit distance of the expected barcode. The code for assigning genotypes to each cell can be found on github at: github.com/yanwu2014/genotyping-matrices Clustering and Cluster Enrichment Clustering was performed on the aggregated counts matrices using the Seurat pipeline. Applicants first filtered the counts matrix for genes that are expressed in at least 2% of cells, and cells that express at least 500 genes. Applicants then normalized the counts matrix, found overdispersed genes, and used a negative binomial linear model to regress away library depth, batch effects, and mitochondrial gene fraction. Applicants performed PCA on the overdispersed genes, keeping the first 20 principal components. Applicants then used the PCs to generate a K Nearest Neighbors graph, with K=30, used the KNN graph to calculate a shared nearest neighbors graph, and used a modularity optimization algorithm on the SNN graph to find clusters. Clusters were recursively merged until all clusters could be distinguished from every other cluster with an out of the box error (oobe) of less than 5% using a random forest classifier trained on the top 15 genes by loading magnitude for the first 20 PCs. Applicants used tSNE on the first 20 PCs to visualize the results.

Cluster enrichment was performed using Fisher's exact test, testing each genotype for over-enrichment in each cluster. The p-value from the Fisher test for each genotype and cluster combination was corrected using the Benjamini-Hochberg method.

Differential Expression, Identification of Significant Genotypes, and Genotype Trimming Applicants used a modified version of the MIMOSCA linear model to analyze the differentially expressed genes for each genotype. In this model, Applicants used the R glmnet package with the multigaussian family, with alpha (the lasso vs ridge parameter) set to 0.5. Lambda (the coefficient magnitude regularization parameter) was set using 5-fold cross validation.

In order to account for unperturbed cells, Applicants "trimmed" the cells in each transcription factor genotype to only include cells that belonged to a cluster that the genotype was enriched for. Specifically, Applicants first obtained a set of transcription factor genotypes with strong cluster enrichment, such that each significantly enriched genotype was enriched for a cluster with an FDR>1e-6, and whose cluster enrichment profile was different from the control mCherry profile with an adjusted chi-squared p-value of less than 1e-6. For each significantly enriched genotype, Applicants only kept cells that were part of a cluster that the genotype was enriched for at FDR<0.01 level. Each genotype can be enriched for more than one cluster. After trimming the significantly enriched genotypes, Applicants repeated the differential expression.

TFs were chosen as significant for downstream analysis if they were enriched for one or more clusters as described, or if the TF drove statistically significant differential expression of greater than 100 genes.

Gene Co Perturbation Network and Module Detection

Applicants took the genes by genotypes coefficients matrix from the regression analysis with trimmed genotypes and used it to calculate the Euclidean distance between genes, using the significant genotypes as features. Applicants then built a k-nearest neighbors graph from the Euclidean distances between genes, with k=30. From this kNN graph, Applicants calculated the fraction of shared nearest neighbors (SNN) for each pair of genes to build and SNN graph. For example, if two genes share 23/30 neighbors, Applicants create an edge between them in the SNN graph with a weight of 23/30=0.767.

To identify gene modules, Applicants used the Louvain modularity optimization algorithm. For each gene module, Applicants identified enriched Gene Ontology terms using Fisher's exact test (Table 5). Applicants also ranked genes in each gene module by the number of enriched Gene Ontology terms the gene is part of, to identify the most biologically significant genes in each module (Table 5). Gene module identities were assigned based on manual inspection of enriched GO terms and the genes within each module. The effect of each genotype on a gene module was calculated by taking the average of the regression coefficients for the genotype and the genes within the module.

Dataset Correlation

To compare how the combined hPSC medium dataset correlated with the five individual datasets, Applicants correlated the regression coefficients of the combined dataset with the coefficients for each individual dataset, subsetting for coefficients that were statistically significant in either the individual dataset, or the combined dataset. Each coefficient represents the effect of a single TF on a single gene. The two datasets for the multilineage lineage screens were correlated in the same manner.

Fitness Effect Analysis

To calculate fitness effects from genomic DNA reads, Applicants first used MagECK to align reads to genotype barcodes and count the number of reads for each genotype in each sample, resulting in a genotypes by samples read counts matrix. Applicants normalized the read counts matrix by dividing each column by the sum of that column, and then calculated log fold-change by dividing each sample by the normalized plasmid library counts, and then taking a log 2 transform. For the stem cell media, Applicants averaged the log fold change across the non MACS sorted samples.

To calculate fitness effects from genotype counts identified from single cell RNA-seq, Applicants used a cell counts matrix instead of a read counts matrix, and repeated the above protocol.

Epithelial Mesenchymal Transition Analysis

Applicants took 200 genes from the Hallmark Epithelial Mesenchymal Transition geneset from MSigDB and ran PCA on those genes with the stem cell medium dataset, visualizing the first two principal components. The first principal component was an EMT-like signature and Applicants used the gene loadings, along with literature research to identify a relevant panel of EMT related genes to display. All analysis code can be found at github.com/yanwu2014/SEUSS-Analysis.

RNA Extraction, and qRT-PCR

RNA was extracted from cells using the RNeasy Mini Kit (Qiagen) as per the manufacturer's instructions. The quality and concentration of the RNA samples was measured using a spectrophotometer (Nanodrop 2000, Thermo Fisher Scientific). cDNA was prepared using the Protoscript II First Strand cDNA synthesis kit (New England Biolabs) in a 20 μl reaction and diluted up to 1:5 with nuclease-free water. qRT-PCR reactions were setup as: 2 μl cDNA, 400 nM of each primer, 2× Kapa SYBR Fast Master Mix (Kapa Biosystems), $H_2O$ up to 20 μl. qRT-PCR was performed using a CFX Connect Real Time PCR Detection System (Bio-Rad) with the thermocycling parameters: 95° C. for 3 min; 95° C. for 3 s; 60° C. for 20 s, for 40 cycles. All experiments were performed in triplicate and results were normalized against a housekeeping gene, GAPDH. Relative mRNA expression levels, compared with GAPDH, were determined by the comparative cycle threshold ($\Delta\Delta C_T$) method. Primers used for qRT-PCR are listed in Table 6.

Immunofluorescence

Cells were fixed with 4% (wt/vol) paraformaldehyde in PBS at room temperature for 30 minutes. Cells were then incubated with a blocking buffer: 5% donkey serum, 0.2% Triton X-100 in PBS for 1 hour at room temperature followed by incubation with primary antibodies diluted in the blocking buffer at 4° C. overnight. Primary antibodies used were: VE-Cadherin (D87F2, Cell Signaling Technology; 1:400). Secondary antibodies used were: DyLight 488 labelled donkey anti-rabbit IgG (ab96891, Abcam; 1:250).

After overnight incubation with primary antibodies, cells were labelled with secondary antibodies diluted in 1% BSA in PBS for 1 hour at 37° C. Nuclear staining was done by incubating cells with DAPI for 5 minutes at room temperature. All imaging was conducted on a Leica DMi8 inverted microscope equipped with an Andor Zyla sCMOS camera and a Lumencor Spectra X multi-wavelength fluorescence light source.

Endothelial Tube Formation Assay

A mCherry expressing H1 cell line was created by transducing H1 cells with a lentivirus containing the EF1α promoter driving expression of the mCherry transgene, internal ribosome entry site (IRES) and a puromycin resistance gene. Cells were then maintained under constant puromycin selection at a dose of 0.75 μg/ml. mCherry labelled H1 cells were transduced with either ETV2 lentivirus or control mCherry lentivirus, hygromycin selection was started on day 2 and cells were used for tube formation assay on day 6.

Growth-factor reduced Matrigel (Corning) was thawed on ice and 250 μl was deposited cold per well of a 24-well plate. The deposited Matrigel was incubated for 60 minutes at 37° C., 5% $CO_2$, to allow for complete gelation and the ETV2-transduced or control cells were then seeded on it at a density of 3.2×10⁵ cells per well in a volume of 500 µl EGM. Imaging was conducted 24 hours after deposition of the cells.

Example 2

Corneal Endothelial Stem Cell Transplant

Skin fibroblasts are isolated from a patient with a corneal eye disease. iPSCs are generated from the fibroblasts using techniques known in the art. Briefly, the isolated fibroblasts are reprogrammed by forced expression of one or more pluripotency genes selected from: OCT3/4, SOX1, SOX2, SOX15, SOX18, KLF1, KLF2, KLF4, KLF5, n-MYC, c-MYC, L-MYC, NANOG, LIN28, and GLIS1.

Next, the iPSCs are directed to differentiate into endothelial cells by introducing expression of ETV2. Expression is introduced by infecting the cells with an AAV virus encoding ETV2. After the cells differentiate into endothelial cells, they are expanded ex vivo and harvested.

The cells are administered to the patient by transplant to the cornea following removal of the diseased corneal tissue. After corneal transplant with the endothelial cells, repair of the cornea is identified by achieving full or partial restoration of corneal function in the patient.

TABLE 1

| GENE | SEQUENCE | SEQ ID NO: | ROLE | REFERENCES |
|---|---|---|---|---|
| mCherry Control | ATGGTGAGCAAGGGCGAGGAGGAT AACATGGCCATCATCAAGGAGTTC ATGCGCTTCAAGGTGCACATGGAG GGCTCCGTGAACGGCCACGAGTTC GAGATCGAGGGCGAGGGCGAGGGC CGCCCCTACGAGGGCACCCAGACC GCCAAGCTGAAGGTGACCAAGGGT GGCCCCCTGCCCTTCGCCTGGGACA TCCTGTCCCCTCAGTTCATGTACGG CTCCAAGGCCTACGTGAAGCACCC CGCCGACATCCCCGACTACTTGAAG CTGTCCTTCCCCGAGGGCTTCAAGT GGGAGCGCGTGATGAACTTCGAGG ACGGCGGCGTGGTGACCGTGACCC AGGACTCCTCCCTGCAGGACGGCG AGTTCATCTACAAGGTGAAGCTGC GCGGCACCAACTTCCCCTCCGACGG CCCCGTAATGCAGAAGAAGACCAT GGGCTGGGAGGCCTCCTCCGAGCG GATGTACCCCGAGGACGGCGCCCT GAAGGGCGAGATCAAGCAGAGGCT GAAGCTGAAGGACGGCGGCCACTA CGACGCTGAGGTCAAGACCACCTA CAAGGCCAAGAAGCCCGTGCAGCT GCCCGGCGCCTACAACGTCAACAT CAAGTTGGACATCACCTCCCACAAC GAGGACTACACCATCGTGGAACAG TACGAACGCGCCGAGGGCCGCCAC TCCACCGGCGGCATGGACGAGCTG TACAAG | 33 | Non-functional control vector | |
| ASCL1 | ATGGAGTCTTCTGCTAAAATGGAGT CCGGAGGCGCGGGACAACAACCAC AACCGCAACCACAACAACCCTTCCT GCCGCCGGCCGCATGTTTTTTCGCG ACCGCTGCTGCTGCTGCAGCGGCG GCGGCTGCTGCCGCCGCGCAATCC GCCCAACAGCAACAACAACAACAG CAGCAGCAGCAACAAGCGCCTCAA CTTCGACCCGCTGCAGACGGGCAG CCCTCAGGGGAGGGCACAAGAGC GCTCCGAAGCAGGTTAAAAGGCAG AGGAGCAGTAGTCCCGAACTGATG CGATGTAAGAGGCGCCTCAATTTTA GCGGTTTTGGTTACTCTTTGCCCCA GCAGCAGCCGGCTGCCGTAGCTCG CCGAAATGAGCGGGAAAGGAACCG CGTTAAACTTGTGAATCTCGGTTTC GCGACACTTCGAGAGCACGTACCA AATGGGGCAGCTAACAAGAAAATG AGTAAAGTTGAGACACTGCGGTCT GCAGTGGAGTATATTAGAGCTCTTC AACAATTGCTTGACGAGCACGATG CCGTATCAGCCGCATTTCAAGCCGG GGTGCTGTCCCCAACAATATCTCCG AACTACAGCAATGATCTTAATAGC ATGGCGGGAAGTCCCGTTTCCTCCT ACTCCTCTGATGAGGGCAGCTACG ACCCTCTCAGTCCCGAGGAGCAAG AGCTTCTTGACTTCACTAACTGGTT C | 34 | Involved in neuronal specification and differentiation. Demonstrated to drive neuronal differentiation from hPSCs | Wilkinson, G. et al. Proneural genes in neocortical development. Neuroscience 253, 256-273 (2013). Chanda, S. et al. Generation of induced neuronal cells by the single reprogramming factor ASCL1. Stem cell reports 3, 282-96 (2014). |

TABLE 1-continued

| GENE | SEQUENCE | SEQ ID NO: | ROLE | REFERENCES |
|---|---|---|---|---|
| ASCL3 | ATGATGGACAACAGAGGCAACTCT AGTCTACCTGACAAACTTCCTATCT TCCCTGATTCTGCCCGCTTGCCACT TACCAGGTCCTTCTATCTGGAGCCC ATGGTCACTTTCCACGTGCACCCAG AGGCCCCGGTGTCATCTCCTTACTC TGAGGAGCTGCCACGGCTGCCTTTT CCCAGCGACTCTCTTATCCTGGGAA ATTACAGTGAACCCTGCCCCTTCTC TTTCCCGATGCCTTATCCAAATTAC AGAGGGTGCGAGTACTCCTACGGG CCAGCCTTCACCCGGAAAAGGAAT GAGCGGGAAAGGCAGCGGGTGAAA TGTGTCAATGAAGGCTACGCCCAG CTCCGACATCATCTGCCAGAGGAGT ATTTGGAGAAGCGACTCAGCAAAG TGGAAACCCTCAGAGCTGCGATCA AGTACATTAACTACCTGCAGTCTCT TCTGTACCCTGATAAAGCTGAGACA AAGAATAACCCTGGAAAAGTTTCC TCCATGATAGCAACCACCAGCCAC CATGCTGACCCTATGTTCAGAATTG TTTGCCCAACTTTCTTGTACAAAGT TGTCCCC | 35 | Involved in salivary gland cell development | Bullard, T. et al. Ascl3 expression marks a progenitor population of both acinar and ductal cells in mouse salivary glands. Dev. Biol. 320, 72-78(2008) |
| ASCL4 | ATGGAGACGCGTAAACCGGCGAA CGGCTGGCCTTGCCATACTCGCTGC GCACCGCGCCCTGGGCGTTCCGG GGACCCTGCCCGGACTCCCGCGGA GGGACCCCCTCAGGGTCGCCCTGC GTCTGGACGCCGCGTGCTGGGAGT GGGCGCGCAGCGGCTGCGCACGGG GATGGCAGTACTTGCCCGTGCCGCT GGACAGCGCCTTCGAGCCCGCCTTC CTCCGCAAGCGCAACGAGCGCGAG CGGCAGCGGGTGCGCTGCGTGAAC GAGGGCTATGCGCGCCTCCGAGAC CACCTGCCCCGGGAGCTGGCAGAC AAGCGCCCTCAGCAAAGTGGAGACG CTCCGCGCTGCCATCGACTACATCA AGCACCTGCAGGAGCTGCTGGAGC GCCAGGCCTGGGGGCTCGAGGGCG CGGCCGGCGCCGTCCCCCAGCGCA GGGCGGAATGCAACAGCGACGGGG AGTCCAAGGCCTCTTCGGCGCCTTC GCCCAGCAGCGAGCCCGAGGAGGG GGGCAGC | 36 | Involved in development of skin | Jonsson, M. et al. Hash4, a novel human achaete-scute homologue found in fetal skin. Genomics 84, 859-866 (2004) |
| ASCL5 | ATGCCGATGGGGGCAGCAGAAAGA GGTGCTGGGCCCCAATCATCTGCAG CACCATGGGCTGGTTCAGAAAAGG CGGCAAAGAGAGGGCCATCAAAAA GCTGGTACCCAAGAGCTGCTGCATC TGATGTCACGTGCCCGACTGGTGGT GATGGAGCTGACCCAAAACCTGGA CCTTTTGGAGGTGGTTTAGCTTTAG GGCCTGCGCCCAGAGGAACAATGA ATAATAATTTCTGCAGGGCCCTTGT TGACAGAAGGCCTTTAGGACCCCCT TCATGTATGCAATTAGGTGTAATGC CACCGCCAAGACAAGCGCCCCTCC CGCCGGCTGAACCCCTTGGAAATGT ACCTTTCCTCCTATACCCTGGCCCA GCTGAACCACCATATTATGATGCAT ATGCTGGTGTTTTCCCATATGTGCC TTTCCCTGGTGCTTTTGGTGTATAT GAATACCCTTTTGAGCCGGCTTTTA TCCAAAAGAGGAATGAAAGAGAGA GACAGAGAGTGAAGTGTGTGAATG AAGGATACGCCAGATTGAGAGGCC ATTTGCCTGGTGCCCTGGCAGAAAA GAGATTATCAAAAGTTGAAACCCT GAGGGCGGCAATCAGATATATAAA ATACCTCCAAGAACTCCTTTCATCA GCACCTGATGGATCGACACCACCG GCTTCAAGAGGTTTACCTGGAACTG | 37 | Paralog of ASCL4 | Wang, C. et al. Systematic analysis of the achaete-scute complex-like gene signature in clinical cancer patients. Molecular and Clinical Oncology 6, (Spandidos Publications, 2017). |

TABLE 1-continued

| GENE | SEQUENCE | SEQ ID NO: | ROLE | REFERENCES |
|---|---|---|---|---|
| | GACCATGCCCTGCACCGCCTGCTAC ACCAAGGCCAGACAGACCTGGAGA TGGAGAAGCAAGAGCACCTTCTTC CCTTGTCCCTGAATCTTCTGAATCA TCATGTTTTTCGCCTTCCCCTTTTTT AGAAAGTGAAGAATCCTGGCA | | | |
| ATF7 | ATGGGAGACGACAGACCGTTTGTG TGCAATGCCCCGGGCTGTGGACAG AGATTTACAAACGAGGACCACCTG GCAGTTCATAAACACAAGCATGAG ATGACATTGAAATTTGGCCCAGCCC GAACTGACTCAGTCATCATTGCAGA TCAAACGCCTACTCCAACTAGATTC CTGAAGAACTGTGAGGAGGTGGGA CTCTTCAATGAACTAGCTAGCTCCT TTGAACATGAATTCAAGAAAGCTG CAGATGAGGATGAGAAAAAGGCAA GAAGCAGGACTGTTGCCAAAAAAC TGGTGGCTGCTGCTGGGCCCCTTGA CATGTCTCTGCCTTCCACACCAGAC ATCAAAATCAAAGAAGAAGAGCCA GTGGAGGTAGACTCATCCCCACCTG ATAGCCCTGCCTCTAGTCCCTGTTC CCCACCACTGAAGGAGAAGGAGGT TACCCCAAAGCCTGTTCTGATCTCT ACCCCCACACCCACCATTGTACGTC CTGGCTCCCTGCCTCTCCACTTGGG CTATGATCCACTTCATCCAACCCTT CCCTCCCCAACCTCTGTCATCACAC AGGCTCCACCATCCAACAGGCAAA TGGGGTCTCCCACTGGCTCCCTCCC TCTTGTCATGCATCTTGCTAATGGA CAGACCATGCCTGTGTTGCCAGGGC CTCCAGTACAGATGCCGTCTGTTAT ATCGCTGGCCAGACCTGTGTCCATG GTGCCCAACATTCCTGGTATCCCTG GCCCACCAGTTAACAGTAGTGGCTC CATTTCTCCCTCTGGCCACCCTATA CCATCAGAAGCCAAGATGAGACTG AAAGCCACCCTAACTCACCAAGTCT CCTCAATCAATGGTGGTTGTGGAAT GGTGGTGGGTACTGCCAGCACCAT GGTGACAGCCCGCCCAGAGCAGAG CCAGATTCTCATCCAGCACCCTGAT GCCCCATCCCCTGCCCAGCCACAG GTCTCACCAGCTCAGCCCACCCCTA GTACTGGGGGGCGACGGCGGCGCA CAGTAGATGAAGATCCAGATGAGC GACGGCAGCGCTTTCTGGAGCGCA ACCGGGCTGCAGCCTCCCGCTGCCG CCAAAAGCGAAAGCTGTGGGTGTC CTCCCTAGAGAAGAAGGCCGAAGA ACTCACTTCTCAGAACATTCAGCTG AGTAATGAAGTCACATTACTACGC AATGAGGTGGCCCAGTTGAAACAG CTACTGTTAGCTCATAAAGACTGCC CAGTCACTGCACTACAGAAAAAGA CTCAAGGCTATTTAGAAAGCCCCA AGGAAAGCTCAGAGCCAACGGGTT CTCCAGCCCCTGTGATTCAGCACAG CTCAGCAACAGCCCCTAGCAATGG CCTCAGTGTTCGCTCTGCAGCTGAA GCTGTGGCCACCTCGGTCCTCACTC AGATGGCCAGCAAAGGACAGAAC TGAGCATGCCGATACAATCGCATGT AATCATGACCCCACAGTCCCAGTCT GCGGGCAGA | 38 | Involved in early cell signaling, binds cAMP response element | Peters, C. S. et al. ATF-7, a novel bZIP protein, interacts with the PRL-1 protein-tyrosine phosphatase. J. Biol. Chem. 276, 13718-26 (2001). Hamard, P.-J. et al. A functional interaction between ATF7 and TAF12 that is modulated by TAF4. Oncogene 24, 3472-3483 (2005). |
| CDX2 | ATGTACGTGAGCTACCTCCTGGACA AGGACGTGAGCATGTACCCTAGCT CCGTGCGCCACTCTGGCGGCCTCAA CCTGGCGCCGCAGAACTTCGTCAGC CCCCCGCAGTACCCGGACTACGGC GGTTACCACGTGGCGGCCGCAGCT GCAGCGGCAGCGAACTTGGACAGC GCGCAGTCCCCGGGGCCATCCTGG | 39 | Involved in trophectoderm specification and differentiation | Strumpf, D. et al. Cdx2 is required for correct cell fate specification and differentiation |

TABLE 1-continued

| GENE | SEQUENCE | SEQ ID NO: | ROLE | REFERENCES |
|------|----------|------------|------|------------|
| | CCGGCAGCGTATGGCGCCCCACTCC GGGAGGACTGGAATGGCTACGCGC CCGGAGGCGCCGCGGCCGCCGCCA ACGCCGTGGCTCACGGCCTCAACG GTGGCTCCCCGGCCGCAGCCATGG GCTACAGCAGCCCCGCAGACTACC ATCCGCACCACCACCCGCATCACC ACCCGCACCACCCGGCCGCCGCGC CTTCCTGCGCTTCTGGGCTGCTGCA AACGCTCAACCCCGGCCCTCCTGGG CCCGCCGCCACCGCTGCCGCCGAG CAGCTGTCTCCCGGCGCCAGCGG CGGAACCTGTGCGAGTGGATGCGG AAGCCGGCGCAGCAGTCCCTCGGC AGCCAAGTGAAAACCAGGACGAAA GACAAATATCGAGTGGTGTACACG GACCACCAGCGGCTGGAGCTGGAG AAGGAGTTTCACTACAGTCGCTACA TCACCATCCGGAGGAAAGCCGAGC TAGCCGCCACGCTGGGGCTCTCTGA GAGGCAGGTTAAAATCTGGTTTCA GAACCGCAGAGCAAAGGAGAGGA AAATCAACAAGAAGAAGTTGCAGC AGCAACAGCAGCAGCAGCCACCAC AGCCGCCTCCGCCGCCACCACAGC CTCCCCAGCCTCAGCCAGGTCCTCT GAGAAGTGTCCCAGAGCCCTTGAG TCCGGTGTCTTCCCTGCAAGCCTCA GTGTCTGGCTCTGTCCCTGGGGTTC TGGGGCCAACTGGGGGGGTGCTAA ACCCCACCGTCACCCAG | | | of trophectoderm in the mouse blastocyst. Development 132, 2093-102 (2005). |
| CRX | ATGATGGCGTATATGAACCCGGGG CCCCACTATTCTGTCAACGCCTTGG CCCTAAGTGGCCCCAGTGTGGATCT GATGCACCAGGCTGTGCCCTACCCA AGCGCCCCCAGGAAGCAGCGGCGG GAGCGCACCACCTTCACCCGGAGC CAACTGGAGGAGCTGGAGGCACTG TTTGCCAAGACCCAGTACCCAGAC GTCTATGCCCGTGAGGAGGTGGCTC TGAAGATCAATCTGCCTGAGTCCAG GGTTCAGGTTTGGTTCAAGAACCGG AGGGCTAAATGCAGGCAGCAGCGA CAGCAGCAGAAACAGCAGCAGCAG CCCCCAGGGGGCCAGGCCAAGGCC CGGCCTGCCAAGAGGAAGGCGGGC ACGTCCCCAAGACCCTCCACAGAT GTGTGTCCAGACCCTCTGGGCATCT CAGATTCCTACAGTCCCCCTCTGCC CGGCCCCTCAGGCTCCCCAACCAC GGCAGTGGCCACTGTGTCCATCTGG AGCCCAGCCTCAGAGTCCCCTTTGC CTGAGGCGCAGCGGGCTGGGCTGG TGGCCTCAGGGCCGTCTCTGACCTC CGCCCCCTATGCCATGACCTACGCC CCGGCCTCCGCTTTCTGCTCTTCCC CCTCCGCCTATGGGTCTCCGAGCTC CTATTTCAGCGGCCTAGACCCCTAC CTTTCTCCCATGGTGCCCCAGCTAG GGGGCCCGGCTCTTAGCCCCCTCTC TGGCCCCTCCGTGGGACCTTCCCTG GCCCAGTCCCCCACCTCCCTATCAG GCCAGAGCTATGGCGCCTACAGCC CCGTGGATAGCTTGGAATTCAAGG ACCCCACGGGCACCTGGAAATTCA CCTACAATCCCATGGACCCTCTGGA CTACAAGGATCAGAGTGCCTGGAA GTTTCAGATCTTG | 40 | Involved in photoreceptor differentiation | Furukawa, T., Morrow, E. M. & Cepko, C. L. Crx, a novel otx-like homeobox gene, shows photoreceptor-specific expression and regulates photoreceptor differentiation. Cell 91, 531-541 (1997). |
| ERG | ATGGCCAGCACTATTAAGGAAGCC TTATCAGTTGTGAGTGAGGACCAGT CGTTGTTTGAGTGTGCCTACGGAAC GCCACACCTGGCTAAGACAGAGAT GACCGCGTCCTCCTCCAGCGACTAT GGACAGACTTCCAAGATGAGCCCA CGCGTCCCTCAGCAGGATTGGCTGT | 41 | Involved in endothelial cell specification and differentiation | Mclaughlin, F. et al. Combined genomic and antisense analysis reveals that |

TABLE 1-continued

| GENE | SEQUENCE | SEQ ID NO: | ROLE | REFERENCES |
|---|---|---|---|---|
| | CTCAACCCCCAGCCAGGGTCACCAT CAAAATGGAATGTAACCCTAGCCA GGTGAATGGCTCAAGGAACTCTCCT GATGAATGCAGTGTGGCCAAAGGC GGGAAGATGGTGGGCAGCCCAGAC ACCGTTGGGATGAACTACGGCAGC TACATGGAGGAGAAGCACATGCCA CCCCCAAACATGACCACGAACGAG CGCAGAGTTATCGTGCCAGCAGAT CCTACGCTATGGAGTACAGACCAT GTGCGGCAGTGGCTGGAGTGGGCG GTGAAAGAATATGGCCTTCCAGAC GTCAACATCTTGTTATTCCAGAACA TCGATGGGAAGGAACTGTGCAAGA TGACCAAGGACGACTTCCAGAGGC TCACCCCCAGCTACAATGCCGACAT CCTTCTCTCACATCTCCACTACCTC AGAGAGACTCCTCTTCCACATTTGA CTTCAGATGATGTTGATAAAGCCTT ACAAAACTCTCCACGGTTAATGCAT GCTAGAAACACAGGGGGTGCAGCT TTTATTTTCCCAAATACTTCAGTAT ATCCTGAAGCTACGCAAAGAATTA CAACTAGGCCAGATTTACCATATGA GCCCCCCAGGAGATCAGCCTGGAC CGGTCACGGCCACCCCACGCCCCA GTCGAAAGCTGCTCAACCATCTCCT TCCACAGTGCCCAAAACTGAAGAC CAGCGTCCTCAGTTAGATCCTTATC AGATTCTTGGACCAACAAGTAGCC GCCTTGCAAATCCAGGCAGTGGCC AGATCCAGCTTTGGCAGTTCCTCCT GGAGCTCCTGTCGGACAGCTCCAA CTCCAGCTGCATCACCTGGGAAGG CACCAACGGGGAGTTCAAGATGAC GGATCCCGACGAGGTGGCCCGGCG CTGGGGAGAGCGGAAGAGCAAACC CAACATGAACTACGATAAGCTCAG CCGCGCCCTCCGTTACTACTATGAC AAGAACATCATGACCAAGGTCCAT GGGAAGCGCTACGCCTACAAGTTC GACTTCCACGGGATCGCCCAGGCC CTCCAGCCCCACCCCCCGGAGTCAT CTCTGTACAAGTACCCCTCAGACCT CCCGTACATGGGCTCCTATCACGCC CACCCACAGAAGATGAACTTTGTG GCGCCCCACCCTCCAGCCCTCCCCG TGACATCTTCCAGTTTTTTTGCTGCC CCAAACCCATACTGGAATTCACCA ACTGGGGTATATACCCCAACACT AGGCTCCCCACCAGCCATATGCCTT CTCATCTGGGCACTTACTAC | | | |
| ESRRG | ATGTCAAACAAAGATCGACACATT GATTCCAGCTGTTCGTCCTTCATCA AGACGGAACCTTCCAGCCCAGCCT CCCTGACGGACAGCGTCAACCACC ACAGCCCTGGTGGCTCTTCAGACGC CAGTGGGAGCTACAGTTCAACCAT GAATGGCCATCAGAACGGACTTGA CTCGCCACCTCTCTACCCTTCTGCT CCTATCCTGGGAGGTAGTGGGCCTG TCAGGAAACTGTATGATGACTGCTC CAGCACCATTGTTGAAGATCCCCAG ACCAAGTGTGAATACATGCTCAACT CGATGCCCAAGAGACTGTGTTTAGT GTGTGGTGACATCGCTTCTGGGTAC CACTATGGGGTAGCATCATGTGAA GCCTGCAAGGCATTCTTCAAGAGG ACAATTCAAGGCAATATAGAATAC AGCTGCCCTGCCACGAATGAATGT GAAATCACAAAGCGCAGACGTAAA TCCTGCCAGGCTTGCCGCTTCATGA AGTGTTTAAAAGTGGGCATGCTGA AAGAAGGGGTGCGTCTTGACAGAG TACGTGGAGGTCGGCAGAAGTACA AGCGCAGGATAGATGCGGAGAACA | 42 | Involved in cardiac development | Alaynick, W. A. et al. ERRγ Directs and Maintains the Transition to Oxidative Metabolism in the Postnatal Heart. Cell Metab. 6, 13-24 (2007). |

TABLE 1-continued

| GENE | SEQUENCE | SEQ ID NO: | ROLE | REFERENCES |
|---|---|---|---|---|
| | GCCCATACCTGAACCCTCAGCTGGT<br>TCAGCCAGCCAAAAAGCCATTGCT<br>CTGGTCTGATCCTGCAGATAACAAG<br>ATTGTCTCACATTTGTTGGTGGCTG<br>AACCGGAGAAGATCTATGCCATGC<br>CTGACCCTACTGTCCCCGACAGTGA<br>CATCAAAGCCCTCACTACACTGTGT<br>GACTTGGCCGACCGAGAGTTGGTG<br>GTTATCATTGGATGGGCGAAGCAT<br>ATTCCAGGCTTCTCCACGCTGTCCC<br>TGGCGGACCAGATGAGCCTTCTGC<br>AGAGTGCTTGGATGGAAATTTTGAT<br>CCTTGGTGTCGTATACCGGTCTCTT<br>TCGTTTGAGGATGAACTTGTCTATG<br>CAGACGATTATATAATGGACGAAG<br>ACCAGTCCAAATTAGCAGGCCTTCT<br>TGATCTAAATAATGCTATCCTGCAG<br>CTGGTAAAGAAATACAAGAGCATG<br>AAGCTGGAAAAGAAGAATTTGTC<br>ACCCTCAAAGCTATAGCTCTTGCTA<br>ATTCAGACTCCATGCACATAGAAG<br>ATGTTGAAGCCGTTCAGAAGCTTCA<br>GGATGTCTTACATGAAGCGCTGCA<br>GGATTATGAAGCTGGCCAGCACAT<br>GGAAGACCCTCGTCGAGCTGGCAA<br>GATGCTGATGACACTGCCACTCCTG<br>AGGCAGACCTCTACCAAGGCCGTG<br>CAGCATTTCTACAACATCAAACTAG<br>AAGGCAAAGTCCCAATGCACAAAC<br>TTTTTTTGGAAATGTTGGAGGCCAA<br>GGTC | | | |
| ETV2 | ATGGATCTTTGGAACTGGGATGAA<br>GCTTCCCCTCAAGAAGTTCCCCCCG<br>GAAATAAACTCGCGGGGCTTGGAA<br>GACTCCCTCGCCTTCCGCAACGCGT<br>CTGGGGCGGATGCCCTGGTGGAGC<br>CTCAGCGGACCCAAACCCTTTGTCT<br>CCAGCGGAGGGGCAAAGTTGGGT<br>TTCTGCTTCCCGGATCTTGCTTTGC<br>AAGGCGATACTCCAACGGCGACGG<br>CAGAGACCTGTTGGAAAGGCACCA<br>GTAGCTCCCTGGCCAGCTTTCCGCA<br>GCTCGATTGGGGGTCAGCCCTTCTC<br>CATCCCGAAGTTCCCTGGGGGGCG<br>GAACCCGACTCCCAAGCCCTTCCCT<br>GGAGTGGTGATTGGACAGATATGG<br>CATGCACAGCCTGGGACAGTTGGT<br>CCGGGGCGTCACAGACATTGGGAC<br>CAGCCCCACTTGGACCGGGGCCTAT<br>CCCCGCAGCAGGAAGCGAAGGAGC<br>TGCTGGTCAGAACTGTGTGCCCGTG<br>GCTGGTGAGGCTACCAGTTGGTCCA<br>GGGCCCAGGCAGCAGGCAGTAACA<br>CCAGCTGGGATTGCTCAGTGGGGC<br>CTGACGGGGATACTTATTGGGGCTC<br>TGGTCTTGGTGGAGAACCGAGAAC<br>GGACTGTACGATAAGTTGGGGCGG<br>TCCAGCTGGGCCTGATTGTACTACG<br>TCATGGAATCCTGGCTTGCACGCCG<br>GCGGCACGACAAGCCTTAAGAGAT<br>ATCAAAGTTCAGCCCTTACAGTTTG<br>CTCAGAACCTTCCCCGCAAAGTGAC<br>CGAGCGTCACTGGCGCGATGTCCTA<br>AAACTAATCATCGAGGGCCGATCC<br>AGTTGTGGCAGTTTTTGCTTGAACT<br>CCTTCACGATGGCGCGAGGAGCAG<br>TTGCATCAGATGGACCGGTAACAG<br>CAGGGAGTTCCAATTGTGTGACCCC<br>AAGGAAGTGGCTCGACTGTGGGGT<br>GAGCGCAAACGGAAGCCTGGTATG<br>AATTACGAAAAGTTGAGTAGGGGT<br>TTGCGATATTACTATAGGCGCGACA | 43 | Involved in haemato-endothelial specification and differentiation, and in vasculogenesis | Lee, D. et al. ER71 acts downstream of BMP, Notch, and Wnt signaling in blood and vessel progenitor specification. Cell Stem Cell 2, 49-507 (2008). |

TABLE 1-continued

| GENE | SEQUENCE | SEQ ID NO: | ROLE | REFERENCES |
|---|---|---|---|---|
| | TCGTTCGAAAGTCCGGTGGTCGAA AGTACACATACAGATTCGGCGGTC GCGTACCATCTCTTGCATACCCTGA TTGCGCAGGCGGGGGTAGGGGTGC GGAAACACAA | | | |
| FLI1 | ATGGACGGGACTATTAAGGAGGCT CTGTCGGTGGTGAGCGACGACCAG TCCCTCTTTGACTCAGCGTACGGAG CGGCAGCCCATCTCCCCAAGGCCG ACATGACTGCCTCGGGGAGTCCTG ACTACGGGCAGCCCCACAAGATCA ACCCCCTCCCACCACAGCAGGAGT GGATCAATCAGCCAGTGAGGGTCA ACGTCAAGCGGGAGTATGACCACA TGAATGGATCCAGGGAGTCTCCGG TGGACTGCAGCGTTAGCAAATGCA GCAAGCTGGTGGGCGGAGGCGAGT CCAACCCCATGAACTACAACAGCT ATATGGACGAGAAGAATGGCCCCC CTCCTCCCAACATGACCACCAACGA GAGGAGAGTCATCGTCCCCGCAGA CCCCACACTGTGGACACAGGAGCA TGTGAGGCAATGGCTGGAGTGGGC CATAAAGGAGTACAGCTTGATGGA GATCGACACATCCTTTTTCCAGAAC ATGGATGGCAAGGAACTGTGTAAA ATGAACAAGGAGGACTTCCTCCGC GCCACCACCCTCTACAACACGGAA GTGCTGTTGTCACACCTCAGTTACC TCAGGGAAAGTTCACTGCTGGCCTA TAATACAACCTCCCACACCGACCA ATCCTCACGATTGAGTGTCAAAGA AGACCCTTCTTATGACTCAGTCAGA AGAGGAGCTTGGGGCAATAACATG AATTCTGGCCTCAACAAAAGTCCTC CCCTTGGAGGGGCACAAACGATCA GTAAGAATACAGAGCAACGGCCCC AGCCAGATCCGTATCAGATCCTGG GCCCGACCAGCAGTCGCCTAGCCA ACCCTGGAAGCGGGCAGATCCAGC TGTGGCAATTCCTCCTGGAGCTGCT CTCCGACAGCGCCAACGCCAGCTG TATCACCTGGGAGGGGACCAACGG GGAGTTCAAAATGACGGACCCCGA TGAGGTGGCCAGGCGCTGGGGCGA GCGGAAAAGCAAGCCCAACATGAA TTACGACAAGCTGAGCCGGGCCCT CCGTTATTACTATGATAAAAACATT ATGACCAAAGTGCACGGCAAAAGA TATGCTTACAAATTTGACTTCCACG GCATTGCCCAGGCTCTGCAGCCACA TCCGACCGAGTCGTCCATGTACAAG TACCCTTCTGACATCTCCTACATGC CTTCCTACCATGCCCACCAGCAGAA GGTGAACTTTGTCCCTCCCCATCCA TCCTCCATGCCTGTCACTTCCTCCA GCTTCTTTGGAGCCGCATCACAATA CTGGACCTCCCCCACGGGGGAAT CTACCCCAACCCCAACGTCCCCGC CATCCTAACACCCACGTGCCTTCAC ACTTAGGCAGCTACTAC | 44 | Involved in haemato-endothelial specification and differentiation | Liu, F. et al. Fli1 Acts at the Top of the Transcriptional Network Driving Blood and Endothelial Development. Curr. Biol. 18, 1234-1240 (2008). |
| FOXA1 | ATGTTGGGCACCGTGAGATGGAG GGGCATGAGACAAGCGACTGGAAT TCCTACTACGCGGATACCCAAGAA GCGTATTCTTCAGTTCCCGTAAGCA ATATGAACTCCGGATTGGGGACA TGAATAGTATGAACACGTATATGA CAATGAATACGATGACCACCAGCG GCAACATGACACCGGCCTCCTTTAA TATGTCATATGCGAACCCTGGTCTT GGCGCTGGCCTCTCACCAGGTGCG GTCGCTGGAATGCCCGGGGGAGC GCCGGAGCGATGAACTCCATGACC GCTGCGGGCGTGACGGCCATGGGT ACGGCCCTTGTCACCCAGTGGAATG | 45 | Involved in branching morphogenesis, development of lung, liver, prostate, and pancreas | Friedman, J. R. et al. The Foxa family of transcription factors in development and metabolism. Cell. Mol. Life Sci. 63, 2317-2328 (2006). |

| GENE | SEQUENCE | SEQ ID NO: | ROLE | REFERENCES |
|---|---|---|---|---|
| | GGCGCTGGCCTCTCACCAGGTGCG<br>GTCGCTGGAATGCCCGGGGGGAGC<br>GCCGGAGCGATGAACTCCATGACC<br>GCTGCGGGCGTGACGGCCATGGGT<br>ACGGCCCTGTCACCCAGTGGAATG<br>GGAGCTATGGGGGCCCAGCAAGCC<br>GCCTCAATGAATGGATTGGGGCCCT<br>ATGCCGCGGCGATGAATCCCTGCAT<br>GTCCCCTATGGCTTATGCCCCCAGC<br>AATTTGGGTCGCAGTAGAGCCGGC<br>GGTGGTGGCGATGCCAAAACCTTC<br>AAGCGAAGTTATCCTCATGCGAAG<br>CCTCCTTATTCATATATATCCTTGAT<br>TACGATGGCGATACAGCAGGCCCC<br>GTCTAAGATGCTGACTCTGAGTGAG<br>ATATACCAGTGGATCATGGACCTTT<br>TTCCTTACTACCGGCAAAACCAACA<br>GAGATGGCAAAACTCAATACGCCA<br>TAGCCTTTCCTTCAATGATTGCTTT<br>GTCAAAGTCGCTCGGAGCCCTGAC<br>AAGCCCGGTAAAGGGTCCTATTGG<br>ACCCTTCATCCAGATAGCGGCAATA<br>TGTTCGAGAATGGTTGTTATCTTAG<br>ACGGCAGAAACGATTCAAATGTGA<br>GAAACAGCCAGGTGCCGGCGGTGG<br>TGGCGGCAGCGGTTCAGGCGGAAG<br>TGGTGCCAAGGGTGGGCCTGAGTC<br>TAGAAAAGACCCCAGCGGAGCAAG<br>CAATCCAAGCGCGGACTCTCCCCTG<br>CACCGCGGTGTTCATGGTAAGACA<br>GGTCAGCTTGAGGGGGCGCCTGCT<br>CCAGGCCCGGCTGCGTCACCGCAA<br>ACACTGGACCATAGTGGAGCTACA<br>GCGACCGGAGGTGCTTCAGAACTC<br>AAGACGCCTGCGTCCTCCACTGCGC<br>CTCCGATCTCCAGTGGTCCCGGTGC<br>ACTTGCCTCTGTTCCTGCATCTCAT<br>CCAGCACACGGACTCGCGCCGCAC<br>GAGTCCCAGCTCCATTTGAAAGGG<br>GACCCACACTACAGCTTTAACCACC<br>CATTCTCTATTAACAATTTGATGTC<br>ATCCTCAGAACAGCAGCATAAACT<br>CGACTTCAAAGCCTATGAACAGGC<br>CCTGCAGTATTCTCCATATGGCTCT<br>ACACTTCCTGCTTCTCTTCCATTGG<br>GGTCTGCAAGTGTGACAACGCGCT<br>CCCCAATCGAGCCAAGTGCCCTCG<br>AGCCTGCTTATTATCAAGGAGTATA<br>TTCCCGACCAGTTTTGAATACAAGT | | | |
| FOXA2 | ATGCTGGGAGCGGTGAAGATGGAA<br>GGGCACGAGCCGTCCGACTGGAGC<br>AGCTACTATGCAGAGCCCGAGGGC<br>TACTCCTCCGTGAGCAACATGAACG<br>CCGGCCTGGGGATGAACGGCATGA<br>ACACGTACATGAGCATGTCGGCGG<br>CCGCCATGGGCAGCGGCTCGGGCA<br>ACATGAGCGCGGGCTCCATGAACA<br>TGTCGTCGTACGTGGGCGCTGGCAT<br>GAGCCCGTCCCTGGCGGGGATGTC<br>CCCCGGCGCGGGCGCCATGGCGGG<br>CATGGGCGGCTCGGCCGGGGCGGC<br>TGGCGTGGCGGGCATGGGGCCGCA<br>CTTGAGTCCCAGCCTGAGCCCGCTC<br>GGGGGGCAGGCGGCCGGGGCCATG<br>GGCGGCCTGGCCCCCTACGCCAAC<br>ATGAACTCCATGAGCCCCATGTACG<br>GGCAGGCGGGCCTGAGCCGCGCCC<br>GCGACCCCAAGACCTACAGGCGCA<br>GCTACACGCACGCAAAGCCGCCCT<br>ACTCGTACATCTCGCTCATCACCAT<br>GGCCATCCAGCAGAGCCCCAACAA<br>GATGCTGACGCTGAGCGAGATCTA<br>CCAGTGGATCATGGACCTCTTCCCC<br>TTCTACCGGCAGAACCAGCAGCGC<br>TGGCAGAACTCCATCCGCCACTCGC<br>TCTCCTTCAACGACTGTTTCCTGAA | 46 | Involved in branching morphogenesis, development of notochord, lung, liver, prostate, and pancreas. | Friedman, J. R. et al. The Foxa family of transcription factors in development and metabolism. Cell. Mol. Life Sci. 63, 2317-2328 (2006). |

TABLE 1-continued

| GENE | SEQUENCE | SEQ ID NO: | ROLE | REFERENCES |
|---|---|---|---|---|
| | GGTGCCCCGCTCGCCCGACAAGCC CGGCAAGGGCTCCTTCTGGACCCTG CACCCTGACTCGGGCAACATGTTCG AGAACGGCTGCTACCTGCGCCGCC AGAAGCGCTTCAAGTGCGAGAAGC AGCTGGCGCTGAAGGAGGCCGCAG GCGCCGCCGGCAGCGGCAAGAAGG CGGCCGCCGGGGCCCAGGCCTCAC AGGCTCAACTCGGGGAGGCCGCCG GGCCGGCCTCCGAGACTCCGGCGG GCACCGAGTCGCCTCACTCGAGCG CCTCCCCGTGCCAGGAGCACAAGC GAGGGGGCCTGGGAGAGCTGAAGG GGACGCCGGCTGCGGCGCTGAGCC CCCCAGAGCCGGCGCCCTCTCCCG GGCAGCAGCAGCAGGCCGCGGCCC ACCTGCTGGGCCCGCCCCACCACCC GGGCCTGCCGCCTGAGGCCCACCT GAAGCCGGAACACCACTACGCCTT CAACCACCCGTTCTCCATCAACAAC CTCATGTCCTCGGAGCAGCAGCACC ACCACAGCCACCACCACCACCAGC CCCACAAAATGGACCTCAAGGCCT ACGAACAGGTGATGCACTACCCCG GCTACGGTTCCCCCATGCCTGGCAG CTTGGCCATGGGCCCGGTCACGAA CAAAACGGGCCTGGACGCCTCGCC CCTGGCCGCAGATACCTCCTACTAC CAGGGGGTGTACTCCCGGCCCATTA TGAACTCCTCTTTG | | | |
| FOXA3 | ATGCTGGGCTCAGTGAAGATGGAG GCCCATGACCTGGCCGAGTGGAGC TACTACCCGGAGGCGGGCGAGGTC TACTCGCCGGTGACCCCAGTGCCCA CCATGGCCCCCCTCAACTCCTACAT GACCCTGAATCCTCTAAGCTCTCCC TATCCCCCTGGGGGGCTCCCTGCCT CCCCACTGCCCTCAGGACCCCTGGC ACCCCCAGCACCTGCAGCCCCCCTG GGGCCCACTTTCCCAGGCCTGGGTG TCAGCGGTGGCAGCAGCAGCTCCG GGTACGGGGCCCCGGGTCCTGGGC TGGTGCACGGGAAGGAGATGCCGA AGGGGTATCGGCGGCCCCTGGCAC ACGCCAAGCCACCGTATTCCTATAT CTCACTCATCACCATGGCCATCCAG CAGGCGCCGGGCAAGATGCTGACC TTGAGTGAAATCTACCAGTGGATCA TGGACCTCTTCCCTTACTACCGGGA GAATCAGCAGCGCTGGCAGAACTC CATTCGCCACTCGCTGTCTTTCAAC GACTGCTTCGTCAAGGTGGCGCGTT CCCCAGACAAGCCTGGCAAGGGCT CCTACTGGGCCCTACACCCCAGCTC AGGGAACATGTTTGAGAATGGCTG CTACCTGCGCCGCCAGAAACGCTTC AAGCTGGAGGAGAAGGTGAAAAAA GGGGCAGCGGGGCTGCCACCACC ACCAGGAACGGGACAGGGTCTGCT GCCTCGACCACCACCCCCGCGGCC ACAGTCACCTCCCCGCCCCAGCCCC CGCCTCCAGCCCCTGAGCCTGAGGC CCAGGGCGGGAAGATGTGGGGGC TCTGGACTGTGGCTCACCCGCTTCC TCCACACCCTATTTCACTGGCCTGG AGCTCCAGGGGAGCTGAAGCTGG ACGCGCCCTACAACTTCAACCACCC TTTCTCCATCAACAACCTAATGTCA GAACAGACACCAGCACCTCCCAAA CTGGACGTGGGGTTTGGGGGCTAC GGGGCTGAAGGTGGGGAGCCTGGA GTCTACTACCAGGGCCTCTATTCCC GCTCTTTGCTTAATGCATCC | 47 | Involved in cell glucose homeostasis | Friedman, J. R. et al. The Foxa family of transcription factors in development and metabolism. Cell. Mol. Life Sci. 63, 2317-2328 (2006). |

TABLE 1-continued

| GENE | SEQUENCE | SEQ ID NO: | ROLE | REFERENCES |
|---|---|---|---|---|
| FOXP1 | ATGATGCAAGAATCTGGGACTGAG ACAAAAAGTAACGGTTCAGCCATC CAGAATGGGTCGGGCGGCAGCAAC CACTTACTAGAGTGCGGCGGTCTTC GGGAGGGGCGGTCCAACGGAGAGA CGCCGGCCGTGGACATCGGGGCAG CTGACCTCGCCCACGCCCAGCAGC AGCAGCAACAGTGGCATCTCATAA ACCATCAGCCCTCTAGGAGTCCCAG CAGTTGGCTTAAGAGACTAATTTCA AGCCCTTGGGAGTTGGAAGTCCTGC AGGTCCCCTTGTGGGGAGCAGTTGC TGAGACGAAGATGAGTGGACCTGT GTGTCAGCCTAACCCTTCCCCATTT | 48 | Involved in development of haematopoetic cells, lung and oesophagus, and neuronal development | Hu, H. et al. Foxp1 is an essential transcriptional regulator of B cell development. Nat. Immunol. 7, 819-826 (2006). Shu, W. et al. Foxp2 and Foxp1 cooperatively regulate lung and esophagus development. Development 134, 1991-2000 (2007). Bacon, C. et al. Brain-specific Foxp1 deletion impairs neuronal development and causes autistic-like behaviour. Mol. Psychiatry 20, 632-639 (2015). |
| GATA1 | ATGGAGTTCCCTGGCCTGGGGTCCC TGGGGACCTCAGAGCCCCTCCCCCA GTTTGTGGATCCTGCTCTGGTGTCC TCCACACCAGAATCAGGGGTTTTCT TCCCCTCTGGGCCTGAGGGCTTGGA TGCAGCAGCTTCCTCCACTGCCCCG AGCACAGCCACCGCTGCAGCTGCG GCACTGGCCTACTACAGGGACGCT GAGGCCTACAGACACTCCCCAGTCT TTCAGGTGTACCCATTGCTCAACTG TATGGAGGGGATCCCAGGGGGCTC ACCATATGCCGGCTGGGCCTACGG CAAGACGGGGCTCTACCCTGCCTCA ACTGTGTGTCCCACCCGCGAGGACT CTCCTCCCCAGGCCGTGGAAGATCT GGATGGAAAAGGCAGCACCAGCTT CCTGGAGACTTTGAAGACAGAGCG GCTGAGCCCAGACCTCCTGACCCTG GGACCTGCACTGCCTTCATCACTCC CTGTCCCCAATAGTGCTTATGGGGG CCCTGACTTTTCCAGTACCTTCTTTT CTCCCACCGGGAGCCCCCTCAATTC AGCAGCCTATTCCTCTCCCAAGCTT CGTGGAACTCTCCCCCTGCCTCCCT GTGAGGCCAGGGAGTGTGTGAACT GCGGAGCAACAGCCACTCCACTGT GGCGGAGGGACAGGACAGGCCACT ACCTATGCAACGCCTGCGGCCTCTA TCACAAGATGAATGGGCAGAACAG GCCCCTCATCCGGCCCAAGAAGCG CCTGATTGTCAGTAAACGGGCAGG TACTCAGTGCACCAACTGCCAGAC GACCACCACGACACTGTGGCGGAG AAATGCCAGTGGGGATCCCGTGTG CAATGCCTGCGGCCTCTACTACAAG CTACACCACCAGCACTACTGTGGTG GCTCCGCTCAGCTCATGAGGGCAC AGAGCATGGCCTCCAGAGGAGGGG | 49 | Involved in erythroid development | Fujiwara, Y., Browne, C. P., Cunniff, K., Goff, S. C. & Orkin, S. H. Arrested development of embryonic red cell precursors in mouse embryos lacking transcription factor GATA-1. PNAS 93, 12355-12358 (1996). |

TABLE 1-continued

| GENE | SEQUENCE | SEQ ID NO: | ROLE | REFERENCES |
|---|---|---|---|---|
| | TGGTGTCCTTCTCCTCTTGTAGCCA GAATTCTGGACAACCCAAGTCTCTG GGCCCCAGGCACCCCCTGGCT | | | |
| GATA2 | ATGGAGGTGGCGCCGGAGCAGCCG CGCTGGATGGCGCACCCGGCCGTG CTGAATGCGCAGCACCCCGACTCA CACCACCCGGGCCTGGCGCACAAC TACATGGAACCCGCGCAGCTGCTG CCTCCAGACGAGGTGGACGTCTTCT TCAATCACCTCGACTCGCAGGGCA ACCCCTACTATGCCAACCCCGCTCA CGCGCGGGCGCGCGTCTCCTACAG CCCCGCGCACGCCCGCCTGACCGG AGGCCAGATGTGCCGCCCACACTT GTTGCACAGCCCGGGTTTGCCCTGG CTGGACGGGGGCAAAGCAGCCCTC TCTGCCGCTGCGGCCCACCACCACA ACCCCTGGACCGTGAGCCCCTTCTC CAAGACGCCACTGCACCCCTCAGCT GCTGGAGGCCCTGGAGGCCCACTC TCTGTGTACCCAGGGGCTGGGGGT GGGAGCGGGGGAGGCAGCGGGAG CTCAGTGGCCTCCCTCACCCCTACA GCAACCCACTCTGGCTCCCACCTTT TCGGCTTCCCACCCACGCCACCCAA AGAAGTGTCTCCTGACCCTAGCACC ACGGGGGCTGCGTCTCCAGCCTCAT CTTCCGCGGGGGTAGTGCAGCCC GAGGAGAGGACAAGGACGGCGTCA AGTACCAGGTGTCACTGACGGAGA GCATGAAGATGGAAAGTGGCAGTC CCCTGCGCCCAGGCCTAGCTACTAT GGGCACCCAGCCTGCTACACACCA CCCCATCCCCACCTACCCCTCCTAT GTGCCGGCGGCTGCCCACGACTAC AGCAGCGGACTCTTCCACCCCGGA GGCTTCCTGGGGGGACCGGCCTCC AGCTTCACCCCTAAGCAGCGCAGC AAGGCTCGTTCCTGTTCAGAAGGCC GGGAGTGTGTCAACTGTGGGGCCA CAGCCACCCCTCTCTGGCGGCGGG ACGGCACCGGCCACTACCTGTGCA ATGCCTGTGGCCTCTACCACAAGAT GAATGGGCAGAACCGACCACTCAT CAAGCCCAAGCGAAGACTGTCGGC CGCCAGAAGAGCCGGCACCTGTTG TGCAAATTGTCAGACGACAACCAC CACCTTATGGCGCCGAAACGCCAA CGGGGACCCTGTCTGCAACGCCTGT GGCCTCTACTACAAGCTGCACAATG TTAACAGGCCACTGACCATGAAGA AGGAAGGGATCCAGACTCGGAACC GGAAGATGTCCAACAAGTCCAAGA AGAGCAAGAAAGGGCGGAGTGCT TCGAGGAGCTGTCAAAGTGCATGC AGGAGAAGTCATCCCCCTTCAGTGC AGCTGCCCTGGCTGGACACATGGC ACCTGTGGGCCACCTCCCGCCCTTC AGCCACTCCGGACACATCCTGCCCA CTCCGACGCCCATCCACCCCTCCTC CAGCCTCTCCTTCGGCCACCCCCAC CCGTCCAGCATGGTGACCGCCATG GGC | 50 | Involved in haematopoetic development | Pimanda, J. E. et al. Gata2, Fli1, and Scl form a recursively wired gene-regulatory circuit during early hematopoietic development. Proc. Natl. Acad. Sci. U. S. A. 104, 17692-7 (2007). Lugus, J. J. et al. GATA2 functions at multiple steps in hemangioblast development and differentiation. Development 134, 393-405 (2007). |
| GATA4 | ATGTACCAGAGCCTGGCTATGGCTG CTAATCATGGACCTCCCCCTGGAGC CTATGAAGCCGGAGGACCTGGCGC TTTTATGCATGGAGCTGGCGCCGCT TCTTCTCCCGTGTATGTGCCTACAC CTAGAGTGCCCAGCAGCGTGCTGG GCCTTTCTTATCTTCAGGGAGGAGG AGCAGGATCTGCTTCTGGCGGAGCT TCAGGCGGATCTTCTGGAGGCGCTG CTTCAGGTGCTGGACCTGGAACTCA ACAGGGATCTCCTGGATGGTCACA GGCAGGAGCTGATGGAGCCGCTTA | 51 | Involved in cardiovascular development | Xin, M. et al. A threshold of GATA4 and GATA6 expression is required for cardiovascular development. Proc. Natl. Acad. Sci. U. S. A. 103, 11189-94 |

TABLE 1-continued

| GENE | SEQUENCE | SEQ ID NO: | ROLE | REFERENCES |
|---|---|---|---|---|
| | TACCCCTCCTCCTGTGAGCCCCAGG<br>TTTAGCTTTCCTGGCACAACAGGCT<br>CTTTAGCTGCCGCTGCTGCTGCAGC<br>CGCAGCTAGAGAAGCAGCTGCATA<br>TTCTAGTGGCGGAGGAGCTGCTGG<br>AGCCGGCTTAGCTGGAAGAGAGCA<br>GTACGGAAGAGCCGGATTTGCCGG<br>AAGCTATAGCAGCCCTTACCCTGCC<br>TATATGGCCGATGTTGGCGCATCTT<br>GGGCAGCCGCCGCAGCAGCTTCTG<br>CAGGACCTTTTGACTCACCTGTGCT<br>TCACTCTCTGCCTGGCAGAGCTAAT<br>CCTGCCGCCAGACATCCCAACCTGG<br>ACATGTTCGACGACTTCAGCGAGG<br>GCAGAGAATGCGTGAACTGCGGAG<br>CCATGAGCACCCCCCTTTGGAGAA<br>GAGACGGCACCGGCCACTACCTTT<br>GCAATGCCTGTGGCCTGTACCACAA<br>GATGAACGGCATCAACAGACCCCT<br>GATCAAGCCCCAGAGAAGACTGAG<br>CGCTAGCAGAAGAGTGGGCCTGTC<br>CTGCGCCAATTGCCAGACCACAAC<br>CACCACACTGTGGAGGAGAAATGC<br>CGAGGGCGAGCCTGTGTGTAACGC<br>CTGTGGACTGTACATGAAGCTGCAC<br>GGCGTGCCCAGACCTCTGGCCATG<br>AGAAAGGAGGGCATCCAGACCAGA<br>AAGAGAAAGCCCAAGAACCTGAAC<br>AAGAGCAAGACCCCCGCTGCTCCTT<br>CTGGAAGCGAGAGCCTGCCTCCAG<br>CCTCTGGAGCCAGCAGCAATAGCT<br>CTAACGCCACCACATCTTCTTCTGA<br>GGGAGATGAGGCCCATCAAAACCGA<br>GCCAGGCCTGAGCAGCCACTACGG<br>CCACAGCTCTAGCGTGAGCCAGAC<br>TTTTAGCGTGTCTGCCATGTCAGGC<br>CACGGACCTAGCATTCACCCTGTGC<br>TGAGCGCCCTGAAGTTGAGCCCAC<br>AGGGCTATGCTTCTCCTGTGTCTCA<br>GAGCCCTCAGACCTCCAGCAAGCA<br>GGACTCCTGGAATTCTCTGGTGCTG<br>GCCGACAGCCACGGCGATATCATC<br>ACCGCC | | | (2006).<br>Rivera-<br>Feliciano, J.<br>et al.<br>Development<br>of heart<br>valves<br>requires<br>Gata4<br>expression in<br>endothelial-<br>derived cells.<br>Development<br>133, 3607-18<br>(2006). |
| GATA6 | ATGGCCCTGACCGACGGCGGATGG<br>TGTCTCCCTAAAAGATTCGGCGCCG<br>CTGGCGCTGATGCTTCTGACAGCAG<br>AGCCTTCCCCGCTAGGGAACCCAG<br>CACACCACCTAGCCCCATCAGCAG<br>CTCAAGCTCTAGCTGTAGCAGAGG<br>CGGAGAGAGAGGACCTGGAGGCGC<br>TTCTAACTGCGGCACACCTCAGCTG<br>GATACAGAAGCCGCCGCCGGACCA<br>CCAGCCAGATCTCTTTTACTTAGCA<br>GCTACGCCAGCCACCCTTTTGGCGC<br>TCCTCATGGACCCTCTGCTCCTGGT<br>GTGGCCGGACCTGGCGGAAACCTG<br>AGCTCTTGGGAGGACCTTCTGCTGT<br>TTACCGACCTGGACCAGGCTGCCAC<br>CGCTAGCAAGCTTCTGTGTGGAGCAG<br>CAGGGGCGCTAAGCTGAGCCCTTTT<br>GCCCCTGAGCAGCCCGAGGAGATG<br>TACCAGACCCTGGCTGCTTTAAGCT<br>CTCAGGGACCTGCCGCTTATGACGG<br>AGCCCCTGGTGGATTTGTTCACTCA<br>GCGGCAGCAGCCGCAGCTGCTGCA<br>GCCGCTGCCAGCTCACCTGTGTATG<br>TGCCTACCACAAGAGTGGGCAGCA<br>TGTTACCTGGACTTCCTTACCATCT<br>GCAGGGCAGCGGAAGCGGCCCTGC<br>TAACCATGCCGGAGGAGCTGGAGC<br>TCACCCCGGATGGCCTCAGGCTTCT<br>GCAGATTCTCCTTCCTTATGGATCTG<br>GAGGAGGAGCAGCTGGAGGGGGA<br>GCTGCAGGACCAGGTGGAGCCGGA<br>AGCGCAGCAGCACATGTGTCTGCC<br>AGATTTCCCTATAGCCCTAGCCCTC | 52 | Involved in<br>cardiac, lung,<br>endoderm and<br>extraembryonic<br>development | Xin, M. et al.<br>A threshold of<br>GATA4 and<br>GATA6<br>expression is<br>required for<br>cardiovascular<br>development.<br>Proc. Natl.<br>Acad. Sci. U.<br>S. A. 103,<br>11189-94<br>(2006).<br>Morrisey, E.<br>E. et al.<br>GATA6<br>regulates<br>HNF4 and is<br>required for<br>differentiation<br>of visceral<br>endoderm in<br>the mouse<br>embryo.<br>Genes Dev.<br>12, 3579-<br>3590 (1998).<br>Koutsourakis,<br>M.;<br>Langeveld,<br>A.; Patient,<br>R.;<br>Beddington, |

TABLE 1-continued

| GENE | SEQUENCE | SEQ ID NO: | ROLE | REFERENCES |
|------|----------|------------|------|------------|
|  | CTATGGCCAATGGCGCTGCTAGAG<br>AACCCGGAGGATATGCTGCGGCAG<br>GCTCTGGCGGCGCTGGCGGAGTTTC<br>TGGAGGTGGATCTTCACTGGCCGCT<br>ATGGGAGGAAGAGAGCCTCAGTAC<br>TCTTCTCTGAGCGCCGCTAGACCAC<br>TGAACGGCACCTATCATCACCACCA<br>CCATCACCATCATCATCACCCCAGC<br>CCTTACTCCCCTTATGTGGGAGCCC<br>CCCTTACACCCGCTTGGCCTGCCGG<br>CCCTTTCGAGACACCTGTGCTGCAC<br>AGCCTTCAGTCTAGAGCTGGCGCAC<br>CTTTACCAGTGCCTAGAGGCCCCTC<br>TGCCGACTTGCTGGAGGATCTGAGC<br>GAGAGCAGAGAGTGCGTGAACTGT<br>GGCAGCATCCAGACACCCCTGTGG<br>AGAAGAGACGGCACCGGCCACTAC<br>CTGTGCAACGCTTGCGGCCTGTACA<br>GCAAGATGAATGGGCTGAGCAGAC<br>CCCTGATCAAGCCCCAGAAGAGGG<br>TGCCCAGCAGCAGACGGCTGGGAC<br>TGAGCTGCGCCAACTGTCATACCAC<br>AACAACCACACTGTGGCGGAGAAA<br>CGCCGAGGGCGAGCCCGTGTGTAA<br>CGCCTGCGGCCTTTACATGAAGCTG<br>CACGGCGTGCCCAGACCTCTGGCC<br>ATGAAGAAGGAGGGAATCCAGACC<br>AGAAAGAGAAAGCCCAAGAACATC<br>AACAAGAGCAAGACCTGCAGCGGC<br>AACAGCAACAACAGCATCCCCATG<br>ACCCCCACCAGCACATCTAGCAAC<br>AGCGACGACTGTAGCAAGAACACA<br>TCACCTACCACCCAGCCCACAGCTA<br>GCGGAGCCGGCGCCCCCGTGATGA<br>CAGGCGCCGGAGAGTCCACACAATC<br>CCGAGAATAGCGAACTGAAGTACT<br>CTGGACAGGACGGACTGTATATCG<br>GCGTGAGCCTGGCTTCTCCCGCCGA<br>GGTGACCAGCTCTGTCAGACCTGAC<br>TCTTGGTGTGCCCTCGCCCTGGCC |  |  | R.; Grosveld,<br>F. The<br>transcription<br>factor<br>GATA6 is<br>essential for<br>early<br>extraembryonic<br>development.<br>Development<br>126, 723-732<br>(1999).<br>Zhang, Y. et<br>al. A Gata6-<br>Wnt pathway<br>required for<br>epithelial<br>stem cell<br>development<br>and airway<br>regeneration.<br>Nat. Genet.<br>40, 862-870<br>(2008). |
| GLI1 | ATGTTCAACTCGATGACCCCACCAC<br>CAATCAGTAGCTATGGCGAGCCCT<br>GCTGTCTCCGGCCCCTCCCCAGTCA<br>GGGGGCCCCCAGTGTGGGGACAGA<br>AGGACTGTCTGGCCCGCCCTTCTGC<br>CACCAAGCTAACCTCATGTCCGGCC<br>CCCACAGTTATGGGCCAGCCAGAG<br>AGACCAACAGCTGCACCGAGGGCC<br>CACTCTTTTCTTCTCCCCGGAGTGC<br>AGTCAAGTTGACCAAGAAGCGGGC<br>ACTGTCCATCTCACCTCTGTCGGAT<br>GCCAGCCTGGACCTGCAGACGGTT<br>ATCCGCACCTCACCCAGCTCCCTCG<br>TAGCTTTCATCAACTCGCGATGCAC<br>ATCTCCAGGAGGCTCCTACGGTCAT<br>CTCTCCATTGGCACCATGAGCCCAT<br>CTCTGGGATTCCCAGCCCAGATGAA<br>TCACCAAAAAGGGCCCTCGCCTTCC<br>TTTGGGGTCCAGCCTTGTGGTCCCC<br>ATGACTCTGCCCGGGGTGGGATGA<br>TCCCACATCCTCAGTCCCGGGGACC<br>CTTCCCAACTTGCCAGCTGAAGTCT<br>GAGCTGGACATGCTGGTTGGCAAG<br>TGCCGGGAGGAACCCTTGGAAGGT<br>GATATGTCCAGCCCCAACTCCACAG<br>GCATACAGGATCCCCTGTTGGGGAT<br>GCTGGATGGGCGGGAGGACCTCGA<br>GAGAGAGGAGAAGCGTGAGCCTGA<br>ATCTGTGTATGAAACTGACTGCCGT<br>TGGGATGGCTGCAGCCAGGAATTT<br>GACTCCCAAGAGCAGCTGGTGCAC<br>CACATCAACAGCGAGCACATCCAC<br>GGGGAGCGGAAGGAGTTCGTGTGC<br>CACTGGGGGGCTGCTCCAGGGAG<br>CTGAGGCCCTTCAAAGCCCAGTAC<br>ATGCTGGTGGTTCACATGCGCAGAC | 53 | Involved in<br>neural stem cell<br>proliferation<br>and neural tube<br>development | Lee, J. et al.<br>Gli1 is a<br>target of<br>Sonic<br>hedgehog that<br>induces<br>ventral neural<br>tube<br>development.<br>Development<br>124, 2537-<br>2552 (1997).<br>Palma, V. et<br>al. Sonic<br>hedgehog<br>controls stem<br>cell behavior<br>in the<br>postnatal and<br>adult brain.<br>Development<br>132, 335-44<br>(2005). |

TABLE 1-continued

| GENE | SEQUENCE | SEQ ID NO: | ROLE | REFERENCES |
|------|----------|------------|------|------------|
| | ACACTGGCGAGAAGCCACACAAGT | | | |
| | GCACGTTTGAAGGGTGCCGGAAGT | | | |
| | CATACTCACGCCTCGAAAACCTGA | | | |
| | AGACGCACCTGCGGTCACACACGG | | | |
| | GTGAGAAGCCATACATGTGTGAGC | | | |
| | ACGAGGGCTGCAGTAAAGCCTTCA | | | |
| | GCAATGCCAGTGACCGAGCCAAGC | | | |
| | ACCAGAATCGGACCCATTCCAATG | | | |
| | AGAAGCCGTATGTATGTAAGCTCCC | | | |
| | TGGCTGCACCAAACGCTATACAGA | | | |
| | TCCTAGCTCGCTGCGAAAACATGTC | | | |
| | AAGACAGTGCATGGTCCTGACGCC | | | |
| | CATGTGACCAAACGGCACCGTGGG | | | |
| | GATGGCCCCCTGCCTCGGGCACCAT | | | |
| | CCATTTCTACAGTGGAGCCCAAGA | | | |
| | GGGAGCGGGAAGGAGGTCCCATCA | | | |
| | GGGAGGAAAGCAGACTGACTGTGC | | | |
| | CAGAGGGTGCCATGAAGCCACAGC | | | |
| | CAAGCCCTGGGGCCCAGTCATCCTG | | | |
| | CAGCAGTGACCACTCCCCGGCAGG | | | |
| | GAGTGCAGCCAATACAGACAGTGG | | | |
| | TGTGGAAATGACTGGCAATGCAGG | | | |
| | GGGCAGCACTGAAGACCTCTCCAG | | | |
| | CTTGGACGAGGGACCTTGCATTGCT | | | |
| | GGCACTGGTCTGTCCACTCTTCGCC | | | |
| | GCCTTGAGAACCTCAGGCTGGACC | | | |
| | AGCTACATCAACTCCGGCCAATAG | | | |
| | GGACCCGGGGTCTCAAACTGCCCA | | | |
| | GCTTGTCCCACACCGGTACCACTGT | | | |
| | GTCCCGCCGCGTGGGCCCCCCAGTC | | | |
| | TCTCTTGAACGCCGCAGCAGCAGCT | | | |
| | CCAGCAGCATCAGCTCTGCCTATAC | | | |
| | TGTCAGCCGCCGCTCCTCCCTGGCC | | | |
| | TCTCCTTTCCCCCCTGGCTCCCCAC | | | |
| | CAGAGAATGGAGCATCCTCCCTGC | | | |
| | CTGGCCTTATGCCTGCCCAGCACTA | | | |
| | CCTGCTTCGGGCAAGATATGCTTCA | | | |
| | GCCAGAGGGGGTGGTACTTCGCCC | | | |
| | ACTGCAGCATCCAGCCTGGATCGG | | | |
| | ATAGGTGGTCTTCCCATGCCTCCTT | | | |
| | GGAGAAGCCGAGCCGAGTATCCAG | | | |
| | GATACAACCCCAATGCAGGGGTCA | | | |
| | CCCGGAGGGCCAGTGACCCAGCCC | | | |
| | AGGCTGCTGACCGTCCTGCTCCAGC | | | |
| | TAGAGTCCAGAGGTTCAAGAGCCT | | | |
| | GGGCTGTGTCCATACCCCACCCACT | | | |
| | GTGGCAGGGGGAGGACAGAACTTT | | | |
| | GATCCTTACCTCCCAACCTCTGTCT | | | |
| | ACTCACCACAGCCCCCCAGCATCA | | | |
| | CTGAGAATGCTGCCATGGATGCTA | | | |
| | GAGGGCTACAGGAAGAGCCAGAAG | | | |
| | TTGGGACCTCCATGGTGGGCAGTG | | | |
| | GTCTGAACCCCTATATGGACTTCCC | | | |
| | ACCTACTGATACTCTGGGATATGGG | | | |
| | GGACCTGAAGGGGCAGCAGCTGAG | | | |
| | CCTTATGGAGCGAGGGGTCCAGGC | | | |
| | TCTCTGCCTCTTGGGCCTGGTCCAC | | | |
| | CCACCAACTATGGCCCCAACCCCTG | | | |
| | TCCCCAGCAGGCCTCATATCCTGAC | | | |
| | CCCACCCAAGAAACATGGGGTGAG | | | |
| | TTCCCTTCCCACTCTGGGCTGTACC | | | |
| | CAGGCCCCAAGGCTCTAGGTGGAA | | | |
| | CCTACAGCCAGTGTCCTCGACTTGA | | | |
| | ACATTATGGACAAGTGCAAGTCAA | | | |
| | GCCAGAACAGGGGTGCCCAGTGGG | | | |
| | GTCTGACTCCACAGGACTGGCACCC | | | |
| | TGCCTCAATGCCCACCCCAGTGAGG | | | |
| | GGCCCCACATCCACAGCCTCTCTT | | | |
| | TTCCCATTACCCCCAGCCCTCTCCT | | | |
| | CCCCAATATCTCCAGTCAGGCCCCT | | | |
| | ATACCCAGCCACCCCCTGATTATCT | | | |
| | TCCTTCAGAACCCAGGCCTTGCCTG | | | |
| | GACTTTGATTCCCCCACCCATTCCA | | | |
| | CAGGGCAGCTCAAGGCTCAGCTTG | | | |
| | TGTGTAATTATGTTCAATCTCAACA | | | |
| | GGAGCTACTGTGGGAGGGTGGGGG | | | |
| | CAGGGAAGATGCCCCCGCCCAGGA | | | |

TABLE 1-continued

| GENE | SEQUENCE | SEQ ID NO: | ROLE | REFERENCES |
|------|----------|------------|------|------------|
| | ACCTTCCTACCAGAGTCCCAAGTTT CTGGGGGGTTCCCAGGTTAGCCCA AGCCGTGCTAAAGCTCCAGTGAAC ACATATGGACCTGGCTTTGGACCCA ACTTGCCCAATCACAAGTCAGGTTC CTATCCCACCCCTTCACCATGCCAT GAAAATTTTGTAGTGGGGGCAAAT AGGGCTTCACATAGGGCAGCAGCA CCACCTCGACTTCTGCCCCCATTGC CCACTTGCTATGGGCCTCTCAAAGT GGGAGGCACAAACCCCAGCTGTGG TCATCCTGAGGTGGGCAGGCTAGG AGGGGGTCCTGCCTTGTACCCTCCT CCCGAAGGACAGGTATGTAACCCC CTGGACTCTCTTGATCTTGACAACA CTCAGCTGGACTTTGTGGCTATTCT GGATGAGCCCCAGGGGCTGAGTCC TCCTCCTTCCCATGATCAGCGGGGC AGCTCTGGACATACCCCACCTCCCT CTGGGCCCCCAACATGGCTGTGG GCAACATGAGTGTCTTACTGAGATC CCTACCTGGGGAAACAGAATTCCTC AACTCTAGTGCC | | | |
| HAND2 | ATGAGTCTGGTAGGTGGTTTTCCCC ACCACCCGGTGGTGCACCACGAGG GCTACCCGTTTGCCGCCGCCGCCGC CGCCAGCCGCTGCAGCCATGAGGA GAACCCCTACTTCCATGGCTGGCTC ATCGGCCACCCCGAGATGTCGCCCC CCGACTACAGCATGGGCCCTGTCCTA CAGCCCCGAGTATGCCAGCGGCAC CGCCAACCGCAAGGAGCGGCGCAG GACTCAGAGCATCAACAGCGCCTT CGCCGAACTGCGCGAGTGCATCCC CAACGTACCCGCCGACACCAAACT CTCCAAAATCAAGACCCTGCGCCTG GCCACCAGCTACATCGCCTACCTCA TGGACCTGCTGGCCAAGGACGACC AGAATGGCGAGGCGGAGGCCTTCA AGGCAGAGATCAAGAAGACCGACG TGAAAGAGGAGAAGAGGAAGAAG GAGCTGAACGAAATCTTGAAAAGC ACAGTGAGCAGCAACGACAAGAAA ACCAAAGGCCGGACGGGCTGGCCG CAGCACGTCTGGGCCCTGGAGCTC AAGCAG | 54 | Involved in cardiac development | Srivastava, D. et al. Regulation of cardiac mesodermal and neural crest development by the bHLH transcription factor, dHAND. Nat. Genet. 16, 154-160 (1997). |
| HNF1A | ATGGTTTCTAAACTGAGCCAGCTGC AGACGGAGCTCCTGGCGGCCCTGC TGGAGTCAGGGCTGAGCAAAGAGG CACTGCTCCAGGCACTGGGTGAGC CGGGGCCCTACCTCCTGGCTGGAG AAGGCCCCCTGGACAAGGGGGAGT CCTGCGGCGGCGGTCGAGGGGAGC TGGCTGAGCTGCCCAATGGGCTGG GGGAGACTCGGGGCTCCGAGGACG AGACGGACGACGATGGGGAAGACT TCACGCCACCCATCCTCAAAGAGCT GGAGAACCTCAGCCCTGAGGAGGC GGCCCACCAGAAAGCCGTGGTGGA GACCCTTCTGCAGGAGGACCCGTG GCGTGTGGCGAAGATGGTCAAGTC CTACTGCAGCAGCACAACATCCC ACAGCGGGAGGTGGTCGATACCAC TGGCCCTCAACCAGTCCCACCTGTCC CAACACCTCAACAAGGGCACTCCC ATGAAGACGCAGAAGCGGGCCGCC CTGTACACCTGGTACGTCCGCAAGC AGCGAGAGGTGGCGCAGCAGTTCA CCCATGCAGGGCAGGGAGGGCTGA TTGAAGAGCCCACAGGTGATGAGC TACCAACCAAGAAGGGGCGGAGGA ACCGTTTCAAGTGGGGCCCAGCATC CCAGCAGATCCTGTTCCAGGCCTAT GAGAGGCAGAAGAACCCTAGCAAG GAGGAGCGAGAGACGCTAGTGGAG | 55 | Involved in liver, kidney, pancreatic and gut development | D' Angelo, A. et al. Hepatocyte nuclear factor 1alpha and beta control terminal differentiation and cell fate commitment in the gut epithelium. Development 137,1573-82 (2010). Servitja, J.-M. et al. Hnf1 alpha (MODY3) controls tissue-specific transcriptional programs and exerts opposed effects on cell growth in pancreatic islets and |

TABLE 1-continued

| GENE | SEQUENCE | SEQ ID NO: | ROLE | REFERENCES |
|------|----------|------------|------|------------|
|  | GAGTGCAATAGGGCGGAATGCATC<br>CAGAGAGGGGTGTCCCCATCACAG<br>GCACAGGGGCTGGGCTCCAACCTC<br>GTCACGGAGGTGCGTGTCTACAACT<br>GGTTTGCCAACCGGCGCAAAGAAG<br>AAGCCTTCCGGCACAAGCTGGCCA<br>TGGACACGTACAGCGGGCCCCCCC<br>CAGGGCCAGGCCCGGGACCTGCGC<br>TGCCCGCTCACAGCTCCCCTGGCCT<br>GCCTCCACCTGCCCTCTCCCCCAGT<br>AAGGTCCACGGTGTGCGCTATGGA<br>CAGCCTGCGACCAGTGAGACTGCA<br>GAAGTACCCTCAAGCAGCGGCGGT<br>CCCTTAGTGACAGTGTCTACACCCC<br>TCCACCAAGTGTCCCCCACGGGCCT<br>GGAGCCCAGCCACAGCCTGCTGAG<br>TACAGAAGCCAAGCTGGTCTCAGC<br>AGCTGGGGGCCCCCTCCCCCCTGTC<br>AGCACCCTGACAGCACTGCACAGC<br>TTGGAGCAGACATCCCCAGGCCTC<br>AACCAGCAGCCCCAGAACCTCATC<br>ATGGGCCTCACTTCCTGGGGTCATGA<br>CCATCGGGCCTGGTGAGCCTGCCTC<br>CCTGGGTCCTACGTTCACCAACACA<br>GGTGCCTCCACCCTGGTCATCGGCC<br>TGGCCTCCACGCAGGCACAGAGTG<br>TGCCGGTCATCAACAGCATGGGCA<br>GCAGCCTGACCACCCTGCAGCCCGT<br>CCAGTTCTCCCAGCCGCTGCACCCC<br>TCCTACCAGCAGCCGCTCATGCCAC<br>CTGTGCAGAGCCATGTGACCCAGA<br>GCCCCTTCATGGCCACCATGGCTCA<br>GCTGCAGAGCCCCCACGCCCTCTAC<br>AGCCACAAGCCCGAGGTGGCCCAG<br>TACACCCACACAGGCCTGCTCCCGC<br>AGACTATGCTCATCACCGACACCAC<br>CAACCTGAGCGCCCTGGCCAGCCTC<br>ACGCCCACCAAGCAGGTCTTCACCT<br>CAGACACTGAGGCCTCCAGTGAGT<br>CCGGGCTTCACACGCCGGCATCTCA<br>GGCCACCACCCTCCACGTCCCCAGC<br>CAGGACCCTGCCGGCATCCAGCAC<br>CTGCAGCCGGCCCACCGGCTCAGC<br>GCCAGCCCCACAGTGTCCTCCAGCA<br>GCCTGGTGCTGTACCAGAGCTCAG<br>ACTCCAGCAATGGCCAGAGCCACC<br>TGCTGCCATCCAACCACAGCGTCAT<br>CGAGACCTTCATCTCCACCCAGATG<br>GCCTCTTCCTCCCAGTTG |  | liver. | Mol.<br>Cell. Biol. 29,<br>2945-59<br>(2009).<br>Si-Tayeb, K.;<br>Lemaigre, F.<br>P.; Duncan, S.<br>A.<br>Organogenesis<br>and<br>Development<br>of the Liver.<br>Dev. Cell 18,<br>175-189<br>(2010).<br>Martovetsky,<br>G., Tee, J. B.<br>& Nigam, S.<br>K. Hepatocyte<br>nuclear<br>factors 4α and<br>1α regulate<br>kidney<br>developmental<br>expression<br>of drug-<br>metabolizing<br>enzymes and<br>drug<br>transporters.<br>Mol.<br>Pharmacol.<br>84, 808-23<br>(2013). |
| HNF1B | ATGGTTAGCAAACTGACATCCCTCC<br>AGCAGGAACTTCTTTCTGCCCTCCT<br>CTCCAGTGGGGTAACCAAAGAGGT<br>ACTGGTCCAGGCTTTGGAGGAGTTG<br>CTCCCCTCACCGAATTTTGGTGTAA<br>AGTTGGAGACTCTCCCCCTCTCCCC<br>TGGTTCTGGAGCAGAGCCGGATAC<br>TAAACCGGTATTTCATACGCTTACA<br>AACGGACACGCAAAGGGTCGGCTT<br>TCAGGTGACGAAGGGTCTGAGGAC<br>GGCGATGATTATGACACCCCGCCC<br>ATCCTCAAAGAACTGCAGGCCCTTA<br>ATACAGAGGAAGCGGCGGAGCAGC<br>GAGCTGAAGTTGACAGAATGCTCT<br>CAGAAGATCCGTGGAGAGCTGCGA<br>AAATGATTAAGGGATATATGCAGC<br>AACATAACATTCCCCAGAGAGAGG<br>TAGTTGATGTTACCGGCCTTAACCA<br>GAGCCACCTGTCTCAGCATCTCAAT<br>AAGGGTACTCCTATGAAAACACAG<br>AAGCGAGCGGCCCTTTACACATGG<br>TACGTGCGGAAGCAACGAGAAATT<br>CTCCGACAGTTCAATCAGACAGTAC<br>AATCTTCAGGGAACATGACGGATA<br>AAAGCTCACAGGATCAGCTCTTGTT<br>TCTCTTCCCCGAGTTCAGCCAACAG<br>TCCCACGGTCCAGGTCAATCTGATG | 56 | Involved in<br>liver, kidney,<br>pancreatic and<br>gut<br>development | D' Angelo, A.<br>et al.<br>Hepatocyte<br>nuclear factor<br>1alpha and<br>beta control<br>terminal<br>differentiation<br>and cell fate<br>commitment<br>in the gut<br>epithelium.<br>Development<br>137, 1573-82<br>(2010).<br>Si-Tayeb, K.;<br>Lemaigre, F.<br>P.; Duncan, S.<br>A.<br>Organogenesis<br>and<br>Development<br>of the Liver.<br>Dev. Cell 18,<br>175-189<br>(2010).<br>Clissold, R. |

TABLE 1-continued

| GENE | SEQUENCE | SEQ ID NO: | ROLE | REFERENCES |
|---|---|---|---|---|
| | ATGCTTGCAGTGAACCTACAAACA AAAAAATGAGGAGGAACAGGTTTA AATGGGGACCGGCCTCTCAGCAGA TACTGTACCAAGCGTACGATCGGC AGAAAAACCCAAGCAAAGAGGAGC GCGAGGCATTGGTCGAGGAGTGTA ATCGGGCCGAGTGCTTGCAACGGG GTGTAAGTCCTAGCAAAGCCCATG GTCTCGGCTCAAACTTGGTCACGGA GGTGAGGGTATATAATTGGTTTGCC AACAGGCGGAAGGAGGAAGCATTC CGGCAAAAGCTGGCGATGGATGCC TACTCAAGCAACCGACACATAGC CTCAACCCTCTGTTGTCACACGGGT CCCCTCATCACCAACCTTCTTCCTC TCCACCCAACAAACTTTCTGGTGTC CGATATTCCCAGCAGGGGAACAAC GAGATAACATCTTCCTCTACTATAA GTCATCACGGAAATTCTGCAATGGT AACGTCACAGAGTGTGTTGCAACA GGTATCACCCGCGTCTCTTGATCCA GGCCACAATCTGTTGAGCCCTGACG GAAAGATGATCTCTGTTTCTGGTGG CGGACTCCCGCCGGTCTCCACACTT ACCAACATACATAGTCTCAGTCATC ATAATCCTCAGCAGAGCCAAAACC TGATTATGACTCCTCTTAGCGGAGT GATGGCTATTGCGCAATCTTTGAAC ACCTCACAAGCACAATCTGTACCCG TCATAAACAGCGTAGCGGGCTCATT GGCGGCGCTCCAACCAGTGCAGTT CTCCCAGCAGCTCCATTCACCCCAT CAACAGCCTCTGATGCAGCAGAGC CCTGGTAGTCACATGGCTCAACAGC CGTTCATGGCAGCTGTCACTCAGCT CCAGAACTCCCATATGTATGCCCAC AAGCAAGAACCACCACAATACAGT CACACATCAAGATTCCCCAGTGCTA TGGTTGTTACTGACACATCCTCTAT CTCAACTCTGACGAACATGTCCAGT AGTAAACAATGTCCTCTGCAAGCAT GG | | | L., Hamilton, A. J., Hattersley, A. T., Ellard, S. & Bingham, C. HNF1B-associated renal and extra-renal disease-an expanding clinical spectrum. Nat. Rev. Nephrol. 11, 102-112 (2014). De Vas, M. G. et al. Hnf1b controls pancreas morphogenesis and the generation of Ngn3+ endocrine progenitors. Development 142, 871-82 (2015). El-Khairi, R. & Vallier, L. The role of hepatocyte nuclear factor 1β in disease and development. Diabetes, Obes. Metab. 18, 23-32 (2016). |
| HNF4A | ATGCGACTCTCCAAAACCCTCGTCG ACATGGACATGGCCGACTACAGTG CTGCACTGGACCCAGCCTACACCAC CCTGGAATTTGAGAATGTGCAGGT GTTGACGATGGCAATGACACGTC CCCATCAGAAGGCACCAACCTCAA CGCGCCCAACAGCGTGGGTGTCAG CGCCCTGTGTGCCATCTGCGGGGAC CGGGCCACGGGCAAACACTACGGT GCCTCGAGCTGTGACGGCTGCAAG GGCTTCTTCCGGAGGAGCGTGCGG AAGAACCACATGTACTCCTGCAGA TTTAGCCGGCAGTGCGTGGTGGAC AAAGACAAGAGGAACCAGTGCCGC TACTGCAGGCTCAAGAAATGCTTCC GGGCTGGCATGAAGAAGGAAGCCG TCCAGAATGAGCGGGACCGGATCA GCACTCGAAGGTCAAGCTATGAGG ACAGCAGCCTGCCCTCCATCAATGC GCTCCTGCAGGCGGAGGTCCTGTCC CGACAGATCACCTCCCCCGTCTCCG GGATCAACGGCGACATTCGGGCGA AGAAGATTGCCAGCATCGCAGATG TGTGTGAGTCCATGAAGGAGCAGC TGCTGGTTCTCGTTGAGTGGGCCAA GTACATCCCAGCTTTCTGCGAGCTC CCCCTGGACGACCAGGTGGCCCTG CTCAGAGCCCATGCTGGCGAGCAC CTGCTGCTCGGAGCCACCAAGAGA TCCATGGTGTTCAAGGACGTGCTGC TCCTAGGCAATGACTACATTGTCCC TCGGCACTGCCCGGAGCTGGCGGA GATGAGCCGGGTGTCCATACGCAT | 57 | Involved in liver, kidney, pancreatic and gut development | Si-Tayeb, K.; Lemaigre, F. P.; Duncan, S. A. Organogenesis and Development of the Liver. Dev. Cell 18, 175-189 (2010). Martovetsky, G., Tee, J. B. & Nigam, S. K. Hepatocyte nuclear factors 4α and 1α regulate kidney developmental expression of drug-metabolizing enzymes and drug transporters. Mol. Pharmacol. 84, 808-23 (2013). Maestro, M. A. et al. Distinct roles |

TABLE 1-continued

| GENE | SEQUENCE | SEQ ID NO: | ROLE | REFERENCES |
|---|---|---|---|---|
| | CCTTGACGAGCTGGTGCTGCCCTTC CAGGAGCTGCAGATCGATGACAAT GAGTATGCCTACCTCAAAGCCATCA TCTTCTTTGACCCAGATGCCAAGGG GCTGAGCGATCCAGGGAAGATCAA GCGGCTGCGTTCCCAGGTGCAGGT GAGCTTGGAGGACTACATCAACGA CCGCCAGTATGACTCGCGTGGCCGC TTTGGAGAGCTGCTGCTGCTGCTGC CCACCTTGCAGGAGCATCCACCTGGCA GATGATCGAGCAGATCCAGTTCATC AAGCTCTTCGGCATGGCCAAGATTG ACAACCTGTTGCAGGAGATGCTGCT GGGAGGTCCGTGCCAAGCCCAGGA GGGGCGGGGTTGGAGTGGGGACTC CCCAGGAGACAGGCCTCACACAGT GAGCTCACCCCTCAGCTCCTTGGCT TCCCCACTGTGCCGCTTTGGGCAAG TTGCT | | | of HNF1b eta, HNF1alpha, and HNF4alpha in regulating pancreas development, beta-cell function and growth. Endocr. Dev. 12,33-45 (2007). Garrison, W. D. et al. Hepatocyte nuclear factor 4alpha is essential for embryonic development of the mouse colon. Gastroenterol ogy 130, 1207-20 (2006). |
| HOXA1 | ATGGACAACGCGCGGATGAATTCC TTCCTCGAGTACCCAATTTTGTCTA GTGGAGACAGTGGCACTTGCAGTG CCCGAGCCTATCCATCAGACCACA GAATTACAACATTCCAAAGCTGTGC GGTGTCAGCCAACAGTTGCGGCGG AGACGACCGCTTCCTGGTCGGAAG AGGGGTTCAAATTGGATCACCTCAC CATCACCATCACCACCACCATCACC ACCCCCAACCGGCGACTTACCAAA CCAGCGGCAATTTGGGCGTGAGCT ATAGCCATTCCTCATGTGGACCTTC CTATGGGTCTCAGAATTTCTCCGCC CCTTATAGCCCATACGCCCTGAACC AAGAGGCCGATGTATCAGGAGGCT ATCCCCAGTGCGCGCCAGCGGTTTA CTCAGGTAATCTTTCTAGCCCGATG GTCCAGCACCACCATCACCATCAA GGTTATGCCGGCGGTGCAGTCGGA TCCCCACAATACATACACCATAGTT ACGGCCAAGAGCACCAATCCCTGG CCCTCGCTACATATAACAACTCACT GTCTCCGCTTCATGCTTCCCACCAA GAAGCTTGTCGGAGTCCCGCCTCAG AAACTTCCTCTCCAGCTCAGACTTT TGATTGGATGAAGGTCAAGCGGAA TCCGCCTAAAACGGGCAAAGTAGG TGAATATGGCTATTTGGGACAGCCT AATGCTGTCCGCACCAATTTCACAA CAAAACAGCTTACTGAACTCGAGA AGGAATTTCATTTTAATAAGTATTT GACTCGAGCGAGACGAGTCGAAAT CGCCGCTAGTCTTCAACTTAACGAG ACCCAGGTTAAGATATGGTTCCAG AACAGAAGAATGAAACAAAAAAA GCGGGAGAAGGAAGGACTCCTCCC TATATCACCAGCCACACCCCCAGGT AACGACGAGAAGGCGGAGGAATCT TCAGAGAAGAGTTCCAGCTCCCCTT GTGTTCCTTCTCCTGGTAGCTCAAC CAGCGATACCCTCACGACGAGTCA C | 58 | Involved in neural and cardiovascular development | Tischfield, M. A. et al. Homozygous HOXA1 mutations disrupt human brainstem, inner ear, cardiovascular and cognitive development. Nat. Genet. 37, 1035-1037 (2005). |
| HOXA10 | ATGTGTCAAGGCAATTCCAAAGGT GAAAACGCAGCCAACTGGCTCACG GCAAAGAGTGGTCGGAAGAAGCGC TGCCCCTACACGAAGCACCAGACA CTGGAGCTGGAGAAGGAGTTTCTG TTCAATATGTACCTTACTCGAGAGC | 59 | Involved function in fertility, embryo viability, and regulation of | Buske, C. et al. Overexpression of HOXA10 perturbs human |

TABLE 1-continued

| GENE | SEQUENCE | SEQ ID NO: | ROLE | REFERENCES |
|---|---|---|---|---|
| | GGCGCCTAGAGATTAGCCGCAGCG TCCACCTCACGGACAGACAAGTGA AAATCTGGTTTCAGAACCGCAGGA TGAAACTGAAGAAAATGAATCGAG AAAACCGGATCCGGGAGCTCACAG CCAACTTTAATTTTTCC | | hematopoetic lineage commitment | lympho-myelopoiesis in vitro and in vivo. Blood 97, 2286-2292 (2001). Satokata, I., Benson, G. & Maas, R. Sexually dimorphic sterility phenotypes in Hoxa10-deficient mice. Nature 374, 460-463 (1995). |
| HOXA11 | ATGGATTTTGATGAGCGTGGTCCCT GCTCCTCTAACATGTATTTGCCAAG TTGTACTTACTACGTCTCGGGTCCA GATTTCTCCAGCCTCCCTTCTTTTCT GCCCCAGACCCCGTCTTCGCGCCCA ATGACATACTCCTACTCCTCCAACC TGCCCAGGTCCAACCCGTGCGCG AAGTGACCTTCAGAGAGTACGCCA TTGAGCCCGCCACTAAATGGCACCC CCGCGGCAATCTGGCCCACTGCTAC TCCGCGGAGGAGCTCGTGCACAGA GACTGCCTGCAGGCGCCCAGCGCG GCCGGCGTGCCTGGCGACGTGCTG GCCAAGAGCTCGGCCAACGTCTAC CACCACCCCACCCCCGCAGTCTCGT CCAATTTCTATAGCACCGTGGGCAG GAACGGCGTCCTGCCACAGGCTTTC GACCAGTTTTTCGAGACAGCCTACG GCACCCCGGAAAACCTCGCCTCCTC CGACTACCCCGGGGACAAGAGCGC CGAGAAGGGGCCCCCGGCGGCCAC GGCGACCTCCGCGGCGGCGGCGGC GGCTGCAACGGGCGCGCCGGCAAC TTCAAGTTCGGACAGCGGCGGCGG CGGCGGCTGCCGGGAGATGGCGGC GGCAGCAGAGGAGAAAGAGCGGC GGCGGCGCCCCGAGAGCAGCAGCA GCCCCGAGTCGTCTTCCGGCCACAC TGAGGACAAGGCCGGCGGCTCCAG TGGCCAACGCACCCGCAAAAAGCG CTGCCCCTATACCAAGTACCAGATC CGAGAGCTGGAACGGGAGTTCTTC TTCAGCGTCTACATTAACAAAGAG AAGCGCCTGCAACTGTCCCGCATGC TCAACCTCACTGATCGTCAAGTCAA AATCTGGTTTCAGAACAGGAGAAT GAAGGAAAAAAAAATTAACAGAGA CCGTTTACAGTACTACTCAGCAAAT CCACTCCTCTTG | 60 | Involved in kidney development | Patterson, L. T., Pembaur, M. & Potter, S. S. Hoxa11 and Hoxd11 regulate branching morphogenesis of the ureteric bud in the developing kidney. Development 2153-2161 (2001). |
| HOXB6 | ATGAGTTCCTATTTCGTGAACTCCA CCTTCCCCGTCACTCTGGCCAGCGG GCAGGAGTCCTTCCTGGGCCAGCTA CCGCTCTATTCGTCGGGCTATGCGG ACCCGCTGAGACATTACCCCGCGCC CTACGGGCCAGGGCCGGGCCAGGA CAAGGGCTTTGCCACTTCCTCCTAT TACCCGCCGGCGGGCGGTGGCTAC GGCCGAGCGGCGCCCTGCGACTAC GGGCCGGCGCCGGCCTTCTACCGC GAGAAAGAGTCGGCCTGCGCACTC TCCGGCGCCGACGAGCAGCCCCCG TTCCACCCCGAGCCGCGGAAGTCG GACTGCGCGCAGGACAAGAGCGTG TTCGGCGAGACAGAAGAGCAGAAG TGCTCCACTCCGGTCTACCCGTGGA TGCAGCGGATGAATTCGTGCAACA GTTCCTCCTTTGGGCCCAGCGGCCG | 61 | Involved in lung and epidermal development | 1. Patterson, L. T., Pembaur, M. & Potter, S. S. Hoxa11 and Hoxd11 regulate branching morphogenesis of the ureteric bud in the developing kidney. Development 2153-2161 (2001). Komuves, L. |

TABLE 1-continued

| GENE | SEQUENCE | SEQ ID NO: | ROLE | REFERENCES |
|---|---|---|---|---|
| | GCGAGGCCGCCAGACATACACACG TTACCAGACGCTGGAGCTGGAGAA GGAGTTTCACTACAATCGCTACCTG ACGCGGCGGCGGCGCATCGAGATC GCGCACGCCCTGTGCCTGACGGAG AGGCAGATCAAGATATGGTTCCAG AACCGACGCATGAAGTGGAAAAAG GAGAGCAAACTGCTCAGCGCGTCT CAGCTCAGTGCCGAGGAGGAGGAA GAAAAACAGGCCGAG | | | G. et al. Changes in HOXB6 homeodomain protein structure and localization during human epidermal development and differentiation. Dev. Dyn. 218, 636-647 (2000). Cardoso, W. V., Mitsialis, S. A., Brody, J. S. & Williams, M. C. Retinoic acid alters the expression of pattern-related genes in the developing rat lung. Dev. Dyn. 207, 47-59 (1996). |
| KLF4 | ATGGCTGTCAGCGACGCGCTGCTCC CATCTTTCTCCACGTTCGCGTCTGG CCCGGCGGGAAGGGAGAAGACACT GCGTCAAGCAGGTGCCCCGAATAA CCGCTGGCGGGAGGAGCTCTCCCA CATGAAGCGACTTCCCCCAGTGCTT CCCGGCCGCCCCTATGACCTGGCGG CGGCGACCGTGGCCACAGACCTGG AGAGCGGCGGAGCCGGTGCGGCTT GCGGCGGTAGCAACCTGGCGCCCC TACCTCGGAGAGAGACCGAGGAGT TCAACGATCTCCTGGACCTGGACTT TATTCTCTCCAATTCGCTGACCCAT CCTCCGGAGTCAGTGGCCGCCACC GTGTCCTCGTCAGCGTCAGCCTCCT CTTCGTCGTCGCCGTCGAGCAGCGG CCCTGCCAGCGCGCCCTCCACCTGC AGCTTCACCTATCCGATCCGGGCCG GGAACGACCCGGGCGTGGCGCCGG GCGGCACGGGCGGAGGCCTCCTCT ATGGCAGGGAGTCCGCTCCCCCTCC GACGGCTCCCTTCAACCTGGCGGAC ATCAACGACGTGAGCCCCTCGGGC GGCTTCGTGGCCGAGCTCCTGCGGC CAGAATTGGACCCGGTGTACATTCC GCCGCAGCAGCCGCAGCCGCCAGG TGGCGGGCTGATGGGCAAGTTCGT GCTGAAGGCGTCGCTGAGCGCCCC TGGCAGCGAGTACGGCAGCCCGTC GGTCATCAGCGTCAGCAAAGGCAG CCCTGACGGCAGCCACCCGGTGGT GGTGGCGCCCTACAACGGCGGGCC GCCGCGCACGTGCCCCAAGATCAA GCAGGAGGCGGTCTCTTCGTGCACC CACTTGGGCGCTGGACCCCCTCTCA GCAATGGCCACCGGCCGGCTGCAC ACGACTTCCCCCTGGGGCGGCAGCT CCCCAGCAGGACTACCCCGACCCT GGGTCTTGAGGAAGTGCTGAGCAG CAGGGACTGTCACCCTGCCCTGCCG CTTCCTCCCGGCTTCCATCCCCACC CGGGGCCCAATTACCCATCCTTCCT GCCCGATCAGATGCAGCCGCAAGT CCCGCCGCTCCATTACCAAGAGCTC ATGCCACCCGGTTCCTGCATGCCAG AGGAGCCCAAGCCAAAGAGGGGAA | 62 | Involved in regulation of pluripotency and development of skin. Reprogramming factor for induction of pluripotency. | Fuchs, E., Segre, J. A. & Bauer, C. Klf4 is a transcription factor required for establishing the barrier function of the skin. Nat. Genet. 22, 356-400 (1999). Jiang, J. et al. A core Klf circuitry regulates self-renewal of embryonic stem cells. Nat. Cell Biol. 10, 353-360 (2008). Takahashi, K. & Yamanaka, S. Induction of pluripotent stem cells from mouse embryonic and adult fibroblast cultures by defined factors. Cell 126, 663-76 (2006). Takahashi, K. et al. Induction of pluripotent stem cells from adult human fibroblasts by |

TABLE 1-continued

| GENE | SEQUENCE | SEQ ID NO: | ROLE | REFERENCES |
|---|---|---|---|---|
| | GACGATCGTGGCCCCGGAAAAGGA CCGCCACCCACACTTGTGATTACGC GGGCTGCGGCAAAACCTACACAAA GAGTTCCCATCTCAAGGCACACCTG CGAACCCACACAGGTGAGAAACCT TACCACTGTGACTGGGACGGCTGTG GATGGAAATTCGCCCGCTCAGATG AACTGACCAGGCACTACCGTAAAC ACACGGGCACCGCCCGTTCCAGT GCCAAAAATGCGACCGAGCATTTT CCAGGTCGGACCACCTCGCCTTACA CATGAAGAGGCATTTT | | | defined factors. Cell 131, 861-72 (2007). Yu, J. et al. Induced Pluripotent Stem Cell Lines Derived from Human Somatic Cells. Science (80-.). 318, 1917-1920 (2007). |
| LHX3 | ATGGAGGCGCGCGGGGAGCTGGGC CCGGCCCGGGAGTCGGCGGGAGGC GACCTGCTGCTAGCACTGCTGGCGC GGAGGGCGGACCTGCGCCGAGAGA TCCCGCTGTGCGCTGGCTGTGACCA GCACATCCTGGACCGCTTCATCCTC AAGGCTCTGGACCGCCACTGGCAC AGCAAGTGTCTCAAGTGCAGCGAC TGCCACACGCCACTGGCCGAGCGC TGCTTCAGCCGAGGGGAGAGCGTT TACTGCAAGGACGACTTTTTCAAGC GCTTCGGGACCAAGTGCGCCGCGT GCCAGCTGGGCATCCCGCCCACGC AGGTGGTGCGCCGCGCCCAGGACT TCGTGTACCACCTGCACTGCTTTGC CTGCGTCGTGTGCAAGCGGCAGCT GGCCACGGGCGACGAGTTCTACCT CATGGAGGACAGCCGGCTCGTGTG CAAGGCGGACTACGAAACCGCCAA GCAGCGAGAGGCCGAGGCCACGGC CAAGCGGCCGCGCACGACCATCAC CGCCAAGCAGCTGGAGACGCTGAA GAGCGCTTACAACACCTCGCCCAA GCCGGCGCGCCACGTGCGCGAGCA GCTCTCGTCCGAGACGGGCCTGGA CATGCGCGTGGTGCAGGTTTGGTTC CAGAACCGCCGGGCCAAGGAGAAG AGGCTGAAGAAGGACGCCGGCCGG CAGCGCTGGGGGCAGTATTTCCGC AACATGAAGCGCTCCCGCGGCGGC TCCAAGTCGGACAAGGACAGCGTT CAGGAGGGGCAGGACAGCGACGCT GAGGTCTCCTTCCCCGATGAGCCTT CCTTGGCGGAAATGGGCCCGGCCA ATGGCCTCTACGGGAGCTTGGGGG AACCCACCCAGGCCTTGGGCCGGC CCTCGGGAGCCCTGGGCAACTTCTC CCTGGAGCATGGAGGCCTGGCAGG CCCAGAGCAGTACCGAGAGCTGCG TCCCGGCAGCCCCTACGGTGTCCCC CCATCCCCCGCCGCCCCGCAGAGC CTCCCTGGCCCCCAGCCCCTCCTCT CCAGCCTGGTGTACCCAGACACCA GCTTGGGCCTTGTGCCCTCGGGAGC CCCCGGCGGGCCCCCACCCATGAG GGTGCTGGCAGGGAACGGACCCAG TTCTGACCTATCCACGGGGAGCAGC GGGGGTTACCCCGACTTCCCTGCCA GCCCCGCCTCCTGGCTGGATGAGGT AGACCACGCTCAGTTCTCAGGCCTC ATGGGCCCAGCTTTCTTGTAC | 63 | Involved in pituitary gland development | Sheng, H. Z. et al. Multistep Control of Pituitary Organogenesis. Science (80-.). 278, 1809-1812 (1997). |
| LMX1A | ATGGAAGGAATCATGAACCCCTAC ACGGCTCTGCCCACCCCACAGCAG CTCCTGGCCATCGAGCAGAGTGTCT ACAGCTCAGATCCCTTCCGACAGG GTCTCACCCCACCCCAGATGCCTGG AGACCACATGCACCCTTATGGTGCC GAGCCCCTTTTCCATGACCTGGATA GCGACGACACCTCCCTCAGTAACCT GGGTGACTGTTTCCTAGCAACCTCA | 64 | Involved in neuronal development | Lin, W. et al. Foxa1 and Foxa2 function both upstream of and cooperatively with Lmx1a and Lmx1b in |

TABLE 1-continued

| GENE | SEQUENCE | SEQ ID NO: | ROLE | REFERENCES |
| --- | --- | --- | --- | --- |
| | GAAGCTGGGCCTCTGCAGTCCAGA GTGGGAAACCCCATTGACCATCTGT ACTCCATGCAGAATTCTTACTTCAC ATCT | | | a feedforward loop promoting meso- diencephalic dopaminergic neuron development. Dev. Biol. 333, 386-396 (2009). Qiaolin, D. et al. Specific and integrated roles of Lmx1a, Lmx1b and Phox2a in ventral midbrain development. Development 138, 3399- 3408 (2011). |
| MEF2C | ATGGGGAGAAAAAAGATTCAGATT ACGAGGATTATGGATGAACGTAAC AGACAGGTGACATTTACAAAGAGG AAATTTGGGTTGATGAAGAAGGCT TATGAGCTGAGCGTGCTGTGTGACT GTGAGATTGCGCTGATCATCTTCAA CAGCACCAACAAGCTGTTCCAGTAT GCCAGCACCGACATGGACAAAGTG CTTCTCAAGTACACGGAGTACAAC GAGCCGCATGAGAGCCGGACAAAC TCAGACATCGTGGAGACGTTGAGA AAGAAGGGCCTTAATGGCTGTGAC AGCCCAGACCCCGATGCGGACGAT TCCGTAGGTCACAGCCCTGAGTCTG AGGACAAGTACAGGAAAATTAACG AAGATATTGATCTAATGATCAGCA GGCAAAGATTGTGTGCTGTTCCACC TCCCAACTTCGAGATGCCAGTCTCC ATCCCAGTGTCCAGCCACAACAGTT TGGTGTACAGCAACCCTGTCAGCTC ACTGGGAAACCCCAACCTATTGCC ACTGGCTCACCCTTCTCTGCAGAGG AATAGTATGTCTCCTGGTGTAACAC ATCGACCTCCAAGTGCAGGTAACA CAGGTGGTCTGATGGGTGGAGACC TCACGTCTGGTGCAGGCACCAGTGC AGGGAACGGGTATGGCAATCCCCG AAACTCACCAGGTCTGCTGGTCTCA CCTGGTAACTTGAACAAGAATATG CAAGCAAAATCTCCTCCCCCAATGA ATTTAGGAATGAATAACCGTAAAC CAGATCTCCGAGTTCTTATTCCACC AGGCAGCAAGAATACGATGCCATC AGTGTCTGAGGATGTCGACCTGCTT TTGAATCAAAGGATAAATAACTCC CAGTCGGCTCAGTCATTGGCTACCC CAGTGGTTTCCGTAGCAACTCCTAC TTTACCAGGACAAGGAATGGGAGG ATATCCATCAGCCATTTCAACAACA TATGGTACCGAGTACTCTCTGAGTA GTGCAGACCTGTCATCTCTGTCTGG GTTTAACACCGCCAGCGCTCTTCAC CTTGGTTCAGTAACTGGCTGGCAAC AGCAACACCTACATAACATGCCAC CATCTGCCCTCAGTCAGTTGGGAGC TTGCACTAGCACTCATTTATCTCAG AGTTCAAATCTCTCCCTGCCTTCTA CTCAAAGCCTCAACATCAAGTCAG AACCTGTTTCTCCTCCTAGAGACCG TACCACCACCCCTTCGAGATACCCA CAACACACGCGCCACGAGGCGGGG AGATCTCCTGTTGACAGCTTGAGCA | 65 | Involved in cardiac development | Lin, Q. et al. Control of mouse cardiac morphogenesis and myogenesis by transcription factor MEF2C. Science 276, 1404-7 (1997). |

TABLE 1-continued

| GENE | SEQUENCE | SEQ ID NO: | ROLE | REFERENCES |
|---|---|---|---|---|
| | GCTGTAGCAGTTCGTACGACGGGA<br>GCGACCGAGAGGATCACCGGAACG<br>AATTCCACTCCCCCATTGGACTCAC<br>CAGACCTTCGCCGGACGAAAGGGA<br>AAGTCCCTCAGTCAAGCGCATGCG<br>ACTTTCTGAAGGATGGGCAACA | | | |
| MESP1 | ATGGCCCAGCCCCTGTGCCCGCCGC<br>TCTCCGAGTCCTGGATGCTCTCTGC<br>GGCCTGGGGCCCAACTCGGCGGCC<br>GCCGCCCTCCGACAAGGACTGCGG<br>CCGCTCCCTCGTCTCGTCCCCAGAC<br>TCATGGGGCAGCACCCCAGCCGAC<br>AGCCCCGTGGCGAGCCCCGCGCGG<br>CCAGGCACCCTCCGGGACCCCCGC<br>GCCCCCTCCGTAGGTAGGCGCGGC<br>GCGCGCAGCAGCCGCCTGGGCAGC<br>GGGCAGAGGCAGAGCGCCAGTGAG<br>CGGGAGAAACTGCGCATGCGCACG<br>CTGGCCCGCGCCCTGCACGAGCTGC<br>GCCGCTTTCTACCGCCGTCCGTGGC<br>GCCCGCGGGCCAGAGCCTGACCAA<br>GATCGAGACGCTGCGCCTGGCTATC<br>CGCTATATCGGCCACCTGTCGGCCG<br>TGCTAGGCCTCAGCGAGGAGAGTC<br>TCCAGCGCCGGTGCCGGCAGCGCG<br>GTGACGCGGGGTCCCCTCGGGGCT<br>GCCCGCTGTGCCCCGACGACTGCCC<br>CGCGCAGATGCAGACACGGACGCA<br>GGCTGAGGGGCAGGGGCAGGGGCG<br>CGGGCTGGGCCTGGTATCCGCCGTC<br>CGCGCCGGGGCGTCCTGGGGATCC<br>CCGCCTGCCTGCCCCGGAGCCCGA<br>GCTGCACCCGAGCCGCGCGACCCG<br>CCTGCGCTGTTCGCCGAGGCGGCGT<br>GCCCGGAAGGGCAGGCGATGGAGC<br>CAAGCCCACCGTCCCCGCTCCTTCC<br>GGGCGACGTGCTGGCTCTGTTGGA<br>GACCTGGATGCCCCTCTCGCCTCTG<br>GAGTGGCTGCCTGAGGAGCCCAAG<br>TTG | 66 | Involved in cardiac development | Bondue, A. et al. Mesp1 Acts as a Master Regulator of Multipotent Cardiovascular Progenitor Specification. Cell Stem Cell 3,69-84 (2008). |
| MITF | ATGCTGGAAATGCTAGAATATAAT<br>CACTATCAGGTGCAGACCCACCTCG<br>AAAACCCCACCAAGTACCACATAC<br>AGCAAGCCCAACGGCAGCAGGTAA<br>AGCAGTACCTTTCTACCACTTTAGC<br>AAATAAACATGCCAACCAAGTCCT<br>GAGCTTGCCATGTCCAAACCAGCCT<br>GGCGATCATGTCATGCCACCGGTGC<br>CGGGGAGCAGCGCACCCAACAGCC<br>CCATGGCTATGCTTACGCTTAACTC<br>CAACTGTGAAAAAGAGGGATTTTA<br>TAAGTTTGAAGAGCAAAACAGGGC<br>AGAGAGCGAGTGCCCAGGCATGAA<br>CACACATTCACGAGCGTCCTGTATG<br>CAGATGGATGATGTAATCGATGAC<br>ATCATTAGCCTAGAATCAAGTTATA<br>ATGAGGAAATCTTGGGCTTGATGG<br>ATCCTGCTTTGCAAATGGCAAATAC<br>GTTGCCTGTCTCGGGAAACTTGATT<br>GATCTTTATGGAAACCAAGGTCTGC<br>CCCCACCAGGCCTCACCATCAGCA<br>ACTCCTGTCCAGCCAACCTTCCCAA<br>CATAAAAGGGAGCTCACAGAGTC<br>TGAAGCAAGAGCACTGGCCAAAGA<br>GAGGCAGAAAAGGACAATCACAA<br>CCTGATTGAACGAAGAAGAAGATT<br>TAACATAAATGACCGCATTAAAGA<br>ACTAGGTACTTTGATTCCCAAGTCA<br>AATGATCCAGACATGCGCTGGAAC<br>AAGGGAACCATCTTAAAAGCATCC<br>GTGGACTATATCCGAAAGTTGCAA<br>CGAGAACAGCAACGCGCAAAAGAA<br>CTTGAAAACCGACAGAAGAAACTG<br>GAGCACGCCAACCGGCATTTGTTGC<br>TCAGAATACAGGAACTTGAAATGC | 67 | Involved in pigment cell and melanocyte differentiation | Widlund, H. R. & Fisher, D. E. Microphthalmia-associated transcription factor: a critical regulator of pigment cell development and survival. Oncogene 22, 3035-3041 (2003). |

TABLE 1-continued

| GENE | SEQUENCE | SEQ ID NO: | ROLE | REFERENCES |
|---|---|---|---|---|
| | AGGCTCGAGCTCATGGACTTTCCCT TATTCCATCCACGGGTCTCTGCTCT CCAGATTTGGTGAATCGGATCATCA AGCAAGAACCCGTTCTTGAGAACT GCAGCCAAGACCTCCTTCAGCATCA TGCAGACCTAACCTGTACAACAACT CTCGATCTCACGGATGGCACCATCA CCTTCAACAACAACCTCGGAACTG GGACTGAGGCCAACCAAGCCTATA GTGTCCCCACAAAAATGGGATCCA AACTGGAAGACATCCTGATGGACG ACACCCTTTCTCCCGTCGGTGTCAC TGATCCACTCCTTTCCTCAGTGTCC CCCGGAGCTTCCAAAACAAGCAGC CGGAGGAGCAGTATGAGCATGGAA GAGACGGAGCACACTTGT | | | |
| MYC | ATGCCCCTCAACGTTAGCTTCACCA ACAGGAACTATGACCTCGACTACG ACTCGGTGCAGCCGTATTTCTACTG CGACGAGGAGGAGAACTTCTACCA GCAGCAGCAGCAGAGCGAGCTGCA GCCCCCGGCGCCCAGCGAGGATAT CTGGAAGAAATTCGAGCTGCTGCC CACCCCGCCCCTGTCCCCTAGCCGC CGCTCCGGGCTCTGCTCGCCCTCCT ACGTTGCGGTCACACCCTTCTCCCT TCGGGGAGACAACGACGGCGGTGG CGGGAGCTTCTCCACGGCCGACCA GCTGGAGATGGTGACCGAGCTGCT GGGAGGAGACATGGTGAACCAGAG TTTCATCTGCGACCCGGACGACGAG ACCTTCATCAAAAACATCATCATCC AGGACTGTATGTGGAGCGGCTTCTC GGCCGCCGCCAAGCTCGTCTCAGA GAAGCTGGCCTCCTACCAGGCTGC GCGCAAAGACAGCGGCAGCCCGAA CCCCGCCCGCGGCCACAGCGTCTG CTCCACCTCCAGCTTGTACCTGCAG GATCTGAGCGCCGCCGCCTCAGAG TGCATCGACCCCTCGGTGGTCTTCC CCTACCCTCTCAACGACAGCAGCTC GCCCAAGTCCTGCGCCTCGCAAGA CTCCAGCGCCTTCTCTCCGTCCTCG GATTCTCTGCTCTCCTCGACGGAGT CCTCCCCGCAGGGCAGCCCCGAGC CCCTGGTGCTCCATGAGGAGACAC CGCCCACCACCAGCAGCGACTCTG AGGAGGAACAAGAAGATGAGGAA GAAATCGATGTTGTTTCTGTGGAAA AGAGGCAGGCTCCTGGCAAAAGGT CAGAGTCTGGATCACCTTCTGCTGG AGGCCACAGCAAACCTCCTCACAG CCCACTGGTCCTCAAGAGGTGCCAC GTCTCCACACATCAGCACAACTACG CAGCGCCTCCCTCCACTCGGAAGG ACTATCCTGCTGCCAAGAGGGTCA AGTTGGACAGTGTCAGAGTCCTGA GACAGATCAGCAACAACCGAAAAT GCACCAGCCCCAGGTCCTCGGACA CCGAGGAGAATGTCAAGAGGCGAA CACACAACGTCTTGGAGCGCCAGA GGAGGAACGAGCTAAAACGGAGCT TTTTTGCCCTGCGTGACCAGATCCC GGAGTTGGAAAACAATGAAAAGGC CCCCAAGGTAGTTATCCTTAAAAAA GCCACAGCATACATCCTGTCCGTCC AAGCAGAGGAGCAAAAGCTCATTT CTGAAGAGGACTTGTTGCGGAAAC GACGAGAACAGTTGAAACACAAAC TTGAACAGCTACGGAACTCTTGTGC G | 68 | Involved in cell proliferation, differentiation and apoptosis. Reprogramming factor for induction of pluripotency. | Pelengaris, S., Khan, M. & Evan, G. c-MYC: more than just a matter of life and death. Nat. Rev. Cancer 2, 764-776 (2002). Takahashi, K. & Yamanaka, S. Induction of pluripotent stem cells from mouse embryonic and adult fibroblast cultures by defined factors. Cell 126,663-76 (2006). Takahashi, K. et al. Induction of pluripotent stem cells from adult human fibroblasts by defined factors. Cell 131,861-72 (2007). Yu, J. et al. Induced Pluripotent Stem Cell Lines Derived from Human Somatic Cells. Science (80-. ). 318, 1917-1920 (2007). |

TABLE 1-continued

| GENE | SEQUENCE | SEQ ID NO: | ROLE | REFERENCES |
|---|---|---|---|---|
| MYCL | ATGGACTACGACTCGTACCAGCACT ATTTCTACGACTATGACTGCGGGGA GGATTTCTACCGCTCCACGGCGCCC AGCGAGGACATCTGGAAGAAATTC GAGCTGGTGCCATCGCCCCCCACGT CGCCGCCCTGGGGCTTGGGTCCCGG CGCAGGGGACCCGGCCCCCGGGAT TGGTCCCCCGGAGCCGTGGCCCGG AGGGTGCACCGGAGACGAAGCGGA ATCCCGGGGCCACTCGAAAGGCTG GGGCAGGAACTACGCCTCCATCAT ACGCCGTGACTGCATGTGGAGCGG CTTCTCGGCCCGGGAACGGCTGGA GAGAGCTGTGAGCGACCGGCTCGC TCCTGGCGCGCCCCGGGGAACCC GCCCAAGGCGTCCGCCGCCCCGGA CTGCACTCCCAGCCTCGAAGCCGGC AACCCGGCGCCCGCCGCCCCCTGTC CGCTGGGCGAACCCAAGACCCAGG CCTGCTCCGGGTCCGAGAGCCCAA GCGACTCGGGTAAGGACCTCCCCG AGCCATCCAAGAGGGGGCCACCCC ATGGGTGGCCAAAGCTCTGCCCCTG CCTGAGGTCAGGCATTGGCTCTTCT CAAGCTCTTGGGCCATCTCCGCCTC TCTTTGGC | 69 | Involved in cell proliferation, differentiation and apoptosis. | Hatton, K. S. et al. Expression and activity of L-Myc in normal mouse development. Mol. Cell. Biol. 16, 1794-804 (1996). |
| MYCN | ATGCCGAGTTGTTCCACGTCTACGA TGCCAGGAATGATATGCAAGAACC CCGACTTGGAGTTTGACTCTTTGCA ACCATGCTTTTATCCGGATGAAGAC GACTTTTATTTCGGCGGCCCGGACA GCACCCCTCCTGGAGAGGACATCT GGAAAAAATTCGAACTTTTGCCTAC ACCCCCACTCAGTCCCTCTCGAGGA TTTGCGGAACACAGCAGTGAACCG CCGTCTTGGGTGACAGAGATGCTCC TCGAGAACGAATTGTGGGGAAGCC CTGCGGAGGAAGACGCTTTCGGGC TCGGTGGACTCGGAGGTCTCACGCC GAACCCAGTCATACTGCAGGATTG CATGTGGTCTGGATTCTCAGCTCGG GAGAAGCTGGAACGGGCAGTTTCT GAGAAACTCCAACATGGCCGGGGC CCTCCAACAGCGGGTTCTACCGCAC AGTCCCTGGTGCTGGAGCCGCTAG TCCCGCGGGGAGAGGCCATGGGGG CGCGGCAGGAGCGGGTAGGGCCGG CGCTGCGTTGCCTGCTGAGCTTGCG CACCCCGCCGCTGAATGTGTAGATC CCGCGGTAGTGTTTCCGTTCCCCGT TAATAAGCGAGAACCGGCACCGGT GCCAGCCGCTCCTGCGTCTGCACCC GCGGCAGGTCCTGCTGTCGCCTCAG GAGCAGGTATTGCCGCTCCTGCAG GGGCACCAGGAGTAGCCCCTCCAA GGCCCGGCGGTAGGCAAACCTCCG GCGGCGACCACAAAGCACTCTCAA CGAGCGGAGAGGATACACTGTCCG ATAGTGATGACGAGGACGACGAAG AGGAGGACGAGGAGGAGGAGATA GATGTTGTCACGGTCGAGAAGCGA AGGAGTTCTTCAAATACAAAAGCG GTAACGACATTCACGATAACAGTA AGACCTAAGAACGCAGCCCTCGGT CCAGGGCGGGCCCAGTCCAGTGAG CTTATACTTAAGCGCTGCCTGCCGA TTCACCAGCAGCATAACTACGCGG CCCCTAGTCCCTACGTTGAGAGCGA GGATGCCCCCCACAAAAAAAAAT AAAGTCTGAAGCGTCCCCCCGCCCC CTGAAATCCGTAATCCCCCCAAAG GCGAAGTCACTCAGTCCCAGGAAT TCAGATTCCGAGGACTCCGAACGG CGGCGGAATCATAACATACTTGAG AGACAACGACGCAATGACCTGAGG | 70 | Involved in cell proliferation and differentiation | Malynn, B. A. et al. N-myc can functionally replace c-myc in murine development, cellular growth, and differentiation. Genes Dev. 14, 1390-9 (2000). Sawai, S. et al. Defects of embryonic organogenesis resulting from targeted disruption of the N-myc gene in the mouse. Development 117, 1445-1455 (1993). Stanton, B. R., Perkins, A. S., Tessarollo, L., Sassoon, D. A. & Parada, L. F. Loss of N-myc function results in embryonic lethality and failure of the epithelial component of the embryo to develop. Genes Dev. 6, 2235-47 (1992). |

TABLE 1-continued

| GENE | SEQUENCE | SEQ ID NO: | ROLE | REFERENCES |
|---|---|---|---|---|
| | TCTTCTTTTTTGACCCTCCGAGATC ACGTCCCCGAGCTGGTTAAGAATG AGAAAGCTGCGAAGGTAGTCATAC TGAAAAAGGCCACCGAGTATGTCC ATAGTTTGCAAGCTGAGGAGCACC AGCTTCTCCTTGAAAAGGAGAAAC TTCAGGCACGACAACAGCAATTGC TGAAAAAGATTGAGCATGCACGCA CTTGT | | | |
| MYOD1 | ATGGAGCTACTGTCGCCACCGCTCC GCGACGTAGACCTGACGGCCCCCG ACGGCTCTCTCTGCTCCTTTGCCAC AACGGACGACTTCTATGACGACCC GTGTTTCGACTCCCCGGACCTGCGC TTCTTCGAAGACCTGGACCCGCGCC TGATGCACGTGGGCGCGCTCCTGA AACCCGAAGAGCACTCGCACTTCC CCGCGGCGGTGCACCCGGCCCCGG GCGCACGTGAGGACGAGCATGTGC GCGCGCCCAGCGGGCACCACCAGG CGGGCCGCTGCCTACTGTGGGCCTG CAAGGCGTGCAAGCGCAAGACCAC CAACGCCGACCGCCGCAAGGCCGC CACCATGCGCGAGCGGCGCCGCCT GAGCAAAGTAAATGAGGCCTTTGA GACACTCAAGCGCTGCACGTCGAG CAATCCAAACCAGCGGTTGCCCAA GGTGGAGATCCTGCGCAACGCCAT CCGCTATATCGAGGGCCTGCAGGCT CTGCTGCGCGACCAGGACGCCGCG CCCCCTGGCGCCGCAGCCGCCTTCT ATGCGCCGGGCCCGCTGCCCCCGG GCCGCGGCGGCGAGCACTACAGCG GCGACTCCGACGCGTCCAGCCCGC GCTCCAACTGCTCCGACGGCATGAT GGACTACAGCGGCCCCCCCGAGCGG CGCCCGGCGGCGGAACTGCTACGA AGGCGCCTACTACAACGAGGCGCC CAGCGAACCCAGGCCCGGGAAGAG TGCGGCGGTGTCGAGCCTAGACTG CCTGTCCAGCATCGTGGAGCGCATC TCCACCGAGAGCCCTGCGGCGCCC GCCCTCCTGCTGGCGGACGTGCCTT CTGAGTCGCCTCCGCGCAGGCAAG AGGCTGCCGCCCCAGCGAGGGAG AGAGCAGCGGCGACCCCACCCAGT CACCGGACGCCGCCCCGCAGTGCC CTGCGGGTGCGAACCCCAACCCGA TATACCAGGTGCTC | 71 | Involved in skeletal muscle specification and differentiation Demonstrated to induce differentiation of hPSCs to skeletal muscle | Tapscott, S. J. The circuitry of a master switch: Myod and the regulation of skeletal muscle gene transcription. Development 132, 2685- 2695 (2005). Abujarour, R. et al. Myogenic differentiation of muscular dystrophy-specific induced pluripotent stem cells for use in drug discovery. Stem Cells Transl. Med. 3,149-60 (2014). |
| MYOG | ATGGAGCTGTATGAGACATCCCCCT ACTTCTACCAGGAACCCCGCTTCTA TGATGGGGAAAACTACCTGCCTGTC CACCTCCAGGGCTTCGAACCACCA GGCTACGAGCGGACGGAGCTCACC CTGAGCCCCGAGGCCCCAGGGCCC CTTGAGGACAAGGGGCTGGGGACC CCCGAGCACTGTCCAGGCCAGTGC CTGCCGTGGGCGTGTAAGGTGTGTA AGAGGAAGTCGGTGTCCGTGGACC GGCGGCGGGCGGCCACACTGAGGG AGAAGCGCAGGCTCAAGAAGGTGA ATGAGGCCTTCGAGGCCCTGAAGA GAAGCACCCTGCTCAACCCCAACC AGCGGCTGCCCAAGGTGGAGATCC TGCGCAGTGCCATCCAGTACATCGA GCGCCTCCAGGCCCTGCTCAGCTCC CTCAACCAGGAGGAGCGTGACCTC CGCTACCGGGGCGGGGCGGGCCC CAGCCAGGGGTGCCCAGCGAATGC AGCTCTCACAGCGCCTCCTGCAGTC CAGAGTGGGGCAGTGCACTGGAGT TCAGCGCCAACCCAGGGGATCATC | 72 | Involved in skeletal muscle specification and differentiation | Pownall, M. E., Gustafsson, M. K. & Emerson, C. P. Myogenic Regulatory Factors and the Specification of Muscle Progenitors in Vertebrate Embryos. Annu. Rev. Cell Dev. Biol. 18,747- 783 (2002). Shi, X. & Garry, D. J. Muscle stem cells in development, |

TABLE 1-continued

| GENE | SEQUENCE | SEQ ID NO: | ROLE | REFERENCES |
|---|---|---|---|---|
| | TGCTCACGGCTGACCCTACAGATGC CCACAACCTGCACTCCCTCACCTCC ATCGTGGACAGCATCACAGTGGAA GATGTGTCTGTGGCCTTCCCAGATG AAACCATGCCCAAC | | | regeneration, and disease. Genes Dev. 20,1692-708 (2006). |
| NEURO D1 | ATGACCAAATCGTACAGCGAGAGT GGGCTGATGGGCGAGCCTCAGCCC CAAGGTCCTCCAAGCTGGACAGAC GAGTGTCTCAGTTCTCAGGACGAG GAGCACGAGGCAGACAAGAAGGA GGACGACCTCGAAGCCATGAACGC AGAGGAGGACTCACTGAGGAACGG GGGAGAGGAGGAGGACGAAGATG AGGACCTGGAAGAGGAGGAAGAA GAGGAAGAGGAGGATGACGATCAA AAGCCCAAGAGACGCGGCCCCAAA AAGAAGAAGATGACTAAGGCTCGC CTGGAGCGTTTTAAATTGAGACGCA TGAAGGCTAACGCCCGGGAGCGGA ACCGCATGCACGGACTGAACGCGG CGCTAGACAACCTGCGCAAGGTGG TGCCTTGCTATTCTAAGACGCAGAA GCTGTCCAAAATCGAGACTCTGCGC TTGGCCAAGAACTACATCTGGGCTC TGTCGGAGATCCTGCGCTCAGGCA AAAGCCCAGACCTGGTCTCCTTCGT TCAGACGCTTTGCAAGGGCTTATCC CAACCCACCACCAACCTGGTTGCG GGCTGCCTGCAACTCAATCCTCGGA CTTTTCTGCCTGAGCAGAACCAGGA CATGCCCCCCACCTGCCGACGGCC AGCGCTTCCTTCCCTGTACACCCCT ACTCCTACCAGTCGCCTGGGCTGCC CAGTCCGCCTTACGGTACCATGGAC AGCTCCCATGTCTTCCACGTTAAGC CTCCGCCGCACGCCTACAGCGCAG CGCTGGAGCCCTTCTTTGAAAGCCC TCTGACTGATTGCACCAGCCCTTCC TTTGATGGACCCCTCAGCCCGCCGC TCAGCATCAATGGCAACTTCTCTTT CAAACACGAACCGTCCGCCGAGTT TGAGAAAAATTATGCCTTTACCATG CACTATCCTGCAGCGACACTGGCA GGGGCCCAAAGCCACGGATCAATC TTCTCAGGCACCGCTGCCCCTCGCT GCGAGATCCCCATAGACAATATTAT GTCCTTCGATAGCCATTCACATCAT GAGCGAGTCATGAGTGCCCAGCTC AATGCCATATTTCATGAT | 73 | Involved in neuronal specification and differentiation Demonstrated to induce neuronal differentiation in hPSCs | Pataskar, A. et al. NeuroD1 reprograms chromatin and transcription factor landscapes to induce the neuronal program. EMBO J. 35, 24-45 (2016). Zhang, Y. et al. Rapid single-step induction of functional neurons from human pluripotent stem cells. Neuron 78, 785-98 (2013). |
| NEURO G1 | ATGCCAGCCCGCCTTGAGACCTGCA TCTCCGACCTCGACTGCGCCAGCAG CAGCGGCAGTGACCTATCCGGCTTC CTCACCGACGAGGAAGACTGTGCC AGACTCCAACAGGCAGCCTCCGCTT CGGGGCCGCCCGCGCCGGCCCGCA GGGGCGCGCCCAATATCTCCCGGG CGTCTGAGGTTCCAGGGGCACAGG ACGACGAGCAGGAGAGGCGGCGGC GCCGCGCCGGACGCGGGTCCGCT CCGAGGCGCTGCTGCACTCGCTGCG CAGGAGCCGGCGCGTCAAGGCCAA CGATCGCGAGCGCAACCGCATGCA CAACTTGAACGCGGCCCTGGACGC ACTGCGCAGCGTGCTGCCCTCGTTC CCCGACGACACCAAGCTCACCAAA ATCGAGACGCTGCGCTTCGCCTACA ACTACATCTGGGCTCTGGCCGAGAC ACTGCGCCTGGCGGATCAAGGGCT GCCCGGAGGCGGTGCCCGGGAGCG CCTCCTGCCGCCGCAGTGCGTCCCC TGCCTGCCCGGTCCCCAAGCCCCG CCAGCGACGCGGAGTCCTGGGGCT CAGGTGCCGCCGCCGCCTCCCCGCT CTCTGACCCCAGTAGCCCAGCCGCC TCCGAAGACTTCACCTACCGCCCCG | 74 | Involved in neuronal specification and differentiation | Bertrand, N., Castro, D. S. & Guillemot, F. Proneural genes and the specification of neural cell types. Nat. Rev. Neurosci. 3, 517-530 (2002). |

TABLE 1-continued

| GENE | SEQUENCE | SEQ ID NO: | ROLE | REFERENCES |
|---|---|---|---|---|
| | GCGACCCTGTTTTCTCCTTCCCAAG CCTGCCCAAAGACTTGCTCCACACA ACGCCCTGTTTCATTCCTTACCAC | | | |
| NEURO G3 | ATGACACCACAACCATCTGGTGCTC CCACAGTCCAGGTGACGCGAGAGA CTGAAAGATCATTCCCACGCGCGTC CGAGGATGAGGTGACATGTCCAAC TAGCGCACCCCCTCTCCTACCCGG ACCCGCGGGAATTGTGCTGAGGCC GAAGAGGGAGGATGCAGAGGAGC ACCAAGGAAACTTCGAGCCCGACG GGGTGGAAGAAGCCGCCCCAAGTC TGAGCTCGCCCTTAGCAAGCAGCG CCGCAGTCGGAGGAAAAAGGCAAA CGACCGGGAAAGGAATAGGATGCA TAATCTTAATTCTGCTCTGGACGCT CTGCGAGGCGTACTTCCTACTTTCC CGGATGACGCGAAATTGACCAAGA TAGAGACTCTCCGGTTTGCACATAA TTACATCTGGGCTCTTACACAAACA CTGAGAATTGCCGATCACAGTCTTT ACGCTCTTGAGCCACCCGCCCCGCA CTGTGGCGAGCTGGGTAGCCCCGG CGGCTCTCCTGGAGACTGGGGGTCT TTGTATTCTCCTGTCAGCCAAGCGG GATCTTTGAGTCCGGCTGCCAGTCT CGAAGAAAGACCCGGACTCCTTGG AGCGACTTTTTCAGCATGTCTGTCC CCTGGCTCATTGGCTTTCTCAGACT TTTTG | 75 | Involved in pancreatic development, and neuronal specification and differentiation | Bertrand, N., Castro, D. S. & Guillemot, F. Proneural genes and the specification of neural cell types. Nat. Rev. Neurosci. 3, 517-530 (2002). Arda, H. E. et al. Gene Regulatory Networks Governing Pancreas Development. Dev. Cell 25, 5-13 (2013). |
| NRL | ATGGCCCTGCCTCCCAGCCCGCTGG CCATGGAATATGTCAATGACTTTGA CTTGATGAAGTTTGAGGTAAAGCG GGAACCCTCTGAGGGCCGACCTGG CCCACCTACAGCCTCACTGGGATCC ACACCTTACAGCTCAGTGCCTCCTT CACCCACCTTCAGTGAACCAGGCAT GGTAGGGGCAACCGAGGGTACACG ACCAGGTTTGGAGGAGCTGTACTG GCTTGCTACCCTGCAGCAGCAGCTT GGGGCTGGGGAGGCATTGGGACTG AGTCCTGAAGAGGCCATGGAGCTA CTGCAAGGTCAGGGCCCAGTCCCT GTTGATGGACCCCATGGTTACTACC CAGGGAGCCCAGAGGAGACAGGAG CCCAGCACGTTCAGTTGGCAGAGC GGTTTTCCGACGCGGCGCTTGTCTC GATGTCTGTGCGAGAACTAAACCG GCAGCTGCGGGGATGCGGGAGAGA CGAGGCTCTACGACTGAAGCAGAG GCGTCGAACGCTGAAGAACCGTGG CTATGCGCAAGCATGTCGTTCCAAG AGGCTGCAACAGAGGCGAGGTCTT GAGGCCGAGCGCGCCCGTCTTGCA GCCCAGCTAGATGCGCTACGAGCT GAAGTAGCACGTTTGGCAAGAGAG CGAGATCTCTACAAGGCTCGCTGTG ACCGGCTAACCTCGAGTGGCCCCG GGTCCGGGGATCCCTCCCACCTTTT CCTCTGCCCAACTTTCTTGTACAAA GTTGTCCCC | 76 | Involved in photoreceptor development | Mears, A. J. et al. Nrl is required for rod photoreceptor development. Nat. Genet. 29, 447-452 (2001). |
| ONECU T1 | ATGAACGCGCAGCTGACCATGGAA GCGATCGGCGAGCTGCACGGGGTG AGCCATGAGCCGGTGCCCGCCCCT GCCGACCTGCTGGGCGGCAGCCCC CACGCGCGCAGCTCCGTGGCGCAC CGCGGCAGCCACCTGCCCCCCGCG CACCCGCGCTCCATGGGCATGGCGT CCCTGCTGGACGGCGGCAGCGGCG GCGGAGATTACCACCACCACCACC GGGCCCCTGAGCACAGCCTGGCCG GCCCCCTGCATCCCACCATGACCAT GGCCTGCGAGACTCCCCCAGGTAT GAGCATGCCCACCACCTACACCAC | 77 | Involved in retinal, liver, gallbladder and pancreatic development | Chakrabarti, S. K., et al. Transcription factors direct the development and function of pancreatic β cells. Trends Endocrinol. Metab. 14, 78-84 (2003). |

TABLE 1-continued

| GENE | SEQUENCE | SEQ ID NO: | ROLE | REFERENCES |
|---|---|---|---|---|
| | CTTGACCCCTCTGCAGCCGCTGCCT<br>CCCATCTCCACAGTCTCGGACAAGT<br>TCCCCCACCATCACCACCACCACCA<br>TCACCACCACCACCCGCACCACCA<br>CCAGCGCCTGGCGGGCAACGTGAG<br>CGGTAGCTTCACGCTCATGCGGGAT<br>GAGCGCGGGCTGGCCTCCATGAAT<br>AACCTCTATACCCCCTACCACAAGG<br>ACGTGGCCGGCATGGGCCAGAGCC<br>TCTCGCCCCTCTCCAGCTCCGGTCT<br>GGGCAGCATCCACAACTCCCAGCA<br>AGGGCTCCCCCACTATGCCCACCCG<br>GGGGCCGCCATGCCCACCGACAAG<br>ATGCTCACCCCCAACGGCTTCGAAG<br>CCCACCACCCGGCCATGCTCGGCC<br>GCCACGGGGAGCAGCACCTCACGC<br>CCACCTCGGCCGGCATGGTGCCCAT<br>CAACGGCCTTCCTCCGCACCATCCC<br>CACGCCCACCTGAACGCCCAGGGC<br>CACGGGCAACTCCTGGGCACAGCC<br>CGGGAGCCCAACCCTTCGGTGACC<br>GGCGCGCAGGTCAGCAATGGAAGT<br>AATTCAGGGCAGATGGAAGAGATC<br>AATACCAAAGAGGTGGCGCAGCGT<br>ATCACCACCGAGCTCAAGCGCTAC<br>AGCATCCCACAGGCCATCTTCGCGC<br>AGAGGGTGCTCTGCCGCTCCCAGG<br>GGACCCTCTCGGACCTGCTGCGCAA<br>CCCCAAACCCTGGAGCAAACTCAA<br>ATCCGGCCGGGAGACCTTCCGGAG<br>GATGTGGAAGTGGCTGCAGGAGCC<br>GGAGTTCCAGCGCATGTCCGCGCTC<br>CGCTTAGCAGCATGCAAAAGGAAA<br>GAACAAGAACATGGGAAGGATAGA<br>GGCAACACACCCAAAAAGCCCAGG<br>TTGGTCTTCACAGATGTCCAGCGTC<br>GAACTCTACATGCAATATTCAAGG<br>AAAATAAGCGTCCATCCAAAGAAT<br>TGCAAATCACCATTTCCCAGCAGCT<br>GGGGTTGGAGCTGAGCACTGTCAG<br>CAACTTCTTCATGAACGCAAGAAG<br>GAGGAGTCTGGACAAGTGGCAGGA<br>CGAGGGCAGCTCCAATTCAGGCAA<br>CTCATCTTCTTCATCAAGCACTTGT<br>ACCAAAGCA | | | Clotman, F. et al. The onecut transcription factor HNF6 is required for normal development of the biliary tract. Development 129,1819-1828 (2002). Sapkota, D. et al. Onecut1 and Onecut2 redundantly regulate early retinal cell fates during development. Proc. Natl. Acad. Sci. U. S. A. 111, E4086-95 (2014). |
| OTX2 | ATGATGTCTTATCTTAAGCAACCGC<br>CTTACGCAGTCAATGGGCTGAGTCT<br>GACCACTTCGGGTATGGACTTGCTG<br>CACCCCTCCGTGGGCTACCCGGGGC<br>CCTGGGCTTCTTGTCCCGCAGCCAC<br>CCCCCGGAAACAGCGCCGGGAGAG<br>GACGACGTTCACTCGGGCGCAGCT<br>AGATGTGCTGGAAGCACTGTTTGCC<br>AAGACCCGGTACCCAGACATCTTC<br>ATGCGAGAGGAGGTGGCACTGAAA<br>ATCAACTTGCCCGAGTCGAGGGTG<br>CAGGTATGGTTTAAGAATCGAAGA<br>GCTAAGTGCCGCCAACAACAGCAA<br>CAACAGCAGAATGGAGGTCAAAAC<br>AAAGTGAGACCTGCCAAAAAGAAG<br>ACATCTCCAGCTCGGGAAGTGAGTT<br>CAGAGAGTGGAACAAGTGGCCAAT<br>TCACTCCCCCCTCTAGCACCTCAGT<br>CCCGACCATTGCCAGCAGCAGTGCT<br>CCTGTGTCTATCTGGAGCCCAGCTT<br>CCATCTCCCCACTGTCAGATCCCTT<br>GTCCACCTCCTCTTCCTGCATGCAG<br>AGGTCCTATCCCATGACCTATACTC<br>AGGCTTCAGGTTATAGTCAAGGAT<br>ATGCTGGCTCAACTTCCTACTTTGG<br>GGGCATGGACTGTGGATCATATTTG<br>ACCCCTATGCATCACCAGCTTCCCG<br>GACCAGGGGCCACACTCAGTCCCA<br>TGGGTACCAATGCAGTCACCAGCC<br>ATCTCAATCAGTCCCCAGCTTCTCT<br>TTCCACCCAGGGGATATGGAGCTTCA | 78 | Involved in photoreceptor differentiation, pineal gland development and induction and specification of forebrain and midbrain | Rhinn, M. et al. Sequential roles for Otx2 in visceral endoderm and neuroectoderm for forebrain and midbrain induction and specification. Development 125, 845-856 (1998). Nishida, A. et al. Otx2 homeobox gene controls retinal photoreceptor cell fate and pineal gland development. Nat. Neurosci. 6,1255-1263 (2003). |

TABLE 1-continued

| GENE | SEQUENCE | SEQ ID NO: | ROLE | REFERENCES |
|---|---|---|---|---|
| | AGCTTGGGTTTTAACTCAACCACTG ATTGCTTGGATTATAAGGACCAAAC TGCCTCCTGGAAGCTTAACTTCAAT GCTGACTGCTTGGATTATAAAGATC AGACATCCTCGTGGAAATTCCAGGT TTTG | | | |
| PAX7 | ATGGCGGCCCTTCCCGGCACGGTAC CGAGAATGATGCGGCCGGCTCCGG GGCAGAACTACCCCCGCACGGGAT TCCCTTTGGAAGTGTCCACCCCGCT TGGCCAAGGCCGGGTCAATCAGCT GGGAGGGGTCTTCATCAATGGGCG ACCCCTGCCTAACCACATCCGCCAC AAGATAGTGGAGATGGCCCACCAT GGCATCCGGCCCTGTGTCATCTCCC GACAGCTGCGTGTCTCCCACGGCTG CGTCTCCAAGATTCTTTGCCGCTAC CAGGAGACCGGGTCCATCCGGCCT GGGGCCATCGGCGGCAGCAAGCCC AGACAGGTGGCGACTCCGGATGTA GAGAAAAAGATTGAGGAGTACAAG AGGGAAAACCAGGCATGTTCAGC TGGGAGATCCGGGACAGGCTGCTG AAGGATGGGCACTGTGACCGAAGC ACTGTGCCCTCAGTGAGTTCGATTA GCCGCGTGCTCAGAATCAAGTTCG GGAAGAAAGAGGAGGAGGATGAA GCGGACAAGAAGGAGGACGACGGC GAAAAGAAGGCCAAACACAGCATC GACGGCATCCTGGGCGACAAAGGG AACCGGCTGGACAGAGGGCTCGGAT GTGGAGTCGGAACCTGACCTCCCA CTGAAGCGCAAGCAGCGACGCAGT CGGACCACATTCACGGCCGAGCAG CTGGAGGAGCTGGAGAAGGCCTTT GAGAGGACCCACTACCCAGACATA TACACCCGCGAGGAGCTGGCGCAG AGGACCAAGCTGACAGAGGCGCGT GTGCAGGTCTGGTTCAGTAACCGCC GCGCCCGTTGGCGTAAGCAGGCAG GAGCCAACCAGCTGGCGGCGTTCA ACCACCTTCTGCCAGGAGGCTTCCC GCCCACCGGCATGCCCACGCTGCC CCCCTACCAGCTGCCGGACTCCACC TACCCCACCACCACCATCTCCCAAG ATGGGGGCAGCACTGTGCACCGGC CTCAGCCCCTGCCACCGTCCACCAT GCACCAGGGCGGGCTGGCTGCAGC GGCTGCAGCCGCCGACACCAGCTC TGCCTACGGAGCCCGCCACAGCTTC TCCAGCTACTCTGACAGCTTCATGA ATCCGGCGGCGCCCTCCAACCACAT GAACCCGGTCAGCAACGGCCTGTC TCCTCAGGTGATGAGCATCTTGGGC AACCCCAGTGCGGTGCCCCCGCAG CCACAGGCTGACTTCTCCATCTCCC CGCTGCATGGCGGCCTGGACTCGG CCACCTCCATCTCAGCCAGCTGCAG CCAGCGGGCCGACTCCATCAAGCC AGGAGACAGCCTGCCCACCTCCCA GGCCTACTGCCCACCCACCTACAGC ACCACCGGCTACAGCGTGGACCCC GTGGCCGGCTATCAGTACGGCCAG TACGGCCAGAGTGAGTGCCTGGTG CCCTGGGCGTCCCCCGTCCCCATTC CTTCTCCCACCCCCAGGGCCTCCTG CTTGTTTATGGAGAGCTACAAGGTG GTGTCAGGGTGGGAATGTCCATTT CACAGATGGAAAAATTGAAGTCCA GCCAGATGGAACAGTTCACC | 79 | Involved in specification and differentiation of satellite cells Demonstrated to induce myogenic precursor differentiation in hPSCs | Darabi, R. et al. Human ES- and iPS-derived myogenic progenitors restore DYSTROPHIN and improve contractility upon transplantation in dystrophic mice. Cell Stem Cell 10, 610-9 (2012). Seale, P., et al. Pax7 Is Required for the Specification of Myogenic Satellite Cells. Cell 102, 777-786 (2000). |

TABLE 1-continued

| GENE | SEQUENCE | SEQ ID NO: | ROLE | REFERENCES |
|------|----------|-----------|------|------------|
| POU1F1 | ATGAGTTGCCAAGCTTTTACTTCGG CTGATACCTTTATACCTCTGAATTC TGACGCCTCTGCAACTCTGCCTCTG ATAATGCATCACAGTGCTGCCGAGT GTCTACCAGTCTCCAACCATGCCAC CAATGTGATGTCTACAGCAACAGG ACTTCATTATTCTGTTCCTTCCTGTC ATTATGGAAACCAGCCATCAACCT ATGGAGTGATGGCAGGTAGTTTAA CCCCTTGTCTTTATAAATTTCCTGA CCACACCTTGAGTCATGGATTTCCT CCTATACACCAGCCTCTTCTGGCAG AGGACCCCACAGCTGCTGATTTCAA GCAGGAACTCAGGCGGAAAAGTAA ATTGGTGGAAGAGCCAATAGACAT GGATTCTCCAGAAATCAGAGAACT TGAAAAGTTTGCCAATGAATTTAAA GTGAGACGAATTAAATTAGGATAC ACCCAGACAAATGTTGGGGAGGCC CTGGCAGCTGTGCATGGCTCTGAAT TCAGTCAAACAACAATCTGCCGATT TGAAAATCTGCAGCTCAGCTTTAAA AATGCATGCAAACTGAAAGCAATA TTATCCAAATGGCTGGAGGAAGCT GAGCAAGTAGGAGCTTTGTACAAT GAAAAAGTGGGAGCAAATGAAAGG AAAAGAAAACGAAGAACAACTATA AGCATTGCTGCTAAAGATGCTCTGG AGAGACACTTTGGAGAACAGAATA AACCTTCTTCTCAAGAGATCATGAG GATGGCTGAAGAACTGAATCTGGA GAAAGAAGTAGTAAGAGTTTGGTT TTGCAACCGGAGGCAGAGAGAAAA ACGGGTGAAAACAAGTCTGAATCA GAGTTTATTTTCTATTTCTAAGGAA CATCTTGAGTGCAGATCAGGCCTCA TGGGCCCAGCTTTCTTGTAC | 80 | Involved in pituitary gland development | Turton, J. P. G. et al. Novel Mutations within the POU1F1 Gene Associated with Variable Combined Pituitary Hormone Deficiency. J. Clin. Endocrinol. Metab. 90, 4762-4770 (2005). |
| POU5F1 | ATGGCGGGACACCTGGCTTCAGATT TTGCCTTCTCGCCCCTCCAGGTGG TGGAGGTGATGGGCCAGGGGGCC GGAGCCGGGCTGGGTTGATCCTCG GACCTGGCTAAGCTTCCAAGGCCCT CCTGGAGGGCCAGGAATCGGGCCG GGGGTTGGGCCAGGCTCTGAGGTG TGGGGGATTCCCCCATGCCCCCGC CGTATGAGTTCTGTGGGGGGATGG CGTACTGTGGGCCCCAGGTTGGAGT GGGGCTAGTGCCCCAAGGCGGCTT GGAGACCTCTCAGCCTGAGGGCGA AGCAGGAGTCGGGGTGGAGAGCAA CTCCGATGGGGCCTCCCCGGAGCCC TGCACCGTCACCCCTGGTGCCGTGA AGCTGGAGAAGGAGAAGCTGGAGC AAAACCCGGAGGAGTCCCAGGACA TCAAAGCTCTGCAGAAAGAACTCG AGCAATTTGCCAAGCTCCTGAAGC AGAAGAGGATCACCCTGGGATATA CACAGGCCGATGTGGGGCTCACCC TGGGGGTTCTATTTGGGAAGGTATT CAGCCAAACGACCATCTGCCGCTTT GAGGCTCTGCAGCTTAGCTTCAAGA ACATGTGTAAGCTGCGCCCTTGCT GCAGAAGTGGGTGGAGGAAGCTGA CAACAATGAAAATCTTCAGGAGAT ATGCAAAGCAGAAACCCTCGTGCA GGCCCGAAAGAGAAAGCGAACCAG TATCGAGAACCGAGTGAGAGGCAA CCTGGAGAATTTGTTCCTGCAGTGC CCGAAACCCACACTGCAGCAGATC AGCCACATCGCCCAGCAGCTTGGG CTCGAGAAGGATGTGGTCCGAGTG TGGTTCTGTAACCGGCGCCAGAAG GGCAAGCGATCAAGCAGCGACTAT GCACAACGAGAGGATTTTGAGGCT GCTGGGTCTCCTTTCTCAGGGGAC | 81 | Involved in regulation of pluripotency and embryogenesis. Reprogramming factor for induction of pluripotency | Boyer, L. A., et al. Core Transcriptional Regulatory Circuitry in Human Embryonic Stem Cells. Cell 122, 947-956 (2005). Takahashi, K. & Yamanaka, S. Induction of pluripotent stem cells from mouse embryonic and adult fibroblast cultures by defined factors. Cell 126,663-76 (2006). Takahashi, K. et al. Induction of pluripotent stem cells from adult human fibroblasts by defined factors. Cell 131,861-72 (2007). Yu, J. et al. |

TABLE 1-continued

| GENE | SEQUENCE | SEQ ID NO: | ROLE | REFERENCES |
|---|---|---|---|---|
| | CAGTGTCCTTTCCTCTGGCCCCAGG GCCCCATTTTGGTACCCCAGGCTAT GGGAGCCCTCACTTCACTGCACTGT ACTCCTCGGTCCCTTTCCCTGAGGG GGAAGCCTTTCCCCCTGTCTCTGTC ACCACTCTGGGCTCTCCCATGCATT CAAAC | | | Induced Pluripotent Stem Cell Lines Derived from Human Somatic Cells. Science (80-.). 318, 1917-1920 (2007). |
| RUNX1 | ATGGCTTCAGACAGCATATTTGAGT CATTTCCTTCGTACCCACAGTGCTT CATGAGAGAATGCATACTTGGAAT GAATCCTTCTAGAGACGTCCACGAT GCCAGCACGAGCCGCCGCTTCACG CCGCCTTCCACCGCGCTGAGCCCAG GCAAGATGAGCGAGGCGTTGCCGC TGGGCGCCCCGGACGCCGGCGCTG CCCTGGCCGGCAAGCTGAGGAGCG GCGACCGCAGCATGGTGGAGGTGC TGGCCGACCACCCGGGCGAGCTGG TGCGCACCGACAGCCCCAACTTCCT CTGCTCCGTGCTGCCTACGCACTGG CGCTGCAACAAGACCCTGCCCATC GCTTTCAAGGTGGTGGCCCTAGGG GATGTTCCAGATGGCACTCTGGTCA CTGTGATGGCTGGCAATGATGAAA ACTACTCGGCTGAGCTGAGAAATG CTACCGCAGCCATGAAGAACCAGG TTGCAAGATTTAATGACCTCAGGTT TGTCGGTCGAAGTGGAAGAGGGAA AAGCTTCACTCTGACCATCACTGTC TTCACAAACCCACCGCAAGTCGCC ACCTACCACAGAGCCATCAAAATC ACAGTGGATGGGCCCCGAGAACCT CGAAGACATCGGCAGAAACTAGAT GATCAGACCAAGCCCGGGAGCTTG TCCTTTTCCGAGCGGCTCAGTGAAC TGGAGCAGCTGCGGCGCACAGCCA TGAGGGTCAGCCCACACCACCCAG CCCCCACGCCCAACCCTCGTGCCTC CCTGAACCACTCCACTGCCTTTAAC CCTCAGCCTCAGAGTCAGATGCAG GATACAAGGCAGATCCAACCATCC CCACCGTGGTCCTACGATCAGTCCT ACCAATACCTGGGATCCATTGCCTC TCCTTCTGTGCACCCAGCAACGCCC ATTTCACCTGGACGTGCCAGCGGCA TGACAACCCTCTCTGCAGAACTTTC CAGTCGACTCTCAACGGCACCCGA CCTGACAGCGTTCAGCGACCCGCG CCAGTTCCCCGCGCTGCCCTCCATC TCCGACCCCCGCATGCACTATCCAG GCGCCTTCACCTACTCCCCGACGCC GGTCACCTCGGGCATCGGCATCGG CATGTCGGCCATGGGCTCGGCCAC GCGCTACCACACCTACCTGCCGCCG CCCTACCCCGGCTCGTCGCAAGCGC AGGGAGGCCCCGTTCCAAGCCAGCT CGCCCTCCTACCACCTGTACTACGG CGCCTCGGCCGGCTCCTACCAGTTC TCCATGGTGGGCGGCGAGCGCTCG CCGCCGCGCATCCTGCCGCCCTGCA CCAACGCCTCCACCGGCTCCGCGCT GCTCAACCCCAGCCTCCCGAACCA GAGCGACGTGGTGGAGGCCGAGGG CAGCCACAGCAACTCCCCCACCAA CATGGCGCCCTCCGCGCGCCTGGA GGAGGCCGTGTGGAGGCCCTAC | 82 | Involved in haematopoetic cell development | Woolf, E. et al. Runx3 and Runx1 are required for CD8 T cell development during thymopoiesis. Proc. Natl. Acad. Sci. U. S. A. 100, 7731-6 (2003). Lacaud, G. et al. Runx1 is essential for hematopoietic commitment at the hemangioblast stage of development in vitro. Blood 100, 458-66 (2002). |
| SIX1 | ATGGTCGATGCTGCCGTCGTTTGGCT TTACGCAGGAGCAAGTGGCGTGCG TGTGCGAGGTTCTGCAGCAAGGCG GAAACCTGGAGCGCCTGGGCAGGT TCCTGTGGTCACTGCCCGCCTGCGA CCACCTGCACAAGAACGAGAGCGT | 83 | Involved in kidney, ear and olfactory epithelium development | Zheng, W. et al. The role of Six1 in mammalian auditory system |

TABLE 1-continued

| GENE | SEQUENCE | SEQ ID NO: | ROLE | REFERENCES |
|---|---|---|---|---|
| | ACTCAAGGCCAAGGCGGTGGTCGC<br>CTTCCACCGCGGCAACTTCCGTGAG<br>CTCTACAAGATCCTGGAGAGCCAC<br>CAGTTCTCGCCTCACAACCACCCCA<br>AACTGCAGCAACTGTGGCTGAAGG<br>CGCATTACGTGGAGGCCGAGAAGC<br>TGTGCGGCCGACCCCTGGGCGCCGT<br>GGGCAAATATCGGGTGCGCCGAAA<br>ATTTCCACTGCCGCGCACCATCTGG<br>GACGGCGAGGAGACCAGCTACTGC<br>TTCAAGGAGAAGTCGAGGGGTGTC<br>CTGCGGGAGTGGTACGCGCACAAT<br>CCCTACCCATCGCCGCGTGAGAAG<br>CGGGAGCTGGCCGAGGCCACCGGC<br>CTCACCACCACCCAGGTCAGCAACT<br>GGTTTAAGAACCGGAGGCAAAGAG<br>ACCGGGCCGCGGAGGCCAAGGAAA<br>GGGAGAACACCGAAAACAATAACT<br>CCTCCTCCAACAAGCAGAACCAAC<br>TCTCTCCTCTGGAAGGGGGCAAGCC<br>GCTCATGTCCAGCTCAGAAGAGGA<br>ATTCTCACCTCCCCAAAGTCCAGAC<br>CAGAACTCGGTCCTTCTGCTGCAGG<br>GCAATATGGGCCACGCCAGGAGCT<br>CAAACTATTCTCTCCCGGGCTTAAC<br>AGCCTCGCAGCCCAGTCACGGCCT<br>GCAGACCCACCAGCATCAGCTCCA<br>AGACTCTCTGCTCGGCCCCCTCACC<br>TCCAGTCTGGTGGACTTGGGGTCC | | | development.<br>Development<br>130, 3989-<br>4000 (2003).<br>Xu, P. et al.<br>Six1 is<br>required for<br>the early<br>organogenesis<br>of mammalian<br>kidney.<br>Development<br>130, 3085-<br>3094 (2003).<br>Ikeda, K. et<br>al. Six1 is<br>essential for<br>early<br>neurogenesis<br>in the<br>development<br>of olfactory<br>epithelium.<br>Dev. Biol.<br>311, 53-68<br>(2007). |
| SIX2 | ATGTCCATGCTGCCCACCTTCGGCT<br>TCACGCAGGAGCAAGTGGCGTGCG<br>TGTGCGAGGTGCTGCAGCAGGGCG<br>GCAACATCGAGCGGCTGGGCCGCT<br>TCCTGTGGTCGCTGCCCGCCTGCGA<br>GCACCTTCACAAGAATGAAAGCGT<br>GCTCAAGGCCAAGGCCGTGGTGGC<br>CTTCCACCGCGGCAACTTCCGCGAG<br>CTCTACAAGATCCTGGAGAGCCAC<br>CAGTTCTCGCCGCACAACCACGCCA<br>AGCTGCAGCAGCTGTGGCTCAAGG<br>CACACTACATCGAGGCGGAGAAGC<br>TGCGCGGCCGACCCCTGGGCGCCG<br>TGGGCAAATACCGCGTGCGCCGCA<br>AATTCCCGCTGCCGCGCTCCATCTG<br>GGACGGCGAGGAGACCAGCTACTG<br>CTTCAAGGAAAAGAGTCGCAGCGT<br>GCTGCGCGAGTGGTACGCGCACAA<br>CCCCTACCCTTCACCCCGCGAGAAG<br>CGTGAGCTGACGGAGGCCACGGGC<br>CTCACCACCACACAGGTCAGCAAC<br>TGGTTCAAGAACCGGCGGCAGCGC<br>GACCGGGCGGCCGAGGCCAAGGAA<br>AGGGAGAACAACGAGAACTCCAAT<br>TCTAACAGCCACAACCCGCTGAAT<br>GGCAGCGGCAAGTCGGTGTTAGGC<br>AGCTCGGAGGATGAGAAGACTCCA<br>TCGGGGACGCCAGACCACTCATCA<br>TCCAGCCCCGCACTGCTCCTCAGCC<br>CGCCGCCCCTGGGCTGCCGTCCCT<br>GCACAGCCTGGGCCACCCTCCGGG<br>CCCCAGCGCAGTGCCAGTGCCGGT<br>GCCAGGCGGAGGTGGAGCGGACCC<br>ACTGCAACACCACCATGGCCTGCA<br>GGACTCCATCCTCAACCCCATGTCA<br>GCCAACCTCGTGGACCTGGGCTCC | 84 | Involved in<br>kidney<br>development | Kobayashi, A.<br>et al. Six2<br>Defines and<br>Regulates a<br>Multipotent<br>Self-<br>Renewing<br>Nephron<br>Progenitor<br>Population<br>throughout<br>Mammalian<br>Kidney<br>Development.<br>Cell Stem<br>Cell 3, 169-<br>181 (2008). |
| SNAI2 | ATGCCGCGCTCCTTCCTGGTCAAGA<br>AGCATTTCAACGCCTCCAAAAAGC<br>CAAACTACAGCGAACTGGACACAC<br>ATACAGTGATTATTTCCCCGTATCT<br>CTATGAGAGTTACTCCATGCCTGTC<br>ATACCACAACCAGAGATCCTCAGC<br>TCAGGAGCATACAGCCCCATCACT<br>GTGTGGACTACCGCTGCTCCATTCC<br>ACGCCCAGCTACCCAATGGCCTCTC<br>TCCTCTTTCCGGATACTCCTCATCTT | 85 | Involved in<br>neural crest<br>development,<br>epithelial-<br>mesenchymal<br>transition, and<br>melanocyte<br>stem cell<br>development | Cobaleda, C.,<br>Pérez-Caro,<br>M., Vicente-<br>Dueñas, C. &<br>Sánchez-<br>García, I.<br>Function of<br>the Zinc-<br>Finger<br>Transcription |

TABLE 1-continued

| GENE | SEQUENCE | SEQ ID NO: | ROLE | REFERENCES |
| --- | --- | --- | --- | --- |
| | TGGGGCGAGTGAGTCCCCCTCCTCC ATCTGACACCTCCTCCAAGGACCAC AGTGGCTCAGAAAGCCCCATTAGT GATGAAGAGGAAAGACTACAGTCC AAGCTTTCAGACCCCCATGCCATTG AAGCTGAAAAGTTTCAGTGCAATTT ATGCAATAAGACCTATTCAACTTTT TCTGGGCTGGCCAAACATAAGCAG CTGCACTGCGATGCCCAGTCTAGAA AATCTTTCAGCTGTAAATACTGTGA CAAGGAATATGTGAGCCTGGGCGC CCTGAAGATGCATATTCGGACCCAC ACATTACCTTGTGTTTGCAAGATCT GCGGCAAGGCGTTTTCCAGACCCTG GTTGCTTCAAGGACACATTAGAACT CACACGGGGAGAAGCCTTTTTCTT GCCCTCACTGCAACAGAGCATTTGC AGACAGGTCAAATCTGAGGGCTCA TCTGCAGACCCATTCTGATGTAAAG AAATACCAGTGCAAAAACTGCTCC AAAACCTTCTCCAGAATGTCTCTCC TGCACAAACATGAGGAATCTGGCT GCTGTGTAGCACAC | | | Factor SNAI2 in Cancer and Development. Annu. Rev. Genet. 41, 41-61 (2007). |
| SOX10 | ATGGCGGAGGAGCAGGACCTATCG GAGGTGGAGCTGAGCCCCGTGGGC TCGGAGGAGCCCCGCTGCCTGTCCC CGGGGAGCGCGCCCTCGCTAGGGC CCGACGGCGGCGGCGGCGGATCGG GCCTGCGAGCCAGCCCGGGGCCAG GCGAGCTGGGCAAGGTCAAGAAGG AGCAGCAGGACGGCGAGGCGGACG ATGACAAGTTCCCCGTGTGCATCCG CGAGGCCGTCAGCCAGGTGCTCAG CGGCTACGACTGGACGCTGGTGCC CATGCCCGTGCGCGTCAACGGCGC CAGCAAAAGCAAGCCGCACGTCAA GCGGCCCATGAACGCCTTCATGGTG TGGGCTCAGGCAGCGCGCAGGAAG CTCGCGGACCAGTACCCGCACCTGC ACAACGCTGAGCTCAGCAAGACGC TGGGCAAGCTCTGGAGGCTGCTGA ACGAAAGTGACAAGCGCCCCTTCA TCGAGGAGGCTGAGCGGCTCCGTA TGCAGCACAAGAAAGACCACCCGG ACTACAAGTACCAGCCCAGGCGGC GGAAGAACGGGAAGGCCGCCCAGG GCGAGGCGGAGTGCCCCGGTGGGG AGGCCGAGCAAGGTGGGACCGCCG CCATCCAGGCCCACTACAAGAGCG CCCACTTGGACCACCGGCACCCAG GAGAGGGCTCCCCCATGTCAGATG GGAACCCCGAGCACCCCTCAGGCC AGAGCCATGGCCCACCCACCCCTC CAACCACCCCGAAGACAGAGCTGC AGTCGGGCAAGGCAGACCCGAAGC GGGACGGGCGCTCCATGGGGGAGG GCGGGAAGCCTCACATCGACTTCG GCAACGTGGACATTGGTGAGATCA GCCACGAGGTAATGTCCAACATGG AGACCTTTGATGTGGCTGAGTTGGA CCAGTACCTGCCGCCCAATGGGCA CCCAGGCCATGTGAGCAGCTACTC AGCAGCCGGCTATGGGCTGGGCAG TGCCCTGGCCGTGGCCAGTGGACA CTCCGCCTGGATCTCCAAGCCACCA GGCGTGGCTCTGCCCACGGTCTCAC CACCTGGTGTGGATGCCAAAGCCC AGGTGAAGACAGAGACCGCGGGGC CCCAGGGGCCCCACACTACACCG ACCAGCCATCCACCTCACAGATCGC CTACACCTCCCTCAGCCTGCCCCAC TATGGCTCAGCCTTCCCCTCCATCT CCCGCCCCCAGTTTGACTACTCTGA CCATCAGCCCTCAGGACCCTATTAT GGCCACTCGGGCCAGGCCTCTGGC CTCTACTCGGCCTTCTCCTATATGG | 86 | Involved in neural crest and neuronal development | Southard-Smith, E. M., Kos, L. & Pavan, W. J. SOX10 mutation disrupts neural crest development in Dom Hirschsprung mouse model. Nat. Genet. 18, 60-64 (1998). Britsch, S. et al. The transcription factor Sox10 is a key regulator of peripheral glial development. Genes Dev. 15, 66-78 (2001). |

TABLE 1-continued

| GENE | SEQUENCE | SEQ ID NO: | ROLE | REFERENCES |
|------|----------|------------|------|------------|
| | GGCCCTCGCAGCGGCCCCTCTACAC GGCCATCTCTGACCCCAGCCCCTCA GGGCCCCAGTCCCACAGCCCCACA CACTGGGAGCAGCCAGTATATACG ACACTGTCCCGGCCC | | | |
| SOX2 | ATGTACAACATGATGGAGACGGAG CTGAAGCCGCCGGGCCCGCAGCAA ACTTCGGGGGGCGGCGGCGGCAAC TCCACCGCGGCGGCGGCCGGCGGC AACCAGAAAAACAGCCCGGACCGC GTCAAGCGGCCCATGAATGCCTTCA TGGTGTGGTCCCGCGGGCAGCGGC GCAAGATGGCCCAGGAGAACCCCA AGATGCACAACTCGGAGATCAGCA AGCGCCTGGGCGCCGAGTGGAAAC TTTTGTCGGAGACGGAGAAGCGGC CGTTCATCGACGAGGCTAAGCGGC TGCGAGCGCTGCACATGAAGGAGC ACCCGGATTATAAATACCGGCCCC GGCGGAAAACCAAGACGCTCATGA AGAAGGATAAGTACACGCTGCCCG GCGGGCTGCTGGCCCCCGGCGGCA ATAGCATGGCGAGCGGGGTCGGGG TGGGCGCCGGCCTGGGCGCGGGCG TGAACCAGCGCATGGACAGTTACG CGCACATGAACGGCTGGAGCAACG GCAGCTACAGCATGATGCAGGACC AGCTGGGCTACCCGCAGCACCCGG GCCTCAATGCGCACGGCGCAGCGC AGATGCAGCCCATGCACCGCTACG ACGTGAGCGCCCTGCAGTACAACT CCATGACCAGCTCGCAGACCTACAT GAACGGCTCGCCCACCTACAGCAT GTCCTACTCGCAGCAGGGCACCCCT GGCATGGCTCTTGGCTCCATGGGTT CGGTGGTCAAGTCCGAGGCCAGCT CCAGCCCCCCTGTGGTTACCTCTTC CTCCCACTCCAGGGCGCCCTGCCAG GCCGGGGACCTCCGGGACATGATC AGCATGTATCTCCCCGGCGCCGAG GTGCCGGAACCCGCCGCCCCCAGC AGACTTCACATGTCCCAGCACTACC AGAGCGGCCCGGTGCCCGGACACGG CCATTAACGGCACACTGCCCCTCTC ACACATG | 87 | Involved in regulation of pluripotency and embryogenesis, and in neuronal development. Reprogramming factor for induction of pluripotency. | Boyer, L. A., et al. Core Transcriptional Regulatory Circuitry in Human Embryonic Stem Cells. Cell 122, 947-956 (2005). Graham, V. et al. SOX2 Functions to Maintain Neural Progenitor Identity. Neuron 39, 749-765 (2003). Wang, Z., Oron, E., Nelson, B., Razis, S. & Ivanova, N. Distinct Lineage Specification Roles for NANOG, OCT4, and SOX2 in Human Embryonic Stem Cells. Cell Stem Cell 10, 440-454 (2012). Takahashi, K. & Yamanaka, S. Induction of pluripotent stem cells from mouse embryonic and adult fibroblast cultures by defined factors. Cell 126, 663-76 (2006). Takahashi, K. et al. Induction of pluripotent stem cells from adult human fibroblasts by defined factors. Cell 131, 861-72 (2007). Yu, J. et al. Induced Pluripotent Stem Cell Lines Derived from Human |

TABLE 1-continued

| GENE | SEQUENCE | SEQ ID NO: | ROLE | REFERENCES |
|------|----------|------------|------|------------|
| | | | | Somatic Cells. Science (80-.). 318, 1917-1920 (2007). |
| SOX3 | ATGCGACCTGTTCGAGAGAACTCAT CAGGTGCGAGAAGCCCGCGGGTTC CTGCTGATTTGGCGCGGAGCATTTT GATAAGCCTACCCTTCCCGCCGGAC TCGCTGGCCCACAGGCCCCCAAGCT CCGCTCCGACGGAGTCCCAGGGCC TTTTCACCGTGGCCGCTCCAGCCCC GGGAGCGCCTTCTCCTCCCGCCACG CTGGCGCACCTTCTTCCCGCCCCGG CAATGTACAGCCTTCTGGAGACTGA ACTCAAGAACCCCGTAGGGACACC CACACAAGCGGCGGGCACCGGCGG CCCCGCAGCCCCGGGAGGCGCAGG CAAGAGTAGTGCGAACGCAGCCGG CGGCGCGAACTCGGGCGGCGGCAG CAGCGGTGGTGCGAGCGGAGGTGG CGGGGGTACAGACCAGGACCGTGT GAAACGGCCCATGAACGCCTTCAT GGTATGGTCCCGCGGGCAGCGGCG CAAAATGGCCCTGGAGAACCCCAA GATGCACAATTCTGAGATCAGCAA GCGCTTGGGCGCCGACTGGAAACT GCTGACCGACGCCGAGAAGCGACC ATTCATCGACGAGGCCAAGCGACT TCGCGCCGTGCACATGAAGGAGTA TCCGGACTACAAGTACCGACCGCG CCGCAAGACCAAGACGCTGCTCAA GAAAGATAAGTACTCCCTGCCCAG CGGCCTCCTGCCTCCCGGTGCCGCG GCCGCCGCCGCCGCTGCCGCGGCC GCAGCCGCTGCCGCCAGCAGTCCG GTGGGCGTGGGCCAGCGCCTGGAC ACGTACACGCACGTGAACGGCTGG GCCAACGGCGCGTACTCGCTGGTG CAGGAGCAGCTGGGCTACGCGCAG CCCCCGAGCATGAGCAGCCCGCCG CCGCCGCCCGCGCTGCCGCCGATG CACCGCTACGACATGGCCGGCCTG CAGTACAGCCCAATGATGCCGCCC GGCGCTCAGAGCTACATGAACGTC GCTGCCGCGGCCGCCGCCGCCTCG GGCTACGGGGGCATGGCGCCCTCA GCCACAGCAGCCGCGGCCGCCGCC TACGGGCAGCAGCCCGCCACCGCC GCGGCCGCAGCTGCGGCCGCAGCC GCCATGAGCCTGGGCCCCATGGGC TCGGTAGTGAAGTCTGAGCCCAGCT CGCCGCCGCCCGCCATCGCATCGC ACTCTCAGCGCGCGTGCCTCGGCGA CCTGCGCGACATGATCAGCATGTAC CTGCCACCCGGCGGGACGCGGCC GACGCCGCCTCTCCGCTGCCCGGCG GTCGCCTGCACGGCGTGCACCAGC ACTACCAGGGCGCCGGGACTGCAG TCAACGGAACGGTGCCGCTGACCC ACATC | 88 | Involved in neuronal and pituitary development | Rizzoti, K. et al. SOX3 is required during the formation of the hypothalamo-pituitary axis. Nat. Genet. 36, 247-255 (2004). |
| SPI1 | ATGTTACAGGCGTGCAAAATGGAA GGGTTTCCCCTCGTCCCCCCTCAGC CATCAGAAGACCTGGTGCCCTATG ACACGGATCTATACCAACGCCAAA CGCACGAGTATTACCCCTATCTCAG CAGTGATGGGGAGAGCCATAGCGA CCATTACTGGGACTTCCACCCCCAC CACGTGCACAGCGAGTTCGAGAGC TTCGCCGAGAACAACTTCACGGAG CTCCAGAGCGTGCAGCCCCGCAG CTGCAGCAGCTCTACCGCCACATGG AGCTGGAGCAGATGCACGTCCTCG ATACCCCATGGTGCCACCCCATCC CAGTCTTGGCCACCAGGTCTCCTAC | 89 | Involved in haematopoetic cell development | Scott, E. W. et al. Requirement of transcription factor PU.1 in the development of multiple hematopoietic lineages. Science 265, 1573-1577 (1994). |

TABLE 1-continued

| GENE | SEQUENCE | SEQ ID NO: | ROLE | REFERENCES |
|------|----------|------------|------|------------|
| | CTGCCCCGGATGTGCCTCCAGTACC CATCCCTGTCCCCAGCCCAGCCCAG CTCAGATGAGGAGGAGGGCGAGCG GCAGAGCCCCCACTGGAGGTGTC TGACGGCGAGGCGGATGGCCTGGA GCCCGGGCCTGGGCTCCTGCCTGGG GAGACAGGCAGCAAGAAGAAGATC CGCCTGTACCAGTTCCTGTTGGACC TGCTCCGCAGCGGCGACATGAAGG ACAGCATCTGGTGGGTGGACAAGG ACAAGGGCACCTTCCAGTTCTCGTC CAAGCACAAGGAGGCGCTGGCGCA CCGCTGGGGCATCCAGAAGGGCAA CCGCAAGAAGATGACCTACCAGAA GATGGCGCGCGCGCTGCGCAACTA CGGCAAGACGGGCGAGGTCAAGAA GGTGAAGAAGAAGCTCACCTACCA GTTCAGCGGCGAAGTGCTGGGCCG CGGGGGCCTGGCCGAGCGGCGCCA CCCGCCCCAC | | | Rosenbauer, F. & Tenen, D. G. Transcription factors in myeloid development: balancing differentiation with transformation. Nat. Rev. Immunol. 7, 105-117 (2007). |
| SPIB | ATGCTCGCCCTGGAGGCTGCACAG CTCGACGGGCCACACTTCAGCTGTC TGTACCCAGATGCGTCTTCTATGA CCTGGACAGCTGCAAGCATTCCAG CTACCCTGATTCAGAGGGGGCTCCT GACTCCCTGTGGGACTGGACTGTGG CCCCACCTGTCCCAGCCACCCCCTA TGAAGCCTTCGACCCGGCAGCAGC CGCTTTTAGCCACCCCCAGGCTGCC CAGCTCTGCTACGAACCCCCCACCT ACAGCCCTGCAGGGAACCTCGAAC TGGCCCCAGCCTGGAGGCCCCGG GGCCTGGCCTCCCCGCATACCCCAC GGAGAACTTCGCTAGCCAGACCCT GGTTCCCCCGGCATATGCCCCGTAC CCCAGCCCTGTGCTATCAGAGGAG GAAGACTTACCGTTGGACAGCCCT GCCCTGGAGGTCTCGGACAGCGAG TCGGATGAGGCCCTCGTGGCTGGCC CCGAGGGGAAGGGATCCGAGGCAG GGACTCGCAAGAAGCTGCGCCTGT ACCAGTTCCTGCTGGGGCTACTGAC GCGCGGGGACATGCGTGAGTGCGT GTGGTGGGTGGAGCCAGGCGCCGG CGTCTTCCAGTTCTCCTCCAAGCAC AAGGAACTCCTGGCGCGCCGCTGG GGCCAGCAGAAGGGGAACCGCAAG CGCATGACCTACCAGAAGCTGGCG CGCGCCCTCCGAAACTACGCCAAG ACCGGCGAGATCCGCAAGGTCAAG CGCAAGCTCACCTACCAGTTCGACA GCGCGCTGCTGCCTGCAGTCCGCCG GGCCTTG | 90 | Involved in differentiation of lymphoid cells | Maroulakou, I. G. & Bowe, D. B. Expression and function of Ets transcription factors in mammalian development: a regulatory network. Oncogene 19, 6432-6442 (2000). |
| SPIC | ATGACGTGTGTTGAACAAGACAAG CTGGGTCAAGCATTTGAAGATGCTT TTGAGGTTCTGAGGCAAACATTCAAC TGGAGATCTTCAGTACTCGCCAGAT TACAGAAATTACCTGGCTTTAATCA ACCATCGTCCTCATGTCAAAGGAA ATTCCAGCTGCTATGGAGTGTTGCC TACAGAGGAGCCTGTCTATAATTGG AGAACGGTAATTAACAGTGCTGCG GACTTCTATTTTGAAGGAAATATTC ATCAATCTCTGCAGAACATAACTGA AAACCAGCTGGTACAACCCACTCTT CTCCAGCAAAAGGGGGGAAAAGGC AGGAAGAAGCTCCGACTGTTTGAA TACCTTCACGAATCCCTGTATAATC CGGAGATGGCATCTTGTATTCAGTG GGTAGATAAAACCAAAGGCATCTT TCAGTTTGTATCAAAAAACAAAGA AAAACTTGCCGAGCTTTGGGGAA AAGAAAAGGCAACAGGAAGACCAT GACTTACCAGAAAATGCCAGGGC ACTCAGAAATTACGGAAGAAGTGG | 91 | Involved in macrophage development | Kohyama, M. et al. Role for Spi-C in the development of red pulp macrophages and splenic iron homeostasis. Nature 457, 318-321 (2009). |

TABLE 1-continued

| GENE | SEQUENCE | SEQ ID NO: | ROLE | REFERENCES |
|---|---|---|---|---|
| | GGAAATTACCAAAATCCGGAGGAA GCTGACTTACCAGTTCAGTGAGGCC ATTCTCCAAAGACTCTCTCCATCCT ATTTCCTGGGGAAAGAGATCTTCTA TTCACAGTGTGTTCAACCTGATCAA GAATATCTCAGTTTAAATAACTGGA ATGCAAATTATAATTATACATATGC CAATTACCATGAGCTAAATCACCAT GATTGC | | | |
| SRY | ATGCAATCATATGCTTCTGCTATGT TAAGCGTATTCAACAGCGATGATTA CAGTCCAGCTGTGCAAGAGAATAT TCCCGCTCTCCGGAGAAGCTCTTCC TTCCTTTGCACTGAAAGCTGTAACT CTAAGTATCAGTGTGAAACGGGAG AAAACAGTAAAGGCAACGTCCAGG ATAGAGTGAAGCGACCCATGAACG CATTCATCGTGTGGTCTCGCGATCA GAGGCGCAAGATGGCTCTAGAGAA TCCCAGAATGCGAAACTCAGAGAT CAGCAAGCAGCTGGGATACCAGTG GAAAATGCTTACTGAAGCCGAAAA ATGGCCATTCTTCCAGGAGGCACA GAAATTACAGGCCATGCACAGAGA GAAATACCCGAATTATAAGTATCG ACCTCGTCGGAAGGCGAAGATGCT GCCGAAGAATTGCAGTTTGCTTCCC GCAGATCCCGCTTCGGTACTCTGCA GCGAAGTGCAACTGGACAACAGGT TGTACAGGGATGACTGTACGAAAG CCACACACTCAAGAATGGAGCACC AGCTAGGCCACTTACCGCCCATCAA CGCAGCCAGCTCACCGCAGCAACG GGACCGCTACAGCCACTGGACAAA GCTG | 92 | Involved in sex determination and spermatogenesis | Polanco, J. C. & Koopman, P. Sry and the hesitant beginnings of male development. Dev. Biol. 302, 13-24 (2007). Koopman, P. et al. Male development of chromosomally female mice transgenic for Sry. Nature 351, 117-121 (1991). |
| TBX5 | ATGGCCGACGCAGACGAGGGCTTT GGCTCTGGCGCACACGCCTCTGGAG CCTGACGCAAAAGACCTGCCCTGC GATTCGAAACCCGAGAGCGCGCTC GGGGCCCCCAGCAAGTCCCCGTCG TCCCCGCAGGCCGCCTTCACCCAGC AGGGCATGGAGGGAATCAAAGTGT TTCTCCATGAAAGAGAACTGTGGCT AAAATTCCACGAAGTGGGCACGGA AATGATCATAACCAAGGCTGGAAG GCGGATGTTTCCCAGTTACAAAGTG AAGGTGACGGGCCTTAATCCCAAA ACGAAGTACATTCTTCTCATGGACA TTGTACCTGCCGACGATCACAGATA CAAATTCGCAGATAATAAATGGTCT GTGACGGGCAAAGCTGAGCCCGCC ATGCCTGGCCGCCTGTACGTGCACC CAGACTCCCCCGCCACCGGGGCGC ATTGGATGAGGCAGCTCGTCTCCTT CCAGAAACTCAAGCTCACCAACAA CCACCTGGACCCATTTGGGCATATT ATTCTAAATTCCATGCACAAATACC AGCCTAGATTACACATCGTGAAAG CGGATGAAAATAATGGATTTGGCT CAAAAAATACAGCGTTCTGCACTC ACGTCTTTCCTGAGACTGCGTTTAT AGCAGTGACTTCCTACCAGAACCA CAAGATCACGCAATTAAAGATTGA GAATAATCCCTTTGCCAAAGGATTT CGGGGCAGTGATGACATGGAGCTG CACAGAATGTCAAGAATGCAAAGT AAAGAATATCCCGTGGTCCCCAGG AGCACCGTGAGGCAAAAAGTGGCC TCCAACCACAGTCCTTTCAGCAGCG AGTCTCGAGCTCTCTCCACCTCATC CAATTTGGGGTCCCAATACCAGTGT GAGAATGGTGTTTCCGGCCCCTCCC AGGACCTCCTGCCTCCACCCAACCC ATACCCACTGCCCCAGGAGCATAG CCAAATTTACCATTGTACCAAGAGG | 93 | Involved in cardiac development | Bruneau, B. G. et al. A Murine Model of Holt-Oram Syndrome Defines Roles of the T-Box Transcription Factor Tbx5 in Cardiogenesis and Disease. Cell 106, 709-721 (2001). |

TABLE 1-continued

| GENE | SEQUENCE | SEQ ID NO: | ROLE | REFERENCES |
|------|----------|------------|------|------------|
| | AAAGAGGAAGAATGTTCCACCACA<br>GACCATCCCTATAAGAAGCCCTAC<br>ATGGAGACATCACCCAGTGAAGAA<br>GATTCCTTCTACCGCTCTAGCTATC<br>CACAGCAGCAGGGCCTGGGTGCCT<br>CCTACAGGACAGAGTCGGCACAGC<br>GGCAAGCTTGCATGTATGCCAGCTC<br>TGCGCCCCCAGCGAGCCTGTGCCC<br>AGCCTAGAGGACATCAGCTGCAAC<br>ACGTGGCCAAGCATGCCTTCCTACA<br>GCAGCTGCACCGTCACCACCGTGC<br>AGCCCATGGACAGGCTACCCTACC<br>AGCACTTCTCCGCTCACTTCACCTC<br>GGGGCCCCTGGTCCCTCGGCTGGCT<br>GGCATGGCCAACCATGGCTCCCCA<br>CAGCTGGGAGAGGGAATGTTCCAG<br>CACCAGACCTCCGTGGCCCACCAG<br>CCTGTGGTCAGGCAGTGTGGGCCTC<br>AGACTGGCCTGCAGTCCCCTGGCAC<br>CCTTCAGCCCCTGAGTTCCTCTAC<br>TCTCATGGCGTGCCAAGGACTCTAT<br>CCCCTCATCAGTACCACTCTGTGCA<br>CGGAGTTGGCATGGTGCCAGAGTG<br>GAGCGACAATAGCTTG | | | |
| TFAP2<br>C | ATGTTGTGGAAAATAACCGATAAT<br>GTCAAGTACGAAGAGGACTGCGAG<br>GATCGCCACGACGGGAGCAGCAAT<br>GGGAATCCGCGGGTCCCCCACCTCT<br>CCTCCGCCGGGCAGCACCTCTACAG<br>CCCCGCGCCACCCCTCTCCCACACT<br>GGAGTCGCCGAATATCAGCCGCCA<br>CCCTACTTTCCCCCTCCCTACCAGC<br>AGCTGGCCTACTCCCAGTCGGCCGA<br>CCCCTACTCGCATCTGGGGAAGC<br>GTACGCCGCCGCCATCAACCCCCTG<br>CACCAGCCGGCGCCCACAGGCAGC<br>CAGCAGCAGGCCTGGCCCGGCCGC<br>CAGAGCCAGGAGGGAGCGGGGCTG<br>CCCTCGCACCACGGGCGCCCGGCC<br>GGCCTACTGCCCCACCTCTCCGGGC<br>TGGAGGCGGGCGCGGTGAGCGCCC<br>GCAGGGATGCCTACCGCCGCTCCG<br>ACCTGCTGCTGCCCCACGCACACGC<br>CCTGGATGCCGCGGGCCTGGCCGA<br>GAACCTGGGGCTCCACGACATGCC<br>TCACCAGATGGACGAGGTGCAGAA<br>TGTCGACGACCAGCACCTGTTGCTG<br>CACGATCAGACAGTCATTCGCAAA<br>GGTCCCATTTCCATGACCAAGAACC<br>CTCTGAACCTCCCCTGTCAGAAGGA<br>GCTGGTGGGGGCCGTAATGAACCC<br>CACTGAGGTCTTCTGCTCAGTCCCT<br>GGAAGATTGTCGCTCCTCAGCTCTA<br>CGTCTAAATACAAAGTGACAGTGG<br>CTGAAGTACAGAGGCGACTGTCCC<br>CACCTGAATGCTTAAATGCCTCGTT<br>ACTGGGAGGTGTTCTCAGAAGAGC<br>CAAATCGAAAAATGGAGGCCGGTC<br>CTTGCGGGAGAAGTTGGACAAGAT<br>TGGGTTGAATCTTCCGGCCGGGAG<br>GCGGAAAGCCGCTCATGTGACTCTC<br>CTGACATCCTTAGTAGAAGGTGAA<br>GCTGTTCATTTGGCTAGGGACTTTG<br>CCTATGTCTGTGAAGCCGAATTTCC<br>TAGTAAACCAGTGGCAGAATATTT<br>AACCAGACCTCATCTTGGAGGACG<br>AAATGAGATGGCAGCTAGGAAGAA<br>CATGCTATTGGCGGCCCAGCAACTG<br>TGTAAAGAATTCACAGAACTTCTCA<br>GCCAAGACCGGACACCCCATGGGA<br>CCAGCAGGCTCGCCCCAGTCTTGGA<br>GACGAACATACAGAACTGCTTGTCT<br>CATTTCAGCCTGATTACCCACGGGT<br>TTGGCAGCCAGGCCATCTGTGCCGC<br>GGTGTCTGCCCTGCAGAACTACATC<br>AAAGAAGCCCTGATTGTCATAGAC | 94 | Involved in trophectoderm development | Cao, Z. et al. Transcription factor AP-2γ induces early Cdx2 expression and represses HIPPO signaling to specify the trophectoderm lineage. Development 142, 1606-15 (2015). |

TABLE 1-continued

| GENE | SEQUENCE | SEQ ID NO: | ROLE | REFERENCES |
|---|---|---|---|---|
| | AAATCCTACATGAACCCTGGAGAC CAGAGTCCAGCTGATTCTAACAAA ACCCTGGAGAAAATGGAGAAACAC AGGAAA | | | |

TABLE 2

| Sample_ID | Description | Media Condition | Estimated Number of Cells | Mean Reads per Cell | Median Genes per Cell |
|---|---|---|---|---|---|
| UP_TF_1 | HighMOI, (−) TRA-1-60 MACS sorted | Pluripotent stem cell medium | 3,640 | 45,983 | 3,317 |
| UP_TF_2 | HighMOI, Unsorted | Pluripotent stem cell medium | 3,505 | 49,750 | 3,843 |
| UP_TF_3 | HighMOI, Unsorted | Pluripotent stem cell medium | 4,223 | 45,403 | 3,972 |
| UP_TF_4 | HighMOI, (−) TRA-1-60 MACS sorted | Pluripotent stem cell medium | 3,461 | 56,290 | 4,475 |
| UP_TF_5 | LowMOI, (−) TRA-1-60 MACS sorted | Pluripotent stem cell medium | 3,748 | 46,895 | 4,165 |
| UP_TF_8 | Library, Endothelial | Endothelial growth medium | 3,563 | 41,056 | 3,698 |
| UP_TF_10 | Library, Multilineage | Multilineage differentiation medium | 2,129 | 70,519 | 5,605 |
| UP_TF_11 | Library, Endothelial | Endothelial growth medium | 6,574 | 23,250 | 3,105 |
| UP_TF_12 | Library, Multilineage | Multilineage differentiation medium | 4,678 | 30,340 | 3,882 |
| UP_TF_13 | KLF Family, cMYC Mutants | Pluripotent stem cell medium | 5,590 | 35,913 | 3,620 |

| Sample_ID | Number of Reads | Valid Barcodes | Reads Mapped Confidently to Exonic Regions | Sequencing Saturation | Fraction Reads in Cells | Median UMI Counts per Cell |
|---|---|---|---|---|---|---|
| UP_TF_1 | 167,381,505 | 97.90% | 65.60% | 17.00% | 55.40% | 11,785 |
| UP_TF_2 | 174,376,238 | 98.40% | 70.30% | 20.80% | 63.90% | 15,985 |
| UP_TF_3 | 191,740,141 | 98.10% | 63.10% | 18.90% | 77.20% | 16,090 |
| UP_TF_4 | 194,819,799 | 98.20% | 66.80% | 25.00% | 78.60% | 19,132 |
| UP_TF_5 | 175,765,276 | 98.10% | 65.70% | 17.70% | 76.90% | 17,349 |
| UP_TF_8 | 146,283,407 | 98.20% | 65.20% | 16.60% | 80.90% | 15,049 |
| UP_TF_10 | 150,135,344 | 98.20% | 68.60% | 20.20% | 83.00% | 27,785 |
| UP_TF_11 | 152,847,871 | 98.20% | 69.40% | 11.20% | 86.80% | 10,681 |
| UP_TF_12 | 141,934,669 | 98.20% | 70.00% | 11.00% | 88.10% | 14,526 |
| UP_TF_13 | 200,756,922 | 98.00% | 66.20% | 15.50% | 78.70% | 14,286 |

TABLE 3

| | Number of Genotyped Cells | | |
|---|---|---|---|
| Genotype | Stem cell media | Endothelial media | Multilineage media |
| ASCL1 | 186 | 78 | 21 |
| ASCL3 | 471 | 150 | 89 |
| ASCL4 | 286 | 90 | 75 |
| ASCL5 | 140 | 64 | 51 |
| ATF7 | 97 | 49 | 45 |
| CDX2 | 267 | 192 | 103 |
| CRX | 292 | 107 | 54 |
| ERG | 62 | 30 | 7 |

TABLE 3-continued

Number of Genotyped Cells

| Genotype | Stem cell media | Endothelial media | Multilineage media |
|---|---|---|---|
| ESRRG | 169 | 98 | 64 |
| ETV2 | 60 | 22 | 21 |
| FLI1 | 55 | 27 | 18 |
| FOXA1 | 53 | 27 | 14 |
| FOXA2 | 89 | 46 | 37 |
| FOXA3 | 255 | 90 | 61 |
| FOXP1 | 413 | 112 | 94 |
| GATA1 | 288 | 111 | 72 |
| GATA2 | 62 | 81 | 60 |
| GATA4 | 71 | 101 | 58 |
| GATA6 | 44 | 44 | 35 |
| GLI1 | 27 | 11 | 16 |
| HAND2 | 310 | 113 | 81 |
| HNF1A | 88 | 45 | 39 |
| HNF1B | 53 | 30 | 41 |
| HOXA1 | 166 | 67 | 57 |
| HOXA10 | 344 | 111 | 66 |
| HOXA11 | 237 | 82 | 47 |
| HOXB6 | 166 | 95 | 44 |
| KLF4 | 298 | 259 | 145 |
| LHX3 | 175 | 76 | 45 |
| LMX1A | 458 | 155 | 82 |
| mCherry | 1689 | 689 | 495 |
| MEF2C | 87 | 49 | 51 |
| MESP1 | 227 | 70 | 55 |
| MITF | 73 | 63 | 45 |
| MYC | 291 | 113 | 36 |
| MYCL | 356 | 112 | 75 |
| MYCN | 50 | 33 | 12 |
| MYOD1 | 197 | 68 | 40 |
| MYOG | 284 | 122 | 81 |
| NEUROD1 | 83 | 46 | 10 |
| NEUROG1 | 154 | 103 | 23 |
| NEUROG3 | 158 | 138 | 41 |
| NRL | 249 | 75 | 49 |
| ONECUT1 | 159 | 109 | 58 |
| OTX2 | 293 | 95 | 47 |
| PAX7 | 86 | 56 | 28 |
| POU1F1 | 126 | 61 | 50 |
| POU5F1 | 78 | 30 | 24 |
| RUNX1 | 139 | 47 | 43 |
| SIX1 | 260 | 119 | 66 |
| SIX2 | 295 | 103 | 84 |
| SNAI2 | 485 | 96 | 50 |
| SOX10 | 83 | 54 | 30 |
| SOX2 | 137 | 53 | 27 |
| SOX3 | 137 | 56 | 31 |
| SPI1 | 264 | 142 | 67 |
| SPIB | 199 | 70 | 47 |
| SPIC | 147 | 80 | 35 |
| SRY | 166 | 61 | 65 |
| TBX5 | 149 | 112 | 35 |
| TFAP2C | 90 | 58 | 34 |

TABLE 4

Enrichment p-value for each genotype in clusters using Fisher's exact test

| | C6 | C2 | C5 | C3 | C1 | C7 | C4 |
|---|---|---|---|---|---|---|---|
| CDX2 | 0.999581 | 0.502321 | 1 | 1 | 1 | 3.42E−58 | 1 |
| KLF4 | 0.688329 | 1.12E−27 | 1 | 1 | 1 | 1 | 3.82E−21 |
| FOXA1 | 0.848222 | 1 | 1 | 8.00E−08 | 1 | 1 | 1 |
| FOXA2 | 0.559116 | 1 | 1 | 2.56E−15 | 1 | 0.788874 | 1 |
| GATA2 | 0.002284 | 1 | 1.57E−10 | 1 | 1 | 0.91906 | 0.832613 |
| GATA4 | 0.009787 | 0.781098 | 1.13E−09 | 1 | 0.553072 | 1 | 0.822422 |
| GATA6 | 0.03266 | 0.23167 | 0.000147 | 1 | 1 | 1 | 1 |
| SOX10 | 0.017774 | 0.043271 | 1 | 1 | 1 | 0.12661 | 1 |
| NEUROD1 | 0.280233 | 1 | 1 | 1 | 1 | 0.34423 | 1 |
| ETV2 | 0.016254 | 1 | 1 | 1 | 1 | 0.054486 | 1 |
| SPIB | 9.93E−07 | 1 | 0.29024 | 0.190193 | 1 | 1 | 1 |
| SOX3 | 1.53E−05 | 1 | 1 | 1 | 1 | 1 | 0.063768 |
| NEUROG3 | 6.23E−06 | 1 | 1 | 0.502271 | 1 | 0.50894 | 1 |
| TBX5 | 1.71E−07 | 1 | 1 | 0.449045 | 1 | 1 | 1 |
| MYOD1 | 3.73E−07 | 1 | 1 | 1 | 1 | 1 | 0.115324 |
| MYC | 9.91E−05 | 0.611641 | 1 | 1 | 0.394338 | 0.779857 | 1 |
| ESRRG | 5.02E−12 | 0.233929 | 1 | 1 | 0.58849 | 1 | 1 |
| TFAP2C | 6.90E−05 | 1 | 0.541387 | 1 | 1 | 1 | 0.638171 |
| GLI1 | 0.017877 | 1 | 1 | 1 | 1 | 1 | 0.380973 |
| NEUROG1 | 0.00162 | 1 | 1 | 1 | 1 | 0.620425 | 1 |
| ASCL5 | 9.82E−08 | 0.737393 | 1 | 1 | 1 | 0.353463 | 1 |
| FOXA3 | 3.08E−15 | 1 | 1 | 0.644816 | 1 | 1 | 1 |
| ATF7 | 2.03E−09 | 1 | 1 | 0.534822 | 1 | 1 | 1 |
| HOXA10 | 2.36E−09 | 1 | 0.4436 | 0.673452 | 0.599648 | 1 | 0.85978 |
| SOX2 | 4.01E−06 | 1 | 0.461875 | 1 | 1 | 1 | 1 |
| ONECUT1 | 2.98E−11 | 1 | 1 | 0.626421 | 1 | 1 | 0.822422 |
| RUNX1 | 3.65E−07 | 1 | 1 | 1 | 0.450277 | 1 | 0.364314 |
| SIX2 | 8.69E−16 | 1 | 0.888323 | 1 | 1 | 0.677188 | 0.710842 |
| HOXA11 | 4.51E−09 | 1 | 1 | 1 | 1 | 0.860947 | 0.406197 |
| SPIC | 1.28E−06 | 1 | 1 | 1 | 1 | 1 | 0.648778 |
| MYCL | 2.52E−22 | 1 | 1 | 1 | 1 | 1 | 1 |
| FOXP1 | 9.41E−17 | 0.702249 | 1 | 0.795614 | 0.374912 | 0.980162 | 1 |
| SNAI2 | 4.89E−09 | 1 | 1 | 0.681398 | 1 | 0.616212 | 1 |
| HNF1A | 7.52E−11 | 1 | 1 | 1 | 1 | 1 | 1 |
| LMX1A | 2.74E−19 | 1 | 1 | 0.845485 | 1 | 1 | 0.912434 |
| ERG | 0.164469 | 1 | 1 | 1 | 1 | 1 | 1 |
| HAND2 | 7.41E−17 | 1 | 1 | 1 | 1 | 0.653393 | 1 |
| MITF | 2.07E−10 | 1 | 0.643049 | 1 | 1 | 1 | 1 |
| PAX7 | 1.57E−05 | 1 | 1 | 1 | 1 | 0.692249 | 1 |

TABLE 4-continued

Enrichment p-value for each genotype in clusters using Fisher's exact test

| | C6 | C2 | C5 | C3 | C1 | C7 | C4 |
|---|---|---|---|---|---|---|---|
| SIX1 | 1.58E-14 | 0.822135 | 1 | 1 | 0.599648 | 1 | 1 |
| OTX2 | 3.17E-08 | 0.708559 | 1 | 1 | 1 | 1 | 0.754072 |
| SPI1 | 5.65E-12 | 0.826686 | 1 | 1 | 1 | 0.767724 | 1 |
| GATA1 | 2.36E-13 | 0.847734 | 1 | 1 | 1 | 1 | 0.629688 |
| MYOG | 7.41E-17 | 1 | 1 | 0.746058 | 1 | 0.966092 | 1 |
| HNF1B | 1.21E-06 | 1 | 1 | 1 | 0.434855 | 1 | 1 |
| POU1F1 | 2.52E-14 | 1 | 1 | 1 | 1 | 1 | 1 |
| FLI1 | 0.000193 | 1 | 1 | 1 | 1 | 1 | 1 |
| HOXA1 | 3.20E-15 | 1 | 1 | 1 | 1 | 1 | 1 |
| SRY | 1.01E-17 | 1 | 1 | 1 | 1 | 1 | 1 |
| CRX | 4.15E-13 | 1 | 1 | 1 | 1 | 0.896121 | 1 |
| ASCL1 | 0.000199 | 1 | 1 | 1 | 1 | 1 | 1 |
| NRL | 9.14E-09 | 1 | 1 | 1 | 0.494018 | 0.872071 | 1 |
| LHX3 | 1.65E-11 | 1 | 1 | 1 | 1 | 1 | 1 |
| MESP1 | 2.47E-11 | 1 | 1 | 1 | 0.534212 | 1 | 0.805949 |
| HOXB6 | 3.05E-08 | 1 | 1 | 1 | 1 | 1 | 1 |
| ASCL4 | 3.41E-17 | 1 | 1 | 1 | 0.646165 | 0.956545 | 1 |
| MYCN | 0.00932 | 1 | 1 | 1 | 1 | 1 | 1 |
| MEF2C | 3.40E-10 | 1 | 1 | 1 | 1 | 1 | 0.78156 |
| POU5F1 | 3.21E-06 | 1 | 1 | 1 | 1 | 1 | 1 |
| ASCL3 | 3.49E-19 | 1 | 1 | 1 | 0.707836 | 1 | 1 |
| mCherry | 1.64E-91 | 0.99443 | 0.961129 | 0.996934 | 0.263601 | 0.994961 | 0.947099 |

TABLE 5

| Module | Description | n_genes |
|---|---|---|
| GM1 | Cytoskeleton and polarity | 444 |
| GM2 | Ion transport | 973 |
| GM3 | Chromatin accessibility | 1568 |
| GM4 | Signaling pathways | 873 |
| GM5 | Neuron differentiation | 444 |
| GM6 | Notch pathway | 859 |
| GM7 | Embryonic development | 509 |
| GM8 | Mitochondrial metabolism and translation | 2242 |
| GM9 | Ribosome biogenesis | 190 |
| GM10 | Growth factor response | 492 |
| GM11 | Pluripotent state | 234 |

TABLE 6

| Gene | Forward Primer (5'→3') | SEQ ID NO: | Reverse Primer (5'→3') | SEQ ID NO: |
|---|---|---|---|---|
| CDH5 | AGACCACGCCTCTGTCATGTACCAAATC | 95 | CACGATCTCATACCTGGCCTGCTTC | 113 |
| PECAM1 | GGTCAGCAGCATCGTGGTCAACATAAC | 96 | TGGAGCAGGACAGGTTCAGTCTTTCA | 114 |
| VWF | TCTCCGTGGTCCTGAAGCAGACATA | 97 | AGGTTGCTGCTGGTGAGGTCATT | 115 |
| KDR | AGCCATGTGGTCTCTCTGGTTGTGTATG | 98 | GTTTGAGTGGTGCCGTACTGGTAGGA | 116 |
| NANOG | TTTGTGGGCCTGAAGAAAACT | 99 | AGGGCTGTCCTGAATAAGCAG | 117 |
| POU5F1 | CTTGAATCCCGAATGGAAAGGG | 100 | GTGTATATCCCAGGGTGATCCTC | 118 |
| SOX2 | TACAGCATGTCCTACTCGCAG | 101 | GAGGAAGAGGTAACCACAGGG | 119 |
| DNMT3B | GAGTCCATTGCTGTTGGAACCG | 102 | ATGTCCCTCTTGTCGCCAACCT | 120 |
| SALL2 | CAGCGGAAACCCCAACAGTTA | 103 | GAGGGTCAGTAGAACATGCGT | 121 |
| DPPA4 | GACCTCCACAGAGAAGTCGAG | 104 | TGCCTTTTTCTTAGGGCAGAG | 122 |
| VIM | AGTCCACTGAGTACCGGAGAC | 105 | CATTTCACGCATCTGGCGTTC | 123 |
| CDH1 | CGAGAGCTACACGTTCACGG | 106 | GGGTGTCGAGGGAAAAATAGG | 124 |
| CDH2 | AGCCAACCTTAACTGAGGAGT | 107 | GGCAAGTTGATTGGAGGGATG | 125 |
| EPCAM | TGATCCTGACTGCGATGAGAG | 108 | CTTGTCTGTTCTTCTGACCCC | 126 |
| LAMC1 | GGCAACGTGGCCTTTTCTAC | 109 | AGTGGCAGTTACCCATTCCTG | 127 |
| SPP1 | GAAGTTTCGCAGACCTGACAT | 110 | GTATGCACCATTCAACTCCTCG | 128 |

TABLE 6-continued

| Gene | Forward Primer (5'→3') | SEQ ID NO: | Reverse Primer (5'→3') | SEQ ID NO: |
|---|---|---|---|---|
| THY1 | ATCGCTCTCCTGCTAACAGTC | 111 | CTCGTACTGGATGGGTGAACT | 129 |
| TPM2 | CTGAGACCCGAGCAGAGTTTG | 112 | TGAATCTCGACGTTCTCCTCC | 130 |

REFERENCES

1. Xu, J., Du, Y. & Deng, H. Direct lineage reprogramming: strategies, mechanisms, and applications. *Cell Stem Cell* 16, 119-34 (2015).
2. Davis, Robert L; Weintraub, Harold; Lassar, A. B. Expression of a single transfected cDNA converts fibroblasts to myoblasts. *Cell* 51, 987-1000 (1987).
3. Takahashi, K. & Yamanaka, S. Induction of pluripotent stem cells from mouse embryonic and adult fibroblast cultures by defined factors. *Cell* 126, 663-76 (2006).
4. Takahashi, K. et al. Induction of pluripotent stem cells from adult human fibroblasts by defined factors. *Cell* 131, 861-72 (2007).
5. Yu, J. et al. Induced Pluripotent Stem Cell Lines Derived from Human Somatic Cells. *Science* 318, 1917-1920 (2007).
6. Wernig, M. et al. In vitro reprogramming of fibroblasts into a pluripotent ES-cell-like state. *Nature* 448, 318-324 (2007).
7. Maherali, N. et al. Directly Reprogrammed Fibroblasts Show Global Epigenetic Remodeling and Widespread Tissue Contribution. *Cell Stem Cell* 1, 55-70 (2007).
8. Park, I.-H. et al. Reprogramming of human somatic cells to pluripotency with defined factors. *Nature* 451, 141-146 (2008).
9. Pang, Z. P. et al. Induction of human neuronal cells by defined transcription factors. *Nature* 476, 220-223 (2011).
10. Sugimura, R. et al. Haematopoietic stem and progenitor cells from human pluripotent stem cells. *Nature* 545, 432-438 (2017).
11. Yang, N. et al. Generation of pure GABAergic neurons by transcription factor programming. *Nat. Methods* 14, 621-628 (2017).
12. Sugimura, R. et al. Haematopoietic stem and progenitor cells from human pluripotent stem cells. *Nature* 545, 432-438 (2017).
13. Zhang, Y. et al. Rapid single-step induction of functional neurons from human pluripotent stem cells. *Neuron* 78, 785-98 (2013).
14. Abujarour, R. et al. Myogenic differentiation of muscular dystrophy-specific induced pluripotent stem cells for use in drug discovery. *Stem Cells Transl. Med.* 3, 149-60 (2014).
15. Chanda, S. et al. Generation of induced neuronal cells by the single reprogramming factor ASCL1. *Stem Cell Reports* 3, 282-96 (2014).
16. Kolodziejczyk, A. A., Kim, J. K., Svensson, V., Marioni, J. C. & Teichmann, S. A. The technology and biology of single-cell RNA sequencing. *Mol. Cell* 58, 610-20 (2015).
17. Mohr, S., Bakal, C. & Perrimon, N. Genomic screening with RNAi: results and challenges. *Annu. Rev. Biochem.* 79, 37-64 (2010).
18. Shalem, O., Sanjana, N. E. & Zhang, F. High-throughput functional genomics using CRISPR-Cas9. *Nat. Rev. Genet.* 16, 299-311 (2015).
19. Adamson, B. et al. A Multiplexed Single-Cell CRISPR Screening Platform Enables Systematic Dissection of the Unfolded Protein Response. *Cell* 167, 1867-1882.e21 (2016).
20. Dixit, A. et al. Perturb-Seq: Dissecting Molecular Circuits with Scalable Single-Cell RNA Profiling of Pooled Genetic Screens. *Cell* 167, 1853-1866.e17 (2016).
21. Jaitin, D. A. et al. Dissecting Immune Circuits by Linking CRISPR-Pooled Screens with Single-Cell RNA-Seq. *Cell* 167, 1883-1896.e15 (2016).
22. Xie, S., Duan, J., Li, B., Zhou, P. & Hon, G. C. Multiplexed Engineering and Analysis of Combinatorial Enhancer Activity in Single Cells. *Mol. Cell* 66, 285-299.e5 (2017).
23. Datlinger, P. et al. Pooled CRISPR screening with single-cell transcriptome readout. *Nat. Methods* 14, 297-301 (2017).
24. Macosko, E. Z. et al. Highly Parallel Genome-wide Expression Profiling of Individual Cells Using Nanoliter Droplets. *Cell* 161, 1202-1214 (2015).
25. Nishiyama, A. et al. Uncovering Early Response of Gene Regulatory Networks in ESCs by Systematic Induction of Transcription Factors. *Cell Stem Cell* 5, 420-433
26. Blondel, V. D., Guillaume, J.-L., Lambiotte, R. & Lefebvre, E. Fast unfolding of communities in large networks. *arXiv* 1-12 (2008). doi:10.1088/1742-5468/2008/10/P10008
27. Orkin, S. H. & Hochedlinger, K. Chromatin connections to pluripotency and cellular reprogramming. Cell 145, 835 (2011).
28. Busskamp, V. et al. Rapid neurogenesis through transcriptional activation in human stem cells. *Mol Syst Blol* 10, (2014).
29. Velkey, J. M. & O'Shea, K. S. Expression of Neurogenin 1 in mouse embryonic stem cells directs the differentiation of neuronal precursors and identifies unique patterns of down-stream gene expression. *Dev. Dyn.* 242, 230-53 (2013).
30. Castro, D. S. et al. A novel function of the proneural factor Ascl1 in progenitor proliferation identified by genome-wide characterization of its targets. *Genes Dev.* 25, 930-45 (2011).
31. Tapscott, S. J. The circuitry of a master switch: Myod and the regulation of skeletal muscle gene transcription. *Development* 132, 2685-2695 (2005).
32. Treutlein, B. et al. Dissecting direct reprogramming from fibroblast to neuron using single-cell RNA-seq. *Nature* 534, 391-5 (2016).
33. Niwa, H. et al. Interaction between Oct3/4 and Cdx2 Determines Trophectoderm Differentiation. *Cell* 123, 917-929 (2005).
34. Pelengaris, S., Khan, M. & Evan, G. c-MYC: more than just a matter of life and death. *Nat. Rev. Cancer* 2, 764-776 (2002).
35. McConnell, B. B. & Yang, V. W. Mammalian Kruppel-like factors in health and diseases. *Physiol. Rev.* 90, 1337-81 (2010).

36. Tiwari, N. et al. Klf4 Is a Transcriptional Regulator of Genes Critical for EMT, Including Jnk1 (Mapk8). *PLoS One* 8, e57329 (2013).
37. Zhang, B. et al. KLF5 activates microRNA 200 transcription to maintain epithelial characteristics and prevent induced epithelial-mesenchymal transition in epithelial cells. *Mol. Cell. Biol.* 33, 4919-35 (2013).
38. Gumireddy, K. et al. KLF17 is a negative regulator of epithelial-mesenchymal transition and metastasis in breast cancer. *Nat. Cell Biol.* 11, 1297-304 (2009).
39. Liu, Y.-N. et al. Critical and reciprocal regulation of KLF4 and SLUG in transforming growth factor β-initiated prostate cancer epithelial-mesenchymal transition. *Mol. Cell. Biol.* 32, 941-53 (2012).
40. Li, R. et al. A Mesenchymal-to-Epithelial Transition Initiates and Is Required for the Nuclear Reprogramming of Mouse Fibroblasts. *Cell Stem Cell* 7, 51-63 (2010).
41. Barrallo-Gimeno, A., Nieto, M. A. & Ip, Y. T. The Snail genes as inducers of cell movement and survival: implications in development and cancer. *Development* 132, 3151-61 (2005).
42. Subramanian, A. et al. Gene set enrichment analysis: a knowledge-based approach for interpreting genome-wide expression profiles. *Proc. Natl. Acad. Sci.* 102, 15545-15550 (2005).
43. Morita, R. et al. ETS transcription factor ETV2 directly converts human fibroblasts into functional endothelial cells. *Proc. Natl. Acad. Sci.* 112, 160-165 (2015).
44. Li, W. et al. MAGeCK enables robust identification of essential genes from genome-scale CRISPR/Cas9 knockout screens. *Genome Biol.* 15, 554 (2014)

What is claimed is:

1. A method of performing a high throughput gene overexpression screen, the method comprising:
   (a) transducing target cells with a barcoded open reading frame (ORF) library of transcription factor (TF) genes comprising viral particles, wherein each of the viral particles comprises an isolated polynucleotide or vector comprising:
      (i) a polynucleotide encoding an open reading frame (ORF) of a TF gene, wherein the polynucleotide is operably linked to a nucleic acid encoding a 2A peptide;
      (ii) a nucleic acid encoding a selectable marker; and
      (iii) a nucleic acid barcode located downstream of the selectable marker; wherein the nucleic acid barcode is located 3' to the polynucleotide encoding the ORF of the TF gene and wherein the TF gene is a wild type TF gene, an engineered TF gene, or a mutated TF gene;
   (b) performing single cell RNA sequencing (scRNA-seq) on the transduced target cells to identify overexpressed nucleic acid barcodes;
   (c) determining a fitness effect in the transduced target cells, wherein determining the fitness effect comprises determining the effect of an ORF expression on cell proliferation, viability, rate of senescence, apoptosis, DNA repair mechanism, genome stability, gene transcription, or stress response, and
   (d) identifying transduced target cells comprising a significant ORF, wherein the significant ORF exhibits a cluster enrichment with a false discovery rate (FDR) of less than $10^{-6}$; and a cluster enrichment profile different from a non-TF control with a FDR less than $10^{-6}$ based on a Fisher's exact test when expressed in the target cells; and
   wherein the target cells are mammalian cells selected from equine cells, bovine cells, canine cells, murine cells, porcine cells, feline cells, or human cells.

2. The method of claim 1, further comprising identifying the effect of TF overexpression on a gene-to-gene co-perturbation network.

3. The method of claim 2, further comprising segmenting the co-perturbation network into functional gene modules.

4. The method of claim 1, wherein the target cells are stem cells.

5. The method of claim 1, wherein the TF gene drives differential expression of more than 100 genes.

6. The method of claim 1, wherein the isolated polynucleotide or vector further comprises a 3'-long terminal repeat (LTR) region and wherein the nucleic acid barcode is located about 200 base pairs upstream of the 3'-LTR region.

7. The method of claim 1, wherein the selectable marker is operably linked to the TF via the 2A peptide.

8. The method of claim 1, wherein the isolated polynucleotide or vector further comprises a nucleic acid encoding an expression control element.

9. The method of claim 8, wherein the expression control element is a promoter or wherein the expression control element is a translation elongation factor 1A (EF1A) promoter.

10. The method of claim 1, wherein the TF gene is a wild type TF gene.

11. The method of claim 10, wherein the wild type TF gene encodes a developmentally critical TF selected from ASCL1, ASCL3, ASCL4, ASCL5, ATF7, CDX2, CRX, ERG, ESRRG, ETV2, FLI1, FOXA1, FOXA2, FOXA3, FOXP1, GATA1, GATA2, GATA4, GATA6, GLI1, HAND2, HNF1A, HNF1B, HNF4A, HOXA1, HOXA10, HOXA11, HOXB6, KLF4, LHX3, LMX1A, MEF2C, MESP1, MITF, MYC, MYCL, MYCN, MYOD1, MYOG, NEUROD1, NEUROG1, NEUROG3, NRL, ONECUT1, OTX2, PAX7, POU1F1, POU5F1, RUNX1, SIX1, SIX2, SNAI2, SOX10, SOX2, SOX3, SPI1, SPIB, SPIC, SRY, TBX5, or TFAP2C.

12. The method of claim 1, wherein the library comprises at least 10, at least 20, at least 30, at least 40, at least 50, at least 60, at least 70, at least 80, at least 90, or at least 100 nucleic acids or vectors.

13. The method of claim 1, wherein the target cells are embryonic stem cells (ESCs) or induced pluripotent stem cells (iPSCs).

* * * * *

UNITED STATES PATENT AND TRADEMARK OFFICE
CERTIFICATE OF CORRECTION

PATENT NO. : 11,912,986 B2
APPLICATION NO. : 17/028836
DATED : February 27, 2024
INVENTOR(S) : Prashant Mali et al.

It is certified that error appears in the above-identified patent and that said Letters Patent is hereby corrected as shown below:

In the Claims

At Column 261, Line 24: replace "(0 RF)" with --(ORF)--

Signed and Sealed this
Eighth Day of October, 2024

Katherine Kelly Vidal
*Director of the United States Patent and Trademark Office*